(12) United States Patent
Nukaya et al.

(10) Patent No.: US 12,090,252 B2
(45) Date of Patent: *Sep. 17, 2024

(54) METHOD FOR PRODUCING RETINAL TISSUES

(71) Applicants: RIKEN, Wako (JP); SUMITOMO PHARMA CO., LTD., Osaka (JP)

(72) Inventors: Daiki Nukaya, Tokyo (JP); Mototsugu Eiraku, Wako (JP); Yuiko Kinose, Wako (JP); Akishi Onishi, Wako (JP); Masayo Takahashi, Wako (JP); Yoshiki SASAI, Wako (JP)

(73) Assignees: RIKEN, Wako (JP); SUMITOMO PHARMA CO., LTD., Osaka (JP)

( * ) Notice: Subject to any disclaimer, the term of this patent is extended or adjusted under 35 U.S.C. 154(b) by 938 days.

This patent is subject to a terminal disclaimer.

(21) Appl. No.: 16/647,441

(22) PCT Filed: Sep. 14, 2018

(86) PCT No.: PCT/JP2018/034314
§ 371 (c)(1),
(2) Date: Mar. 13, 2020

(87) PCT Pub. No.: WO2019/054514
PCT Pub. Date: Mar. 21, 2019

(65) Prior Publication Data
US 2021/0154370 A1 May 27, 2021

(30) Foreign Application Priority Data
Sep. 14, 2017 (JP) .................. 2017-177188

(51) Int. Cl.
*A61L 27/38* (2006.01)
*C12N 5/0793* (2010.01)
*G01N 33/50* (2006.01)

(52) U.S. Cl.
CPC ....... *A61L 27/3895* (2013.01); *A61L 27/3891* (2013.01); *C12N 5/062* (2013.01); *G01N 33/5088* (2013.01); *A61L 2430/16* (2013.01); *A61L 2430/32* (2013.01); *C12N 2501/155* (2013.01); *C12N 2501/395* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 7,285,415 B2 | 10/2007 | Keirstead et al. | |
| 10,066,203 B2 | 9/2018 | Fryer et al. | |
| 10,307,444 B2 | 6/2019 | Lanza et al. | |
| 10,501,724 B2 * | 12/2019 | Nakano | C12N 5/0621 |
| 10,570,370 B2 | 2/2020 | Park et al. | |
| 11,001,802 B2 | 5/2021 | Fryer et al. | |
| 2003/0207450 A1 | 11/2003 | Young et al. | |
| 2004/0009593 A1 | 1/2004 | Keirstead et al. | |
| 2006/0122111 A1 | 6/2006 | Furukawa | |
| 2007/0196919 A1 | 8/2007 | Reh et al. | |
| 2008/0044901 A1 | 2/2008 | Sasai et al. | |
| 2009/0053809 A1 | 2/2009 | Zander et al. | |
| 2009/0215177 A1 | 8/2009 | Fryer et al. | |
| 2010/0009442 A1 | 1/2010 | Sasai et al. | |
| 2011/0081719 A1 | 4/2011 | Gamm et al. | |
| 2011/0091869 A1 | 4/2011 | Sasai et al. | |
| 2011/0274662 A1 | 11/2011 | Malcuit et al. | |
| 2013/0040330 A1 | 2/2013 | Sasai et al. | |
| 2014/0294778 A1 | 10/2014 | Lanza et al. | |
| 2014/0308743 A1 | 10/2014 | Sasai et al. | |
| 2014/0341864 A1 | 11/2014 | Nakano et al. | |
| 2015/0132787 A1 | 5/2015 | Sasai et al. | |
| 2016/0030490 A1 | 2/2016 | Lanza et al. | |
| 2016/0175361 A1 | 6/2016 | Lanza et al. | |

(Continued)

FOREIGN PATENT DOCUMENTS

AU 2014345110 A1 6/2016
AU 2014378349 A1 9/2016

(Continued)

OTHER PUBLICATIONS

Kelley, Matthew et al. Regulation of Proliferation and Photoreceptor Differentiation in Fetal Human Retinal Cell Cultures. Investigative Ophthalmology & Visual Science. Jun. 1995. vol. 95 No 2. pp. 1280-1289. (Year: 1995).*

Mellough, Carla et al. Efficient Stage-Specific Differentiation of Human Pluripotent Stem Cells Toward Retinal Photoreceptor Cells. Stem Cells 2012(30). pp. 673-686. (Year: 2012).*

(Continued)

*Primary Examiner* — Nghi V Nguyen

(74) *Attorney, Agent, or Firm* — Leydig, Voit & Mayer, Ltd.

(57) ABSTRACT

The present invention aims to provide a method for suppressing differentiation of ganglion cell, amacrine cell, horizontal cell and/or bipolar cell in a neural retina tissue containing photoreceptor precursor and/or photoreceptor, and the like. A method for suppressing differentiation of a ganglion cell, an amacrine cell, a horizontal cell and/or a bipolar cell in a neural retinal tissue containing a photoreceptor precursor and/or a photoreceptor, including a step of culturing a retinal tissue comprising a neural retinal progenitor cell and in any stage between a differentiation stage immediately after emergence of a ganglion cell and a differentiation stage where emergence rate of a cone photoreceptor precursor reaches maximum in a medium containing a thyroid gland hormone signal transduction pathway agonist.

21 Claims, 10 Drawing Sheets

(56) References Cited

U.S. PATENT DOCUMENTS

| | | | |
|---|---|---|---|
| 2016/0175362 | A1 | 6/2016 | Lanza et al. |
| 2016/0186134 | A1 | 6/2016 | Keller et al. |
| 2016/0186136 | A1 | 6/2016 | Sasai et al. |
| 2016/0251616 | A1 | 9/2016 | Nakano et al. |
| 2016/0376554 | A1 | 12/2016 | Kuwahara et al. |
| 2017/0313976 | A1 | 11/2017 | Kuwahara et al. |
| 2017/0313981 | A1 | 11/2017 | Kuwahara et al. |
| 2017/0319748 | A1 | 11/2017 | Kuwahara et al. |
| 2018/0016552 | A1 | 1/2018 | Park et al. |
| 2018/0228846 | A1 | 8/2018 | Bohana-Kashtan |
| 2018/0245039 | A1 | 8/2018 | Ando et al. |
| 2019/0060370 | A1 | 2/2019 | Lanza et al. |
| 2019/0127690 | A1 | 5/2019 | Kuwahara et al. |
| 2019/0249138 | A1 | 8/2019 | Fryer et al. |
| 2019/0290701 | A1 | 9/2019 | Lanza et al. |
| 2019/0321414 | A1 | 10/2019 | Lanza et al. |
| 2020/0157499 | A1 | 5/2020 | Park et al. |
| 2020/0206387 | A1 | 7/2020 | Takahashi et al. |
| 2020/0277571 | A1 | 9/2020 | Nukaya et al. |
| 2022/0315888 | A1 | 10/2022 | Lako et al. |
| 2022/0364054 | A1 | 11/2022 | Nakano et al. |

FOREIGN PATENT DOCUMENTS

| | | | |
|---|---|---|---|
| CA | 2937129 | A1 | 7/2015 |
| CN | 102747029 | A | 10/2012 |
| CN | 103396993 | A | 11/2013 |
| EP | 3524671 | A1 | 8/2019 |
| JP | 2003-521910 | A | 7/2003 |
| JP | 2011-512797 | A | 4/2011 |
| JP | 2012-245007 | A | 12/2012 |
| JP | 2013-099345 | A | 5/2013 |
| WO | WO 2001/058460 | A1 | 8/2001 |
| WO | WO 2006/053629 | A1 | 5/2006 |
| WO | WO 2009/148170 | A1 | 12/2009 |
| WO | WO 2011/043591 | A2 | 4/2011 |
| WO | WO 2011/055855 | A1 | 5/2011 |
| WO | WO 2013/065763 | A1 | 5/2013 |
| WO | WO 2013/077425 | A1 | 5/2013 |
| WO | WO 2013/183774 | A1 | 12/2013 |
| WO | WO 2014/145108 | A1 | 9/2014 |
| WO | 2015/107738 | A1 | 7/2015 |
| WO | WO 2016/032263 | A1 | 3/2016 |
| WO | WO 2016/063985 | A1 | 4/2016 |
| WO | WO 2016/063986 | A1 | 4/2016 |
| WO | WO 2017/021972 | A1 | 2/2017 |
| WO | WO 2017/183732 | A1 | 10/2017 |
| WO | WO 2019/017492 | A1 | 1/2019 |
| WO | WO 2019/054515 | A1 | 3/2019 |

OTHER PUBLICATIONS

Hasegawa, Yuiko et al. Emergence of dorsal-ventral polarity in ESC-derived retinal tissue. Published by the Company of Biologists Ltd | Development (2016) 143, 3895-3906. (Year: 2016).*
Osakada, Fumitaka et al. Stepwise differentiation of pluripotent stem cells into retinal cells. Nature Protocols. vol. 4 No. 6. pp. 811-824. (Year: 2009).*
Levine et al., "Sonic Hedgehog Promotes Rod Photoreceptor Differentiation in Mammalian Retinal Cells In Vitro," *J. Neurosci.*, 17(16): 6277-6288 (1997).
Yao, "Role of Soluble Factors in Retinal Transplantation," *Section Ophthalmol. Foreign Med. Sci.*, 28(2): 99-103 (2004).
Akopian et al., "Comparison of defined culture systems for feeder cell free propagation of human embryonic stem cells," *In Vitro Cell. Dev. Biol. Anim.*, 46(4-4): 247-258 (2010).
Boucherie et al., "Brief Report: Self-Organizing Neuroepithelium from Human Pluripotent Stem Cells Facilitates Derivation of Photoreceptors," *Stem Cells*, 31(2): 408-414 (2013).
Chambers et al., "Highly efficient neural conversion of human ES and iPS cells by dual inhibition of SMAD signaling," *Nat. Biotechnol.*, 27(3): 275-280 and corrigendum (2009).
Chen et al., "Chemically defined conditions for human iPSCSC derivation and culture," *Nat. Methods*, 8(5): 424-429 (2011).
Denayer et al., "Canonical Wnt Signaling Controls Proliferation of Retinal Stem/Progenitor Cells in Postembryonic *Xenopus* Eyes," *Stem Cells*, 26(8): 2063-2074 (2008).
Eiraku et al., "Self-Organized Formation of Polarized Cortical Tissues from ESCs and Its Active Manipulation by Extrinsic Signals," *Cell Stem Cell*, 3(5): 519-532 (2008).
Eiraku et al., "Self-organizing optic-cup morphogenesis in three-dimensional culture," *Nature*, 472(7341): 51-56 (2011).
Eiraku et al., "Relaxation-expansion model for self-driven retinal morphogenesis," *Bioessays*, 34(1): 17-25 (2012).
Fuhrmann, "Wnt signaling in eye organogenesis," *Organogenesis*, 4(2): 60-67 (2008).
Furuta et al., "BMP4 is essential for lens induction in the mouse embryo," *Genes Dev.*, 12(23): 3764-3775 (1998).
Hasegawa et al., "Emergence of dorsal-ventral polarity in ESC-derived retinal tissue," *Development*, 143(21): 3895-3906 (2016).
Hirami et al., "Generation of retinal cells from mouse and human induced pluripotent stem cells," *Neuroscience Lett.*, 458(3): 126-131 (2009).
Ikeda et al., "Generation of $Rx^+/Pax6^+$ neural retinal precursors from embryonic stem cells," *Proc. Natl. Acad. Sci. U.S.A.*, 102(32): 11331-11336 (2005).
Ikeda et al., "In vitro neuronal differentiation induction using ES cells—telencephalic precursors and neural retinal precursors," *Experimental Medicine*, 24(2): 188-194 and additional figures (2006).
Johe et al., "Single factors direct the differentiation of stem cells from the fetal and adult central nervous system," *Genes Dev.*, 10(24): 3129-3140 (1996).
Kadoshima et al., "Self-organization of axial polarity, inside-out layer pattern, and species-specific progenitor dynamics in human ES cell-derived neocortex," *Proc. Natl. Acad. Sci. U.S.A.*, 110(50): 20284-20289 (2013).
Kelley et al., "Retinoic acid promotes differentiation of photoreceptors in vitro," *Development*, 120(8): 2091-2102 (1994).
Kelley et al., "Regulation of Proliferation and Photoreceptor Differentiation in Fetal Human Retinal Cell Cultures," *Invest. Ophthalmol. Vis. Sci.*, 36(7): 1280-1289 (1995).
Kubo et al., "Wnt2b controls retinal cell differentiation at the ciliary marginal zone," *Development*, 130(3): 587-598 (2003).
Kubo et al., "Hairy1 acts as a node downstream of Wnt signaling to maintain retinal stem cell-like progenitor cells in the chick ciliary marginal zone," *Development*, 136(11): 1823-1833 (2009).
Kuwahara et al., "Generation of a ciliary margin-like stem cell niche from self- organizing human retinal tissue," *Nat Commun.*, 6: 6286 (2015).
Lamba et al., "Efficient generation of retinal progenitor cells from human embryonic stem cells," *Proc. Natl. Acad. Sci. U.S.A.*, 103(34): 12769-12774 (2006).
Lancaster et al., "Cerebral organoids model human brain development and microcephaly," *Nature*, 501(7467): 373-379 (2013).
Lang et al., "Pathways regulating lens induction in the mouse," *Int. J. Dev. Biol.*, 48(8-9): 783-791 (2004).
La Torre et al., "Production and Transplantation of Retinal Cells from Human and Mouse Embryonic Stem Cells," *Methods Mol. Biol.*, 884: 229-246 (2012).
Milam et al., "Histopathology of the Human Retina in Retinitis Pigmentosa," *Prog. Retin. Eye Res.*, 17(2): 175-205 (1998).
Muguruma et al., "Ontogeny-recapitulating generation and tissue integration of ES cell-derived Purkinje cells," *Nat. Neurosci.*, 13(10): 1171-1180 (2010).
Nakagawa et al., "A novel efficient feeder-free culture system for the derivation of human induced pluripotent stem cells," *Sci. Rep.*, 4: 3594 (2014).
Nakano et al., "Self-Formation of Optic Cups and Storable Stratified Neural Retina from Human ESCs," *Cell Stem Cell*, 10(6): 771-785 (2012).
Osakada et al., "Control of neural differentiation from pluripotent stem cells," *Inflammation and Regeneration*, 28(3): 166-173 (2008).
Osakada et al., "Toward the generation of rod and cone photoreceptors from mouse, monkey and human embryonic stem cells," *Nat. Biotechnol.*, 26(2): 215-224 (2008).

(56) References Cited

OTHER PUBLICATIONS

Osakada et al., "In vitro differentiation of retinal cells from human pluripotent stem cells by small-molecule induction," *J. Cell. Sci.*, 122(17): 3169-3179 (2009).
Osakada et al., "Neural Induction and Patterning in Mammalian Pluripotent Stem Cells," *CNS Neurol. Disord. Drug Targets*, 10(4): 419-432 (2011).
Ozair et al., "Neural induction and early patterning in vertebrates," *WIREs Dev. Biol.*, 2(4): 479-498 (2013).
Rothermel et al., "Photoreceptor plasticity in reaggregates of embryonic chick retina: rods depend on proximal cones and on tissue reorganization," *Eur. J. Neurosci.*, 13(5): 949-958 (2001).
Sasai et al., "Self-organization as seen in pattern formation of neural tissue: Challenge to Emergent Biology," *Brain Science Review*, 99-112 (Feb. 2014).
Satoh et al., "The Spatial Patterning of Mouse Cone Opsin Expression Is Regulated by Bone Morphogenetic Protein Signaling through Downstream Effector COUP-TF Nuclear Receptors," *J. Neurosci.*, 29(40): 12401-12411 (2009).
Schulte et al., "The Rod Photoreceptor Pattern Is Set at the Optic Vesicle Stage and Requires Spatially Restricted cVax Expression," *J. Neurosci.*, 25(11): 2823-2381 (2005).
Sehgal et al., "Bone Morphogenetic Protein 7 Increases Chick Photoreceptor Outer Segment Initiation," *Invest. Ophthalmol. Vis. Sci.*, 47(8): 3625-3634 (2006).
Seiler et al., "Visual restoration and transplant connectivity in degenerate rats implanted with retinal progenitor sheets," *Eur J. Neurosci.*, 31(3): 508-520 (2010).
Shirai et al., "Transplantation of human embryonic stem cell-derived retinal tissue in two primate models of retinal degeneration," *Proc. Natl. Acad. Sci. U.S.A.*, 113(1): E81-E90 (2016).
Stephens et al., "Loss of *Adenomatous polyposis coli* (*apc*) Results in an Expanded Ciliary Marginal Zone in the Zebrafish Eye," *Dev. Dyn.*, 239(7): 2066- 2077 (2010).
Suga et al., "Self-formation of functional adenohypophysis in three-dimensional culture," *Nature*, 480(7375): 57-62 (2011).
Trousse et al., "BMP4 Mediates Apoptotic Cell Death in the Developing Chick Eye," *J. Neurosci.*, 21(4): 1292-1301 (2001).
Vugler et al., "Embryonic stem cells and retinal repair," *Mech. Dev.*, 124(11-12): 807-829 (2007).
Watanabe et al., "Directed differentiation of telencephalic precursors from embryonic stem cells," *Nat. Neurosci.*, 8(3): 288-296 (2005).
Wei et al., "Isolation and identification of retinal stem cells in mouse eye," *Journal of Third Military Medical University*, 25(24): 2161-2164 (2003).
Yanai et al., "Differentiation of Human Embryonic Stem Cells Using Size-Controlled Embryoid Bodies and Negative Cell Selection in the Production of Photoreceptor Precursor Cells," *Tissue Eng. Part C Methods*, 19(10): 755-764 (2013).
Yang et al., "Efficient generation of lens progenitor cells and lentoid bodies from human embryonic stem cells in chemically defined conditions," *FASEB J.*, 24(9): 3274-3283 (2010).
Yu et al., "Altered Expression of Genes of the Bmp/Smad and Wnt/Calcium Signaling Pathways in the Cone-only Nrl$^{-/-}$ Mouse Retina, Revealed by Gene Profiling Using Custom cDNA Microarrays," *J. Biol. Chem.*, 279(40): 42211-42220 (2004).
Japanese Patent Office, International Search Report in International Patent Application No. PCT/JP2018/034314 (Dec. 18, 2018).
Japanese Patent Office, International Search Report in International Patent Application No. PCT/JP2018/034315 (Dec. 11, 2018).
Kelley et al., "Ligands of steroid/thyroid receptors induce cone photoreceptors in vertebrate retina," *Development*, 121 (11): 3777-3785 (1995).
McCaffery et al., "Dorsal and ventral retinal territories defined by retinoic acid synthesis, break-down and nuclear receptor expression," *Mech. Dev.*, 82(1-2): 119-130 (1999).
Ng et al., "A thyroid hormone receptor that is required for the development of green cone photoreceptors," *Nat. Genet.*, 27(1): 94-98 (2001).
Zhong et al., "Generation of three-dimensional retinal tissue with functional photoreceptors from human iPSCs," *Nat. Commun.*, 5: 4047 (2014).
Kruczek, "Differentiation and transplantation of mouse embryonic stem cell- derived cone photoreceptor precursors," Thesis Submitted for the Degree of Doctor of Philosophy, University College London (2016).
Mustafi et al., "Transcriptome analysis reveals rod/cone photoreceptor specific signatures across mammalian retinas," *Hum. Mol. Genet.*, 25(20): 4376-4388 (2016).
Osakada et al., "Stepwise differentiation of pluripotent stem cells into retinal cells," *Nat. Protoc.*, 4(6): 811-824 (2009).
Ueda et al., "Generation of three-dimensional retinal organoids expressing rhodopsin and S- and M-cone opsins from mouse stem cells," *Biochem. Biophys. Res. Commun.*, 495(4): 2595-2601 (2018).
Zhou et al., "Differentiation of human embryonic stem cells into cone photoreceptors through simultaneous inhibition of BMP, TGFβ and Wnt signaling," *Development*, 142(19): 3294-3306 (2015).
European Patent Office, Extended European Search in European Patent Application No. 18856535.2 (May 10, 2021).
European Patent Office, Extended European Search in European Patent Application No. 18855704.5 (May 10, 2021).
Freese et al., "Wnt Signaling in Development and Disease," *Neurobiol. Dis.*, 38(2): 148-153 (2010).
Eldar-Finkelman et al., "GSK-3 Inhibitors: Preclinical and Clinical Focus on CNS," *Frontiers in Molecular Neuroscience*, 4: 32 (2011).
Rimkus et al., "Targeting the Sonic Hedgehog Signaling Pathway: Review of Smoothened and GLI Inhibitors," *Cancers*, 8: 22 (2016).
Ruiz et al., "Glycogen Synthase Kinase-3 Inhibitors: Preclinical and Clinical Focus on CNS—A Decade Onward," *Frontiers in Molecular Neuroscience*, 14:792364 (2022).
Tocris Bioscience, "Glycogen Synthase Kinase 3 Inhibitors" catalog webpage printout (retrieved from internet on Dec. 29, 2023).
Tocris Bioscience, "Hedgehog Signaling Inhibitors" catalog webpage printout (retrieved from internet on Dec. 29, 2023).

\* cited by examiner

METHOD FOR PRODUCING RETINAL TISSUES

CROSS-REFERENCE TO RELATED APPLICATIONS

This patent application is the U.S. national phase of International Patent Application No. PCT/JP2018/034314, filed Sep. 14, 2018, which claims the benefit of Japanese Patent Application No. 2017-177188, filed on Sep. 14, 2017, which are incorporated by reference in their entireties herein.

TECHNICAL FIELD

The present invention relates to a retinal tissue containing bipolar cell, amacrine cell, ganglion cell, horizontal cell and the like at a lower proportion and photoreceptor precursor or photoreceptor at a higher proportion, and suitable for transplantation, and a production method thereof.

BACKGROUND ART

It is known that, in diseases in which visual loss or visual field defect is caused by degeneration or loss of photoreceptors, such as retinal pigment denaturation and the like, while photoreceptors are associated with degeneration and loss, bipolar cells that receive signals from photoreceptors first and other retinal cells remain in the retinal tissue for a certain period of time after degeneration and loss of photoreceptors (non-patent document 1). To achieve a therapeutic effect in regenerative medicine by transplanting retinal tissue containing photoreceptors and photoreceptor precursors, therefore, it is considered preferable that retinal tissue-derived photoreceptors and photoreceptor precursors to be transplanted come into contact with bipolar cells of the patient (recipient) to form synapse, that is, to form a retinal neural circuit (non-patent document 2). Thus, the development of a retinal tissue suitable for transplantation, in which bipolar cells derived from patient's retinal tissue and photoreceptors derived from the retinal tissue to be transplanted can efficiently form synapses, and a production method thereof is strongly demanded.

On the other hand, it has been reported that, when differentiating a retinal cells collected from the fetus into photoreceptor precursors, a retinal tissue containing neural retinal progenitor cells was dispersed, and adhesion culture was performed by adding retinoic acid and triiodothyronine (T3), which is one of thyroid gland hormones (non-patent document 3). It has also been reported that, when rat retinal tissue was dispersed and adhesion culture was performed in the presence of retinoic acid, amacrine cells decreased (non-patent document 4).

However, whether thyroid gland hormones influence differentiation of bipolar cell, ganglion cell, horizontal cell and the like has not been known.

In addition, a method for preparing a retinal tissue suitable for transplantation by adjusting the proportion of cells such as amacrine cell, bipolar cell, ganglion cell, horizontal cell and the like, and photoreceptor precursor and photoreceptor, which are induced from stem cells and contained in a retinal tissue having a steric structure, has not been known.

DOCUMENT LIST

Non-Patent Documents non-patent document 1: Prog Retin Eye Res, 17(2), 175-205(1998)
non-patent document 2: Proc Natl Acad Sci USA, 113(1), E81-90(2016)
non-patent document 3: Invest Ophthalmol Vis Sci, 36(7), 1280-1289(1995)
non-patent document 4: Development 120(8), 2091-2102 (1994)

SUMMARY OF THE INVENTION

Problems to be Solved by the Invention

A problem of the present invention is to provide a retinal tissue suitable for transplantation, in which bipolar cells derived from patient's retinal tissue and photoreceptors derived from the retinal tissue to be transplanted can efficiently form synapses, and a production method thereof.

Means of Solving the Problems

It is known that, in diseases in which visual loss or visual field defect is caused by degeneration or loss of photoreceptors, such as retinal pigment denaturation and the like, while photoreceptors are associated with degeneration and loss, bipolar cells that receive signals from photoreceptors first and other retinal cells remain in the retinal tissue for a certain period of time after degeneration and loss of photoreceptors (non-patent document 1). To achieve a therapeutic effect in regenerative medicine by transplanting retinal tissue containing photoreceptor precursors, therefore, it is considered preferable that retinal tissue-derived photoreceptors to be transplanted come into contact with bipolar cells of the patient (recipient) to form synapse via synaptic terminals of the aforementioned photoreceptor precursors (or photoreceptors), that is, to form a retinal neural circuit (non-patent document 2).

It has also been reported that transplanted retinal tissue can engraft at the transplanted site and adopt a characteristic rosette-like structure, and that the basement membrane side of photoreceptor precursor (or photoreceptor) (i.e., synaptic terminal side of photoreceptor precursor or photoreceptor) can contact bipolar cells of the recipient and form synapses (non-patent document 2). Retinal tissue includes bipolar cells, as well as amacrine cells, ganglion cells, and horizontal cells. These cells are located on the basement membrane side of neural retinal tissue from the layer where photoreceptor precursor is present (outer nuclear layer). Thus, when the transplanted retinal tissue adopts a rosette-like structure, bipolar cells, amacrine cells, ganglion cells and horizontal cells derived from the transplanted retinal tissue are located between the photoreceptor precursor derived from the transplanted retinal tissue and bipolar cell of the recipient.

Thus, the inventors considered that when photoreceptor derived from the transplanted retinal tissue tries to contact bipolar cells of the recipient, the bipolar cells, amacrine cells, ganglion cells and horizontal cells derived from the transplanted retinal tissue cell could be a spatial or physical obstacle. In addition, when bipolar cells are present in the neural retinal tissue to be transplanted, photoreceptor and bipolar cells form a circuit in the transplanted neural retinal tissue and the photoreceptor derived from the transplanted retinal tissue may not be able to efficiently form a neural circuit with the bipolar cells of the recipient. From these, they considered that the proportion of the bipolar cells, amacrine cells, ganglion cells and horizontal cells in the neural retinal tissue to be transplanted is preferably as small as possible.

That is, the present inventors considered that the probability of contact and synapse formation between bipolar cells derived from the retinal tissue of the recipient and photoreceptor derived from the retinal tissue to be transplanted can be increased by reducing the proportion of these unnecessary cells in the retinal tissue used for transplantation and conducted intensive studies. As a result, they have found that cells unnecessary for synapse formation with the biological transplant site contained in a retinal tissue can be reduced and the ratio of photoreceptor precursor can be increased by suspension culture of a retinal tissue containing neural retinal progenitor cell and in a differentiation stage where ganglion cells have not emerged or immediately after emergence thereof in a medium containing a thyroid gland hormone signal transduction pathway agonist, followed by maturation, which resulted in the completion of the present invention. In addition, a neural retinal tissue with a high proportion of photoreceptor precursor in all cells contained in the neural retina, and a high proportion of cone photoreceptor precursor in the photoreceptor precursor could be further obtained by adding a dorsalization signal transmitter in addition to a thyroid gland hormone signal transduction pathway agonist.

That is, the present invention relates to the following:

[1] A method for suppressing differentiation of a ganglion cell, an amacrine cell, a horizontal cell and/or a bipolar cell in a neural retinal tissue comprising a photoreceptor precursor and/or a photoreceptor, the method comprising a step of culturing a retinal tissue comprising a neural retinal progenitor cell and in any stage between a differentiation stage immediately after emergence of a ganglion cell and a differentiation stage where an emergence rate of a cone photoreceptor precursor reaches maximum in a medium containing a thyroid gland hormone signal transduction pathway agonist;

[2] the method of the above-mentioned [1], wherein the culture in the medium containing a thyroid gland hormone signal transduction pathway agonist is performed up to a differentiation stage where a rod photoreceptor precursor and/or a bipolar cell emerge(s);

[3] the method of the above-mentioned [1], wherein the culture in the medium containing a thyroid gland hormone signal transduction pathway agonist is performed up to a differentiation stage where an outer plexiform membrane is formed;

[4] the method of the above-mentioned [1], wherein the culture in the medium containing a thyroid gland hormone signal transduction pathway agonist is performed up to a differentiation stage where a Muller cell emerges;

[5] the method of any of the above-mentioned [1] to [4], wherein the method suppresses formation of a PAX6-negative/CHX10-strongly positive cell and a PAX6-positive/CHX10-negative cell;

[6] the method of any of the above-mentioned [1] to [5], wherein the neural retinal tissue is derived from a stem cell;

[7] the method of the above-mentioned [6], wherein the stem cell is a pluripotent stem cell;

[8] the method of the above-mentioned [6], wherein the stem cell is a somatic stem cell obtained from an adult retina;

[9] the method of any of the above-mentioned [1] to [8], wherein the thyroid gland hormone signal transduction pathway agonist is triiodothyronine;

[10] the method of the above-mentioned [9], wherein the triiodothyronine has a concentration of 1-100 nM;

[11] the method of any of the above-mentioned [1] to [10], wherein the retinal tissue containing a neural retinal progenitor cell and in a differentiation stage immediately after emergence of a ganglion cell is a retinal tissue having a neural retinal progenitor cell content of not less than 50% based on the total number of cells;

[12] the method of any of the above-mentioned [1] to [11], wherein a method for the culture is suspension culture;

[13] a method for producing a matured neural retinal tissue, or a neural retinal tissue that can be matured into a matured neural retinal tissue, the method comprising (1) a step of culturing a retinal tissue in an initial developmental stage in a medium to obtain a retinal tissue containing a neural retinal progenitor cell and in any stage between a differentiation stage immediately after emergence of a ganglion cell and a differentiation stage where an emergence rate of a cone photoreceptor precursor reaches maximum, and (2) a step of culturing the retinal tissue obtained in step (1) in a medium containing a thyroid gland hormone signal transduction pathway agonist;

[14] the production method of the above-mentioned [13], wherein the medium in step (1) and/or the medium in at least a part of step (2) is a medium containing a dorsalization signal transmitter at a concentration that suppresses expression of a ventral marker;

[15] the production method of the above-mentioned [13] or [14], wherein the medium in step (2) comprises a dorsalization signal transmitter at a concentration that suppresses expression of a ventral marker;

[16] the production method of any of the above-mentioned [13] to [15], wherein the medium in step (1) comprises a dorsalization signal transmitter at a concentration that suppresses expression of a ventral marker;

[17] the production method of any of the above-mentioned [13] to [16], wherein the matured neural retinal tissue has the following characteristics (i)-(iii):

(i) a proportion of the number of cells of the photoreceptor precursor and the photoreceptor is not less than 40% based on the total number of cells;

(ii) a content of the cone photoreceptor precursor and the cone photoreceptor contained in the photoreceptor precursor and the photoreceptor is not less than 70%; and (iii) a proportion of the number of cells of a bipolar cell, a ganglion cell, an amacrine cell and a horizontal cell is not more than 30% based on the total number of cells;

[18] the production method of any of the above-mentioned [13] to [16], wherein the neural retinal tissue that can be matured into a matured neural retinal tissue has the following characteristics (i)-(ii):

(i) a proportion of the number of cells of the photoreceptor precursor and the photoreceptor (CRX-positive cells) is not less than 11%, preferably not less than 20%, based on the total number of cells; and (ii) a proportion of the number of cells of a CRX-positive and TRβ2-positive cell is not less than 7%, preferably not less than 10%, based on the total number of cells; and culture is continued for 30-50 days, preferably 30-40 days, after recognition of emergence of the cone photoreceptor precursor;

[19] the production method of any of the above-mentioned [13] to [16], wherein the neural retinal tissue that can be matured into a matured neural retinal tissue has the following characteristics (i)-(ii):
(i) a proportion of the photoreceptor precursor and the photoreceptor (CRX-positive cells) is not less than 25% based on the total number of cells; and
(ii) the photoreceptor precursor and/or the photoreceptor (CRX-positive cell) are/is in contact with an apical surface, and at least two cells are present side by side along a straight line vertical to the tangent line of the apical surface; and culture is continued for 55-80 days, preferably 55-70 days, after recognition of emergence of the cone photoreceptor precursor;

[20] the production method of any of the above-mentioned [13] to [17], wherein the step (2) includes the following step (2-1) and (2-2):
(2-1) a step of culturing the retinal tissue obtained in step (1) in a medium containing a thyroid gland hormone signal transduction pathway agonist up to day 30-80 after recognition of emergence of the cone photoreceptor precursor, and
(2-2) a step of culturing the retinal tissue obtained in step (2-1) in a medium optionally containing a thyroid gland hormone signal transduction pathway agonist for 60-120 days;

[21] the production method of the above-mentioned [20], wherein the medium used in step (2-2) is a medium containing a thyroid gland hormone signal transduction pathway agonist and/or a dorsalization signal transmitter at a concentration that suppresses expression of a ventral marker;

[22] the production method of any of the above-mentioned [13] to [21], wherein the dorsalization signal transmitter is BMP4;

[23] the production method of the above-mentioned [22], wherein the BMP4 has a concentration of 0.05-0.45 nM;

[24] the production method of any of the above-mentioned [13] to [21], wherein the dorsalization signal transmitter is Cyclopamine-KAAD;

[25] the production method of the above-mentioned [24], wherein a concentration of the Cyclopamine-KAAD is 0.01-100 μM;

[26] the production method of any of the above-mentioned [20] to [25], wherein the medium used in step (2-2) is a medium for maintaining a continuous epithelial structure;

[27] a neural retinal tissue comprising an ectopic CRX-positive cell obtained by the production method of any of the above-mentioned [13] to [26];

[28] a neural retinal tissue comprising a cone photoreceptor and a cone photoreceptor precursor, and having the following characteristics (1)-(3):
(1) a proportion of the number of cells of the photoreceptor precursor and the photoreceptor is not less than 11%, preferably not less than 20%, of the total number of cells;
(2) an ectopic photoreceptor precursor and/or a photoreceptor emerging on a basement membrane side from a neuroblastic layer are/is contained; and
(3) it is a neural retinal tissue cultured for 30-50 days after first emergence of the cone photoreceptor precursor, and is free of a CRX-positive and NRL-positive photoreceptor or a photoreceptor precursor;

[29] the neural retinal tissue of the above-mentioned [28], wherein a proportion of the number of cells of the cone photoreceptor precursor and cone photoreceptor is not less than 7%, preferably not less than 10%, of the total number of cells;

[30] the neural retinal tissue of the above-mentioned [28] or [29], wherein the neuroblastic layer is CHX10-positive and PAX6-positive, or Ki67-positive;

[31] the neural retinal tissue of any of the above-mentioned [28] to [30], wherein the number of cells of the ectopic photoreceptor precursor and the photoreceptor on the basement membrane side from the neuroblastic layer (NBL) per a given area is ¹/₁₀ to 10 times the number of cells of the photoreceptor precursor and the photoreceptor in a region on the apical surface side including NBL;

[32] a neural retinal tissue having the following characteristics (1)-(4):
(1) a CRX-positive cell content is not less than 25%;
(2) a photoreceptor precursor (CRX-positive cell) is in contact with an apical surface, and at least two cells are present side by side along a straight line vertical to the tangent line of the apical surface;
(3) a cone photoreceptor precursor and/or a cone photoreceptor, and a bipolar cell are contained and a Muller cell is not contained; and
(4) a neural retinal progenitor cell in a stage of differentiating into a rod photoreceptor precursor and/or a bipolar cell is contained;

[33] the neural retinal tissue of the above-mentioned [32], further having the following characteristic (5):
(5) an ectopic photoreceptor precursor is present on a basement membrane side from a neuroblastic layer (NBL);

[34] a matured neural retinal tissue comprising a cone photoreceptor precursor and/or a cone photoreceptor, and having the following characteristics (1)-(5):
(1) it is in a differentiation stage permitting detection of Muller cell;
(2) a content of a ganglion cell, an amacrine cell, and a horizontal cell is not more than 30%;
(3) a content of a bipolar cell is not more than 10%;
(4) a content of a ganglion cell, an amacrine cell, a horizontal cell, and a bipolar cell is not less than 30%; and
(5) a proportion of the number of cells of a photoreceptor precursor and a photoreceptor is not less than 40% of the total number of cells;

[35] the neural retinal tissue of the above-mentioned [34], comprising an ectopic photoreceptor layer formed on a cell layer on a basement membrane side;

[36] the matured neural retinal tissue of the above-mentioned [34] or [35], wherein a content of a PAX6-negative/CHX10-strongly positive cell and a PAX6-positive/CHX10-negative cell is not more than 30%;

[37] the matured neural retinal tissue of any of the above-mentioned [34] to [36], wherein a proportion of the number of cells of an ectopic photoreceptor precursor and/or the photoreceptor is not less than 30% of the number of an outer nuclear layer;

[38] the matured neural retinal tissue of any of the above-mentioned [34] to [37], wherein a content of the cone photoreceptor precursor and the cone photoreceptor contained in the photoreceptor precursor and the photoreceptor is not less than 70%;

[39] the matured neural retinal tissue of any of the above-mentioned [34] to [38], wherein a proportion of the number of cells of the CRX-positive cell is not less than 40% based on the total number of cells;

[40] the neural retinal tissue of any of the above-mentioned [27] to [33] or the matured neural retinal tissue of any of the above-mentioned [34] to [39], wherein not less than 50% of a layer structure of the neural retinal tissue form a continuous epithelial structure;

[41] the neural retinal tissue of the above-mentioned [40], wherein the retinal tissue has a diameter in the major axis direction of not less than 0.6 mm;

[42] a neural retinal tissue that can be matured into the matured neural retinal tissue of any of the above-mentioned [34] to [41] by culturing;

[43] a pharmaceutical composition for transplantation, comprising the neural retinal tissue of any of the above-mentioned [27] to [33] and [40] to [42] or the matured neural retinal tissue of any of the above-mentioned [34] to [41];

[44] a method for treating or preventing a disease with visual loss or visual field defect, comprising transplanting the neural retinal tissue of any of the above-mentioned [27] to [33] and [40] to [42] or the matured neural retinal tissue of any of the above-mentioned [34] to [41] to an animal;

[45] use of the neural retinal tissue of any of the above-mentioned [27] to [33] and [40] to [42] or the matured neural retinal tissue of any of the above-mentioned [34] to [41] as a reagent for evaluation of toxicity or efficacy.

Effect of the Invention

According to the present invention, a retinal tissue containing bipolar cell, amacrine cell, ganglion cell, horizontal cell and the like at a lower proportion and photoreceptor precursor at an increased proportion can be produced. In one embodiment of the present invention, the proportion of cone photoreceptor precursor among the photoreceptor precursors in the aforementioned retinal tissue can be increased. In one embodiment of the present invention, moreover, photoreceptor precursor or cone photoreceptor precursor emerges ectopically and is located on the basement membrane side of retina layer where bipolar cell, amacrine cell, ganglion cell and the like are present, and when transplanted, highly efficient formation of a neural circuit with bipolar cells derived from patients can be expected. Thus, the retinal tissue of the present invention is useful for treating a disease in which visual loss or visual field defect is caused by degeneration or loss of photoreceptors, such as retinal pigment denaturation and the like.

BRIEF DESCRIPTION OF THE DRAWINGS

In FIG. 2, T3 was added to 60 nM, BMP4 was added to 0.15 nM, and Cyclopamine-KAAD was added to 500 nM, in the medium.

In FIG. 3, T3 was added to 60 nM, and BMP4 was added to 0.45 nM, in the medium.

In FIG. 4, T3 was added to 60 nM, BMP4 was added to 0.15 nM, and Cyclopamine-KAAD was added to 500 nM, in the medium.

Figure 5:
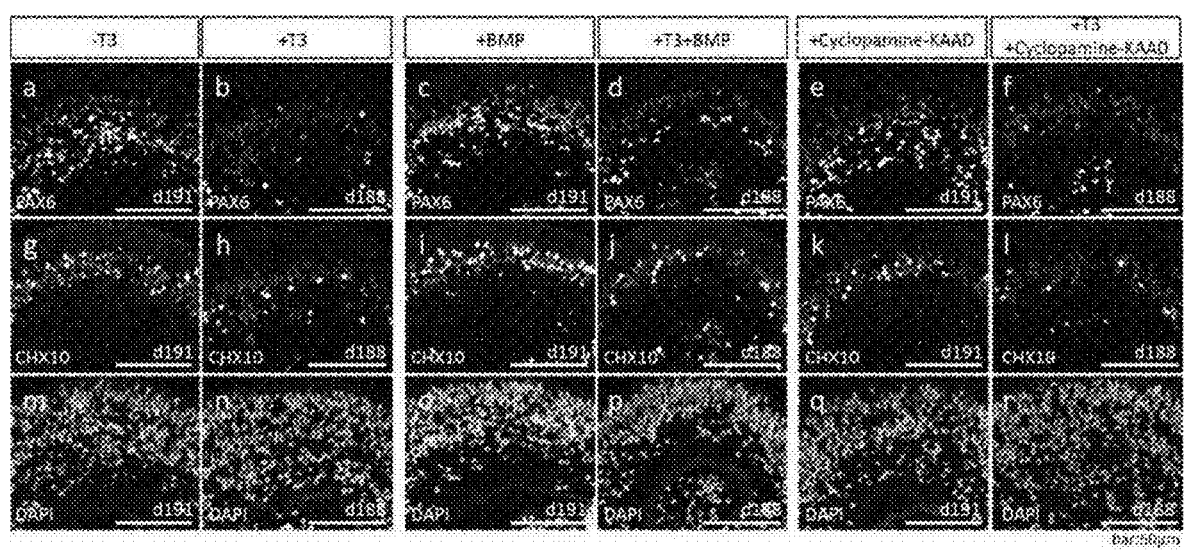

FIG. 5 shows an example of culturing a cell aggregates containing a retinal tissue produced from human ES cells up to about day 188-191 from the start of suspension culture, which is the differentiation stage where Muller cells are observed, preparing a section of the recovered cell aggregates containing the retinal tissue, and performing immunostaining by a conventional method using an anti-PAX6 antibody, an anti-CHX10 antibody, and DAPI. It is clear that any of the amacrine cell, ganglion cell or horizontal cell in the neural retinal tissue (PAX6-positive/CHX10-negative cell) and bipolar cell (PAX6-negative/CHX10-strongly positive cell) remarkably decreased when T3 was added (+T3; b, h, n, +T3+BMP; d, j, p, +T3+Cyclopamine-KAAD; f, l, r) as compared to when T3 was not added (−T3; a, g, m, +BMP; c i, o, +cyclopamine-KAAD; e, k, q). In FIG. 5, T3 was added to 60 nM, BMP4 was added to 0.15 nM, and Cyclopamine-KAAD was added to 500 nM, in the medium.

Figure 6:
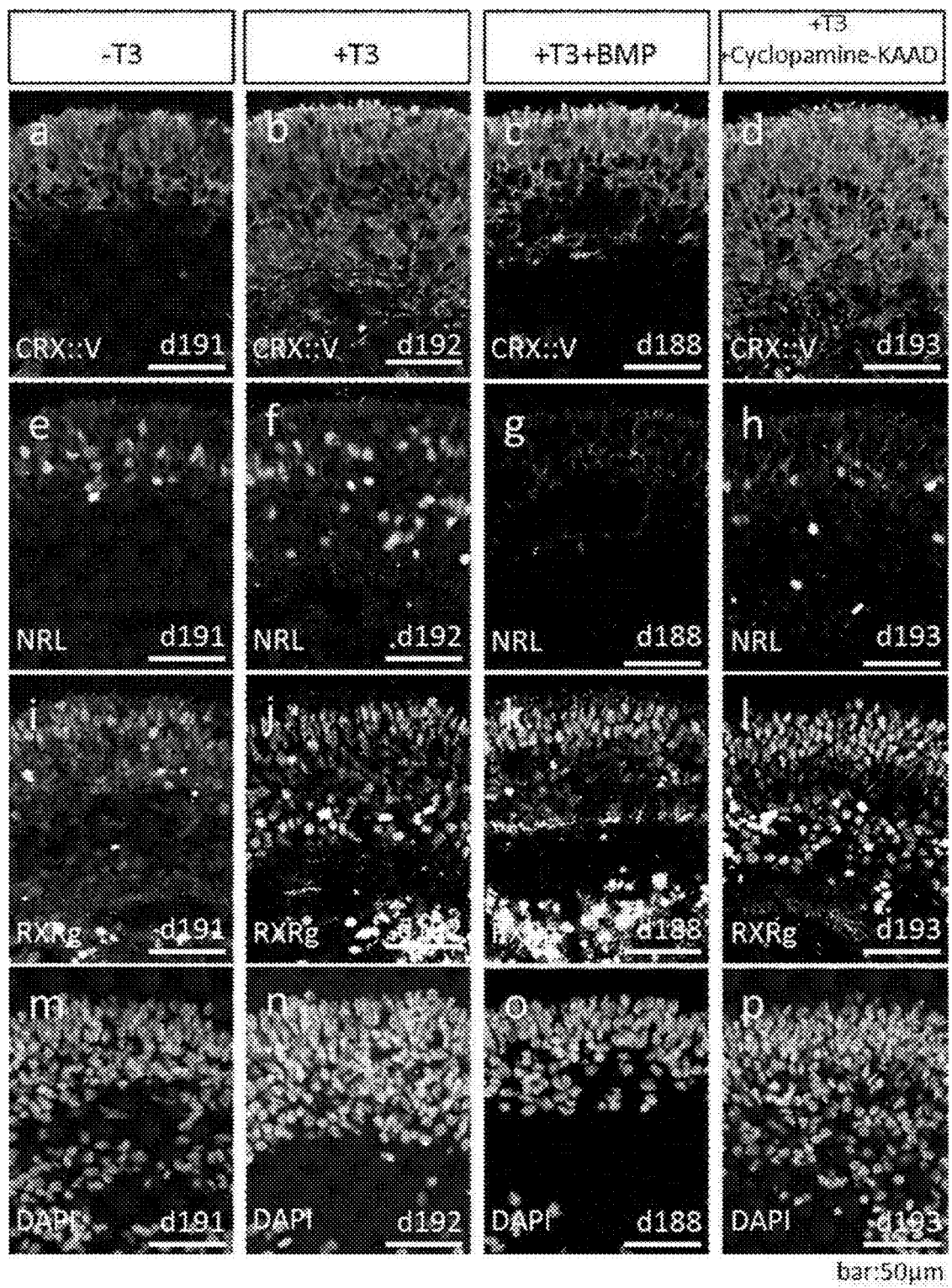

FIG. 6 shows the analysis results (a-p) of RXR-γ-positive and NRL-negative cell (cone photoreceptor precursor) in GFP-positive cell, i.e., CRX:Venus-positive cells, or NRL-positive cell (rod photoreceptor precursor) in CRX:Venus-positive cells by culturing cell aggregates containing retinal tissue produced from human ES cells up to day 188-193 from the start of suspension culture, which is the differentiation stage where Muller cells are observed, preparing a section of the recovered cell aggregates containing the retinal tissue, and performing immunostaining by a conventional method using an anti-GFP antibody (detecting CRX:Venus protein), an anti-NRL antibody, an anti-RXR-γ antibody, and DAPI. Compared to the T3 no-addition group (−T3; a, e, i, m), it is clear that the proportion of photoreceptor precursor and cone photoreceptor precursor which are CRX:Venus-positive cells increased in T3 addition group (+T3; b, f, j, n, +T3+BMP; c, g, k, o, +T3+Cyclopamine-KAAD; d, h, l, p). Particularly, when BMP4 was added as a dorsalization signal transmitter in addition to T3 (+T3+BMP; c, g, k, o), the cells on the basement membrane side decreased as compared to the T3 addition group, and it is clear that the proportion of photoreceptor precursor and cone photoreceptor precursor increased. It is clear that rod photoreceptor precursor was scarcely observed at this time. In FIG. 6, T3 was added to 60 nM, BMP4 was added to 0.15 nM, and Cyclopamine-KAAD was added to 500 nM, in the medium.

Figure 7:
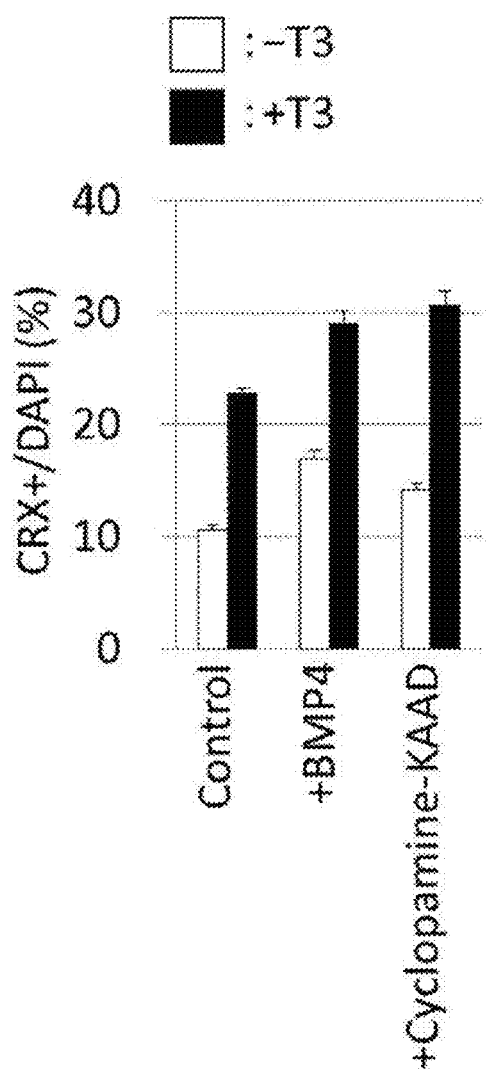
Figure 7:
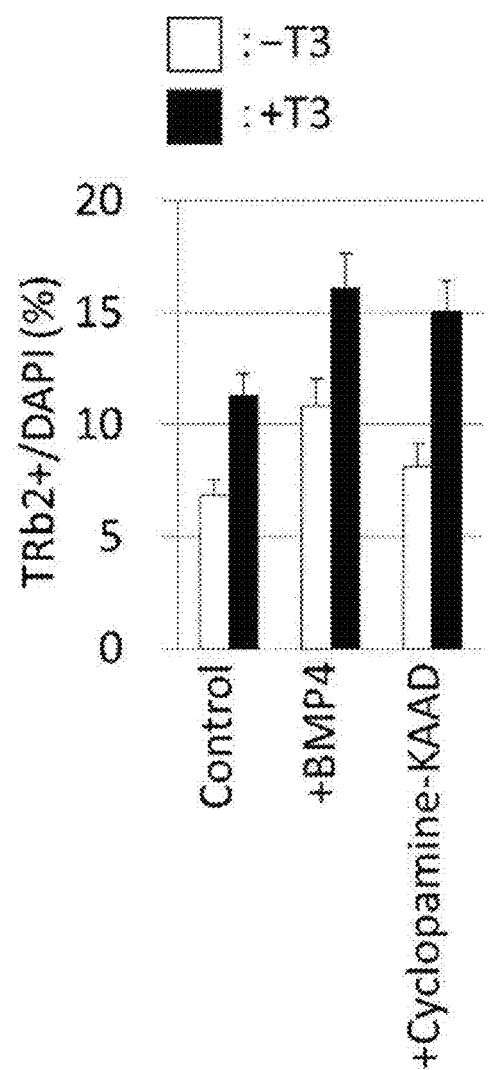

FIG. 7 shows the results obtained by culturing cell aggregates containing a retinal tissue produced from human ES cells up to about day 70 from the start of suspension culture, preparing a section of a cell aggregate containing retinal tissue, performing immunostaining by a conventional method using an anti-CRX antibody, an anti-TRβ2 antibody, and DAPI, and measuring the number of CRX-positive cells contained in the retinal tissue and the number of TRβ2-positive cells among CRX-positive cells using image analysis software (Image J). Compared to no addition of T3 (white bar), it is clear that CRX-positive cell, CRX-positive and TRβ2-positive cell, namely, photoreceptor precursor, cone photoreceptor precursor all increased in the group added with T3 (black bar). Also, it is clear that CRX-positive cell, CRX-positive and TRβ2-positive cell, namely, photoreceptor precursor, cone photoreceptor precursor, all further increased in a group added with dorsalization signal transmitter (BMP4, Cyclopamine-KAAD) in addition to T3 as compared to when dorsalization signal transmitter was not added in addition to T3. In FIG. 7, T3 was added to 60 nM, BMP4 was added to 0.15 nM, and Cyclopamine-KAAD was added to 500 nM, in the medium.

Figure 8:
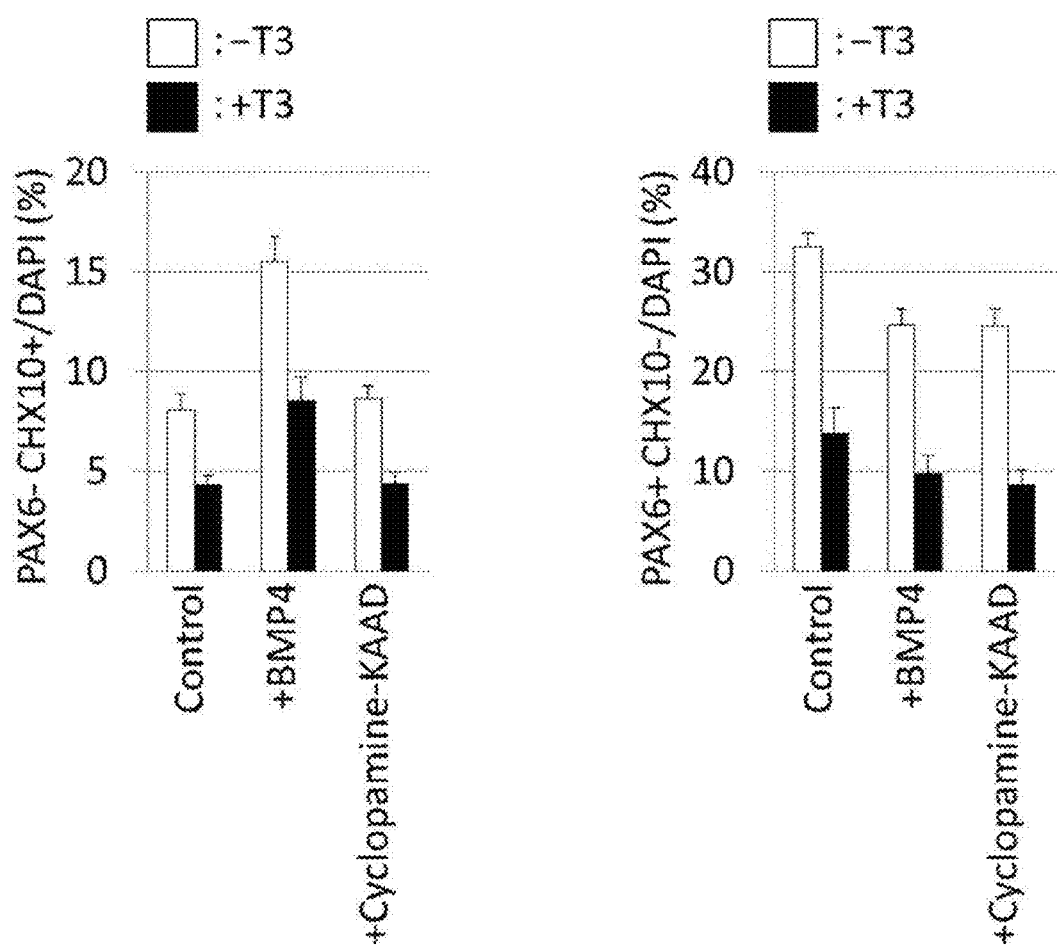

FIG. 8 shows the results obtained by culturing cell aggregates containing retinal tissue produced from human ES cells up to about day 190 from the start of suspension culture, which is the differentiation stage where Muller cells are observed, preparing a section of the recovered cell aggregates containing the retinal tissue, performing immunostaining by a conventional method using an anti-PAX6 antibody, an anti-CHX10 antibody, and DAPI, and measuring, in the neural retinal tissue, the proportion of PAX6-positive/CHX10-negative cells and PAX6-negative/CHX10-strongly positive cell, namely, any of amacrine cell, ganglion cell and horizontal cell, and bipolar cells by the use of image analysis software (Image J). Compared to when T3 was not added (white bar), it is clear that the proportions of any of the amacrine cell, ganglion cell and horizontal cell (PAX6-positive/CHX10-negative cell) and bipolar cell (PAX6-negative/CHX10-strongly positive cell) both decreased in a group added with T3 (black bar). In a group added with BMP4 as a dorsalization signal transmitter in addition to T3, the proportion of bipolar cell (PAX6-negative/CHX10-strongly positive cell) increased somewhat, but the proportion of any of the amacrine cell, ganglion cell and horizontal cell (PAX6-positive/CHX10-negative cell) decreased as compared to when a dorsalization signal transmitter was not added in addition to T3, and it is clear that the total of the bipolar cell (PAX6-negative/CHX10-strongly positive cell) and any of the amacrine cell, ganglion cell and horizontal cell (PAX6-positive/CHX10-negative cell) scarcely changed. On the other hand, in a group added with Cyclopamine-KAAD as a dorsalization signal transmitter in addition to T3, the proportion of bipolar cell (PAX6-negative/CHX10-strongly positive cell) did not change but the proportion of any of the amacrine cell, ganglion cell and horizontal cell (PAX6-positive/CHX10-negative cell) decreased as compared to when a dorsalization signal transmitter was not added in addition to T3, and it is clear that the proportion of the total of the bipolar cell (PAX6-negative/CHX10-strongly positive cell) and any of the amacrine cell, ganglion cell and horizontal cell (PAX6-positive/CHX10-negative cell) decreased. In FIG. 8, T3 was added to 60 nM, BMP4 was added to 0.15 nM, and Cyclopamine-KAAD was added to 500 nM, in the medium.

Figure 9:
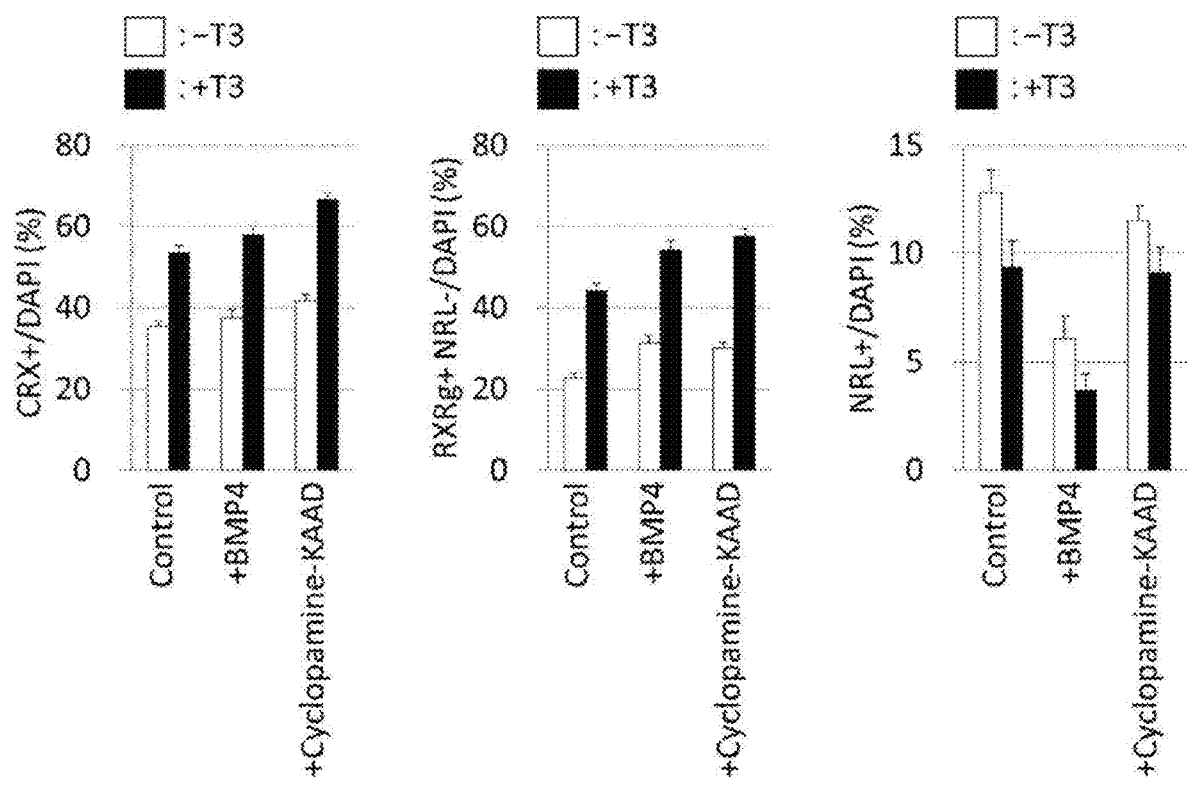

FIG. 9 shows the results obtained by culturing cell aggregates containing retinal tissue produced from human ES cells up to about day 190 from the start of suspension culture, which is the differentiation stage where Muller cells are observed, preparing a section of the recovered cell aggregates containing the retinal tissue, performing immunostaining by a conventional method using an anti-GFP antibody (detecting CRX:Venus protein), an anti-NRL antibody, an anti-RXR-γ antibody, and DAPI, and measuring the proportion of GFP-positive cell, namely, CRX:Venus-positive cell (photoreceptor precursor), and RXR-γ-positive and NRL-negative cell (cone photoreceptor precursor) in CRX:Venus-positive cells, or NRL-positive cell (rod photoreceptor precursor) in CRX:Venus-positive cells by the use of image analysis software (Image J). It is clear that the proportion of both photoreceptor precursor and cone photoreceptor precursor increased in a group added with T3 (black bar) as compared to when T3 was not added (white bar). It is also clear that the proportion of both photoreceptor precursor and cone photoreceptor precursor increased in a group added with a dorsalization signal transmitter in addition to T3 as compared to when not added with a dorsalization signal transmitter in addition to T3. Particularly, the proportion of rod photoreceptor precursor was small when BMP4 was added as a dorsalization signal transmitter in addition to T3 as compared to when a dorsalization signal transmitter was not added in addition to T3, and it is clear that the proportion of cone photoreceptor precursor is high. On the other hand, when Cyclopamine-KAAD was added as a dorsalization signal transmitter in addition to T3, the proportion of rod photoreceptor precursor did not change much as compared to when not added with a dorsalization signal transmitter in addition to T3, and it is clear that the proportion of photoreceptor precursor and cone photoreceptor precursor is higher. In FIG. 9, T3 was added to 60 nM, BMP4 was added to 0.15 nM, and Cyclopamine-KAAD was added to 500 nM, in the medium.

Figure 10:
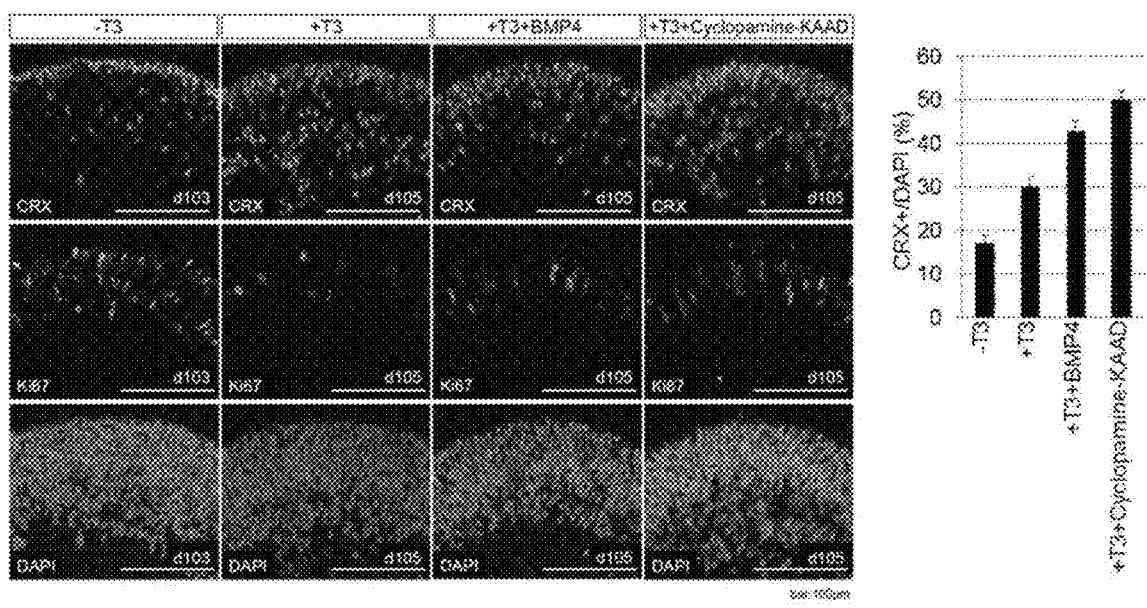

FIG. 10 shows the results obtained by culturing cell aggregates containing a retinal tissue produced from human ES cells up to about day 100-105 from the start of suspension culture, preparing a section of a cell aggregate containing retinal tissue, performing immunostaining using an anti-CRX antibody, an anti-Ki67 antibody, or DAPI staining including staining of the cell nucleus, and measuring with a fluorescent microscope. It is a graph showing the results of measurement of the proportion of CRX-positive cell contained in a neural retinal tissue prepared under similar conditions by the use of image analysis software (Image J). From FIG. 10, CRX-positive cell as a photoreceptor precursor remarkably increased in the retinal tissue in +T3 group (group added with T3) as compared to the retinal tissue in −T3 group (group added with T3) and, particularly, it is clear that the thickness of photoreceptor precursor layer present on the apical surface is almost 2 or 3 times larger in +T3 group as compared to −T3 group. It is also clear that +T3+BMP4 group (group added with BMP4 in addition to T3) and +T3+Cyclopamine-KAAD group (group added with Cyclopamine-KAAD in addition to T3) are similar to these results. In addition, even a neural retinal tissue in a stage about day 100 from the start of suspension culture showed a layer containing a Ki67-positive proliferative neural retinal progenitor cell, namely, a neuroblastic layer, and it is clear that, as compared to the retinal tissue of −T3 group, in the retinal tissue of +T3 group, many ectopic photoreceptor precursors are contained in a retinal tissue in sites other than the apical surface (photoreceptor layer, outer nuclear layer) where photoreceptor precursor is originally present in the fetal stage, namely, a neuroblastic layer where Ki67-positive neural retinal progenitor cells are present and ganglion cell layer on the basement membrane side therefrom. It is clear that such results are similar to those in +T3+Cyclopamine-KAAD group. On the other hand, such ectopic photoreceptor precursor was found in +T3+BMP4 group but not so much in +T3+BMP4 group as compared to +T3 group and +T3+Cyclopamine-KAAD group. Thus, it is suggested that the emergence of the photoreceptor precursor decreased in this differentiation stage as compared to +T3 group and +T3+Cyclopamine-KAAD. From the graph, it is clear that the proportion of CRX-positive cell contained in the neural retinal tissue increases in the order of −T3 group, +T3 group, +T3+BMP4 group, and +T3+Cyclopamine-KAAD group. From these, it is clear that the thyroid gland hormone signal transduction pathway agonist has an action to increase photoreceptor precursor in retinal tissue on around day 100 from the start of suspension culture, and that when the thyroid gland hormone signal transduction pathway agonist and the dorsalization signal transmitter are acted in combination, photoreceptor precursor can be further increased as compared to when the thyroid gland hormone signal transduction pathway agonist is acted alone. In FIG. 10, T3 was added to 60 nM, BMP4 was added to 0.15 nM, and Cyclopamine-KAAD was added to 500 nM, in the medium.

Figure 1:
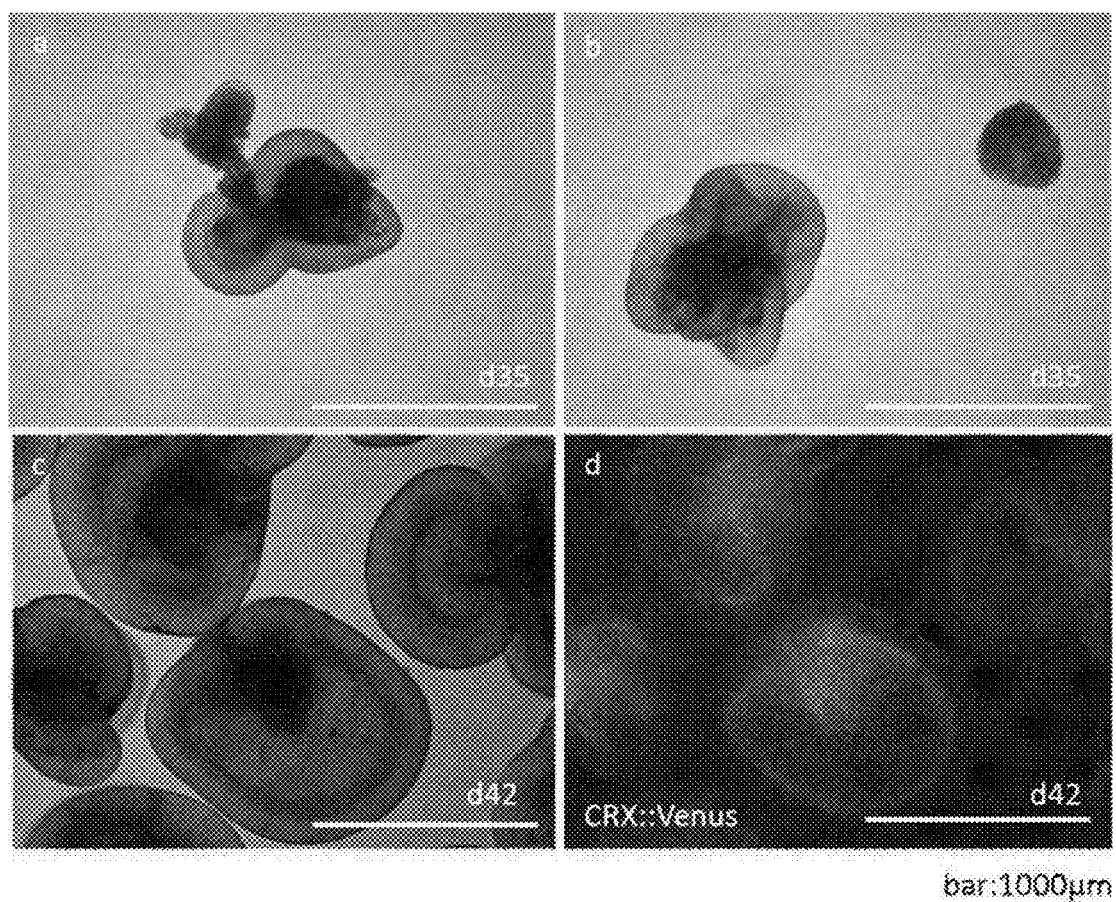
FIG. 1 shows images of cell aggregates containing a retinal tissue produced from human ES cells which were taken by a fluorescence stereo microscope on day 35 (a, b) and day 42 (c, d) from the start of suspension culture. Therein, a and b are images obtained by excising cell aggregates containing retinal tissue with tweezers on day 35 from the start of suspension culture and photographed with a fluorescent stereomicroscope, and c and d are images confirming that cells with fluorescence of CRX:Venus protein, that is, photoreceptor precursors, emerged in cell aggregates containing retinal tissue on day 42 from the start of suspension culture.
Figures 1, 11:
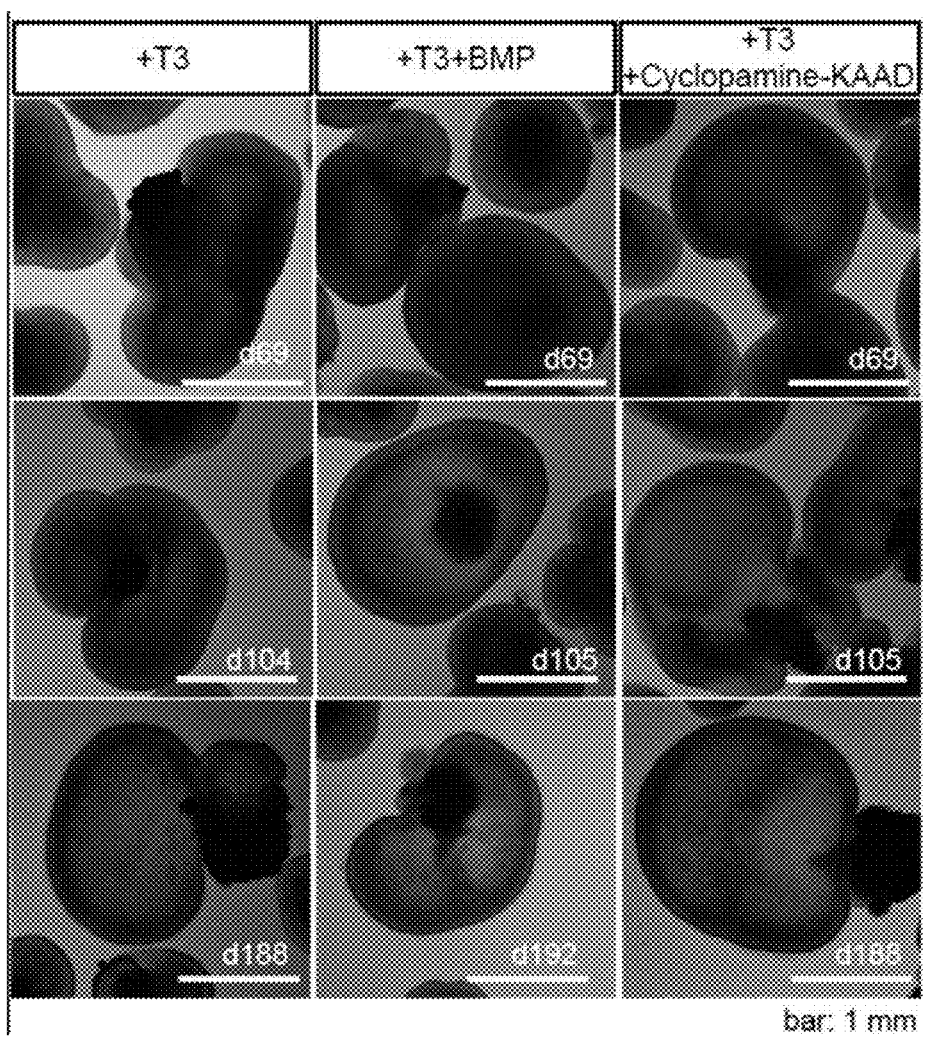
Figures 2, 11:
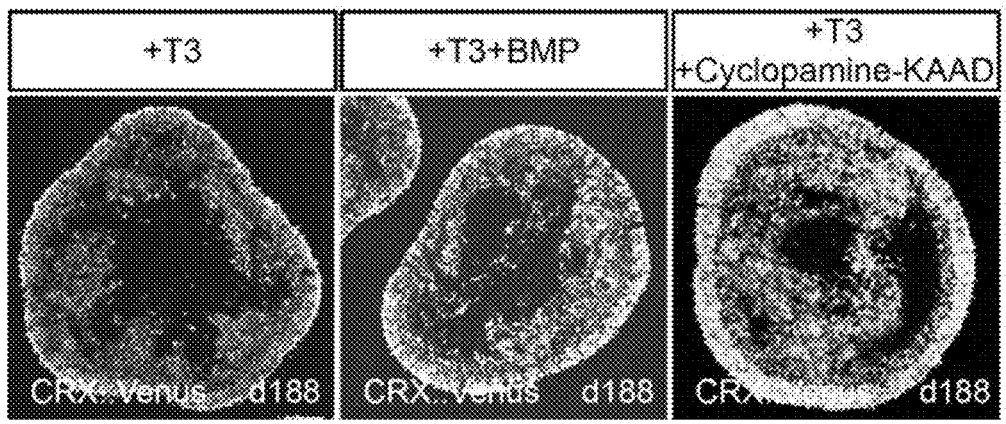
Figures 3, 11:
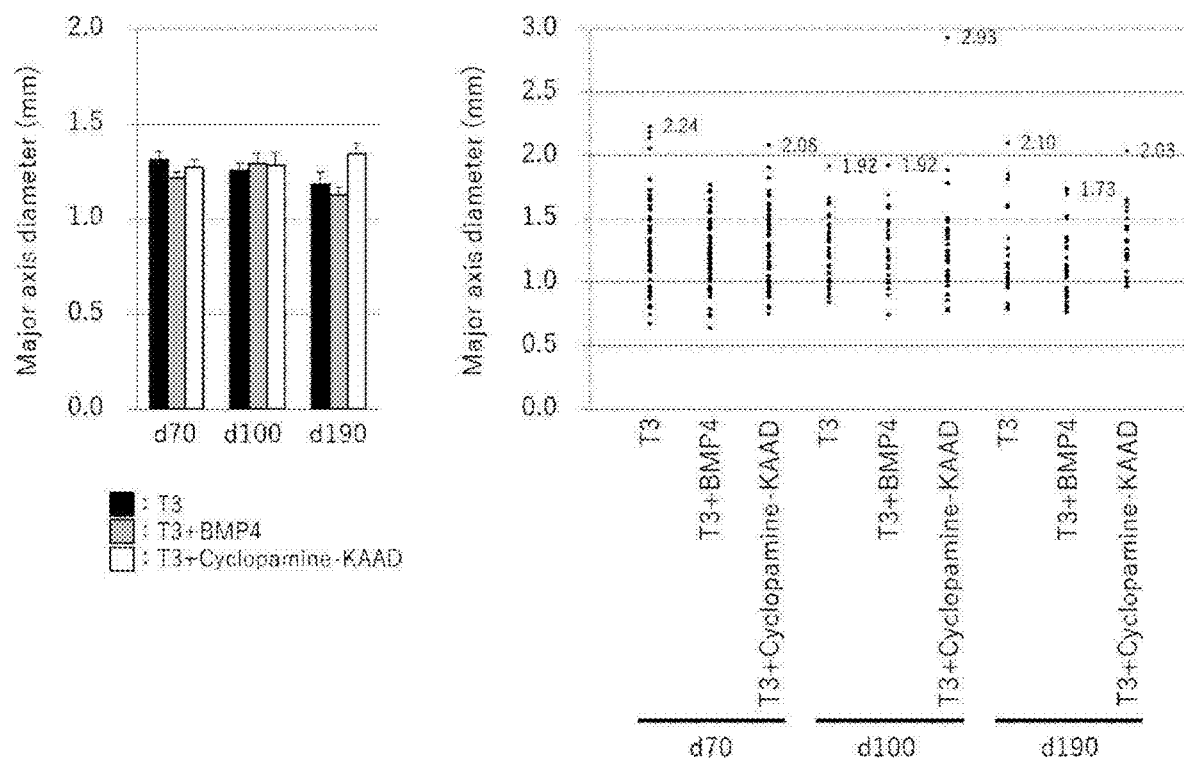

FIG. 11-1 shows the results obtained by culturing cell aggregates containing a retinal tissue produced from human ES cells up to about day 69, about day 104-105, about day 188-192, from the start of suspension culture, followed by observation and analysis. FIG. 11-1 shows images by a fluorescence stereo microscope of cell aggregates containing a retinal tissue cultured for the number of indicated days from the start of suspension culture (e.g., up to day 69 is indicated as d69). From this image, it is clear that a cell aggregate with a diameter of at least not less than 2 mm, containing a retinal tissue is contained under any conditions and at any number of days.

Figure 2:
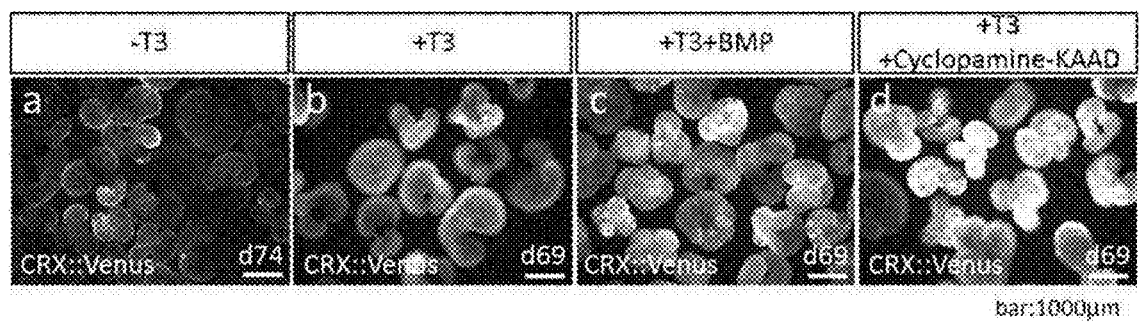
FIG. 2 shows images (a-d) of cell aggregates containing a retinal tissue produced from human ES cells which were taken by a fluorescence stereo microscope after culturing up to day 69-74 from the start of suspension culture. Compared to T3 no-addition group (−T3; a), the fluorescence emitted by CRX:Venus is strong in T3 addition group (+T3; b), and it is clear that CRX:Venus-positive cell increased. When a dorsalization signal transmitter was added in addition to T3 (+T3+BMP; c, +T3+Cyclopamine-KAAD; d), it is clear that CRX:Venus-positive cell further increased as compared to the T3 addition group. Particularly, it is clear that CRX:Venus-positive cell further increased in +T3+Cyclopamine-KAAD group as compared to +T3+BMP group. It has been reported that differentiation of a cell aggregate containing a retinal tissue cultured in vitro progresses in almost the same order and period as in the development of human retina, and CRX:Venus-positive cell that emerges at this differentiation stage is cone photoreceptor precursor among photoreceptor precursors.

FIG. 11-2 shows the results obtained by culturing cell aggregates containing a retinal tissue produced from human ES cells up to about day 188 from the start of suspension culture, preparing a section of a cell aggregate containing retinal tissue, performing immunostaining by a conventional method using an anti-GFP antibody, and observing with a fluorescent microscope. From this Figure, it is clear that CRX:Venus-positive cells stained with an anti-GFP antibody, namely, photoreceptor precursors or photoreceptors, are continuously and regularly arranged under any conditions on the surface of a cell aggregate containing the retinal tissue. That is, it is clear that cell aggregates containing these retinal tissues are retinal tissues having a continuous epithelial structure and free of a rosette-like structure even on at least day 188 from the start of suspension culture. From this Figure, it is further clear that not only photoreceptor layer (outer nuclear layer) near the apical surface but also many ectopic photoreceptor precursors were found.

Figure 3:
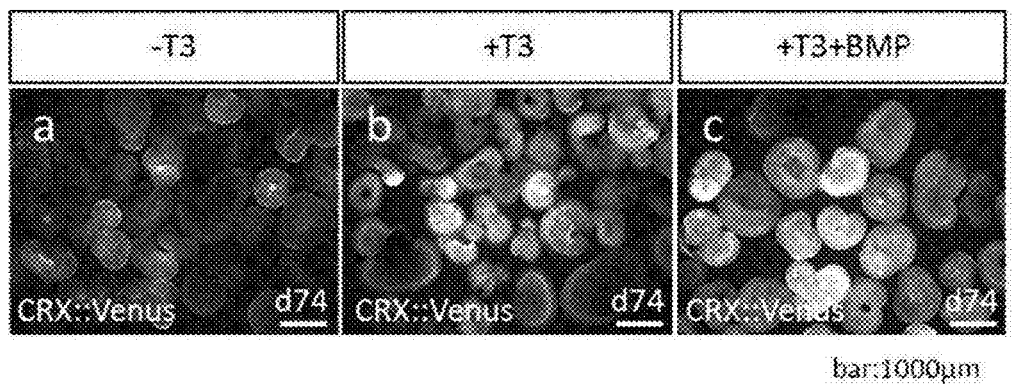
FIG. 3 shows images (a-c) of cell aggregates containing a retinal tissue produced from human ES cells which were taken by a fluorescence stereo microscope after culturing in the presence of 100 nM 9-cis retinoic acid from day 38 when photoreceptor precursor started to emerge up to day 74 from the start of suspension culture. Compared to T3 no-addition group (−T3; a), the fluorescence emitted by CRX:Venus is strong in T3 addition group (+T3; b), and it is clear that CRX:Venus-positive cell increased. When a dorsalization signal transmitter was added in addition to T3 (+T3+BMP; c), it is clear that CRX:Venus-positive cell further increased as compared to the T3 addition group. It has been reported that differentiation a cell aggregate containing a retinal tissue cultured in vitro progresses in almost the same order and period as in the development of human retina, and CRX:Venus-positive cell that emerges at this differentiation stage is cone photoreceptor precursor among photoreceptor precursors.

FIG. 11-3 shows the results obtained by culturing cell aggregates containing a retinal tissue produced from human ES cells up to about day 70, 100, 190 from the start of suspension culture, observing with a fluorescent microscope, obtaining images, measuring the diameter in the major axis of the obtained images by the use of analysis software, calculating the mean of cell aggregate containing the retinal tissue (graph, left side) and plotting same in a graph (right side). From the left side graph, it is clear that any cell aggregate containing a retinal tissue under any conditions and at any stage has a size of not less than 1.1 mm on average. On the other hand, from the right graph, it is clear that the majority are cell aggregates containing retinal tissues of not less than 1.0 mm, and cell aggregates containing retinal tissues of not less than 1.5 mm were easily found. In addition, among cell aggregates containing retinal tissue, those with a large major axis diameter reach nearly 3.0 mm (2.93 mm).

DESCRIPTION OF EMBODIMENTS

1. Definition

In the present specification, "stem cell" means an undifferentiated cell having differentiation potency and proliferative capacity (particularly self-renewal competence) maintaining the same differentiation potency even after cell division. The stem cell includes subpopulations such as pluripotent stem cell, multipotent stem cell, unipotent stem cell and the like according to the differentiation potency. Pluripotent stem cell refers to a stem cell capable of being cultured in vitro and having a potency to differentiate into any cell lineage belonging to three germ layers (ectoderm, mesoderm, endoderm) (pluripotency). The multipotent stem cell means a stem cell having a potency to differentiate into plural types of tissues or cells, though not all kinds. The unipotent stem cell means a stem cell having a potency to differentiate into a particular tissue or cell.

Pluripotent stem cell can be induced from fertilized egg, clone embryo, germ stem cell, stem cell in a tissue and the like. Examples of the pluripotent stem cell include embryonic stem cell (ES cell), EG cell (embryonic germ cell), induced pluripotent stem cell (iPS cell) and the like.

Embryonic stem cell was first established in 1981, and has also been applied to the generation of knockout mouse since 1989. In 1998, human embryonic stem cell was established, which is also being utilized for regenerative medicine. ES cell can be produced by culturing an inner cell mass on a feeder cell or in a medium containing LIF. The production methods of ES cell are described in, for example, WO 96/22362, WO 02/101057, U.S. Pat. Nos. 5,843,780, 6,200,806, 6,280,718 and the like. Embryonic stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from Incorporated Administrative Agency RIKEN, and D3 cell line, which is a mouse embryonic stem cell, is available from ATCC.

Nuclear transfer ES cell (ntES cell), which is one of the ES cells, can be established from a clone embryo produced by transplanting the nucleus of a somatic cell into an enucleated egg.

The "induced pluripotent stem cell" (to be also referred to as iPS cell) in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of plural genes selected from the group consisting of reprogramming genes including Oct3/4, Sox2, Klf4, Myc (c-Myc, N-Myc, L-Myc), Glis1, Nanog, Sal14, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc (Stem Cells, 2013; 31:458-466).

Induced pluripotent stem cell was established by Yamanaka et al. in mouse cell in 2006 (Cell, 2006, 126(4), pp. 663-676). In 2007, induced pluripotent stem cell was also established from human fibroblast, and has pluripotency and self-renewal competence similar to those of embryonic stem cells (Cell, 2007, 131(5), pp. 861-872; Science, 2007, 318(5858), pp. 1917-1920; Nat. Biotechnol., 2008, 26(1), pp. 101-106). The induction method of induced pluripotent stem cell has been variously improved thereafter (e.g., mouse iPS cell: Cell. 2006 Aug. 25; 126(4):663-76, human iPS cell: Cell. 2007 Nov. 30; 131(5):861-72).

Besides the production method of induced pluripotent stem cell based on direct reprogramming by gene expression, induced pluripotent stem cell can also be obtained from somatic cell by the addition of a compound and the like (Science, 2013, 341, pp. 651-654).

It is also possible to obtain established induced pluripotent stem cell and, for example, human induced pluripotent cell lines established by Kyoto University such as 201B7 cell, 201B7-Ff cell, 253G1 cell, 253G4 cell, 1201C1 cell, 1205D1 cell, 1210B2 cell or, 1231A3 cell, Ff-I01 cell, QHJI01 cell and the like are available from Kyoto University.

While the somatic cell used for obtaining induced pluripotent stem cell is not particularly limited, tissue-derived fibroblast, blood-lineage cells (e.g., peripheral blood mononuclear cell, T cell), hepatocyte, pancreatic cell, intestinal epithelial cell, smooth muscle cell and the like can be mentioned. As the fibroblast, those derived from corium and the like can be mentioned.

When induced pluripotent stem cell is produced by reprogramming by the expression of several kinds of genes, the means for gene expression is not particularly limited. Examples of the aforementioned means include an infection method using a virus vector (e.g., retrovirus vector, lentivirus vector, Sendaivirus vector, adenovirus vector, adeno-associated virus vector), a gene transfer method using a plasmid vector (e.g., plasmid vector, episomal vector) (e.g., calcium phosphate method, lipofection method, RetroNectin method, electroporation method), a gene transfer method using an RNA vector (e.g., calcium phosphate method, lipofection method, electroporation method), a method with direct injection of protein and the like.

The pluripotent stem cell to be used in the present invention is preferably ES cell or induced pluripotent stem cell, more preferably induced pluripotent stem cell.

The pluripotent stem cell to be used in the present invention is preferably a pluripotent stem cell of primates (e.g., human, monkey), preferably a human pluripotent stem cell. Therefore, the pluripotent stem cell to be used in the present invention is preferably a human ES cell or human induced pluripotent stem cell (human iPS cell), most preferably a human induced pluripotent stem cell (human iPS cell).

As the stem cell to be used in the present invention, the stem cell (e.g., somatic stem cell) present in the retina of an adult can also be collected and used.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of retinal cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODOSHA CO., LTD. (1995); and so on.

To be specific, for example, the genomic DNA containing the target gene to be modified (e.g., cell marker gene, histocompatibility antigen gene, disease-related gene and so on) is isolated, and a targeting vector used for homologous recombination of the target gene is produced using the isolated genomic DNA. The produced targeting vector is introduced into stem cells and the cells that showed homologous recombination between the target gene and the targeting vector are selected, whereby stem cells having the modified gene on the chromosome can be produced.

Examples of the method for isolating genomic DNA containing the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic DNA containing the target gene can also be isolated using genomic DNA library screening system (manufactured by Genome Systems), Universal GenomeWalker Kits (manufactured by CLONTECH) and so on. A polynucleotide encoding the target protein can also be used instead of genome DNA. The polynucleotide can be obtained by amplifying the corresponding polynucleotide by the PCR method.

Production of targeting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targeting vector, any of replacement type or insertion type can be used. As the selection method, methods such as positive selection, promoter selection, negative selection, polyA selection and so on can be used.

Examples of a method for selecting the desired homologous recombinant from the selected cell lines include Southern hybridization method, PCR method and so on for the genomic DNA.

The "suspension culture" or "suspension culture method" in the present invention refers to culturing while maintaining a state in which cells or cell aggregates are suspended in a culture medium and a method of performing the culture. That is, suspension culture is performed under conditions in which cells or cell aggregates are not adhered to a culture vessel and the like, and culturing performed under conditions permitting adhesion to a culture vessel and the like (adhesion culture or adhesion culture method) is not included in the category of suspension culture. In this case, adhesion of cell means that a strong cell-substratum junction is formed between a cell or cell aggregate and a culture vessel. More particularly, suspension culturing refers to culturing under conditions in which a strong cell-substratum junction is not formed between a cell or cell aggregate and a culture vessel, and "adhesion culture" refers to culturing under conditions in which a strong cell-substratum junction is formed between a cell or cell aggregate and a culture vessel material and the like.

In a cell aggregate in suspension culture, a planar cell-cell adhesion is formed (plane attachment). In cell aggregates in suspension culture, a cell-substratum junction is hardly formed with a culture vessel and the like and, even if it is formed, its contribution is small. In some embodiment, in a cell aggregate in suspension culture an endogenous cell-substratum junction is present inside the aggregate, but a cell-substratum junction is hardly formed with a culture vessel and the like and, even if it is formed, its contribution is small. From such aspect, one embodiment of "suspension culture" is, for example, a culture method in which a cell aggregate is fixed on a thin needle equipment or the like that works as a scaffold for cell aggregates and cultured in equipment filled with a culture medium. Examples of the culture method include a method using a bio 3D printer "Regenova (registered trade mark)" manufactured by Cyfuse Biomedical K.K., reported at 29AB-pm009, the 136th Annual Meeting of the Pharmaceutical Society of Japan.

The planar cell-cell adhesion means that a cell attaches to another cell via planes. More particularly, the planar cell-cell adhesion means that, for example, not less than 1%, preferably not less than 3%, more preferably not less than 5%, of the surface area of a cell adheres to the surface of another cell. A surface of a cell can be observed by staining with a reagent (e.g., DiI) that stains membranes, immunostaining of cell adhesion molecules (e.g., E-cadherin and N-cadherin).

The culture vessel to be used when performing suspension culture is not particularly limited as long as it enables "culturing in suspension" and those of ordinary skill in the art can appropriately determine same. Examples of such culture vessel include flask, tissue culture flask, dish, petri dish, tissue culture dish, multidish, microplate, microwell plate, micropore, multiplate, multiwell plate, chamber slide, schale, tube, tray, culture bag, spinner flask, roller bottle and so on. To enable suspension culture, these culture vessels are preferably non-cell-adhesive. Non-cell-adhesive culture vessels include culture vessels whose surfaces have not undergone an artificial treatment for improving the cell adhesiveness (e.g., coating treatment with extracellular matrix such as basement membrane preparation, laminin, entactin, collagen, gelatin etc., and the like, or with polymer such as polylysine, polyornithine etc. and the like or surface processing such as positive electric charge treatment and the like), and the like. As a non-cell-adhesive culture vessel, culture vessels whose surfaces have been artificially treated to decrease adhesiveness to the cells (e.g., superhydrophilic treatment with MPC polymer and the like, protein low adsorption treatment etc.) and the like can be used. Rotation culture using spinner flask, roller bottle and the like may be performed. The culture surface of the culture vessel may be a flat bottom or may have concaves and convexes.

On the other hand, as an incubator used for adhesion culture, culture vessels whose surfaces have undergone an artificial treatment for improving the cell adhesiveness (e.g., surface treatment with extracellular matrix such as basement membrane preparation, laminin, entactin, collagen, gelatin, Matrigel, Synthemax, vitronectin and the like, and the like, or coating treatment with polymer such as polylysine, polyornithine and the like or positive electric charge treatment and the like), and the like can be mentioned.

In the present specification, an aggregate of cells (cell cluster or cell aggregate) is not particularly limited as long as plural cells are adhered to each other to form a cluster, and may be a cluster formed by assembly of cells dispersed in a medium, or derived from a colony formed by cell culture, or a cell cluster formed by newly budding from other cell cluster. The cell aggregate also encompasses embryoid body, sphere and spheroid. Preferably, a planar cell-cell adhesion is formed in the aggregate of cells. In some embodiments, cells sometimes form a cell-cell junction or a cell adhesion, for example, adherence junction, in some or all of the aggregates. The aggregate also includes a cell population as a derivative obtained from the aforementioned cell cluster.

The "uniformed aggregates" means that the size of each aggregate is constant when plural aggregates are cultured, and that the variance in the length of the maximum diameter is small when the size of the aggregates are evaluated by the length of the maximum diameter. More specifically, it means that not less than 75% of aggregates in the whole aggregate population are within mean±100%, preferably mean±50%, more preferably mean±20%, of the maximum diameter in the population of the aggregates.

To "form uniformed cell aggregates" means to "rapidly aggregate a given number of dispersed cells" to form cell aggregates uniform in size, when gathering the cells to form cell aggregates and culturing the aggregates in suspension. That is, when an aggregate of pluripotent stem cells is formed by rapidly gathering the pluripotent stem cells, an epithelium-like structure can be formed with good reproducibility in the cells induced and differentiated from the formed aggregate. To be specific, a cell aggregate having an epithelium-like structure can be formed by rapidly aggregating pluripotent stem cells in a serum-free medium (SFEBq method (Serum-free Floating culture of Embryoid Body-like aggregates with quick reaggregation)).

Examples of the experimental operation to form the aggregate include a method involving keeping cells in a small space by using a plate with small wells (e.g., plate with wells having a base area of about 0.1-2.0 cm$^2$ when calculated in terms of flat bottom; 96 well plate), micropore and so on, a method involving aggregating cells by centrifugation for a short time using a small centrifugation tube and the like.

As a plate with small wells, for example, 24 well plate (area of about 1.88 cm$^2$ when calculated in terms of flat bottom), 48 well plate (area of about 1.0 cm$^2$ when calculated in terms of flat bottom), 96 well plate (area of about 0.35 cm$^2$ when calculated in terms of flat bottom, inner diameter about 6-8 mm), and 384 well plate can be mentioned. Preferred is 96 well plate. As a shape of the plate with small wells, the shape of the bottom surface when the well is seen from above is, for example, polygon, rectangle, ellipse, true circle, preferably true circle. As a shape of the plate with small wells when the well is seen from the side well, the shape of the bottom surface is preferably a structure having high outer circumference and low inner concave. The shape includes, for example, U-bottom, V-bottom, p-bottom, preferably U-bottom or V-bottom, most preferably V-bottom. As a plate with small wells, a cell culture dish (e.g., 60 mm-150 mm dish, culture flask) with a concave convex, or dent on the bottom surface (e.g., EZSPHERE (AGC TECHNO GLASS CO., LTD.)) may also be used. The bottom surface of a plate with small wells is preferably a non-cell-adhesive bottom surface, preferably the aforementioned non-cell-adhesive-coated bottom surface.

"Dispersion" means that cells and tissues are separated into small cell debris (not less than 2 cells and not more than 100 cells, preferably not more than 50 cells) or single cells by dispersion treatments such as enzyme treatment, physical treatment and the like. A certain number of dispersed cells mean a collection of a certain number of cell debris or single cells. Examples of the method for dispersing pluripotent stem cells include mechanical dispersion treatment, cell dispersing solution treatment, and cell protecting agent addition treatment. These treatments may be performed in combination. It is preferable to perform a cell dispersing solution treatment and then a mechanical dispersion treatment. Examples of the method for the mechanical dispersion treatment include pipetting treatment and scraping operation with a scraper.

The "tissue" in the present specification refers to a structure of a cell population having a structure in which plural types of cells having different morphologies and properties are sterically arranged in a given pattern.

In the present specification, the "retinal tissue" means a tissue in which at least plural types of retinal cells (in the case of retinal progenitor cell, other retinal cells may not be contained), such as photoreceptors, horizontal cells, bipolar cells, amacrine cells, ganglion cells, retinal pigment epithelial cells, Muller cells, progenitor cells of these (neural retina progenitor cell or retinal progenitor cell) and the like, which constitute respective retinal layers in retina in vivo, are sterically arranged in layers. Which retinal layer is constituted by respective cells can be confirmed by a known method, for example, the presence or absence of the expression of a cell marker or the level thereof, and the like.

In the present specification, the "retinal tissue" includes retinal tissue obtained by inducing differentiation of pluripotent stem cells and retinal tissue derived from a living body. Specifically, epithelial tissues which are obtained by suspension culture of cell aggregates formed from pluripotent stem cells under appropriate differentiation-inducing conditions and contain retinal progenitor cells and/or neural retinal progenitor cell formed on the surface of the aforementioned aggregate, and a part of the cell aggregate can be mentioned.

In the present specification, the "cell aggregate containing retinal tissue" is not particularly limited as long as it is a cell aggregate containing the aforementioned retinal tissue.

In the present invention, the "retinal layer" means optional each layer constituting the retina. Specific examples thereof include retinal pigment epithelial layer and neural retinal layer, and the neural retinal layer includes outer limiting membrane, photoreceptor layer (outer nuclear layer), outer plexiform layer, inner nuclear layer, inner plexiform layer, ganglion cell layer, nerve fiber layer and inner limiting membrane. In addition, in a retinal tissue in a stage between the below-mentioned "retinal tissue in an initial developmental stage" and a matured retinal tissue, a neural retina layer contains a layer containing neural retina progenitor cells which is called a neuroblastic layer in a neural retinal tissue.

In the present invention, the "retinal progenitor cell" refers to a progenitor cell capable of differentiating into any mature retinal cells constituting a retinal tissue, including photoreceptor, horizontal cell, bipolar cell, amacrine cell, ganglion cell, retinal pigment epithelial cell and Muller cell.

In the present invention, the "neural retinal progenitor cell" refers to a cell that is destined to be the inner layer of the optic cup. It includes, for example, a progenitor cell capable of differentiating into any mature cell constituting a neural retinal layer (retinal layer containing retinal layer-specific neuron) that does not contain retinal pigment epithelium.

The photoreceptor precursor, horizontal cell precursor, bipolar cell precursor, amacrine cell precursor, ganglion cell precursor, and retinal pigment epithelial precursor refer to precursor cells committed to differentiate into photoreceptor, horizontal cell, bipolar cell, amacrine cell, ganglion cells, and retinal pigment epithelial cell, respectively. The differentiation stages are continuous and it is difficult to clearly distinguish, for example, the boundary of differentiation stages that shift from photoreceptor precursor to photoreceptor. In the present specification, therefore, photoreceptor, horizontal cell, bipolar cell, amacrine cell, ganglion cell, retinal pigment epithelial cell and the like may include respective precursor cells. Conversely, photoreceptor precursor, horizontal cell precursor, bipolar cell precursor, amacrine cell precursor, ganglion cell precursor, retinal pigment epithelial cell precursor and the like may include respective differentiated cells thereof, namely, photoreceptor, horizontal cell, bipolar cell, amacrine cell, ganglion cell, or retinal pigment epithelial cell and the like.

In the present specification, the "retinal layer-specific neuron" is a cell constituting a retinal layer and is a neuron specific to the retinal layer. Examples of the retinal layer-specific neuron include bipolar cell, ganglion cells, amacrine cell, horizontal cell and photoreceptor, and examples of the photoreceptor include rod photoreceptor (Rod photoreceptor cell) and cone photoreceptor (Cone photoreceptor cell) and the like. Examples of the cone photoreceptor include S-cone photoreceptor that expresses S-opsin and receives blue light, L-cone photoreceptor that expresses L-opsin and receives red light, and M cone photoreceptor that expresses M-opsin and receives green light.

In the present specification, the "retinal cell" is a concept encompassing the aforementioned retinal pigment epithelial cell, Muller cell, photoreceptor, horizontal cell, bipolar cell, amacrine cell, ganglion cell and precursor cell thereof, retinal progenitor cell, and neural retinal progenitor cell, and retinal layer-specific neuron and progenitor cell of the retinal layer-specific neuron and the like.

The cells constituting the aforementioned retinal tissue can be detected or identified using an expressed or non-expressed retinal cell marker as an index.

Examples of the retinal cell marker include genes and proteins that are predominantly expressed in retinal cells, and the following can be exemplified for each cell. Alternatively, a gene or protein that is predominantly expressed in cells other than retinal cell can be used as a negative marker.

Examples of the negative marker of retinal cells such as retinal progenitor cell, neural retinal progenitor cell, photoreceptor precursor and the like include Nkx2.1 expressed in precursor of hypothalamus neuron but not expressed in retinal progenitor cell, Sox1 expressed in hypothalamus neuroepithelium but not expressed in retina and the like.

Examples of the retinal progenitor cell marker include RX (also referred to as RAX) and PAX6.

Examples of the neural retinal progenitor cell marker include RX, PAX6 and CHX10.

Examples of the marker of the retinal layer-specific neuron include Chx10 strongly expressed in bipolar cell, PKCα, Goα, VSX1 and L7 expressed in bipolar cell, TUJ1 and BRN3 expressed in ganglion cell, Calretinin and HPC-1 expressed in amacrine cell, Calbindin expressed in horizontal cell, LIM1 and the like.

Examples of the marker expressed in photoreceptor precursor and photoreceptor include CRX, Recoverin, BLIMP1, OTX2 and the like. Furthermore, a marker expressed in a rod photoreceptor and a rod photoreceptor precursor is, for example, NRL, Rhodopsin or the like. Therefore, for example, using a CRX-positive cell being NRL-positive as an index, rod photoreceptor and rod photoreceptor precursor can be identified. As a marker expressed in cone photoreceptor, cone photoreceptor precursor and ganglion cell, RXR-γ can be mentioned. As a marker expressed in cone photoreceptor and cone photoreceptor precursor, TRβ2, or TRβ1 can be mentioned. For example, cone photoreceptor precursor can be identified using coexpression of TRβ2 and CRX, or TRβ1 and CRX as an index. A cone photoreceptor precursor coexpresses RXR-γ and CRX, and can also be identified using the absence of NRL expression as an index.

OC1 (ONECUT1/HNF6) and OC2 (ONECUT2) are necessary for differentiation of a cone photoreceptor precursor, and are factors that are transiently expressed during differentiation. They are also expressed in a part of ganglion cell, horizontal cell, and a part of amacrine cell. For example, when cone photoreceptor precursor or cone photoreceptor that expresses OC1 and OC2 and precursor of horizontal cell are differentiated into cone photoreceptor precursor or cone photoreceptor and horizontal cell, the expression of OC1 and OC2 decreases in the cone photoreceptor precursor or cone photoreceptor, whereas the expression of OC1 and OC2 increases in the horizontal cell. Therefore, the differentiation efficiency of the cone photoreceptor precursor can be determined by measuring the expression level or proportion thereof.

That a cone photoreceptor and a cone photoreceptor precursor are induced and the retinal tissue is at the stage before emergence of rod photoreceptor precursor can be confirmed using CRX-positive cell being NRL-negative and TRβ2-positive, or being NRL-negative and RXR-γ-positive as an index. OTX2 is a marker expressed in a photoreceptor precursor and photoreceptor, as well as bipolar cell, and can be utilized as a marker for cone photoreceptor precursor and cone photoreceptor when the OTX2-positive cell contained in the neural retinal tissue is CHX10-negative and NRL-negative. On the other hand, of the OTX2-positive cells contained in a neural retinal tissue, NRL-positive cell can be identified as a rod photoreceptor precursor and a rod photoreceptor.

As the S cone photoreceptor marker, S-opsin can be mentioned, as the L cone photoreceptor marker, L-opsin can be mentioned, and as the M cone photoreceptor marker, M-opsin can be mentioned.

Examples of the marker commonly expressed in horizontal cell, amacrine cell and ganglion cell include PAX6 and the like.

In addition, examples of the marker of a retinal cell contained in a retinal tissue include RPE65 expressed in retinal pigment epithelial cell, MITF and PAX6, CRABP and CRALBP expressed in Muller cell and the like.

The dorsal marker and ventral marker in a retinal tissue mean a gene and a protein that are expressed in tissues respectively corresponding to the dorsal and ventral sides in a retinal tissue.

Examples of the dorsal marker include markers such as TBX5, TBX3, TBX2, COUP-TF II, CYP26A1, CYP26C1, ALDH1A1 and the like which are expressed in the dorsalization region of a neural retinal tissue among the retinal tissues. Of these, COUP-TF II can be classified as the "most dorsal marker", and ALDH1A1 is also a factor whose expression level increases as it approaches the region. In addition, examples of the ventral marker include markers such as VAX2, COUP-TF I, ALDH1A3 and the like that are expressed in the ventral region of neural retinal tissue.

The "serum-free medium" in the present specification means a medium not containing an unadjusted or unpurified serum. In the present specification, a medium containing purified blood-derived components and animal tissue-derived components (e.g., growth factor) is also included in the serum-free medium unless unadjusted or unpurified serum is contained therein.

The "serum-free conditions" in the present specification means conditions free of unadjusted or unpurified serum, specifically, conditions using a serum-free medium.

The serum-free medium here may contain a serum replacement. Examples of the serum replacement include one appropriately containing albumin, transferrin, fatty acid, collagen precursor, trace element, 2-mercaptoethanol or 3'-thiolglycerol, or equivalents of these etc., and so on. Such serum replacement may be prepared by, for example, the method described in WO 98/30679. The serum replacement may be a commercially available product. Examples of such commercially available serum replacement include KNOCKOUT™ serum replacement medium (Life Technologies, hereinafter sometimes to be indicated as KSR), Chemically-defined Lipid concentrated (manufactured by Life Technologies) and GLUTAMAX™ L-glutamine substitute supplement (manufactured by Life Technologies), B27 (manufactured by Life Technologies), N2 (manufactured by Life Technologies).

The serum-free medium may appropriately contain a fatty acid or lipid, amino acid (e.g., non-essential amino acids), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 0.5% to about 30%, preferably about 1% to about 20%) of commercially available KSR (manufactured by Life Technologies) may be used as such serum-free medium (e.g., medium of 1:1 mixture of F-12 medium and IMDM medium supplemented with 10% KSR and 450 μM 1-monothioglycerol). As a product equivalent to KSR, the medium disclosed in JP-A-2001-508302 can be mentioned.

The "serum-containing medium" in the present specification means a medium containing unadjusted or unpurified serum. The medium may contain a fatty acid, lipid, amino acid (e.g., non-essential amino acids), vitamin, growth factor, cytokine, antioxidant, 2-mercaptoethanol, 1-monothioglycerol, pyruvic acid, buffering agent, inorganic salts and so on. In addition, a serum-containing medium can be used in the step of maintaining retinal cell or retinal tissue produced by the present invention (Cell Stem Cell, 10(6), 771-775 (2012)).

Known growth factors, proteins, additives or chemical substances that promote proliferation and the like may be added to the aforementioned serum-free medium or serum-containing medium. Examples of the known growth factor and protein include EGF, FGF, IGF, insulin and the like. Examples of additives that promote proliferation include N2 supplement (N2, Invitrogen), B27 supplement (Invitrogen), and the like. Examples of chemical substances that promote proliferation include retinoids (e.g., retinoic acid or a derivative thereof), taurine, glutamine and the like.

In the present specification, "xeno-free" means conditions eliminating components derived from species different from that of the cell to be cultured.

In the present invention, the "medium containing substance X" and "in the presence of substance X" refer to a medium supplemented with an exogenous substance X or a medium containing an exogenous substance X, or in the presence of an exogenous substance X. That is, when the cells or tissues present in the medium endogenously express, secrete or produce substance X, the endogenous substance X is distinguished from the exogenous substance X, and a medium free of exogenous substance X is understood to fall outside the category of the "medium containing substance X", even when it contains endogenous substance X.

For example, the "medium containing a thyroid gland hormone signal transduction pathway agonist" is a medium added with an exogeneous thyroid gland hormone signal transduction pathway agonist or a medium containing an exogeneous thyroid gland hormone signal transduction pathway agonist. The "in the presence of thyroid gland hormone signal transduction pathway agonist" means in the presence of an exogenous thyroid gland hormone signal transduction pathway agonist. The "medium free of a BMP signal transduction pathway inhibitor" is a medium not added with an exogenous BMP signal transduction pathway inhibitor or a medium not containing an exogenous BMP signal transduction pathway inhibitor.

In the present specification, the thyroid gland hormone signal transduction pathway agonist is a substance capable of enhancing the signal transduction mediated by thyroid gland hormone, and is not particularly limited as long as it can enhance the thyroid gland hormone signal transduction pathway. Examples of the thyroid gland hormone signal transduction pathway agonist include triiodothyronine (hereinafter sometimes to be abbreviated as T3), thyroxine (hereinafter sometimes to be abbreviated as T4), thyroid gland hormone receptor (preferably TRβ receptor) agonist and the like.

As the thyroid gland hormone receptor agonist well known to those of ordinary skill in the art, compounds such as diphenylmethane derivative, diarylether derivative, pyridazine derivative, pyridine derivative, indole derivative and the like described in WO 97/21993, WO 2004/066929, WO 2004/093799, WO 2000/039077, WO 2001/098256, WO 2003/018515 WO 2003/084915 WO 2002/094319, WO 2003/064369, JP-A-2002-053564, JP-A-2002-370978, JP-A-2000-256190, WO 2007/132475, WO 2007/009913, WO 2003/094845, WO 2002/051805 or WO 2010/122980 can be mentioned.

2. Production Method of Retinal Tissue in Initial Developmental Stage

In the present specification, the "initial developmental stage" means a stage where retinal progenitor cells have emerged but ganglion cells have not emerged. Here, neural retinal progenitor cells may have emerged.

That is, in this stage, RX (RAX)-positive and PAX6-positive cells (and may further be CHX10-positive cells) are included, and TUJ1-positive cells, BRN3-positive cells and cells positive for at least two kinds of markers from tUJ1, BRN3 and PAX6 are not included. The "retinal tissue in an initial developmental stage" is not particularly limited as long as it includes retinal progenitor cells and/or neural retinal progenitor cell, that is, cells that can differentiate into photoreceptors and ganglion cells, and ganglion cells are not included. It may include a ciliary marginal zone structure.

When the retinal tissue in an initial developmental stage is produced in accordance with, for example, the starting material production methods 5 to 7 described later, it corresponds to day 22 (d22) to day 33 (d33) after the start of suspension culture. When the tissue is produced in accordance with the starting material production methods 1 to 4, it corresponds to day 12 (d12) to day 27 (d27) after the start of suspension culture.

The "retinal tissue in an initial developmental stage" can be identified by confirming the expression state of a retinal progenitor cell marker, a neural retinal progenitor cell, and a ganglion cell marker.

The retinal tissue in an initial developmental stage encompasses one corresponding to an "optic vesicle", or an retinal tissue at "the initial stage of an optic cup" containing an RX-positive, PAX6-positive and CHX10-positive neural retinal progenitor cell and free of a ganglion cell, which tissue shows differentiation somewhat progressed from optic vesicle.

Examples of the retinal tissue in the initial developmental stage include a retinal tissue that is differentiated from pluripotent stem cells, contains retinal progenitor cells or neural retinal progenitor cells, and is in a differentiation stage in which ganglion cells have not emerged. Furthermore, a retinal tissue in an initial developmental stage may contain a cell that can differentiate into a photoreceptor or nerve cell. A method for producing a retinal tissue in an initial developmental stage is not particularly limited, and may be a culture method by either suspension culture or adhesion culture.

Specifically, an aggregate containing retinal progenitor cell or neural retinal progenitor cell, which is obtained by suspension culturing an aggregate (cell cluster) prepared from pluripotent stem cells such as ES cell, iPS cell and the like by the SFEBq method (see Nat Commun. 6:6286 (2015)) in the presence of a differentiation-inducer such as BMP4 and the like can be mentioned.

The retinal tissue in an initial developmental stage may be a cell induced from a cell population containing a neuroepithelial cell. The aforementioned cell population can also be obtained by inducing differentiation from pluripotent stem cells such as ES cell, iPS cell and the like, or by collecting stem cells present in an adult retina and inducing differentiation of same.

A retinal tissue in an initial developmental stage is specifically a retinal tissue containing retinal progenitor cell marker-positive (preferably, RX-positive and PAX6-positive) retinal progenitor cell, or a neural retinal progenitor cell marker-positive (preferably, CHX10-positive and PAX6-positive and RX-positive) neural retinal progenitor cell in a proportion of not less than 30%, preferably not less than 50%, more preferably not less than 80%, further preferably not less than 90%, further more preferably not less than 99%, of the total number of cells contained in the retinal tissue, and is a retinal tissue containing a ganglion cell marker-positive (preferably, BRN3-positive) ganglion cell in a proportion of not more than 40%, preferably not more than 20%, not more than 10%, not more than 5%, more preferably not more than 1%, further preferably not more than 0.1%, further more preferably not more than 0.01%, of the total number of cells.

A method for producing a retinal tissue in an initial developmental stage from a pluripotent stem cell such as human iPS cell and the like is explained.

Pluripotent stem cells such as human iPS cell and the like can be obtained or produced by a method well known to those of ordinary skill in the art as mentioned above and subjected to maintenance culture and expansion culture. While the maintenance culture and expansion culture of pluripotent stem cells can be performed by suspension culture or adhesion culture, it is preferably performed by adhesion culture. While the maintenance culture and expansion culture of pluripotent stem cells may be performed in the presence of feeder cells or in the absence of feeder cells (feeder free), it is preferably performed in the absence of feeder cells.

A retinal tissue in an initial developmental stage can be produced using pluripotent stem cells subjected to maintenance culture and by a method well known to those of ordinary skill in the art. As this method, the methods described in WO 2013/077425 (& US2014/341864), WO 2015/025967 (& US2016/251616), WO 2016/063985, WO 2016/063986 and WO 2017/183732 and the like can be mentioned. Also, as this method, the methods described in non-patent documents: Proc Natl Acad Sci USA. 111(23): 8518-8523(2014), Nat Commun. 5:4047(2014), Stem Cells. (2017):35(5), 1176-1188 and the like, and the like can be mentioned.

2-1. Starting Material Production Method 1

As one preferable embodiment of production of a retinal tissue in an initial developmental stage, the method described in WO 2015/025967 including the following steps can be mentioned:

(1) the first step of forming a cell aggregate by culturing pluripotent stem cells in suspension in a serum-free medium, and (2) the second step of obtaining an aggregate containing a retinal progenitor cell or a neural retinal progenitor by culturing in suspension the aggregate formed in the first step in a serum-free medium or serum-containing medium not containing an SHH signal transduction pathway agonist and containing a BMP signal transduction pathway agonist.

An aggregate containing a retinal progenitor cell or a neural retinal progenitor which is obtained by the method can be used as a retinal tissue in an initial developmental stage which is a starting material used in the methods of the present invention.

[First Step]

The first step can be performed according to the method described in WO2015/025967 (& US2014/341864). That is, in the first step, a cell aggregate is formed by culturing pluripotent stem cells in suspension in a serum-free medium.

The serum-free medium to be used in the first step is not particularly limited as long as it is as described above. For example, a serum-free medium free of both a BMP signal transduction pathway agonist and a Wnt signal transduction pathway inhibitor can be used. To avoid complicated preparation, for example, a serum-free medium supplemented with an appropriate amount of a commercially available serum replacement such as KSR and so on (e.g., medium of 1:1 mixture of IMDM and F-12, which is supplemented with 10% KSR, 450 μM 1-monothioglycerol and 1× Chemically Defined Lipid Concentrate) is preferably used. As a serum replacement, bovine serum albumin (BSA) can also be added at a concentration of 0.1 mg/mL-20 mg/mL, preferably about 4 mg/mL-6 mg/mL, to a serum-free medium. The amount of KSR to be added to a serum-free medium in the case of human ES cell or human iPS cell is generally about 1% to about 20%, preferably about 2% to about 20%.

The culture conditions such as culture temperature, $CO_2$ concentration and so on in the first step can be appropriately determined. The culture temperature is, for example, about 30° C. to about 40° C., preferably about 37° C. The $CO_2$ concentration is, for example, about 1% to about 10%, preferably about 5%.

The concentration of the pluripotent stem cells usable in the first step can be appropriately set so that an aggregate of the pluripotent stem cells can be more uniformly and efficiently formed. For example, when human ES cells are cultured in suspension using a 96-well plate, a liquid prepared to achieve about $1\times10^3$ to about $1\times10^5$ cells, preferably about $3\times10^3$ to about $5\times10^4$ cells, more preferably about $5\times10^3$ to about $3\times10^4$ cells, further more preferably about $0.9\times10^4$ to $1.2\times10^4$ cells, per well is added to the wells, and the plate is left to stand to form aggregates.

The period for suspension culture necessary for forming an aggregate can be determined as appropriate according to the pluripotent stem cell to be used. To form uniformed cell aggregates, it is desirably as short as possible (e.g., SFEBq method). The steps for the dispersed cells to form cell aggregates can be divided into a step for assembling cells, and a step forming cell aggregates from the assembled cells. The period from the time point of seeding the dispersed cells (i.e., at the time of the start of suspension culture) to assemble cells in case of human ES cell or human iPS cell is, for example, preferably within about 24 hr, more preferably to form aggregate within about 12 hr. The period from the time point of seeding the dispersed cells (i.e., at the time of the start of suspension culture) to form an aggregate in case of pluripotent stem cell (e.g., human iPS cell) is, for example, preferably within about 72 hr, more preferably within about 48 hr. The period for cell aggregate formation can be appropriately adjusted by controlling the tools for aggregating the cells, centrifugation conditions and so on.

Formation of cell aggregates can be determined based on the size and cell number of the aggregates, macroscopic morphology, microscopic morphology by tissue staining analysis and uniformity thereof, expression of differentiation- and undifferentiation-markers and uniformity thereof, control of expression of differentiation marker and synchrony thereof, reproducibility of differentiation efficiency between the aggregates, and so on.

[Second Step]

A second step of obtaining an aggregate containing a retinal progenitor cell or a neural retinal progenitor cell as a retinal tissue in an initial developmental stage by culturing in suspension the aggregate formed in the aforementioned first step in a serum-free medium or serum-containing medium that does not contain an SHH signal transduction pathway agonist and contains a BMP signal transduction pathway agonist is explained.

The medium to be used in the second step is, for example, a serum-free medium or a serum-containing medium not supplemented with an SHH signal transduction pathway agonist but supplemented with a BMP signal transduction pathway agonist. It is not necessary to add a basement membrane preparation. A serum-free medium or serum-containing medium to be used for such medium is not particularly limited as long as it is as mentioned above. To avoid complicated preparation, for example, a serum-free medium supplemented with an appropriate amount of a commercially available serum replacement such as KSR and so on (e.g., medium of 1:1 mixture of IMDM and F-12 supplemented with 10% KSR, 450 µM 1-monothioglycerol and 1× Chemically Defined Lipid Concentrate) is preferably used. As a serum replacement, BSA can also be added at a concentration of 0.1 mg/mL-20 mg/mL, preferably about 4 mg/mL-6 mg/mL, to a serum-free medium. The amount of KSR to be added to a serum-free medium in the case of human ES cell is generally about 1% to about 20%, preferably about 2% to about 20%.

As the serum-free medium to be used in the second step, the serum-free medium used in the first step may be continuously used as it is as long as it is free of a SHH signal transduction pathway agonist, or may be that replaced with a fresh medium. When the serum-free medium free of a BMP signal transduction pathway substance used in the first step is directly used for the second step, a BMP signal transduction pathway agonist may be added to the medium.

The medium "free of a SHH signal transduction pathway agonist" also includes a medium substantially free of a SHH signal transduction pathway agonist, for example, a medium free of a SHH signal transduction pathway agonist at a concentration imparting an adverse influence on selective differentiation into a retinal progenitor cell or a retinal tissue.

The medium "not supplemented with a SHH signal transduction pathway agonist" also includes a medium substantially not supplemented with a SHH signal transduction pathway agonist, for example, a medium not supplemented with a SHH signal transduction pathway agonist at a concentration imparting an adverse effect on selective differentiation into a retinal progenitor cell or a retinal tissue.

Examples of BMP signal transduction pathway agonist used in the second step include BMP proteins such as BMP2, BMP4, BMP7 etc., GDF proteins such as GDF7 etc., anti-BMP receptor antibody, BMP partial peptides and so on. BMP2, BMP4 and BMP7 are available from, for example, R&D Systems, and GDF7 is available from, for example, Wako Pure Chemical Industries, Ltd. The BMP signal transduction pathway agonist is preferably BMP4.

The concentration of the BMP signal transduction pathway agonist used in the second step only need to be a concentration at which differentiation of the cells contained in the aggregates obtained in the aforementioned the first step into retinal cells can be induced. For example, BMP4 is added to the medium such that the concentration is about 0.01 nM to about 1 µM, preferably about 0.1 nM to about 100 nM, more preferably about 1 nM-about 10 nM, further preferably about 1.5 nM (55 ng/mL). When a BMP signal transduction pathway agonist other than BMP4 is used, it is desirably used at a concentration at which a BMP signal transduction pathway activation action equivalent to that of BMP4 at the above-mentioned concentration is exerted.

A BMP signal transduction pathway agonist may be added after about 24 hr or later from the start of the suspension culture in the first step, and may also be added to the medium within several days (e.g., within 15 days) from the start of the suspension culture in the first step. Preferably, a BMP signal transduction pathway agonist is added to the medium at day 1 to day 15, more preferably day 1 to day 9, further preferably day 2 to day 9, further preferably day 3 to day 8, still more preferably day 3 to day 6, further more preferably day 6, from the start of the suspension culture.

After the addition of a BMP signal transduction pathway agonist to the medium and the start of the differentiation induction of cells contained in the aggregate obtained in the first step to a retinal cell, further addition of the BMP signal transduction pathway agonist to the medium is not necessary, and the medium may be exchanged with a serum-free medium or serum-containing medium each free of a BMP signal transduction pathway agonist.

Alternatively, the concentration of the BMP signal transduction pathway agonist in the medium may be varied during the period of the second step. For example, the BMP signal transduction pathway agonist is provided to fall within the above-mentioned range of a concentration at the time of the start of the second step, and the concentration may be gradually or stepwisely decreased at a ratio of 40-60% per 2-4 days.

In a specific embodiment, the medium is partly or entirely exchanged with a medium containing BMP4 on the 1st-9th day, preferably the 2nd-9th day, further preferably the 3rd-8th day, further more preferably the 3rd-6th day, after the start of suspension culture (namely, after the start of the aforementioned first step), the final concentration of BMP4 is adjusted to about 1-10 nM, and the cells can be cultured in the presence of BMP4 for, for example, 1-16 days, preferably 2-9 days, further preferably 6-9 days. It is also possible to culture cells for a longer term, specifically for not less than 20 days, not less than 30 days. That is, in the second step, culture performed in the presence of a BMP signal transduction pathway agonist is appropriately continued for a period until the aggregate obtained in the first step is induced to differentiate into a retinal tissue in an initial developmental stage. Specifically, the retinal tissue in an initial developmental stage can be obtained in 6-12 days after addition of the BMP signal transduction pathway agonist.

Here, the medium can be partly or entirely exchanged about 1 or 2 times with a medium containing BMP4 to maintain the concentration of BMP4 at the same concentration. Alternatively, as mentioned above, the concentration of BMP4 can also be reduced step by step.

In one embodiment, after the start of culturing in a medium containing a BMP signal transduction pathway agonist, the concentration of the BMP signal transduction pathway agonist in the medium can be gradually or stepwisely decreased at a ratio of 40-60% per 2-4 days by exchanging the medium with a serum-free medium or a serum-containing medium, each free of a BMP signal transduction pathway agonist.

Differentiation induction of a retinal tissue in an initial developmental stage can be confirmed by, for example, detecting expression of a retinal progenitor cell marker and a neural retinal progenitor cell marker in the cells in the tissue. The aggregate formed in the first step by using pluripotent stem cells in which a fluorescence reporter protein gene such as GFP was knocked-in into the Rx gene locus is cultured in suspension in the presence of a BMP signal transduction pathway agonist at a concentration necessary for differentiation induction into retinal cell, and fluorescence emitted from the expressed fluorescence reporter protein is detected, whereby the time point when differentiation induction into retinal cell was started can be confirmed.

As one embodiment of the second step, a step of culturing the aggregate formed in the first step in suspension in a serum-free medium or serum-containing medium containing a BMP signal transduction pathway agonist at a concentration necessary for differentiation induction into retinal cell and not containing an SHH signal transduction pathway agonist, until a cell expressing retinal progenitor cell marker or neural retinal progenitor marker (e.g., Rx, Pax6, Chx10) begins emerging, thereby obtaining an aggregate containing retinal progenitor cells or neural retinal progenitor cells as retinal tissues in an initial developmental stage can be mentioned.

In the second step, when a medium exchange operation is performed, for example, an operation to add a fresh medium without discarding the existing medium (medium addition operation), an operation to discard about a half amount of the existing medium (about 40-800 of the volume of the existing medium) and add about a half amount of a fresh medium (40-80% of the volume of the existing medium) (half-medium exchange operation), and an operation to discard about the whole amount of the existing medium (not less than 90% of the amount of the existing medium) and add about the whole amount of a fresh medium (not less than 90% of the amount of the existing medium) (full-medium exchange operation) can be mentioned.

When a particular component (e.g., BMP4) is added at a certain time point, for example, an operation to calculate the final concentration, to discard about a half amount of the existing medium, and to add about a half amount of a fresh medium containing a particular component at a concentration higher than the final concentration (specifically 1.5 times-3.0 times the final concentration, for example, about 2 times the final concentration, (half-medium exchange operation, half-medium exchange) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time point, for example, the medium exchange operation may be performed plural times per day, preferably plural times (e.g., 2-3 times) within 1 hr. Also, when the concentration of a component contained in the existing medium is to be decreased by dilution at a certain time point, the cells or aggregates may be transferred to another culture container.

While the tool used for the medium exchange operation is not particularly limited, for example, pipetter, micropipette, multichannel micropipette, continuous dispenser, and the like can be mentioned. For example, when a 96 well plate is used as a culture vessel, a multichannel micropipette may be used.

In a preferable embodiment, the concentration of a SHH signal transduction pathway agonist in the medium to be used in the second step is, when calculated in terms of SHH signal transduction promoting activity of SAG, not more than 700 nM, preferably not more than 300 nM, more preferably not more than 10 nM, further preferably not more than 0.1 nM. Further preferably, it is free of a SHH signal transduction pathway agonist. The medium "free of a SHH signal transduction pathway agonist" also includes a medium substantially free of a SHH signal transduction pathway agonist, for example, a medium free of a SHH signal transduction pathway agonist at a concentration imparting an adverse influence on selective differentiation into a retinal progenitor cell or a retinal tissue. The medium "not supplemented with a SHH signal transduction pathway agonist" also includes a medium substantially not supplemented with a SHH signal transduction pathway agonist, for example, a medium not supplemented with a SHH signal transduction pathway agonist at a concentration imparting an adverse effect on selective differentiation into a retinal progenitor cell or a retinal tissue.

The culture conditions such as culture temperature, $CO_2$ concentration and so on in the second step can be appropriately determined. The culture temperature is, for example, about 30° C. to about 40° C., preferably about 37° C. The $CO_2$ concentration is, for example, about 1% to about 10%, preferably about 5%.

By such culture differentiation of the cells forming the aggregates obtained in the first step to a retinal tissue in an initial developmental stage can be induced. That an aggregate containing retinal progenitor cells or neural retinal progenitor cell was obtained as a retinal tissue in an initial developmental stage can be confirmed by, for example, detecting the presence of cells expressing Rx, PAX6, which is a retinal progenitor cell marker, or RX, PAX6 or CHX10, which is a neural retinal progenitor cell marker, in the aggregate.

One embodiment of the second step can be a step of culturing the aggregate formed in the first step in suspension in a serum-free medium or serum-containing medium containing a BMP signal transduction pathway agonist at a concentration necessary for differentiation induction into a retinal cell, until a cell expressing Rx gene begins emerging, whereby obtaining an aggregate containing retinal progenitor cells or neural retinal progenitor cells. In one embodiment, the culturing of the second step is performed until not less than 20% (preferably, not less than 30%, not less than 40%, not less than 50%, not less than 60%, not less than 80%) of the cells contained in the aggregate express Rx.

The aggregate obtained by the above-mentioned method can be used as a retinal tissue in an initial developmental stage that is the starting material in the production method of the present invention after culturing in a suspension in a serum-free medium or serum-containing medium not containing any of SHH signal transduction pathway agonist, BMP signal transduction pathway agonist and Wnt signal transduction pathway agonist. The period of the suspension culture is not particularly limited as long as it is a period until emergence of a ganglion cell. It is, for example, 1 day-50 days, preferably 1 day-15 days, more preferably 1 day-7 days.

The medium used in the aforementioned suspension culture is, for example, a serum-free medium or serum-containing medium not supplemented with any of SHH signal transduction pathway agonist, BMP signal transduction pathway agonist and Wnt signal transduction pathway agonist.

The medium "not containing any of SHH signal transduction pathway agonist, BMP signal transduction pathway agonist and Wnt signal transduction pathway agonist" also includes a medium substantially not containing any of SHH signal transduction pathway agonist, BMP signal transduction pathway agonist and Wnt signal transduction pathway agonist, for example, a medium not containing SHH signal transduction pathway agonist, BMP signal transduction pathway agonist or Wnt signal transduction pathway agonist at a concentration that adversely affects selective differentiation into retinal tissue.

The medium "not supplemented with any of SHH signal transduction pathway agonist, BMP signal transduction pathway agonist and Wnt signal transduction pathway agonist" also includes a medium substantially not supplemented with any of SHH signal transduction pathway agonist, BMP signal transduction pathway agonist and Wnt signal transduction pathway agonist, for example, a medium not supplemented with SHH signal transduction pathway agonist, BMP signal transduction pathway agonist or Wnt signal transduction pathway agonist at a concentration that adversely affects selective differentiation into retinal tissue.

A serum-free medium or serum-containing medium to be used for such medium is not particularly limited as long as it is as mentioned above. To avoid complicated preparation, for example, a serum-free medium supplemented with an appropriate amount of a commercially available serum replacement such as KSR and so on (e.g., medium of 1:1 mixture of IMDM and F-12 supplemented with 10% KSR, 450 μM 1-monothioglycerol and 1× Chemically Defined Lipid Concentrate) is preferably used. Bovine serum albumin (BSA) can also be added at a concentration of 0.1 mg/mL-20 mg/mL, preferably about 4 mg/mL-6 mg/mL, to a serum-free medium. The amount of KSR to be added to a serum-free medium in the case of, for example, human ES cell is generally about 1% to about 20%, preferably about 2% to about 20%. To avoid complicated preparation of serum-containing medium, for example, a serum-containing medium supplemented with an appropriate amount of a commercially available serum (e.g., medium of 1:1 mixture of DMDM and F-12, which is supplemented with serum, and N2 supplement) is more preferably used. The amount of serum to be added to a serum-containing medium in the case of human ES cell is generally about 1% to about 20%, preferably about 2% to about 20%. All the above-mentioned media may be used after addition of taurine and the like.

The culture conditions such as culture temperature, $CO_2$ concentration, $O_2$ concentration and the like can be appropriately determined. The culture temperature is, for example, about 30° C. to about 40° C., preferably about 37° C. The $CO_2$ concentration is, for example, about 1% to about 10%, preferably about 5%. The $O_2$ concentration is not less than about 5%, for example, about 20% to about 70%, preferably about 20% to about 60%, more preferably about 20% to about 40%, particularly preferably about 20%.

As described above, that the retinal tissue obtained by the starting material production method 1 is in an initial developmental stage, that is, in a differentiation stage in the initial stage of development in which a retinal progenitor cell or a neural retinal progenitor cell is contained and a ganglion cell has not emerged can be identified by measuring the expression state of at least one of retinal progenitor cell markers such as RX, PAX6 and the like, neural retinal progenitor markers such as CHX10, RX, PAX6 and the like, and ganglion cell markers such as BRN3 and the like. That is, it can be confirmed that, in this differentiation stage, not less than 30%, preferably not less than 50%, more preferably not less than 80%, further preferably not less than 90%, further more preferably not less than 99%, of the whole cells contained in the retinal tissue express retinal progenitor cell marker and/or neural retinal progenitor cell marker, and not more than 40%, preferably not more than 20%, not more than 10%, not more than 5%, not more than 1%, further preferably not more than 0.1%, further more preferably not more than 0.01%, of the whole cells contained in the retinal tissue express ganglion cell marker. At this time, expression of ventral marker and/or most dorsal marker (e.g., ALDH1A3 and/or ALDH1A1) does not pose any problem, and both may be in a differentiation stage that can be suppressed or promoted by a dorsalization signal transmitter.

2-2. Starting Material Production Method 2

As one preferable embodiment of production of retinal tissue in an initial developmental stage, the method described in WO 2016/063985 and WO 2017/183732 and containing the following steps can be mentioned:

(1) a first step of culturing pluripotent stem cells in the absence of feeder cells and in a medium containing 1) a TGFβ, family signal transduction pathway inhibitor and/or an SHH signal transduction pathway agonist, and 2) a factor for maintaining undifferentiated state, (2) a second step of culturing the cells obtained in the first step in suspension to form a cell aggregate, and (3) a third step of culturing the aggregate obtained in the second step in suspension in the presence of a BMP signal transduction pathway agonist to obtain an aggregate containing a retinal progenitor cell or a neural retinal progenitor cell.

An aggregate obtained by this method and containing retinal progenitor cell or neural retinal progenitor cell can be used as a retinal tissue in an initial developmental stage and as a starting material used in the methods of the present invention.

[First Step]

The first step can be performed according to the method described in WO 2016/063985. That is, the absence of feeder cells (hereinafter to be also referred to as feeder-free) in the first step means a condition substantially free of feeder cells (e.g., the ratio of the number of feeder cells relative to the total number of cells is not more than 3%). Preferably, the first step is performed under a condition free of feeder cells. The medium to be used in the first step is not particularly limited as long as it is a medium enabling culturing of pluripotent stem cells to maintain undifferentiated state under feeder-free conditions (feeder-free medium). Preferably, to enable culturing to maintain undifferentiated state, it contains a factor for maintaining undifferentiated state.

The factor for maintaining undifferentiated state is not particularly limited as long as it is a substance having an action to suppress differentiation of pluripotent stem cells. Examples of the factor for maintaining undifferentiated state widely used by those of ordinary skill in the art include a FGF signal transduction pathway agonist, a TGFβ, family signal transduction pathway agonist, insulin and the like. As the FGF signal transduction pathway agonist, fibroblast growth factors (e.g., bFGF, FGF4, FGF8) can be specifically mentioned. As the TGFβ, family signal transduction pathway agonist, a TGFβ, signal transduction pathway agonist, a Nodal/Activin signal transduction pathway agonist can be mentioned. As the TGFβ, signal transduction pathway agonist, TGFβ1, TGFβ2 can be mentioned. As the Nodal/Activin signal transduction pathway agonist, Nodal, Activin A, Activin B can be mentioned. When human pluripotent stem cells (human ES cells, human iPS cells) are cultured, the medium in the first step preferably contains bFGF as a factor for maintaining undifferentiated state.

The factor for maintaining undifferentiated state to be used in the present invention is not particularly limited as long as it is a mammal-derived factor for maintaining undifferentiated state. Preferably, a factor for maintaining undifferentiated state of a mammal of the same species as the cells to be cultured is used. For example, for culturing human pluripotent stem cells, human factor for maintaining undifferentiated states (e.g., bFGF, FGF4, FGF8, EGF, Nodal, Activin A, Activin B, TGFβ, 1, TGFβ, 2 etc.) are used, and an isolated factor for maintaining undifferentiated state can be exogenously added. Alternatively, a factor for maintaining undifferentiated state may be added in advance to the medium to be used in the first step.

The concentration of the factor for maintaining undifferentiated state in the medium to be used in the first step is a concentration capable of maintaining the undifferentiated state of the pluripotent stem cells to be cultured, and can be appropriately determined by those of ordinary skill in the art. For example, specifically, when bFGF is used as a factor for maintaining undifferentiated state in the absence of feeder cells, the concentration thereof is generally about 4 ng-500 ng/mL, preferably about 10 ng-200 ng/mL, more preferably about 30 ng-150 ng/mL.

As a feeder-free medium containing a factor for maintaining undifferentiated state and usable for culturing pluripotent stem cells, many synthetic media have been developed and are commercially available and, for example, Essential 8 medium (manufactured by Life Technologies) can be mentioned. Essential 8 medium is DMEM/F12 medium containing L-ascorbic acid-2-phosphate magnesium (64 mg/l), sodium selenium (14 μg/L), insulin (19.4 mg/l), NaHCO$_3$ (543 mg/l), transferrin (10.7 mg/l), bFGF (100 ng/mL), and a TGFβ, family signal transduction pathway agonist (TGFβ, 1 (2 ng/mL) or Nodal (100 ng/mL)) as additives (Nature Methods, 8, 424-429 (2011)). Examples of other commercially available feeder-free medium include S-medium (manufactured by DS Pharma Biomedical), StemPro (manufactured by Life Technologies), hESF9 (Proc. Natl. Acad. Sci. USA. 2008 Sep. 9; 105(36):13409-14), mTeSR1 (manufactured by STEMCELL Technologies), mTeSR2 (manufactured by STEMCELL Technologies), TeSR-E8 (manufactured by STEMCELL Technologies), and StemFit (manufactured by Ajinomoto Co., Inc.). The present invention can be performed conveniently by using these in the above-mentioned first step.

In the first step, the pluripotent stem cells may be cultured under any conditions of suspension culture and adhesion culture, preferably adhesion culture.

While a culture vessel used for adhesion culture is not particularly limited as long as "adhesion culture" can be performed, a cell adhesive culture vessel is preferable. Cell-adhesive culture vessels include culture vessels whose surfaces have been artificially treated to improve cell adhesiveness, and specifically, the aforementioned culture vessel whose inside is coated with a coating agent can be mentioned. Examples of the coating agent include extracellular matrix such as laminin [including laminin α5β1γ1 (hereinafter laminin 511), laminin α1β1γ1 (hereinafter laminin 111) and the like and laminin fragment (laminin 511E8 etc.)], entactin, collagen, gelatin, vitronectin, Synthemax (Corning Incorporated), Matrigel and the like, or polymer such as polylysine, polyornithine and the like, and the like. It is also possible to use a culture container whose surface is processed by a positive electric charge treatment and the like. Preferred is laminin and more preferred is laminin 511E-8. Laminin 511E-8 can be a commercially available product (e.g., iMatrix-511, Nippi).

The medium to be used in the first step contains a TGFβ family signal transduction pathway inhibitor and/or an SHH signal transduction pathway agonist.

The TGFβ family signal transduction pathway inhibitor refers to a substance that inhibits the TGFβ family signal transduction pathway, i.e., signal transduction pathway transmitted by the Smad family, and specific examples include a TGFβ signal transduction pathway inhibitor, a Nodal/Activin signal transduction pathway inhibitor and a BMP signal transduction pathway inhibitor.

A TGFβ signal transduction pathway inhibitor is not particularly limited as long as it inhibits the signal transduction pathway caused by TGFβ, and may be any of nucleic acid, protein, and low-molecular-weight organic compound. Examples of the inhibitor can include a substance that directly acts on TGFβ (e.g., protein, antibody, aptamer etc.), a substance that suppresses expression of a gene encoding TGFβ (e.g., antisense oligonucleotide, siRNA etc.), a substance that inhibits the binding of a TGFβ receptor and TGFβ, and a substance that inhibits a physiological activity caused by signal transduction by TGFβ receptor (e.g., TGF receptor inhibitor, Smad inhibitor etc.). A protein known as a TGFβ signal transduction pathway inhibitor, Lefty and the like can be mentioned. As a TGFβ signal transduction pathway inhibitor, a compound well known to those of ordinary skill in the art can be used and, specifically, SB431542 (4[4-(1,3-benzodioxol-5-yl)-5-(2-pyridinyl)-1H-imidazol-2-yl]benzamide), LY-364947 (4-[3-(2-pyridinyl)-1H-pyrazol-4-yl]-quinoline), SB-505124 (2-(5-benzo[1,3]dioxol-5-yl-2-tert-butyl-3H-imidazol-4-yl)-6-methylpyridine), A-83-01 (3-(6-methyl-2-pyridinyl)-N-phenyl-4-(4-quinolinyl)-1H-pyrazole-1-carbothioamide) and the like can be mentioned.

The Nodal/Activin signal transduction pathway inhibitor is not particularly limited as long as it inhibits a signal transduction pathway caused by Nodal or Activin, and may be any of nucleic acid, protein, and low-molecular-weight organic compound. Examples of the inhibitor can include a substance that directly acts on Nodal or Activin (e.g., antibody, aptamer etc.), a substance that suppresses expression of a gene encoding Nodal or Activin (e.g., antisense oligonucleotide, siRNA etc.), a substance that inhibits the binding of a Nodal/Activin receptor and Nodal/Activin, and a substance that inhibits a physiological activity caused by signal transduction by Nodal/Activin receptor. As a Nodal/Activin signal transduction pathway inhibitor, a compound well known to those of ordinary skill in the art can be used and, specifically, SB431542, A-83-01 and the like can be mentioned. Also, a protein (Lefty, Cerberus etc.) known as a Nodal/Activin signal transduction pathway inhibitor may be used. A Nodal/Activin signal transduction pathway inhibitor is preferably SB431542, A-83-01 or Lefty.

The BMP signal transduction pathway inhibitor is not particularly limited as long as it inhibits a signal transduction pathway caused by BMP, and those mentioned above can be used. As a BMP signal transduction pathway inhibitor, a compound well known to those of ordinary skill in the art can be used and, specifically, LDN193189 (4-[6-(4-(piperazin-1-yl)phenyl)pyrazolo[1,5-a]pyrimidin-3-yl]quinoline), Dorsomorphin and the like can be mentioned. Also, a protein (Chordin, Noggin etc.) known as a BMP signal transduction pathway inhibitor may be used. A BMP signal transduction pathway inhibitor is preferably LDN193189.

A TGFβ, family signal transduction pathway inhibitor is preferably Lefty, SB431542, A-83-01 or LDN193189.

Plural kinds of TGFβ, family signal transduction pathway inhibitors having different points of action may be used in combination. By combining them, the aggregate quality improving effect is expected to be enhanced. For example, a combination of a TGFβ, signal transduction pathway inhibitor and a BMP signal transduction pathway inhibitor, a combination of a TGFβ, signal transduction pathway inhibitor and a Nodal/Activin signal transduction pathway inhibitor, a combination of a BMP signal transduction pathway inhibitor and a Nodal/Activin signal transduction pathway inhibitor can be mentioned. Preferably, a TGFβ, signal transduction pathway inhibitor is used in combination with a BMP signal transduction pathway inhibitor. A specific preferable combination is, for example, a combination of SB431542 and LDN193189.

The SHH signal transduction pathway agonist is not particularly limited as long as it is a substance capable of enhancing signal transduction mediated by SHH (meaning Sonic hedgehog). For example, proteins belonging to the Hedgehog family (e.g., SHH, Ihh), SHH receptor, SHH receptor agonist, Purmorphamine (PMA), SAG (Smoothened Agonist; N-Methyl-N'-(3-pyridinylbenzyl)-N'-(3-chlorobenzo[b]thiophene-2-carbonyl)-1,4-diaminocyclohexane) and the like can be mentioned. The SHH signal transduction pathway agonist is preferably SAG. The SHH signal transduction pathway agonist is preferably SHH protein (Genbank accession Nos.: NM_000193, NP_000184), SAG or PMA.

A TGFβ, family signal transduction pathway inhibitor and a SHH signal transduction pathway agonist may be used in combination. As a specific combination, a combination of any TGFβ, family signal transduction pathway inhibitor selected from the group consisting of Lefty, 5B431542, A-83-01 and LDN193189, and any SHH signal transduction pathway agonist selected from the group consisting of SHH protein, SAG and PMA can be mentioned. When a TGFβ, family signal transduction pathway inhibitor and a SHH signal transduction pathway agonist are used in combination, cells may be cultured in a medium containing both a TGFβ, family signal transduction pathway inhibitor and a SHH signal transduction pathway agonist, or cells may be treated with either of a TGFβ, family signal transduction pathway inhibitor and a SHH signal transduction pathway agonist, and continuously treated with either or both of them.

The concentrations of the TGFβ, family signal transduction pathway inhibitor and the SHH signal transduction pathway agonist can be appropriately determined to fall within a range capable of affording the aforementioned effects. For example, SB431542 is generally used at a concentration of 0.1 μM-200 μM, preferably 2 μM-50 μM. A-83-01 is generally used at a concentration of 0.05 μM-50 μM, preferably 0.5 μM-5 μM. LDN193189 is generally used at a concentration of 1 nM-2000 nM, preferably 10 nM-300 nM. Lefty is generally used at a concentration of 5 ng/mL-200 ng/mL, preferably 10 ng/mL-50 ng/mL. SHH protein is generally used at a concentration of 20 ng/mL-1000 ng/mL, preferably 50 ng/mL-300 ng/mL. SAG is generally used at a concentration of 1 nM-2000 nM, preferably 10 nM-700 nM, more preferably 30-600 nM. PMA is generally used at a concentration of 0.002-20 μM, preferably 0.02 μM-2 μM.

In one embodiment, a TGFβ, family signal transduction pathway inhibitor can be appropriately used in an amount conferring TGFβ, family signal transduction pathway inhibiting activity equivalent to that of 5B431542 at the aforementioned concentration. In one embodiment, an SHH signal transduction pathway agonist can be appropriately used at a concentration providing SHH signal transduction pathway activating action equivalent to that of SAG at the aforementioned concentration.

A medium to be used in the first step may be a serum-containing medium or a serum-free medium. To avoid contamination with a chemically-undefined component, it is preferably a serum-free medium. To avoid contamination with a chemically-undefined component, a medium to be used for the first step may be a medium whose components are chemically-defined.

In the first step, the pluripotent stem cells may be cultured under any conditions of suspension culture and adhesion culture, preferably adhesion culture.

For culturing pluripotent stem cells under feeder-free conditions in the first step, an appropriate matrix may be used as a scaffold to provide a scaffold in stead of the feeder cells to the pluripotent stem cell. The pluripotent stem cells are subjected to adhesion culture in a cell container whose surface is coated with a matrix as a scaffold.

As a matrix available as a scaffold, laminin (Nat Biotechnol 28, 611-615 (2010)), laminin fragment (Nat Commun 3, 1236 (2012)), basement membrane preparation (Nat Biotechnol 19, 971-974 (2001)), gelatin, collagen, heparan sulfate proteoglycan, entactin, vitronectin and the like can be mentioned.

Preferably, in the culturing of pluripotent stem cells under feeder-free conditions in the first step, the pluripotent stem cells are cultured in an adhered state in a cell container with surface coated with isolated laminin 511 or E8 fragment of laminin 511 (more preferably, E8 fragment of laminin 511).

While the period for the culturing of pluripotent stem cells in the first step is not particularly limited as long as the effect of improving the quality of the aggregate formed in the second step can be achieved, it is generally 0.5-144 hr. The period for the culturing of the pluripotent stem cells in the first step is preferably not less than 1 hr, not less than 2 hr, not less than 6 hr, not less than 12 hr, not less than 18 hr, or not less than 24 hr. The period for the culturing of the pluripotent stem cells in the first step is preferably within 96 hr or within 72 hr. In one embodiment, the period for the culturing of pluripotent stem cells in the first step is preferably 2-96 hr, more preferably 6-48 hr, further preferably 12-48 hr, further more preferably 18-28 hr (e.g., 24 hr). That is, the first step is started 0.5-144 hr (preferably, 18-28 hr) before the start of the second step, and the second step is continuously performed on completion of the first step. In a further embodiment, the period for the culturing of pluripotent stem cells in the first step is preferably 18-144 hr, 24-144 hr, 24-96 hr, or 24-72 hr. When the cells are treated with either of a TGFβ family signal transduction pathway inhibitor and a SHH signal transduction pathway agonist, and continuously treated with the other, the treatment time of each can be set to fall within the range of the aforementioned period for the culturing.

The culture conditions such as culture temperature, and $CO_2$ concentration in the first step can be appropriately determined. The culture temperature is, for example, about 30° C. to about 40° C., preferably about 37° C. The $CO_2$ concentration is, for example, about 1% to about 10%, preferably about 5%.

In a preferable embodiment, the cells obtained in the first step maintain a pluripotent-like state, and the pluripotent-like state is maintained throughout the first step. The pluripotent-like state means a state maintaining at least a part of the characteristics unique to pluripotent stem cells and common to pluripotent stem cells, including pluripotency. The pluripotent-like state does not require strict pluripotency. Specifically, the state expressing all or a part of the markers to be an index of pluripotent state is included in the "pluripotent-like state". As the marker of the pluripotent-like state, Oct3/4-positive, alkaline phosphatase-positive and the like can be mentioned. In one embodiment, a cell maintaining the pluripotent-like state is Oct3/4-positive. It is included in a "cell showing a pluripotent-like state" even when the expression level of Nanog is low as compared to ES cell or iPS cell.

In one embodiment, the cells obtained in the first step are stem cells having a potency to differentiate into at least retinal tissue, retinal cell, retinal progenitor cell, or retinal layer-specific neuron.

In a preferable embodiment, human pluripotent stem cells (e.g., iPS cells) are cultured in an adhered state in the absence of feeder cells and in a serum-free medium containing a TGFβ, family signal transduction pathway inhibitor and/or an SHH signal transduction pathway agonist, and bFGF.

The above-mentioned adhesion culture is preferably performed in a cell container whose surface is coated with laminin 511 or E8 fragment of laminin 511. The TGFβ, family signal transduction pathway inhibitor is preferably a TGFβ, signal transduction pathway inhibitor (e.g., SB431542, A-83-01, Lefty), a Nodal/Activin signal transduction pathway inhibitor (e.g., Lefty, SB431542, A-83-01), a BMP signal transduction pathway inhibitor (e.g., LDN193189, Chordin, Noggin), or a combination thereof (e.g., SB431542 and LDN193189). The TGFβ, family signal transduction pathway inhibitor is more preferably Lefty, SB431542, A-83-01, or LDN193189, or a combination thereof (e.g., SB431542 and LDN193189). The SHH signal transduction pathway agonist is preferably SHH protein, SAG or Purmorphamine (PMA), more preferably SAG. A TGFβ, family signal transduction pathway inhibitor (e.g., Lefty, SB431542, A-83-01, LDN193189) and an SHH signal transduction pathway agonist (e.g., SHH protein, SAG, PMA) may be used in combination. The period for the culturing is 0.5-144 hr (preferably, 18-144 hr, 24-144 hr, 24-96 hr, or 24-72 hr (e.g., 18-28 hr)).

For example, human pluripotent stem cells (e.g., human iPS cells) are subjected to maintenance culture in the absence of feeder cells and in a serum-free medium containing bFGF. The maintenance culture is preferably performed by adhesion culture. The adhesion culture is preferably performed in a cell container whose surface is coated with vitronectin, laminin 511 or E8 fragment of laminin 511. Then, a TGFβ, family signal transduction pathway inhibitor and/or an SHH signal transduction pathway agonist are/is added to the culture, and the culturing is continued. The TGFβ, family signal transduction pathway inhibitor is preferably a TGFβ, signal transduction pathway inhibitor (e.g., SB431542, A-83-01, Lefty), a Nodal/Activin signal transduction pathway inhibitor (e.g., SB431542, A-83-01, Lefty), a BMP signal transduction pathway inhibitor (e.g., LDN193189), or a combination thereof (e.g., SB431542 and LDN193189). The TGFβ, family signal transduction pathway inhibitor is more preferably Lefty, SB431542, A-83-01, or LDN193189, or a combination thereof (e.g., SB431542 and LDN193189). The SHH signal transduction pathway agonist is preferably SHH protein, SAG or PMA. A TGFβ, family signal transduction pathway inhibitor (e.g., Lefty, SB431542, A-83-01, LDN193189) and an SHH signal transduction pathway agonist (e.g., SHH protein, SAG, PMA) may be used in combination. After the addition, the culturing is continued for 0.5-144 hr (preferably, 18-144 hr, 24-144 hr, 24-96 hr, or 24-72 hr (e.g., 18-28 hr)).

[Second Step]

The second step wherein the cells obtained in the first step are cultured in suspension in a medium to form a cell aggregate is explained.

The medium to be used in the second step may be a serum-containing medium or serum-free medium. To avoid contamination of chemically-undefined components, a serum-free medium is preferably used in the present invention. For example, a serum-free medium free of both a BMP signal transduction pathway agonist and a Wnt signal transduction pathway inhibitor can be used. To avoid complicated preparation, for example, a serum-free medium supplemented with an appropriate amount of a commercially available serum replacement such as KSR and so on (e.g., medium of 1:1 mixture of IMDM and F-12, which is supplemented with 10% KSR, 450 μM 1-monothioglycerol and 1× Chemically Defined Lipid Concentrate, or medium of GMEM supplemented with 5%-20% KSR, NEAA, pyruvic acid, 2-mercaptoethanol) is preferably used. The amount of KSR to be added to a serum-free medium in the case of human pluripotent stem cells is generally about 1% to about 30%, preferably about 2% to about 20%.

For formation of an aggregate, dispersed cells are first prepared by a dispersing operation of the cells obtained in the first step. The "dispersed cells" obtained by the dispersing operation refers to a state where, for example, not less than 70% of cells are single cells and not more than 30% of cells are clusters of 2-50 cells. Preferably, as the dispersed cells, a state where not less than 80% of cells are single cells, and not more than 20% of cells are clusters of 2-50 cells can be mentioned. The dispersed cells refer to a state almost free of mutual adhesion (e.g., plane attachment) of cells.

A dispersion operation of the cells obtained in the first step may contain the above-mentioned mechanical dispersion treatment, cell dispersion solution treatment, and cell protecting agent treatment. These treatments may be performed in combination. Preferably, a cell dispersion solution treatment is performed simultaneously with a cell protecting agent treatment and then a mechanical dispersion treatment is performed.

As a cell protecting agent to be used for the cell protecting agent treatment, a FGF signal transduction pathway agonist (e.g., fibroblast growth factor such as bFGF, FGF4, FGF8 and the like), heparin, an IGF signal transduction pathway agonist (e.g., insulin), serum, and serum replacement can be mentioned. As a cell protecting agent for suppressing cell death of pluripotent stem cells (particularly, human pluripotent stem cells) induced by dispersion, a Rho-associated coiled-coil kinase (ROCK) inhibitor or a Myosin inhibitor may be added. To suppress cell death of pluripotent stem cells (particularly, human pluripotent stem cells) induced by dispersion, and protect the cells, a ROCK inhibitor or a Myosin inhibitor may be added from the start of the second step culture. As a ROCK inhibitor, Y-27632, Fasudil (HA1077), H-1152 and the like can be mentioned. As a Myosin inhibitor, Blebbistatin can be mentioned.

As a cell dispersion solution to be used for the cell dispersion treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TRYPLE™ Select cell dispersion solution (manufactured by Life Technologies) and TRYPLE™ Express cell dispersion solution (manufactured by Life Technologies) can also be used.

As a method of mechanical dispersion treatment, a pipetting treatment or scraping by a scraper can be mentioned.

The dispersed cells are suspended in the above-mentioned medium.

Then, a suspension of the dispersed cells is seeded in the above-mentioned culture vessel, and the dispersed cells are cultured under a condition non-adhesive to the culture vessel, whereby plural cells are assembled to form an aggregate. In this case, plural cell aggregates may be simultaneously formed in one culture vessel by seeding the dispersed cells in a comparatively large culture vessel such as a 10 cm dish. However, the size of the aggregates varies in this case. Thus, for example, a given amount of dispersed stem cells are placed in each well of a multiwell plate (U-bottom, V-bottom) such as a 96-well plate, and static culture is performed, whereby the cells are rapidly aggregated to form one aggregate in each well. The aggregates are recovered from plural wells, whereby a population of uniformed aggregates can be obtained (e.g., SFEBq method).

The concentration of the cells in the second step can be appropriately set so that cell aggregates can be more uniformly and efficiently formed. For example, when human cells (e.g., cells obtained from human iPS cell in the first step) are cultured in suspension using a 96-well plate, a liquid prepared to achieve about $1 \times 10^3$ to about $1 \times 10^5$ cells, preferably about $3 \times 10^3$ to about $5 \times 10^4$ cells, more preferably about $4 \times 10^3$ to about $2 \times 10^4$ cells, further preferably about $4 \times 10^3$ to about $1.6 \times 10^4$ cells, further more preferably about $8 \times 10^3$ to about $1.2 \times 10^4$ cells, per well is added to the wells, and the plate is stood to form aggregates.

The culture conditions such as culture temperature, $CO_2$ concentration and so on in the second step can be appropriately determined. The culture temperature is, for example, about 30° C. to about 40° C., preferably about 37° C. The $CO_2$ concentration is, for example, about 1% to about 10%, preferably about 5%.

In the second step, when a medium exchange operation is performed, for example, an operation to add a fresh medium without discarding the existing medium (medium addition operation), an operation to discard about a half amount of the existing medium (about 30-900, for example, 40-60% of the volume of the existing medium) and add about a half amount of a fresh medium (30-90%, for example, about 40-60% of the volume of the existing medium) (half-medium exchange operation), and an operation to discard about the whole amount of the existing medium (not less than 90% of the amount of the existing medium) and add about the whole amount of a fresh medium (not less than 90% of the amount of the existing medium) (full-medium exchange operation) can be mentioned.

While the tool used for the medium exchange operation is not particularly limited, for example, pipetter, micropipette, multichannel micropipette, continuous dispenser, and the like can be mentioned. For example, when a 96 well plate is used as a culture vessel, a multi-channel micropipette may be used.

The period for suspension culture necessary for forming a cell aggregate can be determined as appropriate according to the cell to be used, so that the cells can be aggregated uniformly. To form uniformed cell aggregates, it is desirably as short as possible. The steps for the dispersed cells to form cell aggregates can be divided into a step for assembling cells, and a step for forming cell aggregates from the assembled cells. The period from the time point of seeding the dispersed cells (i.e., at the time of the start of suspension culture) to assembling of the cells, for example, in case of human cells (e.g., stem cells obtained from human iPS cells in the first step), the assembled cells are formed preferably within about 24 hr, more preferably within about 12 hr. The period from the time point of seeding the dispersed cells (i.e., at the time of the start of suspension culture) to form an aggregate in case of human pluripotent stem cells (e.g., human iPS cells) is, for example, preferably within about 72 hr, more preferably within about 48 hr. The period for cell aggregate formation can be appropriately adjusted by controlling the tools for aggregating the cells, centrifugation conditions and so on.

Formation of cell aggregates and uniformity thereof can be determined based on the size and cell number of the aggregates, macroscopic morphology, microscopic morphology by tissue staining analysis and uniformity thereof, expression of differentiation- and undifferentiation-markers and uniformity thereof, control of expression of differentiation marker and synchrony thereof, reproducibility of differentiation efficiency between the aggregates, and so on.

After aggregate formation, the aggregate may be continuously cultured as it is. The period of the suspension culture in the second step may generally be continued until a BMP signal transduction pathway agonist is added. Specifically, it is generally continued for 12 hr-6 days, preferably about 12 hr-3 days.

As one embodiment of the medium to be used in the second step, a medium containing an SHH signal transduction pathway agonist (see WO 2016/063985), a medium containing a Wnt signal transduction pathway inhibitor, or a medium containing a Wnt signal transduction pathway inhibitor and an SHH signal transduction pathway agonist (see WO 2017/183732) can be mentioned. In the first step, pluripotent stem cells are treated with a TGFβ, family signal transduction pathway inhibitor and/or a SHH signal transduction pathway agonist; and in the second step, the cells obtained in the first step are cultured in suspension in a medium (preferably serum-free medium) containing a SHH signal transduction pathway agonist and/or Wnt signal transduction pathway inhibitor to form aggregates, which results in further quality improvement of the aggregate and enhancement of its differentiation potency into retinal tissue. Using this high quality aggregate, an aggregate containing retinal progenitor cell or neural retinal progenitor cell can be induced with high efficiency.

As the SHH signal transduction pathway agonist, those mentioned above can be used. Preferably, the SHH signal transduction pathway agonist is SHH protein, SAG or PMA. The concentration of the SHH signal transduction pathway agonist in the medium can be appropriately determined to fall within a range capable of achieving the aforementioned effects. SAG is generally used at a concentration of 1 nM-2000 nM, preferably 10 nM-700 nM, more preferably 30 nM-600 nM. PMA is generally used at a concentration of 0.002 μM-20 μM, preferably 0.02 μM-2 μM. SHH protein is generally used at a concentration of 20 ng/ml-1000 ng/ml, preferably 50 ng/ml-300 ng/ml. When a SHH signal transduction pathway agonist other than SAG, PMA, and SHH protein is used, it is desirably used at a concentration affording an SHH signal transduction pathway activating action which is equivalent to the above-mentioned concentration of SAG.

The concentration of the SHH signal transduction pathway agonist in the medium may be varied during the period of the second step. For example, the SHH signal transduction pathway agonist is provided to fall within the above-mentioned range of a concentration at the time of the start of the second step, and the concentration may be gradually or stepwisely decreased at a ratio of 40-60% per 2-4 days.

The timing of addition of a SHH signal transduction pathway agonist to the medium is not particularly limited as long as the above-mentioned effects can be afforded, but a higher effect can be obtained when it is added earlier. A SHH signal transduction pathway agonist is added to the medium generally within 6 days, preferably within 3 days, more preferably within 1 day, from the start of the second step, and further preferably at the time of the start of the second step.

The Wnt signal transduction pathway inhibitor is not particularly limited as long as it can suppress signal transduction mediated by Wnt. For example, a substance that directly acts on Wnt or Wnt receptor (anti-Wnt neutralizing antibody, anti-Wnt receptor neutralizing antibody etc.), a substance that suppresses expression of gene encoding Wnt or Wnt receptor (e.g., antisense oligonucleotide, siRNA etc.), a substance that inhibits binding of Wnt receptor and Wnt (soluble Wnt receptor, dominant-negative Wnt receptor etc., Wnt antagonist, Dkk1, Cerberus protein etc.), a substance that inhibits physiological activity caused by signal transduction by Wnt receptor [low-molecular-weight compounds such as CKI-7 (N-(2-aminoethyl)-5-chloroisoquinoline-8-sulfonamide), D4476 (4-[4-(2,3-dihydro-1,4-benzodioxin-6-yl)-5-(2-pyridinyl)-1H-imidazol-2-yl]benzamide), IWR-1-endo (IWR1e) (4-[(3aR,4S,7R,7aS)-1,3,3a,4,7,7a-hexahydro-1,3-dioxo-4,7-methano-2H-isoindol-2-yl]-N-8-quinolinyl-benzamide), and IWP-2 (N-(6-methyl-2-benzothiazolyl)-2-[(3,4,6,7-tetrahydro-4-oxo-3-phenylthieno[3,2-d]pyrimidin-2-yl)thio]acetamide) and the like, and the like] and the like can be mentioned. As a preferred Wnt signal transduction pathway inhibitor, IWR1e is used.

The concentration of the Wnt signal transduction pathway inhibitor in the medium can be appropriately determined to fall within a range capable of achieving the aforementioned effects. IWR1e is added to a medium such that the concentration is about 0.1 µM to about 100 µM, preferably about 0.3 µM to about 30 µM, more preferably about 1 µM to about 10 µM, further preferably about 3 µM. When a Wnt signal transduction pathway inhibitor other than IWR-1-endo is used, it is desirably used at a concentration exhibiting a Wnt signal transduction pathway inhibiting activity equivalent to that of IWR-1-endo at the above-mentioned concentration.

The concentration of the Wnt signal transduction pathway inhibitor in the medium may be varied during the period of the second step. For example, the Wnt signal transduction pathway inhibitor is provided to fall within the above-mentioned range of a concentration at the time of the start of the second step, and the concentration may be gradually or stepwisely decreased at a ratio of 40-60% per 2-4 days.

The timing of addition of a Wnt signal transduction pathway inhibitor to the medium is not particularly limited as long as the above-mentioned effect can be achieved; however, a high effect is achieved when it is added earlier. Wnt signal transduction pathway inhibitor is added to the medium generally within 6 days, preferably within 3 days, more preferably within 1 day, more preferably within 12 hours, from the start of the suspension culture in the second step, and further preferably at the time of the start of the suspension culture in the second step. Specifically, for example, it is possible to add a basal medium to which a Wnt signal transduction pathway inhibitor is added, or exchange a part or the whole of the medium with the basic medium. While the period during which the cells obtained in the first step are treated with the Wnt signal transduction pathway inhibitor in the second step is not particularly limited as long as the above-mentioned effect can be achieved, preferably, the inhibitor is added to the medium when the suspension culture is started in the second step and acted until the end of the second step. Furthermore, the cells can be continuously exposed to the Wnt signal transduction pathway inhibitor even after completion of the second step (that is, during the period of the third step). In one embodiment, the Wnt signal transduction pathway inhibitor may be allowed to continuously act even after completion of the second step (that is, during the period of the third step) until a neuroepithelial tissue and/or a neural tissue is/are formed.

In a preferable embodiment, the human cells obtained in the first step (e.g., cells obtained from human iPS cells in the first step) are subjected to suspension culture in a serum-free medium containing a SHH signal transduction pathway agonist (e.g., SAG, PMA, SHH protein) and/or Wnt signal transduction pathway inhibitor (e.g., IWR1e) to form aggregates. A SHH signal transduction pathway agonist is preferably contained in the medium from the time of the start of suspension culture. A ROCK inhibitor (e.g., Y-27632) may also be added to the medium. The period for the culturing is 12 hr-6 days, preferably 12 hr-3 days. The aggregates formed are preferably uniformed aggregates.

For example, the human cells obtained in the first step (e.g., cells obtained from human iPS cells in the first step) are recovered, dispersed into single cells or a state close thereto in a serum-free medium containing a SHH signal transduction pathway agonist (e.g., SAG, PMA) and/or Wnt signal transduction pathway inhibitor (e.g., IWR1e), and subjected to suspension culture. The serum-free medium may contain a ROCK inhibitor (e.g., Y-27632). A suspension of human stem cells (e.g., stem cells derived from human iPS cells) is seeded in the above-mentioned culture vessel and the dispersed cells are cultured under conditions where they are non-adhesive to the culture vessel, whereby plural cells are assembled to form an aggregate. The period for the culturing is 12 hr-6 days (preferably 12 hr-3 days). The aggregates formed are preferably uniformed aggregates.

By performing the second step in this manner, aggregates of the cells obtained in the first step, or the cells derived therefrom can be formed. The aggregate obtained in the second step have higher quality than the one formed by a treatment without a TGFβ family signal transduction pathway inhibitor and/or a SHH signal transduction pathway agonist is not performed in the first step. To be specific, a population of spherical cell aggregates having a smooth surface and a dense inside, and having a high ratio of uncollapsed aggregates can be obtained. In one embodiment, when aggregates (e.g., not less than 100 aggregates) are randomly selected on day 6 from the start of the second step, the ratio of non-cystic aggregates is, for example, not less than 70%, preferably not less than 80%.

The aggregate obtained in the second step has a potency to differentiate into a retinal tissue.

In one preferable embodiment, in the first step, pluripotent stem cells are treated with a TGFβ signal transduction pathway inhibitor, and in the second step, the cells obtained in the first step are subjected to suspension culture in a medium containing a SHH signal transduction pathway agonist (e.g., SAG, PMA, SHH protein) and/or Wnt signal transduction pathway inhibitor (e.g., IWR1e). Preferably, 5B431542 or A-83-01 may be used here as a TGFβ signal transduction pathway inhibitor.

In one preferable embodiment, in the first step, pluripotent stem cells are treated with a BMP signal transduction pathway inhibitor, and in the second step, the cells obtained in the first step are subjected to suspension culture in a medium free of a SHH signal transduction pathway agonist (e.g., SAG, PMA, SHH protein). Preferably, LDN193189 may be used here as a BMP signal transduction pathway inhibitor.

In one preferable embodiment, in the first step, pluripotent stem cells (e.g., human pluripotent stem cell) are treated with a TGFβ family signal transduction pathway inhibitor (e.g., a TGFβ signal transduction pathway inhibitor (e.g., Lefty, SB431542, A-83-01), a Nodal/Activin signal transduction pathway inhibitor (e.g., Lefty, SB431542, A-83-01), a BMP signal transduction pathway inhibitor (e.g., LDN193189), or a combination thereof (e.g., SB431542 and LDN193189) etc.); a SHH signal transduction pathway agonist (e.g., SHH protein, SAG, PMA); or a combination of a TGFβ family signal transduction pathway inhibitor (e.g., Lefty, 5B431542, A-83-01, LDN193189) and an SHH signal transduction pathway agonist (e.g., SHH protein, SAG, PMA) and, in the second step, suspension culture of the cells obtained in the first step is performed in a medium containing an SHH signal transduction pathway agonist (e.g., SAG, PMA, SHH protein).

In another embodiment, in the first step, pluripotent stem cells (e.g., human pluripotent stem cells) are treated with a TGFβ family signal transduction pathway inhibitor (e.g., a TGFβ signal transduction pathway inhibitor (e.g., a Lefty, 5B431542, A-83-01), a Nodal/Activin signal transduction pathway inhibitor (e.g., Lefty, 5B431542, A-83-01), a BMP signal transduction pathway inhibitor (e.g., LDN193189), or a combination thereof (e.g., 5B431542 and LDN193189) etc.); a SHH signal transduction pathway agonist (e.g., SHH protein, SAG, PMA); or a combination of a TGFβ family signal transduction pathway inhibitor (e.g., Lefty, 5B431542, A-83-01, LDN193189) and an SHH signal transduction pathway agonist (e.g., SHH protein, SAG, PMA) and, in the second step, suspension culture of the cells obtained in the first step is performed in a medium free of a SHH signal transduction pathway agonist (e.g., SAG, PMA, SHH protein).

In any embodiment, the medium in the second step preferably contains a ROCK inhibitor (e.g., Y-27632).

[Third Step]

The aggregate obtained in the second step is cultured in suspension in the presence of a BMP signal transduction pathway agonist, whereby an aggregate containing a retinal progenitor cell or a neural retinal progenitor cell can be obtained. In this step, production can be performed according to the second step of the aforementioned starting material production method 1.

In one embodiment, when the concentration of the SHH signal transduction pathway agonist added to the medium in the second step is comparatively low (e.g., not more than 700 nM for SAG, and a concentration conferring SHH signal transduction pathway activating action equivalent to or lower than that of SAG at the above-mentioned concentration, for other SHH signal transduction pathway agonists), medium exchange is not necessary, and a BMP signal transduction pathway agonist (e.g., BMP4) may be added to the medium used in the second step. On the other hand, when the concentration of the SHH signal transduction pathway agonist is comparatively high (e.g., exceeding 700 nM or not less than 1000 nM for SAG, and a concentration conferring a SHH signal transduction pathway activating action equivalent to that of SAG at the above-mentioned concentration, for other SHH signal transduction pathway agonists), it is desirable to exchange the medium with a fresh medium containing a BMP signal transduction pathway agonist (e.g., BMP4) to suppress an influence of the SHH signal transduction pathway agonist remaining when a BMP signal transduction pathway agonist is added.

In a preferable embodiment, the concentration of a SHH signal transduction pathway agonist in the medium to be used in the third step is, when calculated in terms of SHH signal transduction promoting activity of SAG, not more than 700 nM, preferably not more than 300 nM, more preferably not more than 10 nM, further preferably not more than 0.1 nM. Further preferably, it is free of a SHH signal transduction pathway agonist. The medium "free of a SHH signal transduction pathway agonist" also includes a medium substantially free of a SHH signal transduction pathway agonist, for example, a medium free of a SHH signal transduction pathway agonist at a concentration imparting an adverse influence on selective differentiation into a retinal progenitor cell or a retinal tissue. The medium "free of a SHH signal transduction pathway agonist" also includes a medium substantially not supplemented with a SHH signal transduction pathway agonist, for example, a medium not supplemented with a SHH signal transduction pathway agonist at a concentration imparting an adverse influence on selective differentiation into a retinal progenitor cell or a retinal tissue.

In a preferable embodiment of the production of a retinal tissue in the initial developmental stage, in the first step, human pluripotent stem cells (e.g., human iPS cells) are cultured in an adhered state in the absence of feeder cells in a serum-free medium containing a TGFβ, signal transduction pathway inhibitor (e.g., 5B431542, A-83-01) and bFGF; in the second step, the cells are cultured in suspension in a serum-free medium containing a SHH signal transduction pathway agonist (e.g., SAG, PMA, SHH protein); and in the third step, the aggregate is cultured in suspension in a serum-free medium containing a BMP signal transduction pathway agonist (e.g., BMP4).

In addition, in a preferable embodiment of the production of a retinal tissue in the initial developmental stage, in the first step, human pluripotent stem cells (e.g., human iPS cells) are cultured in an adhered state in the absence of feeder cells in a serum-free medium containing a BMP signal transduction pathway inhibitor (e.g., LDN193189) and bFGF; in the second step, the cells are cultured in suspension in a serum-free medium free of or containing a SHH signal transduction pathway agonist (e.g., SAG, PMA); and in the third step, the aggregate is cultured in suspension in a serum-free medium containing a BMP signal transduction pathway agonist (e.g., BMP4).

In a preferable embodiment of the production of a retinal tissue in the initial developmental stage, in the first step, human pluripotent stem cells (e.g., human iPS cells) are cultured in an adhered state in the absence of feeder cells in a serum-free medium containing a SHH signal transduction pathway agonist (e.g., SAG, PMA) and bFGF for preferably not less than 1 day and not more than 6 days, further preferably 2-4 days, in the second step, the cells are cultured in suspension in a serum-free medium containing a SHH signal transduction pathway agonist (e.g., SAG, PMA), and in the third step, the aggregates are cultured in suspension in a serum-free medium containing a BMP signal transduction pathway agonist (e.g., BMP4).

In a preferable embodiment of the production of a retinal tissue in the initial developmental stage, in the first step, human pluripotent stem cells (e.g., human iPS cells) are cultured in an adhered state in the absence of feeder cells in a serum-free medium containing
  a TGFβ family signal transduction pathway inhibitor
    (e.g., a TGFβ signal transduction pathway inhibitor (e.g., Lefty, SB431542, A-83-01), a Nodal/Activin signal transduction pathway inhibitor (e.g., Lefty, SB431542, A-83-01), a BMP signal transduction pathway inhibitor (e.g., LDN193189), or a combination thereof (e.g., SB431542 and LDN193189) etc.);
a SHH signal transduction pathway agonist (e.g., SHH protein, SAG, PMA); or
a combination of a TGFβ family signal transduction pathway inhibitor (e.g., Lefty, 5B431542, A-83-01, LDN193189) and a SHH signal transduction pathway agonist (e.g., SHH protein, SAG, PMA); and
bFGF,
in the second step, the cells obtained the first step are cultured in suspension in a serum-free medium containing a SHH signal transduction pathway agonist (e.g., SAG, PMA, SHH protein) to form a cell aggregate, and
in the third step, the aggregate is cultured in suspension in a serum-free medium containing a BMP signal transduction pathway agonist (e.g., BMP4) to give an aggregate containing a retinal progenitor cell or a neural retinal progenitor cell.

2-3. Starting Material Production Method 3

As one preferable embodiment of production of retinal tissue in an initial developmental stage, the method described in WO 2016/063986 and containing the following steps can also be mentioned:

(1) a first step of culturing pluripotent stem cells in the absence of feeder cells and in a medium containing a factor for maintaining undifferentiated state,
(2) a second step of culturing the pluripotent stem cells obtained in the first step in suspension in the presence of a SHH signal transduction pathway agonist to form a cell aggregate, and
(3) a third step of culturing the aggregate obtained in the second step in suspension in the presence of a BMP signal transduction pathway agonist to obtain an aggregate containing a retinal progenitor cell or neural retinal progenitor cell.

[First Step]

The first step can be performed according to the method described in WO 2016/063986. That is, in the first step, human pluripotent stem cells, preferably human induced pluripotent stem cells (iPS cells) or human embryonic stem cells (ES cell) are cultured in the absence of feeder cells and in a medium containing a factor for maintaining undifferentiated state. The absence of feeder cells (feeder-free) in the first step means a condition substantially free of feeder cells (e.g., the ratio of the number of feeder cells relative to the total number of cells is not more than 3%). Preferably, the first step is performed under a condition free of feeder cells.

The medium to be used in the first step is not particularly limited as long as it is a medium enabling culturing of pluripotent stem cells to maintain undifferentiated state under feeder-free conditions (feeder-free medium). Preferably, to enable culturing to maintain undifferentiated state, it contains a factor for maintaining undifferentiated state. For example, it is a medium containing a factor for maintaining undifferentiated state, and free of a TGFβ family signal transduction pathway inhibitor and an SHH signal transduction pathway agonist.

As the factor for maintaining undifferentiated state and feeder-free medium, those described in the aforementioned starting material production method 2 can be mentioned.

While the period for the culturing of pluripotent stem cells in the first step is not particularly limited as long as the effect of improving the quality of the aggregate formed in the second step can be achieved, it is generally 0.5-144 hr, preferably 2-96 hr, more preferably 6-48 hr, further preferably 12-48 hr, further more preferably 18-28 hr (e.g., 24 hr). That is, the first step is started 0.5-144 hr (preferably, 18-28 hr) before the start of the second step, and the second step is continuously performed on completion of the first step.

In the first step, the medium may be exchanged as appropriate, and one embodiment specifically includes a method including medium exchange every 1-2 days. Here, for example, the medium may be exchanged with a medium free of the cell protecting agent or an agent suppressing cell death such as ROCK inhibitor and the like.

The culture conditions such as culture temperature, $CO_2$ concentration and so on in the first step can be appropriately determined. The culture temperature is, for example, about 30° C. to about 40° C., preferably about 37° C. The $CO_2$ concentration is, for example, about 1% to about 10%, preferably about 5%.

In one preferable embodiment, human pluripotent stem cells (e.g., human iPS cells) are cultured in an adhered state in the absence of feeder cells and in a serum-free medium containing bFGF. The adhesion culture is preferably performed in a cell container with surface coated with laminin 511, E8 fragment of laminin 511 or vitronectin. The adhesion culture is preferably performed using Essential 8, TeSR medium, mTeSR medium, mTeSR-E8 medium, or StemFit medium, more preferably Essential 8 or StemFit medium, as a feeder-free medium.

[Second Step]

The second step in which the pluripotent stem cells obtained in the first step are cultured in suspension in the presence of a SHH signal transduction pathway agonist to form a cell aggregate of pluripotent stem cells may be performed according to the method described in the second step of the above-mentioned starting material production method 2.

[Third Step]

The third step can be performed according to the second step of the aforementioned starting material production method 1, or the third step of the aforementioned starting material production method 2.

2-4. Starting Material Production Method 4

As one preferable embodiment of production of a retinal tissue in an initial developmental stage, the method described in WO 2013/077425 and including the following steps can also be mentioned:

(1) a first step of forming an aggregate of pluripotent stem cells by culturing pluripotent stem cells in suspension in a serum-free medium containing a Wnt signal transduction pathway inhibitor, and
(2) a second step of obtaining an aggregate containing a retinal progenitor cell or a neural retinal progenitor cell by culturing in suspension the aggregate formed in the first step in a serum-free medium containing a basement membrane preparation.

The starting material production method 4 can be performed according to the description of WO 2013/077425 (& US2014/341864).

[First Step]

As the Wnt signal transduction pathway inhibitor, those mentioned above can be mentioned.

The concentration of the Wnt signal transduction pathway inhibitor used here may be any as long as it is a concentration at which an aggregate of pluripotent stem cells can be formed. For example, in the case of general Wnt signal transduction pathway inhibitors such as IWR1e and the like, the concentration is 0.1 μM-100 μM, preferably 1 μM-10 μM, more preferably about 3 μM.

A Wnt signal transduction pathway inhibitor may be added to a serum-free medium before the start of the suspension culture, or may be added to a serum-free medium within several days (e.g., within 5 days) after the start of the suspension culture. Preferably, a Wnt signal transduction pathway inhibitor is added to a serum-free medium within 5 days, more preferably 3 days, after the start of the suspension culture, most preferably simultaneously with the start of the suspension culture. The suspension culture is performed until 18 days, more preferably 12 days, after the start of the suspension culture with addition of a Wnt signal transduction pathway inhibitor.

Culture conditions such as culture temperature, $CO_2$ concentration and the like can be appropriately set. The culture temperature is not particularly limited and it is, for example, about 30° C.-about 40° C., preferably about 37° C. The $CO_2$ concentration is, for example, about 1%-about 10%, preferably about 5%.

The concentration of the pluripotent stem cells can be appropriately determined by those of ordinary skill in the art so that aggregates of pluripotent stem cells can be more uniformly and efficiently formed. The concentration of the pluripotent stem cells during formation of the aggregate is not particularly limited as long as it is a concentration at which a uniform aggregate of stem cells can be formed. For example, when human ES cells are cultured in suspension using a 96-well plate, a liquid prepared to achieve about $1\times10^3$ to about $5\times10^4$ cells, preferably about $3\times10^3$ to about $3\times10^4$ cells, more preferably about $5\times10^3$ to about $2\times10^4$ cells, most preferably about $9\times10^3$, per well is added, and the plate is stood to form aggregates.

The period for suspension culture necessary for forming an aggregate can be determined as appropriate according to the pluripotent stem cell to be used as long as the cells can be rapidly aggregated. To form uniformed cell aggregates, it is desirably as short as possible (e.g., SFEBq method). For example, in the case of a human ES cell or human iPS cell, it is desirable to form an aggregate preferably within 24 hr, more preferably within 12 hr. The period for cell aggregate formation can be appropriately adjusted by those of ordinary skill in the art by controlling the tools for aggregating the cells, centrifugation conditions and so on.

Formation of aggregates of pluripotent stem cells can be determined by those of ordinary skill in the art based on the size of the aggregate and the number of cells therein, macroscopic morphology, microscopic morphology by tissue staining analysis and uniformity thereof, expression of differentiation and undifferentiation markers and uniformity thereof, control of expression of differentiation marker and synchrony thereof, reproducibility of differentiation efficiency between aggregates, and so on.

[Second Step]

The second step to obtain an aggregate containing a retinal progenitor cell or a neural retinal progenitor cell by culturing the aggregate formed in the first step in suspension in a serum-free medium containing a basement membrane preparation is explained.

The "basement membrane preparation" refers to one containing basement membrane-constituting components having a function to control cell morphology, differentiation, growth, motility, expression of function and so on which are similar to those of epithelial cell, when intended cells capable of forming a basement membrane are plated thereon and cultured. Here, the "basement membrane constituting components" refers to extracellular matrix molecules in the form of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of a preferable basement membrane preparation include products commercially available as basement membrane component (e.g., Matrigel (hereinafter sometimes referred to as Matrigel)), and extracellular matrix molecules known as basement membrane components (e.g., laminin, type IV collagen, heparan sulfate proteoglycan, entactin and so on).

Matrigel is a basement membrane preparation derived from Engelbreth Holm Swarn (EHS) mouse sarcoma. The main component of Matrigel is laminin, type IV collagen, heparan sulfate proteoglycan, and entactin. In addition to these, TGF-β, fibroblast growth factor (FGF), tissue plasminogen activator, and a growth factor naturally produced by EHS tumor are contained. The "growth factor reduced product" of Matrigel has a lower growth factor concentration than common Matrigel, and the standard concentration thereof is <0.5 ng/ml for EGF, <0.2 ng/ml for NGF, <5 pg/ml for PDGF, 5 ng/ml for IGF1, and 1.7 ng/ml for TGF-β. In starting material production method 4, "growth factor reduced product" is preferably used.

The concentration of the basement membrane preparation added to the serum-free medium in the suspension culture in the second step is not particularly limited as long as the epithelial structure of neural tissue (e.g., retinal tissue) is stably maintained. For example, when Martigel is used, it is preferably a volume of 1/20 to 1/200, more preferably about 1/100, of the culture medium. The basement membrane preparation may already be added to the medium at the start of culturing an aggregate of pluripotent stem cells. Preferably, it is added to the serum-free medium within 5 days, more preferably within 2 days, after the start of suspension culture.

The serum-free medium used in the second step may be the serum-free medium used in the first step as it is or may be that exchanged with a new serum-free medium.

When the serum-free medium used in the first step is directly used in this step, the "basement membrane preparation" may be added to the medium.

The serum-free medium used for the suspension culture in the first step and the second step is not particularly limited as long as it is as mentioned above. However, to avoid complicated preparation, for example, a serum-free medium (GMEM or DMEM, 0.1 mM 2-mercaptoethanol, 0.1 mM non-essential amino acid Mix, 1 mM sodium pyruvate) supplemented with an appropriate amount of commercially available KSR is preferably used as such serum-free medium. The dose of KSR in the serum-free medium is not particularly limited and, for example, it is generally 1-20%, preferably 2-20%, in the case of a human ES cell.

The culture conditions such as culture temperature, $CO_2$ concentration and so on in the second step can be appropriately determined. While the culture temperature is not particularly limited, it is, for example, about 30° C. to about 40° C., preferably about 37° C. The $CO_2$ concentration is, for example, about 1% to about 10%, preferably about 5%.

The aggregate obtained in the second step can be used as a retinal tissue in an initial developmental stage. To increase the content of a retinal progenitor cell or neural retinal progenitor cell contained therein, after suspension culture in a serum-free medium containing a basement membrane preparation, the following third step can be performed, and the obtained aggregate can also be used as a retinal tissue in an initial developmental stage:

(3) the third step of culturing the aggregate cultured in the second step in suspension in a serum-containing medium.

The serum-containing medium used in the third step may be the serum-free medium used in the second step for culture to which a serum is directly added or may be exchanged with a new serum-containing medium.

The serum added to the medium in the third step may be, for example, mammalian serum such as bovine serum, calf serum, fetal bovine serum, equine serum, foal serum, fetal equine serum, rabbit serum, baby rabbit serum, fetal rabbit serum, human serum and the like, and the like.

The serum is added on day 7 or later, more preferably on day 9 or later, most preferably on day 12, from the start of suspension culture (i.e., the first step). The serum concentration is 1-30%, preferably 3-20%, more preferably about 10%.

The serum-containing medium used in the third step is not particularly limited as long as it is as described above. The aforementioned serum-free medium (GMEM or DMEM, 0.1 mM 2-mercaptoethanol, 0.1 mM non-essential amino acid Mix, 1 mM sodium pyruvate) supplemented with serum is preferably used.

In addition, an appropriate amount of a commercially available serum replacement such as KSR and the like may be added to the serum-containing medium and used.

In the third step, the production efficiency of the retinal tissue in an initial developmental stage can be increased by adding an SHH signal transduction pathway agonist in addition to the serum.

The SHH signal transduction pathway agonist is not particularly limited as long as it can enhance signal transduction mediated by SHH, and includes those described above.

The concentration of the SHH signal transduction pathway agonist used in this step is, for example, 0.1 nM-10 µM, preferably 10 nM-1 µM, more preferably about 100 nM, in the case of general SHH signal transduction pathway agonists such as SAG and the like.

The thus-obtained aggregate can also be used as a retinal tissue in an initial developmental stage.

In one preferable embodiment of production of a retinal tissue in an initial developmental stage, after performing the aforementioned third step, the following fourth step can be performed, and the obtained optic cup-like structure can also be used as a retinal tissue in an initial developmental stage:

(4) the fourth step of culturing the aggregate cultured in the third step in suspension in a serum-free medium or serum-containing medium containing an SHH signal transduction pathway agonist and a Wnt signal transduction pathway agonist.

The SHH signal transduction pathway agonist is not particularly limited as long as it can enhance signal transduction mediated by SHH, and includes those described above.

The concentration of the SHH signal transduction pathway agonist used here is, for example, 0.1 nM-10 µM, preferably 10 nM-1 µM, more preferably about 100 nM, in the case of general SHH signal transduction pathway agonists such as SAG and the like.

The Wnt signal transduction pathway agonist is not particularly limited as long as it can enhance signal transduction mediated by Wnt and includes, for example, proteins belonging to the Wnt family (e.g., Wnt1, Wnt3A, Wnt7A, Wnt2B), Wnt receptor, Wnt receptor agonist, anti-Wnt receptor antibody, Wnt partial peptide, β catenin signal transmitter, GSK3β inhibitor (e.g., 6-Bromoindirubin-3'-oxime (BIO), CHIR99021 (6-[[2-[[4-(2,4-dichlorophenyl)-5-(5-methyl-1H-imidazol-2-yl)-2-pyrimidinyl]amino]ethyl]amino]-3-pyridincarbonitrile), Kenpaullone) and the like.

The concentration of the Wnt signal transduction pathway agonist used here is, for example, 0.1 µM-100 µM, preferably 1 µM-30 µM, more preferably about 3 µM, in the case of general Wnt signal transduction pathway agonists such as CHIR99021 and the like.

The SHH signal transduction pathway agonist and the Wnt signal transduction pathway agonist are added on day 12 or later and until day 25, preferably on day 15 and up to day 18, after the start of suspension culture (start of the first step). At this time, it is preferable to use a medium that does not contain a Wnt signal transduction pathway inhibitor added in the aggregate formation step.

On day 18 or later from the start of suspension culture, an optic cup-like structure is formed in a protuberance state from the inside of the aggregate. The optic cup-like structure produced by the above-mentioned fourth step can also be used as a retinal tissue in an initial developmental stage which is used as a starting material in the method of the present invention.

The aggregate obtained in the above-mentioned fourth step is subjected to suspension culture in a serum-free medium or serum-containing medium not containing an SHH signal transduction pathway agonist or a Wnt signal transduction pathway agonist for 1 to 20 days, and can also be used as a retinal tissue in an initial developmental stage which is used as a starting material in the methods of the present invention. Neural tissues other than the retinal tissue may be simultaneously formed by the present starting material production method. These may express a Wnt signal transduction pathway agonist and the like which are dorsalization signal transmitters. For this reason, preferably, to eliminate the influence of the Wnt signal transduction pathway agonist that is an excessive dorsalization signal transmitter and the like, the optic cup-like structure present on the surface of the aggregate can also be physically cut out from the aggregate by using tweezers, scissors, injection needle, razor, one analogous thereto and the like.

2-5. Starting Material Production Method 5

The retinal tissue in an initial developmental stage may contain a ciliary marginal zone structure, and a retinal tissue in an initial developmental stage containing a ciliary marginal zone structure can be produced by the method described in WO 2015/087614 (& US2016/376554).

To be specific, a cell aggregate containing a retinal tissue in which Chx10-positive cells are present in a proportion of 20% or more and 100% or less of the retinal tissue [for example, in the production methods of the starting material production methods 1-4, a cell aggregate corresponding to about day 9-60, preferably day 9-40 from the start of suspension culture, further preferably about day 15-20, for example, day 18, from the start of suspension culture], and obtained by a step of culturing a cell aggregate in a serum-free medium or serum-containing medium each containing a Wnt signal transduction pathway agonist and a FGF signal transduction pathway inhibitor for only a period before the emergence of a RPE65 gene-expressing cell, or an aggregate containing a ciliary marginal zone-like structure which is obtained by a step of further culturing the obtained "cell aggregate in which a RPE65 gene-expressing cell has not emerged" in a serum-free medium or a serum-containing medium not containing a Wnt signal transduction pathway agonist can also be used as a retinal tissue in an initial developmental stage which is used as a starting material in the methods of the present invention.

Specifically, for example, an aggregate containing a ciliary marginal zone structure, which is prepared by the following method, is also included in the retinal tissue in an initial developmental stage:

(1) a method for producing an aggregate containing a ciliary marginal zone-like structure, which includes a step of culturing a cell aggregate containing a retinal tissue in which Chx10-positive cells are present in a proportion of 20% or more and 100% or less of the retinal tissue in a serum-free medium or serum-containing medium each containing a Wnt signal transduction pathway agonist and an FGF signal transduction pathway inhibitor for only a period before the emergence of a RPE65 gene-expressing cell, after which culturing the obtained "cell aggregate in which a RPE65 gene-expressing cell has not emerged" in a serum-free medium or serum-containing medium each not containing a Wnt signal transduction pathway agonist.

A "cell aggregate containing a retinal tissue in which Chx10-positive cells are present in a proportion of 20% or more and 100% or less of the retinal tissue" can be obtained by the method described in the aforementioned starting material production methods 1-4. That is, the cell aggregate is an aggregate containing a retinal tissue in an initial developmental stage. For example, a retinal tissue in an initial developmental stage, namely, "a cell aggregate containing a retinal tissue in which Chx10-positive cells are present in a proportion of 20% or more and 100% or less of the retinal tissue" can be obtained by culturing for 6-15 days in the presence of a BMP signal transduction pathway agonist such as BMP4 and the like in the second step of the starting material production method 1 or the third step of the starting material production method 2 or 3. The above-mentioned "step of culturing a cell aggregate containing a retinal tissue in which Chx10-positive cells are present in a proportion of 20% or more and 100% or less of the retinal tissue in a serum-free medium or serum-containing medium each containing a Wnt signal transduction pathway agonist and an FGF signal transduction pathway inhibitor for only a period before the emergence of a RPE65 gene-expressing cell" is preferably started before not less than 50%, preferably not less than 80%, more preferably not less than 90%, further more preferably not less than 99%, of the cells contained in the retinal tissue can express RPE65 gene by continuously culturing in a serum-free medium or serum-containing medium each containing a Wnt signal transduction pathway agonist and a FGF signal transduction pathway inhibitor (e.g., for not less than 30 days), that is, before the above-mentioned proportion of the cells contained in the retinal tissue can differentiate into retinal pigment epithelium. Specifically, it is started by 40 days, preferably 30 days, more preferably 20 days, after the start of the suspension culture.

The thus-obtained cell aggregate can be used as the "cell aggregate containing a retinal tissue in which Chx10-positive cells are present in a proportion of 20% or more and 100% or less of the aforementioned retinal tissue" in this step.

First, "a cell aggregate containing a retinal tissue in which Chx10-positive cells are present in a proportion of 20% or more and 100% or less of the retinal tissue" is cultured according to the method described in WO 2015/087614 and in a serum-free medium or serum-containing medium each containing a Wnt signal transduction pathway agonist and a FGF signal transduction pathway inhibitor for only a period before the emergence of a RPE65 gene-expressing cell. As a preferable culture here, suspension culture can be mentioned.

As a serum-free medium, a serum-free medium which is a basal medium supplemented with N2 or KSR can be mentioned. More specifically, a serum-free medium which is a DMEM/F-12 medium supplemented with N2 supplement (N2, Invitrogen) can be mentioned. As the serum-containing medium, a serum-containing medium which is a basal medium supplemented with fetal bovine serum can be mentioned.

The culture conditions such as culture temperature, $CO_2$ concentration can be appropriately set. The culture temperature is, for example, in the range of about 30° C. to about 40° C., preferably, for example, about 37° C. The $CO_2$ concentration is, for example, in the range of about 1% to about 10%, preferably, for example, about 5%.

When the above-mentioned cell aggregate is cultured in a serum-free medium or serum-containing medium, the Wnt signal transduction pathway agonist to be contained in the medium is not particularly limited as long as it can enhance signal transduction mediated by Wnt, and those mentioned above can be recited.

The concentration of the Wnt signal transduction pathway agonist to be contained in a serum-free medium or serum-containing medium in the case of a common Wnt signal transduction pathway agonist such as CHIR99021 is, for example, in the range of about 0.1 µM to about 100 µM, preferably, for example, in the range of about 1 µM to about 30 µM, more preferably, for example, about 3 µM.

When the above-mentioned "cell aggregate containing a retinal tissue" is cultured in a serum-free medium or serum-containing medium, the FGF signal transduction pathway inhibitor to be contained in the medium is not particularly limited as long as it can inhibit signal transduction mediated by FGF. Examples of the FGF signal transduction pathway inhibitor include FGF receptor, FGF receptor inhibitor (e.g., SU-5402, AZD4547, BGJ398), MAP kinase cascade inhibiting substance (e.g., MEK inhibitor, MAPK inhibitor, ERK inhibitor), PI3 kinase inhibitor, Akt inhibitor and so on.

The concentration of the FGF signal transduction pathway inhibitor contained in a serum-free medium or serum-containing medium only needs to be a concentration at which differentiation of the cells forming an aggregate of pluripotent stem cells into retinal cells can be induced. For example, in the case of SU-5402, it is added to the medium at a concentration of about 0.1 µM to about 100 µM, preferably about 1 µM to about 30 µM, more preferably about 5 µM.

In the present specification, "culturing for only a period before the emergence of a RPE65 gene-expressing cell" means culturing only in the whole or a part of the period before the emergence of a RPE65 gene-expressing cell. That is, culturing only in the whole or a part of the period (any period) during which the aforementioned "cell aggregate containing a retinal tissue" in the culture system is constituted by cells that do not substantially express RPE65 gene suffices. By employing such culturing, a cell aggregate in which a RPE65 gene-expressing cell has not emerged can be obtained. The "cell aggregate in which a RPE65 gene-expressing cell has not emerged" includes a "cell aggregate in which a RPE65 gene-expressing cell has not emerged at all" and a "cell aggregate in which a RPE65 gene-expressing cell does not substantially emerge". As the "cell aggregate in which a RPE65 gene-expressing cell does not substantially emerge", a cell aggregate in which the proportion of RPE65- positive cells in the retinal tissue contained in the cell aggregate is not more than about 1% can be mentioned.

To determine such particular period, the aforementioned "cell aggregate containing a retinal tissue" is used as a sample, and the presence or absence of expression of RPE65 gene contained in the sample or the level thereof may be measured by a general genetic engineering method or a biochemical method. Specifically, for example, the presence or absence of expression of RPE65 gene or the level thereof can be examined by subjecting a cryosection of the aforementioned "cell aggregate containing a retinal tissue" to an immunostaining method using an antibody against RPE65 protein.

As a "period before the emergence of a RPE65 gene-expressing cell", for example, a period during which the ratio of Chx10-positive cells present in the above-mentioned retinal tissue decreases as compared to that at the time of start of the culturing of the aforementioned cell aggregate in a serum-free medium or serum-containing medium each containing a Wnt signal transduction pathway agonist and a FGF signal transduction pathway inhibitor, and falls within the range of 30% to 0% can be mentioned. As the "cell aggregate in which a RPE65 gene-expressing cell has not emerged", a cell aggregate in which Chx10-positive cells are present in the above-mentioned retinal tissue in a proportion of within 30% to 0% of the tissue can be mentioned.

While the number of days of the "period before the emergence of a RPE65 gene-expressing cell" varies depending on the kind of the Wnt signal transduction pathway agonist and the FGF signal transduction pathway inhibitor, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 2 days to 6 days, further specifically 3 days to 5 days. When a serum-containing medium (e.g., serum-containing medium which is a basal medium supplemented with fetal bovine serum) is used, the aforementioned period is preferably, for example, within 12 days, more preferably, for example, 6 days to 9 days.

The thus-obtained aggregate can be used as a retinal tissue in an initial developmental stage which is used as a starting material in the method of the present invention.

Then, the "cell aggregate in which a RPE65 gene-expressing cell has not emerged" obtained by culturing as mentioned above may be further cultured in a serum-free medium or serum-containing medium without containing a Wnt signal transduction pathway agonist for 1 day-50 days (corresponding to "between a differentiation stage immediately after emergence of a ganglion cell and a differentiation stage where emergence rate of a cone photoreceptor precursor reaches maximum"), preferably 1 day-15 days (corresponding to within about 5 days from emergence of ganglion cell), further preferably 1 day-7 days (corresponding to stage where ganglion cell begins to emerge), and then used as a retinal tissue in an initial developmental stage which is used as a starting material in the method of the present invention. As for the culture method, WO 2015/087614 (e.g., paragraph [0076]-[0079]) can be referred to.

2-6. Starting Material Production Method 6

A retinal tissue in an initial developmental stage and containing a ciliary marginal zone structure which can be used as a starting material in the production method of the present invention can also be produced by the method described in WO 2013/183774 (&US2015/132787).

Specifically, an aggregate obtained by a step of culturing a cell aggregate containing a retinal tissue, in which Chx10-positive cells are present in a proportion of 20% or more and 100% or less of the retinal tissue, in a serum-free medium or serum-containing medium each containing a Wnt signal transduction pathway agonist for only a period before the emergence of a RPE65 gene-expressing cell, or further, an aggregate containing a ciliary marginal zone-like structure which is obtained by a step of culturing the obtained "cell aggregate in which a RPE65 gene-expressing cell has not emerged" in a serum-free medium or serum-containing medium each free of a Wnt signal transduction pathway agonist is also a retinal tissue in the initial developmental stage.

As the "cell aggregate containing a retinal tissue in which Chx10-positive cells are present in a proportion of 20% or more and 100% or less of the retinal tissue" which can be used as the starting material here, and a "Wnt signal transduction pathway agonist", those used in the above-mentioned starting material production method 5 can be mentioned.

As preferable culture, suspension culture can be mentioned. As a preferable medium, a serum-free medium can be mentioned.

The culture conditions such as culture temperature, $CO_2$ concentration and the like can be appropriately set. The culture temperature is, for example, in the range of about 30° C. to about 40° C., preferably, for example, about 37° C. The $CO_2$ concentration is, for example, in the range of about 1% to about 10%, preferably, for example, about 5%.

The Wnt signal transduction pathway agonist to be contained in the medium is not particularly limited as long as it can enhance signal transduction mediated by Wnt, and those mentioned above can be recited.

The concentration of the Wnt signal transduction pathway agonist to be contained in a serum-free medium or serum-containing medium in the case of a common Wnt signal transduction pathway agonist such as CHIR99021 is, for example, in the range of about 0.1 μM to 100 μM, preferably, for example, in the range of about 1 μM to 30 μM, more preferably, for example, about 3 μM.

In the same manner as in the production method 5 except that an FGF signal transduction pathway inhibitor may not be contained, the cell aggregate is "cultured for only a period before the emergence of a RPE65 gene-expressing cell".

As a preferable "period before the emergence of a RPE65 gene-expressing cell", for example, a period during which the ratio of Chx10-positive cells present in the above-mentioned retinal tissue is within the range of 50% to 1% can be mentioned. In this case, the "cell aggregate in which a RPE65 gene-expressing cell has not emerged" is a cell aggregate in which Chx10-positive cells are present in the above-mentioned retinal tissue in a proportion of within 50% to 1% of the tissue.

While the number of days of the "period before the emergence of a RPE65 gene-expressing cell" varies depending on the kind of the Wnt signal transduction pathway agonist, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 2 days to 6 days, further specifically 3 days to 5 days. When a serum-containing medium (e.g., serum-containing medium which is a basal medium supplemented with fetal bovine serum) is used, the aforementioned period is preferably, for example, within 12 days, more preferably, for example, 6 days to 9 days.

The thus-obtained aggregate can be used as a retinal tissue in an initial developmental stage which is used as a starting material in the method of the present invention. The "cell aggregate in which a RPE65 gene-expressing cell has not emerged" obtained by culturing as mentioned above may be directly used as a retinal tissue in an initial developmental stage. It may be further cultured in a serum-free medium or serum-containing medium without containing a Wnt signal transduction pathway agonist for 1 day-50 days, preferably 1 day-15 days, further preferably 1 day-7 days, and then used as an aggregate containing a retinal tissue in an initial developmental stage. As for the culture method, WO 2015/087614 (e.g., paragraph [0076]-[0079]) can be referred to.

2-7. Starting Material Production Method 7

The retinal tissue in an initial developmental stage may contain a ciliary marginal zone structure, and a retinal tissue in an initial developmental stage containing a ciliary marginal zone structure can be produced by the method described in WO 2015/107738 (and U.S. patent application Ser. No. 15/112,187). Specifically, for example, a retinosphere prepared by a method containing the following step can also be used as a retinal tissue in an initial developmental stage which is used as a starting material in the method of the present invention:

(1) a step of obtaining a retinosphere by proliferation culturing in suspension the cells obtained from a cell aggregate containing a ciliary marginal zone-like structure induced to differentiate from a pluripotent stem cell.

The "cell aggregate containing a ciliary marginal zone-like structure induced to differentiate from a pluripotent stem cell" can be produced according to the above-mentioned starting material production method 5 or 6. The cells obtained therefrom are dispersed and cultured in suspension to give a retinosphere.

Examples of the cells include cells obtained by dispersing the above-mentioned "cell aggregate containing a ciliary marginal zone-like structure induced to differentiate from a pluripotent stem cell", cells obtained by dispersing the ciliary marginal zone-like structure separated from the aforementioned cell aggregate, and cells obtained by dispersing the cells sorted from the aforementioned cell aggregate. When such cells are cultured in suspension at a low density in the presence of a growth factor or the like, a single cell or a spherical cell aggregate derived from a small number of cells of about 2 to 10 cells, namely, retinosphere, is formed. For a method for producing a retinosphere, WO 2015/107738 (and US patent application Ser. No. 15/112,187) can be referred to.

Specifically, the dispersed cells can be cultured in suspension in a serum-free medium or serum-containing medium supplemented with an additive for nerve cell culture and a growth factor. As a medium, preferably, a serum-free medium or serum-containing medium containing one or more substances selected from the group consisting of an FGF signal transduction pathway agonist and an EGF signal transduction pathway agonist can be mentioned. Examples of the FGF signal transduction pathway agonist used here include FGF proteins such as FGF1, bFGF, FGF4, FGF7, FGF8, FGF9 and the like and heparine as an auxiliary agent of FGF signal and the like. Examples of the EGF signal transduction pathway agonist include EGF, TGF-alpha and the like.

A retinosphere produced as mentioned above can be used as a retinal tissue in an initial developmental stage that is the starting material in the production method of the present invention since it contains a retinal progenitor cell or a neural retinal progenitor cell, like retinal tissues. In addition, a retinosphere suspension cultured in a serum-free medium or serum-containing medium containing a BMP signal transduction pathway agonist (e.g., BMP4) after the above-mentioned step (1) can also be used as a retinal tissue in an initial developmental stage to be the starting material of the production method of the present invention. Then, the retinosphere obtained as mentioned above may be further cultured in a serum-free medium or serum-containing medium without containing a Wnt signal transduction pathway agonist for 1 day-50 days, preferably 1 day-15 days, further preferably 1 day-7 days, and then the obtained cell aggregate may be used as a retinal tissue in an initial developmental stage.

3. Production of Retinal Tissue Containing Neural Retinal Progenitor Cell, and in any Stage Between Differentiation Stage Immediately after Emergence of Ganglion Cell and Differentiation Stage where Emergence Rate of Cone Photoreceptor Precursor Reaches Maximum (Starting Material Usable in the Method of the Present Invention [1])

The "retinal tissue containing a neural retinal progenitor cell, and in any stage between a differentiation stage immediately after emergence of a ganglion cell and a differentiation stage where emergence rate of a cone photoreceptor precursor reaches maximum" which is used in the above-mentioned present invention [1] is explained in the following.

The retinal tissue when starting culture in a medium containing a thyroid gland hormone signal transduction pathway agonist is not particularly limited as long as it is in a differentiation stage where the proportion of PAX6-negative and CHX10-strongly positive cell (e.g., bipolar cell), and PAX6-positive and CHX10-negative cell (e.g., any cell of amacrine cell, ganglion cell, and horizontal cell) can be reduced, and the proportion of photoreceptor precursor and/or photoreceptor can be increased, when cultured in a medium containing a thyroid gland hormone signal transduction pathway agonist and differentiated and matured to the extent that Muller cell is recognized. However, a retinal tissue "containing a neural retinal progenitor cell, and in any stage between a differentiation stage immediately after emergence of a ganglion cell and a differentiation stage where emergence rate of a cone photoreceptor precursor reaches maximum" is preferably used as mentioned below.

Specifically, a retinal tissue "containing a neural retinal progenitor cell, and in a differentiation stage immediately after emergence of a ganglion cell" is, for example, a retinal tissue containing photoreceptor, and a neural retinal progenitor cell (e.g., CHX10-positive, RX-positive and PAX6-positive cell) that can be differentiated into at least 2, preferably not less than 5, more preferably not less than 6, cells of retinal pigment epithelial cell, ganglion cell, horizontal cell, amacrine cell, bipolar cell and Muller cell, in a differentiation stage immediately after CHX10, preferably RX, PAX6 and CHX10, which are markers of neural retinal progenitor cell, are detected at a detectable level, and TUJ1, BRN3 and the like, which are markers of ganglion cell, are detected at a detectable level. The retinal tissue may contain a retinal progenitor cell.

Whether it is "a differentiation stage immediately after emergence of a ganglion cell" can be determined by specifying the period when a BRN3-positive cell (ganglion cell marker) starts to emerge in a neural retinal tissue. Specifically, "a differentiation stage immediately after emergence of a ganglion cell" is, for example, within about 10 days, preferably about 5 days, more preferably 1 day, further more preferably 1 hr, from the detection of the ganglion cell marker. For example, it is a retinal tissue in which not less than 30%, preferably not less than 50%, more preferably not less than 70%, further preferably not less than 80%, further more preferably not less than 90%, particularly preferably not less than 99%, of the total number of cells contained in the retinal tissue is neural retinal progenitor cell, a ganglion cell marker-positive (preferably, BRN3-positive) cell is detected, and the proportion thereof is not more than 40%, preferably not more than 20%, not more than 10%, not more than 5%, more preferably not more than 1%, further preferably not more than 0.1%, further more preferably not more than 0.01%, of the total number of cells. The retinal tissue may contain a retinal progenitor cell.

For example, as the retinal tissue "containing a neural retinal progenitor cell, and in a differentiation stage immediately after emergence of a ganglion cell", when it is produced by the method described in the above-mentioned starting material production methods 1-4, a retinal tissue corresponding to about day 27-day 40, preferably day 28-day 37, more preferably day 28-33, from the start of suspension culture can be mentioned.

When it is produced, for example, by the method described in the above-mentioned starting material production methods 5-7, a retinal tissue corresponding to about day 33-day 45, preferably about day 33-day 42, more preferably day 33-day 38, from the start of suspension culture (corresponding to about day 11-day 23, preferably day 11-day 20, more preferably day 11-day 16, from the start of culture in a serum-free medium or serum-containing medium not containing Wnt signal transduction pathway agonist) can be mentioned.

As one embodiment of the retinal tissue "containing a neural retinal progenitor cell, and in a differentiation stage immediately after emergence of a ganglion cell" of the present specification, a retinal tissue in a stage where photoreceptor precursor or cone photoreceptor precursor starts to emerge, for example, CRX-positive cell or CRX-positive and TRβ2-positive cell starts to emerge, can be mentioned.

When it is produced, for example, by the method described in the above-mentioned starting material production methods 1-4, a retinal tissue corresponding to about day 30-day 45, preferably about day 30-day 40, from the start of suspension culture can be mentioned.

When it is produced, for example, by the method described in the above-mentioned starting material production methods 5-7, a retinal tissue corresponding to about day 35-day 45, preferably about day 35-day 42, from the start of suspension culture (corresponding to about day 13-day 23, preferably day 13-day 20, from the start of culture in a serum-free medium or serum-containing medium not containing Wnt signal transduction pathway agonist) can be mentioned.

As one embodiment of the retinal tissue in "a differentiation stage where emergence rate of a cone photoreceptor precursor reaches maximum" of the present specification, specifically, a retinal tissue in a differentiation stage at least one day before the "retinal tissue in a differentiation stage where emergence rate of cone photoreceptor precursor reaches maximum" can be mentioned. Here, the "retinal tissue in a differentiation stage where emergence rate of cone photoreceptor precursor reaches maximum" is a differentiation stage corresponding to 30-50 days, preferably 30-40 days, after recognition of the emergence of cone photoreceptor precursor or cone photoreceptor.

As a retinal tissue when starting culture in a medium containing a thyroid gland hormone signal transduction pathway agonist, a retinal tissue in a differentiation stage as early as possible after "containing a neural retinal progenitor cell and in a differentiation stage immediately after emergence of a ganglion cell" can be preferably used as mentioned below. Therefore, as "a retinal tissue up to a differentiation stage where emergence rate of a cone photoreceptor precursor reaches maximum", a retinal tissue in a stage preferably not less than 10 days, more preferably not less than 20 days, further more preferably not less than 30 days, not less than 40 days, before the differentiation stage where the emergence rate of cone photoreceptor precursor reaches maximum, and ganglion cell has emerged, namely, "a retinal tissue containing a neural retinal progenitor cell, and in any differentiation stage between a differentiation stage immediately after emergence of a ganglion cell and a stage where photoreceptor precursor or cone photoreceptor precursor starts to emerge" can be preferably mentioned.

The "retinal tissue containing a neural retinal progenitor cell, and in any stage between a differentiation stage immediately after emergence of a ganglion cell and a differentiation stage where emergence rate of a cone photoreceptor precursor reaches maximum" corresponds to, for example, about day 27-day 69, preferably day 28-day 60, more preferably day 28-day 50, further more preferably day 28-day 40, day 28-day 35, from the start of culture in a medium containing a BMP signal transduction pathway agonist (e.g., BMP4) by the methods described in the above-mentioned starting material production method 1 (WO 2015/025967), starting material production method 2 (WO 2016/063985) and starting material production method 3 (WO 2016/063986).

For example, by the methods described in the above-mentioned starting material production method 4 (WO 2013/077425), the aforementioned differentiation stage corresponds to about day 27-day 69, preferably day 28-day 60, more preferably day 28-day 50, further more preferably day 28-day 40, day 28-day 35, from the start of culture in a medium containing a basement membrane preparation (e.g., Matrigel).

For example, by the method described in the above-mentioned starting material production method 5 (WO 2015/087614), starting material production method 6 (WO 2013/183774) or starting material production method 7 (WO 2015/107738), the aforementioned differentiation stage corresponds to a stage where a retinal tissue containing a RPE65-positive ciliary marginal zone structure is obtained, and corresponds to about day 33-day 74, preferably about day 33-day 65, more preferably day 33-day 55, further more preferably day 33-day 45, day 33-day 40, from the start of suspension culture. It corresponds to about day 11-day 52, preferably day 11-day 43, more preferably day 11-day 33, further more preferably day 11-day 23, day 11-day 18, from the start of culture in a serum-free medium or serum-containing medium not containing a Wnt signal transduction pathway agonist after completion of culture in the presence of a Wnt signal transduction pathway agonist by the method described in the above-mentioned starting material production method 5 (WO 2015/087614), starting material production method 6 (WO 2013/183774) or starting material production method 7 (WO 2015/107738).

That is, the step of producing "a retinal tissue in an initial developmental stage", and a step of culturing "a retinal tissue in an initial developmental stage" and producing "a retinal tissue containing a neural retinal progenitor cell, and in any stage between a differentiation stage immediately after emergence of a ganglion cell and a differentiation stage where emergence rate of a cone photoreceptor precursor reaches maximum" may be continuously performed without interruption between the steps and without identifying or isolating a retinal tissue in an initial developmental stage.

4. Method for Suppressing Differentiation of Bipolar Cell, Amacrine Cell, Ganglion Cell and/or Horizontal Cell As one embodiment of the present invention, a method for suppressing differentiation of bipolar cell, ganglion cell, amacrine cell and/or horizontal cell in a neural retinal tissue containing a photoreceptor precursor and/or a photoreceptor can be mentioned.

According to the method for suppressing differentiation of the present invention, it is possible to reduce the proportion of the number of cells of at least one of ganglion cell, amacrine cell, horizontal cell, bipolar cell, and progenitor cells of these, or the total number of these cells in a neural retinal tissue containing a photoreceptor precursor and/or a photoreceptor and increase the proportion of photoreceptor precursor and photoreceptor, by culturing "a retinal tissue containing a neural retinal progenitor cell and in a differentiation stage immediately after emergence of a ganglion cell", namely, "a cell aggregate containing a neural retinal progenitor cell, and in a differentiation stage immediately after emergence of a ganglion cell" in a medium containing a thyroid gland hormone signal transduction pathway agonist. In addition, it is possible to reduce the proportion of the number of cells of the bipolar cells and increase the proportion of photoreceptor precursor and photoreceptor by the differentiation suppressive method of the present invention.

Furthermore, it is possible to form an ectopic photoreceptor layer (also referred to as photoreceptor precursor layer) in a cell layer on the basement membrane side such as an inner nuclear layer where bipolar cell and amacrine cell and the like are present, and a ganglion cell layer where ganglion cells are present, among respective layers constituting the retinal tissue, and a retinal tissue suitable for transplantation because, upon transplantation, the spatial or physical distance between the bipolar cells of the recipient and the photoreceptor precursor contained in the transplanted retinal tissue is short can be produced.

It is known to those of ordinary skill in the art that, in a stage after differentiation and maturation to a level showing Muller cell in a neural retinal tissue, which is one embodiment of the retinal tissue for transplantation and containing a photoreceptor precursor and/or a photoreceptor, PAX6-negative/CHX10-strongly positive cell is a bipolar cell, and PAX6-positive/CHX10-negative cell is a ganglion cell, amacrine cell or horizontal cell. In the present specification, therefore, in a neural retinal tissue for transplantation and containing a photoreceptor precursor, whether the proportion of bipolar cell, amacrine cell, ganglion cell and/or horizontal cell unnecessary for transplantation could be reduced can be known by specifying the proportion of, for example, PAX6-negative/CHX10-strongly positive cell and/or PAX6-positive/CHX10-negative cell contained in a retinal tissue in a stage after differentiation and maturation to a level showing Muller cell. In addition, whether the Muller cell can be recognized in the retinal tissue can be confirmed by the presence of, for example, CRALBP-positive cell and/or CRABP-positive cell.

The concentration of the thyroid gland hormone signal transduction pathway agonist to be added here is not particularly limited as long as it is a concentration that suppresses differentiation of bipolar cell, and any of amacrine cell, ganglion cell and horizontal cell, does not suppress differentiation of photoreceptor precursor. It can be appropriately determined by measuring the proportion of the number of cells with positive markers of bipolar cell, amacrine cell, ganglion cell and/or horizontal cell, and the number of cells with a positive marker of photoreceptor precursor.

The concentration of the thyroid gland hormone signal transduction pathway agonist to be added can be determined such that PAX6-negative/CHX10-strongly positive cells are not more than 8%, preferably, not more than 6%, more preferably not more than 5%, of all cells contained in a neural retinal tissue in the late differentiation stage after differentiation of the level showing, for example, emergence of Muller cells (e.g., corresponding to about day 180-200 from the start of suspension culture when a retinal tissue produced by the method described in the above-mentioned starting material production method 1-3, 4, or 5-7 is the starting material). Alternatively, the concentration of the thyroid gland hormone signal transduction pathway agonist can be determined such that the proportion of PAX6-positive/CHX10-negative cell is not less than 30%, preferably not less than 20%, more preferably not more than 15%. Alternatively, the concentration of the thyroid gland hormone signal transduction pathway agonist can be determined such that the proportion of photoreceptor (or photoreceptor precursor) is not less than 40%, preferably not less than 45%, more preferably not less than 50%.

Alternatively, the concentration of the thyroid gland hormone signal transduction pathway agonist can be determined such that, for example, in a retinal tissue in a differentiation stage where the emergence rate of cone photoreceptor precursor (e.g., CRX-positive and TRβ2-positive cell, or CRX-positive and RXR-γ-positive cell) reaches maximum (namely, differentiation stage corresponding to 30-50 days, preferably 30-40 days, after recognition of emergence of cone photoreceptor precursor, or, for example, differentiation stage corresponding to on about day 60-70 from the start of suspension culture when a retinal tissue produced by the method described in starting material production methods 1-4 is used as the starting material, differentiation stage corresponding to on about day 65-75 from the start of suspension culture when a retinal tissue produced by the method described in starting material production methods 5-7 is used as the starting material), an ectopic photoreceptor precursor that emerges on the basement membrane side from the neuroblastic layer (NBL) is observed, and the ratio per unit area of the number of cells of photoreceptor precursors that emerge on the apical surface side containing NBL and the number of cells of photoreceptor, and the number of cells of ectopic photoreceptor precursors that emerge on the basement membrane side from NBL and the number of cells of photoreceptor is 10:1 to 1:10, preferably 2:1 to 1:2, more preferably 10:7 to about 7:10. Here, the "proportion per unit area" can be identified by the following procedures. 1) A neural retinal tissue and cells contained therein are identified by a section preparation method and a method such as immunostaining and the like, conventionally performed by a person skilled in the art 2) CRX-positive cells contained in the neural retinal tissue per a given area (i.e., per unit area) are measured using image analysis software and the like and compared. In this way, the ratio per unit area of the number of cells of photoreceptor precursors that emerge on the apical surface side containing NBL, and the number of cells of ectopic photoreceptor precursors that emerge on the basement surface side from NBL can be compared. Here, the neural retinal tissue can be identified by combining with a marker of the above-mentioned neural retinal tissue and the cells contained in the neural retinal tissue, identifying the apical surface, basement membrane and/or region where the DAPI-positive cell nucleus is present, and comparing the positional relationship. Examples of the apical surface marker include atypical-PKC (hereinafter to be abbreviated as aPKC), E-cadherin, N-cadherin, and examples of the basement membrane marker include Laminin, Type-IV Collagen, heparan sulfate proteoglycan, Entactin and the like, and antibodies against these markers and the like can be utilized. NBL can be roughly identified from the retinal structure as a layer in which neural retinal progenitor cell proliferates. It may also be identified using an antibody against CHX10, RX, PAX6 and/or Ki67 as a layer in which neural retinal progenitor cell present in NBL and/or proliferated cell contained in neural retina are/is present.

Alternatively, the concentration of the thyroid gland hormone signal transduction pathway agonist to be added can be determined such that the proportion of photoreceptor precursor (CRX-positive cell) in a retinal tissue in the differentiation stage (differentiation stage where the emergence rate of cone photoreceptor precursor (e.g., CRX-positive and TRβ2-positive cell, or CRX-positive and RXR-γ-positive cell) reaches maximum) is not less than 11%, preferably not less than 15%, further preferably not less than 20%, of the whole cells contained in the neural retinal tissue. Alternatively, the concentration can be determined such that the proportion of the CRX-positive and TRβ2-positive cells in the retinal tissue in this differentiation stage is not less than 7%, preferably not less than 10%, further preferably not less than 11%, of the whole cells contained in the neural retinal tissue.

When T3 is used as a thyroid gland hormone signal transduction pathway agonist, for example, it can be added to a medium to fall within the range of 0.1-1000 nM. A concentration showing a thyroid gland hormone signal transduction promoted activity corresponding to that of T3 at a concentration of preferably 1-500 nM; more preferably 10-100 nM; further preferably 30-90 nM; further more preferably about 60 nM can be mentioned.

When T4 is used as a thyroid gland hormone signal transduction pathway agonist, for example, it can be added to a medium to fall within the range of 1 nM-500 μM; preferably 50 nM-50 μM; more preferably 500 nM-5 μM.

Alternatively, the concentration of the thyroid gland hormone signal transduction pathway agonist to be added can be determined such that the proportion of a photoreceptor precursor (CRX-positive cell) in a retinal tissue in a differentiation stage where a rod photoreceptor precursor (or bipolar cell) starts to emerge is not less than 20%, preferably not less than 25%, further preferably not less than 30%, based on all cells contained in the neural retinal tissue. Alternatively, in a retinal tissue in the differentiation stage, the concentration of the thyroid gland hormone signal transduction pathway agonist to be added may be set such that at least two cells on average, preferably not less than 3 cells on average, more preferably not less than 4 cells on average, are photoreceptor precursors (CRX-positive cells) along a straight line vertical to the tangent line of the apical surface. Preferably, the concentration of the thyroid gland hormone signal transduction pathway agonist to be added can be determined such that the retinal tissue in the differentiation stage contains the ectopic photoreceptor precursor on the basement membrane side from NBL.

The timing to start culturing in a medium containing a thyroid gland hormone signal transduction pathway agonist is not particularly limited as long as it is before a differentiation stage that can reduce the proportion of PAX6-negative and CHX10-strongly positive cell (e.g., bipolar cell), and PAX6-positive and CHX10-negative cell (e.g., any cell of amacrine cell, ganglion cell, and horizontal cell) and a differentiation stage where the proportion of the photoreceptor precursor and/or photoreceptor can be increased, when cultured in a medium containing a thyroid gland hormone signal transduction pathway agonist and differentiated and matured until Muller cell is recognized. It is preferably any stage between the aforementioned differentiation stage containing a neural retinal progenitor cell and immediately after emergence of a ganglion cell and a differentiation stage where emergence rate of a cone photoreceptor precursor reaches maximum.

Here, the "differentiation stage where emergence rate of a cone photoreceptor precursor reaches maximum" is specifically, for example, a retinal tissue in a differentiation stage at least one day before the "differentiation stage where emergence rate of cone photoreceptor precursor reaches maximum".

As for the timing to start culturing in a medium containing a thyroid gland hormone signal transduction pathway agonist, the neural retinal tissue to be the starting material is preferably cultured by the earliest possible differentiation stage after "a differentiation stage containing a neural retinal progenitor cell, and immediately after emergence of a ganglion cell". Thus, the timing of "a differentiation stage where emergence rate of a cone photoreceptor precursor reaches maximum" is preferably not less than 10 days, more preferably not less than 20 days, further more preferably not less than 30 days, and not less than 40 days, before the differentiation stage where emergence rate of a cone photoreceptor precursor reaches maximum and ganglion cell has emerged, namely, specifically preferably from "a differentiation stage containing a neural retinal progenitor cell, and immediately after emergence of a ganglion cell" to "a stage where a photoreceptor precursor or cone photoreceptor precursor starts to emerge".

A differentiation stage immediately after emergence of a ganglion cell, namely, when a ganglion cell or cone photoreceptor precursor starts to emerge can be determined by suspension culturing an aggregate containing a retinal tissue containing a neural retinal progenitor cell and in a differentiation stage where a ganglion cell has not emerged in a culture medium, and identifying the time when ganglion cell, cone photoreceptor precursor, or photoreceptor precursor marker-positive cell initially emerges. Specifically, for example, a retinal tissue under differentiation is collected at given intervals (e.g., one day) (e.g., 26 days, 27 days, 28 days, 29 days, 30 days, 31 days, 32 days, 33 days, 34 days, 35 days, 36 days, 37 days, 38 days, 39 days, 40 days, 41 days, 42 days from the start of culture), fixed with paraformaldehyde and the like, and cryosections are prepared. The cryosections are stained with, for example, an anti-BRN3 antibody, anti-CRX antibody, an anti-TRβ2 antibody, an anti-RXR-γ antibody and the like, the nucleus is simultaneously stained with DAPI and the like, and the time when ganglion cell (BRN3-positive cell), cone photoreceptor precursor (CRX and RXR-γ, or CRX and TRβ2-positive cell), or photoreceptor precursor (CRX-positive cell) emerges can be identified.

A person skilled in the art can specify the above-mentioned differentiation stage where emergence rate of cone photoreceptor precursor reaches maximum by immunostaining with cone photoreceptor precursor marker, nuclear staining with DAPI and the like.

Specifically, for example, the retinal tissue undergoing differentiation is collected at certain intervals (e.g., 1-20 days) (e.g., 40 days, 50 days, 60 days, 70 days, 80 days after the start of culture), and fixed with para-formaldehyde and the like and frozen sections are prepared. The frozen sections are stained with, for example, anti-CRX antibody, anti-TRβ2 antibody, anti-RXR-γ antibody and the like, the nucleus is simultaneously stained with DAPI and the like, and the proportion of the cone photoreceptor precursors (i.e., cells expressing CRX and RXR-γ, or CRX and TRβ2) can be determined. At this time, the ratio of the number of cone photoreceptor precursor marker-positive cells that emerge in the above-mentioned certain period to the total number of cells, that is, the emergence ratio, is determined at plural times (timing). As a result, the period when the proportion of emergence of cone photoreceptor precursor marker-positive cells is the highest can be specified as "when emergence rate of cone photoreceptor precursor reaches maximum".

In addition, BrdU, EdU and the like which are incorporated into the cells in a proliferation period (here, retinal progenitor cell or neural retinal progenitor cell having proliferation ability) are added to a culture medium for a particular period (e.g., 1-7 days), the proportion of the cells that incorporated BrdU, EdU and the like and differentiated into cells that express the aforementioned cone photoreceptor precursor marker is measured by immunostaining and the like well known to those skilled in the art, and the relationship between the proportion and the differentiation stage (e.g., period (stage) when the proportion is the highest etc.) is determined, whereby "when emergence rate of cone photoreceptor precursor reaches maximum" can be identified.

Specifically, for example, it can be identified by the following procedures:
1) a step of culturing by adding BrdU or Edu for any one day to a culture medium for cultivating a retinal tissue in any differentiation stage (e.g., adding BrdU every other day such as at 40 days-41 days, 41 days-42 days, 42 days-43 days, from the start of culture, and culturing for 1 day is repeated for 80 days from the start of culture), recovering the retinal tissue immediately thereafter and measuring the proportion of CRX and RXR-γ-positive cells or the proportion of CRX and TRβ2-positive cells in BrdU or EdU-positive cells;
2) a step of comparing the measurement results, and identifying a retinal tissue in which a ratio of increase in CRX and RXR-γ-positive cells, or a ratio of increase in CRX and TRβ2-positive cells, in BrdU or EdU-positive cells is the highest; and
3) a step of identifying the period of addition of BrdU or EdU to the culture medium (e.g., 1 day) when culturing the retinal tissue in which a ratio of increase in CRX and RXR-γ-positive cells, or a ratio of increase in CRX and TRβ2-positive cells, in BrdU or EdU-positive cells is the highest as "when emergence rate of cone photoreceptor precursor reaches maximum".

Specifically, the "differentiation stage where emergence rate of cone photoreceptor precursor reaches maximum" corresponds to 30 to 50 days, preferably 30 to 40 days, after emergence of cone photoreceptor precursor is observed.

When the method of the present invention is practiced, it is preferable to previously identify the above-mentioned "time when the emergence rate of a cone photoreceptor precursor reaches maximum" by the use of a medium not containing a thyroid gland hormone signal transduction pathway agonist.

When a cell aggregate prepared from a pluripotent stem cell is used, particularly when retinal tissues produced by the methods described in starting material production methods 1-4 are used, culturing in a medium containing a thyroid gland hormone signal transduction pathway agonist is started specifically within 60-65 days from the first emergence of a photoreceptor precursor (within about 95 days from the start of suspension culture); preferably within 30-40 days from the first emergence of a photoreceptor precursor (within about 60-70 days from the start of suspension culture, the upper limit is until the emergence rate of a cone photoreceptor precursor reaches maximum); more preferably when a photoreceptor precursor first emerges, or before then (within about 30-40 days from the start of suspension culture; further more preferably immediately after emergence of ganglion cell (about day 28-33 from the start of suspension culture).

When a cell aggregate prepared from a pluripotent stem cell is used, particularly when retinal tissues produced by the methods described in starting material production methods 5-7 are used, culturing in a medium containing a thyroid gland hormone signal transduction pathway agonist is started specifically within 60-65 days from the first emergence of a photoreceptor precursor (within about 100 days from the start of suspension culture); preferably within 30-40 days from the first emergence of a photoreceptor precursor (within about 65-75 days from the start of suspension culture, the upper limit is until the emergence rate of a cone photoreceptor precursor reaches maximum); more preferably when a photoreceptor precursor first emerges, or before then (within about 35-42 days from the start of suspension culture; or immediately after emergence of ganglion cell (about day 33-38 from the start of suspension culture).

Culturing in the presence of a thyroid gland hormone signal transduction pathway agonist is preferably continued for a period of emergence of a cone photoreceptor precursor from a neural retinal progenitor cell.

The period of emergence of the cone photoreceptor precursor can be determined by adding BrdU or EdU and the like to be incorporated into the proliferated cells in the retinal tissue to be the target to a culture medium, and identifying using an antibody whether the cell that has incorporated BrdU or EdU and the like expresses a marker of the cone photoreceptor precursor. For example, BrdU is added for a given period (e.g., 1 day from day 30, 1 day from day 40, 1 day from day 50, 1 day from day 60, 1 day from day 70, 1 day from day 80, 1 day from day 90 etc.) to the medium, retinal tissue is analyzed immediately thereafter, and when BrdU-positive and cone photoreceptor precursor marker-positive cell can be observed, then the period of BrdU addition can be identified as a period of emergence of the cone photoreceptor precursor.

More specifically, a period of 65 days-70 days after a differentiation stage where cone photoreceptor precursor first starts to differentiate can be mentioned.

In addition, as the period of culturing in a medium containing a thyroid gland hormone signal transduction pathway agonist, a "period when differentiation into bipolar cell, amacrine cell, ganglion cell and/or horizontal cell is possible" can be mentioned. The period can be identified as a period when bipolar cell, amacrine cell, ganglion cell and/or horizontal cell newly emerge(s) from a neural retinal progenitor cell.

Specifically, it can be determined by adding BrdU or EdU and the like to be incorporated into the cells in a retinal tissue in an initial developmental stage to a culture medium, and identifying using an antibody whether the cell (here, neural retinal progenitor cell) that has incorporated BrdU or EdU and the like expresses a marker of the amacrine cell, ganglion cell and/or horizontal cell. For example, BrdU is added for a given period (e.g., 1 day from day 60, 1 day from day 70, 1 day from day 90, 1 day from day 110, 1 day from day 130, etc. from the start of suspension culture) to the medium, retinal tissue is analyzed immediately thereafter, and when BrdU-positive and positive to the markers of amacrine cell, ganglion cell and/or horizontal cell can be observed, then the period of BrdU addition (the very day in case of 1 day) can be identified as a period (day) when amacrine cell, ganglion cell and/or horizontal cell can emerge.

As the timing when amacrine cell, ganglion cell and/or horizontal cell start(s) to emerge, aggregates containing retinal tissue may be cultured in suspension in a culture medium, and the timing of first emergence of amacrine cell, ganglion cell and/or horizontal cell marker-positive cell may be identified. As the marker, in addition to the ganglion cell marker BRN3 and the like, for example, PTF1a which is commonly expressed in precursor cells of amacrine cell and horizontal cell can be used.

Culturing in the presence of a thyroid gland hormone signal transduction pathway agonist is preferably continued during the period when differentiation of neural retinal progenitor cell into PAX6-negative/CHX10-strongly positive cell, and PAX6-positive/CHX10-negative cell and the like, namely, bipolar cell, and any of amacrine cell, ganglion cell, and horizontal cell, is possible. When a cone photoreceptor precursor is produced, culturing in the presence of a thyroid gland hormone signal transduction pathway agonist may be continued until the desired cell is obtained.

For example, a period from when usually ganglion cell first starts to differentiate, i.e., a differentiation stage immediately after emergence (or a differentiation stage where photoreceptor precursor first starts to differentiate; for example, corresponding to 30-40 days from the start of suspension culture in the above-mentioned starting material production methods 1-4, 35-42 days in the above-mentioned starting material production methods 5-7) to at least a differentiation stage where emergence rate of cone photoreceptor precursor at initial development reaches maximum; preferably, a period from a differentiation stage where ganglion cell first starts to differentiate (or a differentiation stage where photoreceptor precursor first starts to differentiate) to a differentiation stage where bipolar cell (or rod photoreceptor precursor) differentiates can be mentioned. Here, the stage where bipolar cell (or rod photoreceptor precursor) starts to emerge can be determined by those of ordinary skill in the art by specifying the stage where CHX10-strongly positive and PAX6-negative cell which is a bipolar cell marker starts to emerge (or specifying the stage where NRL-positive and CRX-positive cell which is a rod photoreceptor precursor marker starts to emerge) using a conventional method such as immunostaining and the like. Specifically, the stage where bipolar cell (or rod photoreceptor precursor) starts to emerge is a differentiation stage within 20 days, preferably 15 days, more preferably 10 days, further preferably 5 days, from emergence of a bipolar cell (or rod photoreceptor precursor), and is a differentiation stage containing a neural retinal progenitor cell in a stage of differentiation into a bipolar cell (or rod photoreceptor precursor). Whether the neural retinal progenitor cell is in a stage of differentiation into a bipolar cell (or rod photoreceptor precursor) can be determined by adding, to a culture medium, BrdU or EdU and the like to be incorporated into neural retinal cells as the proliferated cells in the retinal tissue and identifying using an antibody whether the cell that has incorporated BrdU or EdU and the like expresses a marker of the bipolar cell (or rod photoreceptor precursor). For example, BrdU is added for a given period (e.g., 1 day from day 90, 91, 92, 93, 94-day 110 from the start of suspension culture, etc.) to the medium, retinal tissue is analyzed immediately thereafter, and when BrdU-positive and bipolar cell (or rod photoreceptor precursor) marker-positive cell can be observed, then the period (the very day in case of 1 day) of BrdU addition can be identified as a stage containing a neural retinal tissue in a stage of differentiation into a bipolar cell (or rod photoreceptor precursor). Alternatively, it may be identified as a stage where a bipolar cell (or rod photoreceptor precursor) marker-positive cell is detected, and a BLIMP1-positive cell known to be transiently expressed in a photoreceptor precursor is detected. At this time, since thyroid gland hormone signal transduction pathway agonist has an action of suppressing the emergence of a bipolar cell (or rod photoreceptor precursor), it is preferable to identify the above-mentioned stage in advance using a medium not containing a thyroid gland hormone signal transduction pathway agonist. More specifically, a period of 35 days-45 days from the differentiation stage where ganglion cell first starts to differentiate (or a differentiation stage where photoreceptor precursor first starts to differentiate); preferably a period of 65 days-70 days from the differentiation stage where ganglion cell first starts to differentiate (or a differentiation stage where photoreceptor precursor first starts to differentiate), can be mentioned.

From the aspect of suppressing differentiation of a rod photoreceptor precursor, it is preferable to add a thyroid gland hormone signal transduction pathway agonist for a period from when ganglion cell first starts to differentiate, i.e., a differentiation stage immediately after emergence of ganglion cell (or a differentiation stage where photoreceptor precursor first starts to differentiate; corresponding to day 30-45 days from the start of suspension culture) to a differentiation stage where outer plexiform layer is formed, i.e., until outer plexiform layer marker is expressed, preferably until Muller cell emerges, i.e., until Muller cell marker is expressed. More specifically, a period of 90-100 days, preferably 150-160 days and or later from the differentiation stage where ganglion cell first starts to differentiate, i.e., a differentiation stage immediately after emergence of ganglion cell (or a differentiation stage where photoreceptor precursor first starts to differentiate) can be mentioned.

From the aspect of increasing the proportion of cone photoreceptor precursor and not reducing the proportion of rod photoreceptor precursor, it is preferable to add a thyroid gland hormone signal transduction pathway agonist for a period from when ganglion cell first starts to differentiate, i.e., a differentiation stage immediately after emergence of ganglion cell (or a differentiation stage where photoreceptor precursor first starts to differentiate) to a differentiation stage where emergence rate of cone photoreceptor precursor reaches maximum. More specifically, a period up to 30 days-50 days, preferably 30 days-40 days from a differentiation stage where ganglion cell first starts to differentiate (or a differentiation stage where photoreceptor precursor first starts to differentiate) can be mentioned.

In addition, it is also possible to culture continuously in the presence of a thyroid gland hormone signal transduction pathway agonist for a period up to the use (e.g., transplantation to recipient) of the obtained retinal tissue. More specifically, a period for differentiating from a differentiation stage where ganglion cell first starts to differentiate, i.e., immediately after emergence of ganglion cell (or a differentiation stage where photoreceptor precursor first starts to differentiate) until a stage where a retinal tissue containing photoreceptor precursor and/or photoreceptor can be transplanted to a recipient can be mentioned. That is, culturing in the presence of a thyroid gland hormone signal transduction pathway agonist until the final stage of production of a cell aggregate for transplantation is also one of the preferable embodiments.

For example, as the retinal tissue "in a differentiation stage immediately after emergence of a ganglion cell", when it is produced by the method described in the above-mentioned starting material production methods 1-4, a retinal tissue corresponding to about day 27-day 40, preferably day 28-day 37, more preferably day 28-33, from the start of suspension culture can be mentioned. When it is produced by the method described in the above-mentioned starting material production methods 5-7, a retinal tissue corresponding to about day 33-day 45, preferably about day 33-day 42, more preferably day 33-day 38, from the start of suspension culture (corresponding to about day 11-day 23, preferably day 11-day 20, more preferably day 11-day 16, from the start of culture in a serum-free medium or serum-containing medium not containing Wnt signal transduction pathway agonist) can be mentioned.

For example, a retinal tissue in "a differentiation stage where photoreceptor precursor first starts to differentiate", when it is produced by the method described in the above-mentioned starting material production methods 1-4, a retinal tissue corresponding to about day 30-day 45, preferably about day 30-day 40, from the start of suspension culture can be mentioned. When it is produced by the method described in any of the above-mentioned starting material production methods 5-7, a retinal tissue corresponding to about day 35-day 45, preferably about day 35-day 42, from the start of suspension culture (corresponding to about day 13-day 23, preferably day 13-day 20, from the start of culture in a serum-free medium or serum-containing medium not containing Wnt signal transduction pathway agonist) can be mentioned.

Further, in the aggregate containing the retinal tissue formed by the method for suppressing differentiation of the present invention, as for when the outer plexiform layer is formed, that is, when the outer plexiform layer marker is expressed, after completion of the suspension culture as mentioned above, the aggregate before and after the culture is used as a sample, and the presence or absence of expression of PSD95 gene contained in the sample or the degree thereof can be measured and compared by a conventional genetic engineering technique or a biochemical technique. Specifically, a method for immunostaining frozen sections of an "aggregate containing retinal tissue" before and after culturing by using an antibody against PSD95 protein is used, and when a PSD95 protein-positive region is observed on the basement membrane side of a photoreceptor layer (outer nuclear layer), it can be determined that an outer plexiform layer has been formed. Whether Muller cell is observed in the aggregate containing retinal tissue formed by the method for suppressing differentiation of the present invention can be determined by confirming the presence of, for example, CRALBP-positive cell and/or CRABP-positive cell.

Also, as preferable one embodiment of the present invention, a method including culturing a retinal tissue containing a neural retinal progenitor cell, and in any stage between a differentiation stage immediately after emergence of a ganglion cell and a differentiation stage where emergence rate of a cone photoreceptor precursor reaches maximum in a medium containing a thyroid gland hormone signal transduction pathway agonist such as T3 and the like to increase, in a neural retinal tissue in a stage where emergence rate of a cone photoreceptor precursor reaches maximum, the proportion of cone photoreceptor precursor such that CRX-positive cell, and CRX-positive and TRβ2-positive cone photoreceptor precursor are not less than about 22% and about 11%, respectively, of the total number of cells contained in the retinal tissue, thus suppressing differentiation of bipolar cell, amacrine cell, ganglion cell and/or horizontal cell can be mentioned.

Also, as preferable one embodiment of the present invention, a method including culturing a retinal tissue containing a neural retinal progenitor cell, and in any stage between a differentiation stage immediately after emergence of a ganglion cell and a differentiation stage where emergence rate of a cone photoreceptor precursor reaches maximum in a medium containing a thyroid gland hormone signal transduction pathway agonist such as T3 and the like and a dorsalization signal transmitter such as BMP or Cyclopamine-KAAD and the like to increase, in a neural retinal tissue in a stage where emergence rate of a cone photoreceptor precursor reaches maximum, the proportion of cone photoreceptor precursor such that CRX-positive photoreceptor precursor, and CRX-positive and TRβ2-positive cone photoreceptor precursor are not less than about 29% and not less than about 15%, respectively, of the total number of cells contained in the retinal tissue, thus suppressing differentiation of bipolar cell, amacrine cell, ganglion cell and/or horizontal cell can be mentioned.

Also, as preferable another one embodiment of the present invention, a method including culturing a retinal tissue containing a neural retinal progenitor cell, and in any stage between a differentiation stage immediately after emergence of a ganglion cell and a differentiation stage where emergence rate of a cone photoreceptor precursor reaches maximum in a medium containing a thyroid gland hormone signal transduction pathway agonist such as T3 and the like to increase, in a retinal tissue in a differentiation stage matured to the level that Muller cell marker (CRABP, CRALBP and the like)-positive cell is observed, the proportions of CRX-positive photoreceptor precursor, and CRX-positive and RXR-γ-positive and NRL-negative cone photoreceptor precursor are not less than about 53% and not less than about 44%, respectively, of the total number of cells contained in the retinal tissue, thus suppressing differentiation of bipolar cell, amacrine cell, ganglion cell and/or horizontal cell can be mentioned.

Also, as preferable one embodiment of the present invention, a method including culturing a retinal tissue containing a neural retinal progenitor cell, and in any stage between a differentiation stage immediately after emergence of a ganglion cell and a differentiation stage where emergence rate of a cone photoreceptor precursor reaches maximum in a medium containing a thyroid gland hormone signal transduction pathway agonist such as T3 and the like and a dorsalization signal transmitter such as BMP, Cyclopamine-KAAD and the like to increase, in a retinal tissue in a differentiation stage differentiated to the level that Muller cell marker (CRABP, CRALBP and the like)-positive cell is observed, the proportions of CRX-positive photoreceptor precursor, and CRX-positive and RXR-γ-positive and NRL-negative cone photoreceptor precursor are each not less than about 50% of the total number of cells contained in the retinal tissue, thus suppressing differentiation of bipolar cell, amacrine cell, ganglion cell and/or horizontal cell can be mentioned.

Further, in the method of the present invention for suppressing differentiation of ganglion cell, amacrine cell, horizontal cell and/or bipolar cell, the proportion of PAX6-positive and CHX10-negative cell can be further decreased without changing the proportion of CHX10-strongly positive and PAX6-negative cell by culturing in a medium containing T3 which is a thyroid gland hormone signal transduction pathway agonist and/or Cyclopamine-KAAD which is a dorsalization signal transmitter (e.g., see Example 8). When culturing in a medium containing any of a dorsalization signal transmitter and a thyroid gland hormone signal transduction pathway agonist, the order of adding these substances to the culture medium may be any and is not particularly limited.

As the retinal tissue and the neural retinal tissue in the method for suppressing differentiation of the present invention, stem cell-derived retinal tissue and neural retinal tissue can be mentioned. As the stem cell, the aforementioned pluripotent stem cell, or a stem cell derived from biological retina can be mentioned. As the pluripotent stem cell, ES cell or induced pluripotent stem cell (iPS cell) can be preferably mentioned.

5. Addition of Dorsalization Signal Transmitter

According to the method for suppressing differentiation of ganglion cell and the like of the present invention (the above-mentioned [1]-[12] and the above-mentioned 4.) and the method for producing a neural retinal tissue (the above-mentioned [13]-[26] and the below-mentioned 6.) (hereinafter to be also referred to collectively as the method of the present invention), emergence of cone photoreceptor precursor can be promoted and the proportion of photoreceptor precursor and/or cone photoreceptor precursor can be enhanced by culturing in a medium containing a dorsalization signal transmitter, as compared to when a dorsalization signal transmitter is not added, irrespective of the presence or absence of addition of the above-mentioned thyroid gland hormone signal transduction pathway agonist. That is, as compared to a method including allowing the above-mentioned thyroid gland hormone signal transduction pathway agonist to act alone, the proportion of cone photoreceptor precursor can be further increased among the photoreceptor precursors contained in the retinal tissue, and the proportion of at least one of bipolar cell, amacrine cell, ganglion cell, horizontal cell and progenitor cells of these, or the total number of these cells can be reduced by culturing in a medium containing a dorsalization signal transmitter in combination with a thyroid gland hormone signal transduction pathway agonist.

The following explains the method, timing and period of addition of a dorsalization signal transmitter. The method, timing and period of addition of the dorsalization signal transmitter can be determined independently of the presence or absence, timing and period of addition of a thyroid gland hormone signal transduction pathway agonist.

The proportion of a cone photoreceptor precursor in a photoreceptor precursor and a photoreceptor comprised in a retinal tissue can be increased by culturing a retinal tissue, in an initial developmental stage to a stage where an emergence rate of a cone photoreceptor precursor reaches maximum, in a medium containing a dorsalization signal transmitter at a concentration sufficient to suppress expression of a ventral marker.

As the aforementioned "ventral marker", VAX2, COUP-TF I and ALDH1A3 can be specifically mentioned.

The above-mentioned "most dorsal marker" means a marker that is expressed in a cell present in the most dorsal region of a retinal tissue in the stage of development, and is also a marker that shows an increased expression by an excessive or relatively strong dorsalization signal. Specific examples of the most dorsal marker in a retinal tissue include RPE65, MITF or COUP-TF II expressed in a cell differentiated into a retinal pigment epithelial cell or a precursor thereof due to an excessive dorsalization signal, preferably COUP-TF II expressed in a neural retinal tissue due to a comparatively strong dorsalization signal and the like.

Here, the "concentration sufficient to suppress expression of a ventral marker" can be easily determined by those of ordinary skill in the art. For example, using a method such as immunostaining and the like using an antibody against the above-mentioned ventral marker and the like, a region showing expression of the above-mentioned ventral marker as compared to when a dorsalization signal transmitter is added is analyzed using image analysis software Image J and the like in a retinal tissue in any stage between a stage where a photoreceptor precursor first emerges and a stage where emergence rate of cone photoreceptor precursor reaches maximum, for example, a retinal tissue in a stage where emergence rate of cone photoreceptor precursor reaches maximum, and a concentration of the dorsalization signal transmitter at which a region showing suppression of the expression increases can be appropriately determined as a concentration appropriate for increasing the proportion of the cone photoreceptor precursor. That is, the concentration of the dorsalization signal transmitter to be added can be determined such that a region showing expression of the above-mentioned ventral marker is not more than 50%, preferably not more than 20%, more preferably not more than 1%, further more preferably not more than 0.01%, in a neural retinal tissue containing photoreceptor precursor and/or photoreceptor. Alternatively, using as an index a retinal tissue ventralized by a ventralization signal transmitter BMP signal transduction pathway inhibitor and showing high expression of a ventral marker such as ALDH1A3 and the like, the concentration of the dorsalization signal transmitter to be added can be determined such that the gene expression level of ALDH1A3 is not more than 50%, preferably not more than 20%, more preferably not more than 5%, compared to the index.

The "concentration that does not induce most dorsal marker" can be appropriately determined by those of ordinary skill in the art. For example, using a method such as immunostaining and the like using an antibody against the above-mentioned most dorsal marker and the like, a region showing the expression of the above-mentioned most dorsal marker in a retinal tissue in a stage where the emergence rate of cone photoreceptor precursor reaches maximum is analyzed using image analysis software such as Image J and the like, and the concentration of the dorsalization signal transmitter is appropriately determined such that a region not showing induction of the expression of the most dorsal marker (wherein "not showing induction of expression" means not more than $\frac{1}{5}$, preferably not more than $\frac{1}{10}$, further preferably not more than 1/50, as compared to the expression level of the most dorsal neural retinal tissue in vivo) is not less than 50%, preferably not less than 80%, more preferably not less than 90%, further more preferably not less than 99%, of the neural retinal tissue.

One embodiment is a method for increasing a proportion of a cone photoreceptor precursor in a photoreceptor precursor and a photoreceptor comprised in a retinal tissue, comprising a step of culturing a retinal tissue, in an initial developmental stage to a stage where an emergence rate of a cone photoreceptor precursor reaches maximum, in a medium comprising a dorsalization signal transmitter at a concentration sufficient to promote expression of a dorsal marker.

The "concentration sufficient to promote expression of a dorsal marker" can be easily determined by those of ordinary skill in the art. For example, it can be easily determined by analyzing the expression level of the above-mentioned dorsal marker protein or gene (mRNA). To be specific, various concentrations of a dorsalization signal transmitter is added to a medium, and a concentration at which the dorsal expression level or gene expression level becomes the highest can be determined by immunostaining or quantitative PCR.

For example, the concentration of the dorsalization signal transmitter can be determined to be a concentration at which the expression of CYP26A1 and/or CYP26C1 is most strongly induced. To be specific, it is a concentration at which the expression level of CYP26A1 is not less than 1.2 times, preferably not less than 1.5 times, more preferably not less than 2 times, compared to a retinal tissue in which ventralization is performed by the aforementioned BMP signal transduction pathway inhibitor and the expression of CYP26A1 is suppressed. When the concentration of the dorsalization signal transmitter is determined based on the expression level of CYP26A1 and/or CYP26C1, retinoic acids such as all trans retinoic acids, 9-cis retinoic acid and the like excessively induce expression of these genes irrespective of the degree of dorsalization, and make it difficult to determine the concentration of the dorsalization signal transmitter. Therefore, determination using a medium substantially free of retinoic acids is preferable.

On the other hand, in the case of ALDH1A1, ALDH1A1 is weakly expressed in the CYP26A1-positive region, and the expression level becomes continuously higher as it becomes closer to the dorsal side. That is, it is a marker showing a higher expression level in the COUP-TF II-positive region, which is most dorsal in the neural retinal tissues, as compared to CYP26A1 or CYP26C1-positive region. Accordingly, expression of ALDH1A1 is desirably not too high. To be specific, in a stage where emergence rate of cone photoreceptor precursor reaches maximum, the frequency of ALDH1A1-positive cell is not more than about 1%. That is, it is desirable to adjust the concentration of the dorsalization signal transmitter to a concentration that renders the expression of ALDH1A1 sufficiently low in this stage.

Here, the "concentration that renders the expression of ALDH1A1 sufficiently low" can be determined by those of ordinary skill in the art. For example, using a method such as immunostaining and the like conventionally performed using an antibody against ALDH1A1 and the like, a region showing the expression of ALDH1A1 in a retinal tissue in a stage where the emergence rate of cone photoreceptor precursor reaches maximum is analyzed using image analysis software such as Image J and the like, and a concentration at which the region is not more than 50%, preferably not more than 20%, more preferably not more than 10%, further more preferably not more than 1%, of a neural retinal tissue in the retinal tissue can be determined. Alternatively, such gene expression level of the retinal tissue can be measured by quantitative PCR and the like. That is, for example, when BMP4 at a comparatively high concentration of 0.45 nM-1.35 nM is added, expression of ALDH1A1 is excessively induced. Accordingly, a concentration at which the expression level of ALDH1A1 is preferably 30%, more preferably 15%, further more preferably not more than 10%, of that when differentiation induction is performed by adding 1.35 nM BMP4 can be determined.

In one embodiment of the present invention, the "dorsalization signal transmitter at a concentration that suppresses expression of a ventral marker, and does not induce expression of the most dorsal marker" is a dorsalization signal transmitter at a concentration such that, in a retinal tissue in a stage where an emergence rate of cone photoreceptor precursor relative to the cells contained in the retinal tissue reaches maximum, the proportion of the number of cells that express OC2 relative to the total number of cells contained in the neural retinal tissue is suppressed to about 20%-70%, preferably about 30%-70%, more preferably about 50%-65% compared to that when a dorsalization signal transmitter is not added, or about 30%-60%, preferably about 40%-50% compared to that when the aforementioned BMP signal transduction pathway inhibitor is added. Alternatively, a dorsalization signal transmitter at a concentration such that a OC2 protein expression level of OC2-positive cell is suppressed to about 20%-70%, preferably about 30%-70%, more preferably about 30-40% compared to that when a dorsalization signal transmitter is not added and/or the aforementioned BMP signal transduction pathway inhibitor is added can be mentioned.

Here, the proportion of the number of OC2-positive cells contained in the neural retinal tissue can be determined by those of ordinary skill in the art by performing conventionally possible immunostaining and the like by using an anti OC2 antibody, DAPI and the like, measuring the number of OC2-positive cells, the number of DAPI-positive cells and the like, and identifying the ratio thereof contained in a neural retinal tissue. The expression level of OC2 protein can be determined by those of ordinary skill in the art by performing conventionally possible immunostaining and the like by using an anti OC2 antibody, DAPI and the like, and analyzing the region stained by an anti OC2 antibody by using image analysis software such as Image J and the like to identify the signal intensity of OC2-positive cells. Alternatively, the proportion of the number of OC2-positive cells contained in a neural retinal tissue and/or the OC2 protein expression level of OC2-positive cell may be identified by analysis using conventional flow cytometry using an antibody against OC2 protein.

When a thyroid gland hormone signal transduction pathway agonist is added to a medium, OC2-positive cells increase, whereas the mean of OC2 protein expression level decreases. When setting the concentration of a dorsalization signal transmitter, therefore, it is preferable to determine the concentration in advance using a medium not containing a thyroid gland hormone signal transduction pathway agonist.

On the other hand, when the concentration of a dorsalization signal transmitter is determined using ALDH1A1, ALDH1A3, COUP-TFI, COUP-TF II and the like as an index, a thyroid gland hormone signal transduction pathway agonist may be added to the medium. However, since the effect of the thyroid gland hormone signal transduction pathway agonist on ventralization and dorsalization is unknown, it is preferable to determine the concentration of a dorsalization signal transmitter in advance using a medium not containing a thyroid gland hormone signal transduction pathway agonist.

A person skilled in the art can specify the above-mentioned "stage where photoreceptor precursor first emerges" by immunostaining with photoreceptor precursor marker and/or cone photoreceptor precursor marker, nuclear staining with DAPI and the like. Specifically, for example, the retinal tissue undergoing differentiation is fixed with para-formaldehyde and the like, and frozen sections are prepared. The frozen sections are stained with, for example, CRX antibody, TRβ2 antibody, RXR-γ antibody and the like, the nucleus is simultaneously stained with DAPI and the like, and the stage where photoreceptor precursor and/or cone photoreceptor precursor first emerge/emerges in the retinal tissue is identified.

A person skilled in the art can specify the above-mentioned "stage where emergence rate of cone photoreceptor precursor reaches maximum" by immunostaining with photoreceptor precursor marker and/or cone photoreceptor precursor marker, nuclear staining with DAPI and the like.

Specifically, for example, the retinal tissue undergoing differentiation is collected at certain intervals (e.g., 1-20 days) (e.g., 40 days, 50 days, 60 days, 70 days, 80 days after the start of culture), and fixed with para-formaldehyde and the like and frozen sections are prepared. The frozen sections are stained with, for example, CRX antibody, TRβ2 antibody, RXR-γ antibody and the like, the nucleus is simultaneously stained with DAPI and the like, and the proportion of the number of cone photoreceptor precursors (i.e., the number of CRX and RXR-γ, or cells expressing CRX and TRβ2) based on the total number of cells contained in the neural retinal tissue is determined. At this time, the ratio of the number of cone photoreceptor precursor marker-positive cells that emerge in the above-mentioned certain period to the total number of cells, that is, the emergence ratio, is determined at plural times (timing). As a result, the period when the proportion of emergence of cone photoreceptor precursor marker-positive cells is the highest can be specified as "a stage where emergence rate of cone photoreceptor precursor reaches maximum".

In addition, BrdU, EdU and the like which are incorporated into the cells in a proliferation period (here, retinal progenitor cell or neural retinal progenitor cell having proliferation ability) are added to a culture medium for a particular period (e.g., 1-7 days), the proportion of the cells that incorporated BrdU, EdU and the like and differentiated into cells that express the aforementioned cone photoreceptor precursor marker is measured by immunostaining and the like well known to those skilled in the art, and the period when the emergence rate of the cone photoreceptor precursor is the highest is determined from the proportion, whereby "a stage where emergence rate of cone photoreceptor precursor reaches maximum" can be identified. Specifically, for example, BrdU, Edu and the like are added to a culture medium for cultivating a retinal tissue in any differentiation stage and the retinal tissue is cultured for any one day. The next day, the retinal tissue is recovered and the proportion of CRX and RXR-γ-positive cells or the proportion of CRX and TRβ2-positive cells in BrdU or EdU-positive cells is measured. The day of addition of BrdU or EdU that yields the highest proportion of the cells in the neural retinal tissue can be identified as "a stage where emergence rate of cone photoreceptor precursor reaches maximum".

Specifically, the "stage where emergence rate of cone photoreceptor precursor reaches maximum" corresponds to 30 to 50 days, preferably 30 to 40 days, after emergence of cone photoreceptor precursor is observed.

In the method of the present invention, the step of culturing in a medium containing a dorsalization signal transmitter may be performed in any period between the "initial developmental stage" and the "stage where emergence rate of cone photoreceptor precursor reaches maximum", and the timing of start of the step and period thereof are not limited as long as they are within this period. As the time of start of the step, it is preferably started within about 40 days, more preferably days, from the initial developmental stage, further more preferably in the initial developmental stage.

The medium used when culturing the retinal tissue in an initial developmental state in the presence of the dorsalization signal transmitter is not particularly limited as long as it does not contain a substance that inhibits the effect of the dorsalization signal transmitter in an amount capable of inhibiting the aforementioned effect, and a medium obtained by appropriately adding an additive as necessary to a commercially available medium for cell culture can be used. The medium is preferably a medium capable of maintaining a continuous epithelial structure of a retinal tissue. A specifically usable medium includes, for example, a medium added with Wnt2b, Neurobasal medium, a medium containing Neurobasal medium and the like, and may be a Neurobasal medium added with Wnt2b. A medium for maintaining a continuous epithelial tissue explained below can be used.

The aforementioned medium may or may not contain retinoids (e.g., retinoic acid or a derivative thereof), but in one embodiment, it may contain 9-cis retinoic acid. A more preferred embodiment is a medium that substantially does not contain retinoids, preferably retinoids biosynthesized by ALDH1A3 and which inhibits differentiation of cone photoreceptor precursor. Specific examples of the retinoids that are biosynthesized by ALDH1A3 and inhibit differentiation of cone photoreceptor precursor include all-trans retinoic acid (to be also referred to as atRA) and the like.

The concentration of the dorsalization signal transmitter contained in the medium may be a concentration affording a BMP signal transduction pathway activating action that does not suppress emergence of a cone photoreceptor precursor. The concentration of a dorsalization signal transmitter that does not suppress emergence of a cone photoreceptor precursor can be appropriately set by the proportion of a cone photoreceptor precursor that emerges in a neural retinal tissue and the like. To be specific, it can be set such that not less than 10%, preferably not less than 13%, more preferably not less than 16%, on average of the total number of cells are photoreceptor precursors in a neural retinal tissue 30-50 days, preferably 30-40 days, after emergence of a photoreceptor precursor. Specifically, when a BMP signal transduction pathway agonist, particularly BMP4, is used as a dorsalization signal transmitter, BMP4 is used at a concentration of preferably 0.01 nM-0.90 nM, further preferably 0.05 nM-0.45 nM.

The concentration of the dorsalization signal transmitter contained in the medium may also be a concentration affording a Wnt signal transduction pathway activating action that does not prohibits emergence of a retinal pigment epithelial cell. The concentration of the dorsalization signal transmitter that prohibits emergence of a retinal pigment epithelial cell is specifically, for example, a concentration affording a Wnt signal pathway activating action equivalent to that of 0.01 nM-0.90 nM, preferably 0.05 nM-0.45 nM, BMP4.

When the medium is substantially free of exogenous retinoids such as 9-cis retinoic acid and the like, a dorsalization signal transmitter contained in the medium is preferably 0.05 nM-0.15 nM, further preferably 0.1 nM-0.15 nM, BMP4. In addition, Wnt signal transduction pathway agonist may be allowed to act at a concentration that affords a BMP signal transduction pathway activating action equivalent to BMP4 at preferably 0.05 nM-0.15 nM, further preferably 0.1 nM-0.15 nM.

When the medium contains retinoids such as 9-cis retinoic acid and the like, a dorsalization signal transmitter to be contained in the medium is, for example, BMP4 at preferably 0.15 nM-0.90 nM, further preferably 0.15 nM-0.45 nM. In addition, a Wnt signal transduction pathway agonist may be allowed to act at a concentration that affords a BMP signal transduction pathway activating action equivalent to BMP4 at preferably 0.15 nM-0.90 nM, further preferably 0.15 nM-0.45 nM.

As the dorsalization signal transmitter, an SHH signal transduction pathway inhibitor that inhibits ventralization signal transduction can be mentioned. As the SHH signal transduction pathway inhibitor, SHH receptor antagonist, SHH dominant-negative form, antibody against SHH signal transduction pathway agonist, soluble SHH receptor and the like can be mentioned. As the SHH signal transduction pathway inhibitor, GANT58, GANT61, Jervine, SANT-1, Veratramine, Cyclopamine, Cyclopamine-KAAD (GENES & DEVELOPMENT 16:2743-2748) and the like can be specifically mentioned. As a preferable SHH signal transduction pathway inhibitor, Cyclopamine-KAAD can be mentioned. The concentration of Cyclopamine-KAAD contained in the medium is specifically 0.01 μM-5 μM, further preferably 0.2 μM-1 μM.

In addition, as the dorsalization signal transmitter, the above-mentioned BMP signal transduction pathway agonist, the above-mentioned Wnt signal transduction pathway agonist and/or the above-mentioned SHH signal transduction pathway inhibitor that inhibits ventralization signal transduction may be used in combination. When an SHH signal transduction pathway inhibitor that inhibits the above-mentioned ventralization signal transduction is used as the dorsalization signal transmitter, it is preferably used in combination with the above-mentioned BMP signal transduction pathway agonist and/or the above-mentioned Wnt signal transduction pathway agonist to prepare a retinal tissue containing a cone photoreceptor precursor at a higher ratio.

The period of culturing in a medium containing a dorsalization signal transmitter may be any as long as the effect of the dorsalization signal transmitter continues until the period when a rod photoreceptor precursor emerges when cultured in the absence of the dorsalization signal transmitter, and can be appropriately determined to be typically not less than 4 days, preferably not less than 20 days, more preferably not less than 70 days. Specifically, culturing for, for example, 50 days-170 days is possible. Further specifically, culturing for 70 days-100 days is possible; however, a longer period of addition is preferable to suppress emergence of a rod photoreceptor precursor.

The cone photoreceptor precursor can be matured into L cone photoreceptor, M cone photoreceptor or S cone photoreceptor. Preferably, a neural retinal tissue rich in L cone photoreceptor and M cone photoreceptor can be obtained by culturing cone photoreceptor precursor in the presence of a dorsalization signal transmitter. At this time, to mature into L cone photoreceptor and M cone photoreceptor, it is more preferable to differentiate by simultaneously combining thyroid gland hormone signal transduction pathway agonist, and to mature into S cone photoreceptor, it is preferable to differentiate in a medium substantially free of thyroid gland hormone signal transduction pathway agonist. It is further preferable to differentiate in a serum-free medium.

To induce selective differentiation into L cone photoreceptor or M cone photoreceptor, it is preferable to use a BMP4 signal transmitter as a dorsalization signal transmitter, and it is added to the culture medium at a final concentration of not less than 0.01 nM and not more than 100 nM, preferably not less than 0.05 nM and not more than 10 nM, more preferably not less than 0.1 nM and not more than 1.5 nM. When T3 is used as a thyroid gland hormone signal transduction pathway agonist, it is allowed to act at a concentration of not less than 0.01 nM and not more than 100 nM, preferably not less than 0.5 nM and not more than 10 nM, more preferably not less than 2 nM and not more than 10 nM. When T4 is used as a thyroid gland hormone signal transduction pathway agonist, it is allowed to act at a concentration of T4 showing an action equivalent to the above-mentioned T3. The period of culture by simultaneously combining a dorsalization signal transmitter and a thyroid gland hormone signal transduction pathway agonist is not particularly limited, and it is typically not less than 50 days, preferably not less than 70 days, more preferably not less than 100 days, further more preferably not less than 150 days. As the time of starting culturing by simultaneously combining a dorsalization signal transmitter and a thyroid gland hormone signal transduction pathway agonist, culturing is started after 100 days, preferably after 150 days, from the first emergence of photoreceptor precursor, and culturing is performed by simultaneously combining a dorsalization signal transmitter and a thyroid gland hormone signal transduction pathway agonist until usually after 250 days, preferably after 300 days, more preferably after 400 days, after the first emergence of a photoreceptor precursor. To mature a cone photoreceptor precursor into an L cone photoreceptor or M cone photoreceptor, it is preferably cocultured with retinal pigment epithelium or a conditioned medium (condition medium) after culturing the retinal pigment epithelium is used.

Conversely, a photoreceptor precursor (cone photoreceptor precursor or cone photoreceptor, rod photoreceptor precursor or rod photoreceptor) in the retinal tissue can also be maintained in a state before differentiation into L cone photoreceptor, M cone photoreceptor and/or S cone photoreceptor and before final maturation and a state in which a molecule necessary for light response such as visual pigment and the like is not expressed or produced. It is known that a photoreceptor precursor is connected to a bipolar cell along with maturation. Thus, in this way, the connection between the photoreceptor precursor and the bipolar cell in the retinal tissue to be transplanted is suppressed, and when the retinal tissue is transplanted, the connection efficiency of the photoreceptor precursor in the prepared retinal tissue and the recipient bipolar cell can be increased. To be specific, the state before the final maturation can be maintained by culturing in a medium free of glutamic acid, more preferably a medium free of glutamic acid and aspartic acid, further preferably a medium free of a neurotransmitter such as glutamic acid, aspartic acid and the like. Further more preferably, the state that has not reached the final maturation can be maintained by culturing in a medium containing a serum, specifically, a medium containing not less than 5%, preferably not less than 10% of a serum. As said medium, the below-mentioned medium for maintaining a continuous epithelial tissue can be specifically mentioned. While the serum used here is not particularly limited, specifically, fetal bovine serum (FBS) can be mentioned.

That is, a method for suppressing final maturation of photoreceptor precursor, including a step of culturing a retinal tissue containing a photoreceptor precursor in a medium not containing a neurotransmitter and containing a serum is also within the scope of the present invention.

As the dorsalization signal transmitter, the above-mentioned Wnt signal transduction pathway agonist can also be used. Specifically in this case, the following steps (1) and (2) may be repeated:

(1) the above-mentioned Wnt signal transduction pathway agonist is added to the medium and cultured for 1-5 days, preferably 1-3 days;

(2) culturing in a medium substantially free of the above-mentioned Wnt signal transduction pathway agonist is performed for 1-15 days, 1-10 days, preferably 1-7 days or 5-10 days. In this way, the intensity of Wnt signal can be adjusted.

6. Method for Producing Neural Retinal Tissue

In one embodiment of the present invention, a production method of a matured neural retinal tissue, or a neural retinal tissue that can be matured into a matured neural retinal tissue, which contains the following steps can be mentioned:

(1) a step of culturing a retinal tissue in an initial developmental stage in a medium to obtain a retinal tissue containing a neural retinal progenitor cell, and in any stage between a differentiation stage immediately after emergence of a ganglion cell and a differentiation stage where emergence rate of a cone photoreceptor precursor reaches maximum, and (2) a step of culturing the retinal tissue obtained in step (1) in a medium containing a thyroid gland hormone signal transduction pathway agonist.

As another embodiment of the present invention, a production method of a matured neural retinal tissue, or neural retinal tissue that can be matured into a matured neural retinal tissue wherein the medium in the above-mentioned step (1) and/or the medium in at least a part of step (2) are/is a medium containing a dorsalization signal transmitter at a concentration that suppresses expression of a ventral marker can be mentioned. That is, a production method of a matured neural retinal tissue, or neural retinal tissue that can be matured into a matured neural retinal tissue containing the following steps:

(1) a step of culturing a retinal tissue in an initial developmental stage in a medium, containing a neural retinal progenitor cell to obtain a retinal tissue in any stage between a differentiation stage immediately after emergence of a ganglion cell and a differentiation stage where emergence rate of a cone photoreceptor precursor reaches maximum, (2) a step of culturing the retinal tissue obtained in step (1) in a medium containing a thyroid gland hormone signal transduction pathway agonist, wherein the medium in the above-mentioned step (1) and/or the medium in at least a part of step (2) are/is a medium containing a dorsalization signal transmitter at a concentration that suppresses expression of a ventral marker can be mentioned.

Explanation follows hereunder.

In the above-mentioned step (1), a method of producing "a retinal tissue in an initial developmental stage" is as described in the above-mentioned 2. In addition, a step of obtaining "the retinal tissue containing a neural retinal progenitor cell and in a differentiation stage immediately after emergence of a ganglion cell" in step (1), and a step of obtaining a retinal tissue in "a differentiation stage where emergence rate of a cone photoreceptor precursor reaches maximum" from the differentiation stage are as described in the above-mentioned 3. A specific embodiment of the step of culturing in a medium containing a thyroid gland hormone signal transduction pathway agonist in the above-mentioned step (2) is as described in the above-mentioned 4.

The concentration, addition method, timing and period of "a dorsalization signal transmitter at a concentration that suppresses expression of a ventral marker" in the above-mentioned step (1) and/or step (2) are as described in the above-mentioned 5.

The "matured neural retinal tissue" is a neural retinal tissue that contains cone photoreceptor precursor and/or cone photoreceptor, rod photoreceptor precursor and/or rod photoreceptor, ganglion cell, amacrine cell, horizontal cell, bipolar cell and Muller cell, and forms a layer structure. As one embodiment of the matured neural retinal tissue prepared by the method described in the present specification, a neural retinal tissue having the following characteristics can be mentioned:

(i) Muller cell is contained;

(ii) the proportion of bipolar cell (specifically PAX6-negative and CHX10-strongly positive cell), ganglion cell, amacrine cell and horizontal cell (specifically PAX6-positive and CHX10-negative cell) is not less than 30%, preferably not more than 25%, more preferably not less than 20%, further more preferably not more than 14%, based on the total number of cells;

(iii) the proportion of ganglion cell, amacrine cell and horizontal cell (specifically PAX6-positive and CHX10-negative cell) is not less than 30%, preferably not less than 20%, more preferably not more than 15%, further more preferably not more than 10%, based on the total number of cells;

(iv) the proportion of bipolar cell (specifically PAX6-negative and CHX10-strongly positive cell) is not more than 10%, preferably not more than 5%, based on the total number of cells;

(v) the proportion of CRX-positive photoreceptor precursor and photoreceptor is not less than 40%, preferably not less than 50%, further preferably not less than 53%, more preferably not less than 57%, further more preferably not less than 66%, of the total number of cells;

(vi) the proportion of cone photoreceptor precursor and cone photoreceptor to photoreceptor precursor and photoreceptor is not less than 70%;

(vii) an ectopic photoreceptor precursor or photoreceptor is present in a region corresponding to the basement membrane side from the outer nuclear layer;

(viii) CRABP or CRALBP-positive cell is contained; and (ix) the number of RXR-γ-positive and NRL-negative cells in CRX-positive cells is not less than 32%, preferably not less than 40%, more preferably not less than 54%, further more preferably 57%.

The "neural retinal tissue that can be matured into a matured neural retinal tissue" is not limited as long as it is a neural retinal tissue that can be matured into a matured neural retinal tissue by differentiation and maturation to achieve the same proportion as the cells constituting the aforementioned "matured neural retinal tissue" and the same structure as the aforementioned "matured neural retinal tissue" by culturing under appropriate conditions.

"At least a part of the step of step (2)" when a dorsalization signal transmitter is added shows any period contained in step (2), and the length of the period is not limited. The period may be continuous or intermittent.

Specifically, culturing in a medium containing a dorsalization signal transmitter can be performed in the whole period of step (1), a partial period of step (2), the whole period of step (2), the whole period of step (1) and a partial period of step (2), or the whole period of step (1) and the whole period of step (2).

In step (1), emergence of a neural retinal progenitor cell can be detected by well-known markers such as RX, PAX6, CHX10 and the like, and the number of days required for step (1) can be determined as appropriate. When, for example, an aggregate containing a retinal tissue is formed from a pluripotent stem cell as a starting material by suspension culture by the method described in the above-mentioned starting material production methods 1-4, it corresponds to day 12-day 18, specifically, for example, day 15-day 18, from the start of suspension culture.

When, for example, an aggregate containing a retinal tissue is formed from a pluripotent stem cell as a starting material by suspension culture by the method described in the above-mentioned starting material production methods 5, 6 and/or 7, it corresponds to day 22-day 30, specifically for example, days 22-25 (corresponding to about day 0-day 8, specifically days 0-3, from the start of culture in a serum-free medium or serum-containing medium not containing Wnt signal transduction pathway agonist).

The emergence of ganglion cell can be detected by well-known markers such as BRN and the like, and the number of days required for step (1) can be determined as appropriate. When, for example, an aggregate containing a retinal tissue is formed from a pluripotent stem cell as a starting material by suspension culture by the method described in the above-mentioned starting material production methods 1-4, the stage where a ganglion cell emerges, namely, a differentiation stage immediately after emergence of ganglion cell, corresponds to day 27-day 40, preferably day 28-day 37, more preferably day 28-day 33, from the start of suspension culture.

For example, when an aggregate containing a retinal tissue is formed by suspension culture using a pluripotent stem cell as a starting material by the method described in the above-mentioned starting material production methods 5, 6 and/or 7, it specifically corresponds to day 33-day 45, preferably about day 33-42, more preferably day 33-38, from the start of suspension culture (corresponding to about day 11-23, preferably day 11-20, more preferably day 11-16, from the start of culture in a serum-free medium or serum-containing medium not containing Wnt signal transduction pathway agonist).

The differentiation stage immediately after emergence of a ganglion cell is a differentiation stage where the proportion of a neural retinal progenitor cell detected by well-known markers such as RX, PAX6 and CHX10 and the like after emergence of ganglion cell is not less than 30%, preferably not less than 50%, more preferably not less than 70%, further preferably not less than 80%, further more preferably not less than 90%, particularly preferably not less than 99%, of the total number of cells, and the proportion of a ganglion cell marker-positive (preferably, BRN3-positive) ganglion cell is not more than 40%, preferably not less than 20%, not more than 10%, not more than 5%, more preferably not more than 1%, further preferably not more than 0.1%, further more preferably not more than 0.01%, of the total number of cells, or within about 10 days, preferably within about 5 days, more preferably within about 1 day, further more preferably within 1 hr, after emergence of a ganglion cell.

In one embodiment of the present invention, when T3 is used as a thyroid gland hormone signal transduction pathway agonist in step (2), for example, it can be added to a medium to fall within the range of 0.1 nM to 1000 nM. The concentration is preferably 1-500 nM; more preferably 10-100 nM; further preferably 30-90 nM; further more preferably about 60 nM.

That is, as the concentration of the thyroid gland hormone signal transduction pathway agonist, a concentration showing thyroid gland hormone signal transduction promoting activity corresponding to T3 at a concentration of 0.1-1000 nM, preferably 1-500 nM, more preferably 10-100 nM, further preferably 30-90 nM, further more preferably about 60 nM, can be mentioned. The thyroid gland hormone signal transduction promoting activity here can be appropriately determined, for example, as a concentration that suppresses differentiation of bipolar cell, and any of amacrine cell, ganglion cell and horizontal cell and does not suppress differentiation of photoreceptor precursor, as described above.

That is, for example, in a neural retinal tissue in a late stage of differentiation to the extent that Muller cell has emerged (e.g., corresponding to about day 180-200 from the start of suspension culture when a retinal tissue produced by the method described in the above-mentioned starting material production methods 1-3, 4, 5-7 is the starting material), the concentration of the thyroid gland hormone signal transduction pathway agonist can be determined such that PAX6-negative/CHX10-strongly positive cells are not more than 8%, preferably, not more than 6%, more preferably not more than 5%. Alternatively, the concentration of the thyroid gland hormone signal transduction pathway agonist can be determined such that the proportion of PAX6-positive/CHX10-negative cell is not less than 30%, preferably not less than 20%, more preferably not more than 15%, further more preferably not more than 10%. Alternatively, the concentration thyroid gland hormone signal transduction pathway agonist can be determined such that the proportion of photoreceptor (or photoreceptor precursor) is not less than 40%, preferably not less than 45%, more preferably not less than 50%, further more preferably not less than 57%, not less than 66%.

Alternatively, the concentration of the thyroid gland hormone signal transduction pathway agonist may be determined as a concentration such that, for example, in a retinal tissue in a differentiation stage where the emergence rate of cone photoreceptor precursor (e.g., CRX-positive and TRβ2-positive cell, or CRX-positive and RXR-γ-positive) reaches maximum (namely, differentiation stage corresponding to 30-50 days, preferably 30-40 days, after recognition of the emergence of cone photoreceptor precursor, or for example, about day 60-70 from the start of suspension culture when a retinal tissue produced by the method described in the starting material production methods 1-4 is the starting material, or a differentiation stage corresponding to about day 65-75 from the start of suspension culture when a retinal tissue produced by the method described in the starting material production methods 5-7 is the starting material), ectopic photoreceptor precursor that emerges on the basement membrane side from the neuroblastic layer (NBL) is observed, and the proportion of the photoreceptor precursor that emerges on the apical surface side containing a neuroblastic layer (NBL) is at a certain level, preferably the same level, as compared to the proportion of the ectopic photoreceptor precursor that emerges on the basement membrane side from NBL. Specifically, the concentration of the thyroid gland hormone signal transduction pathway agonist may be set such that the ratio of the proportion per area of photoreceptor precursors contained in the basement membrane side from NBL and the apical surface side containing NBL is 10:1 to 1:10, preferably 2:1 to 1:2, more preferably about 10:7 to 7:10.

Alternatively, the concentration of the thyroid gland hormone signal transduction pathway agonist to be added can be determined such that the proportion of photoreceptor precursor which is CRX-positive cell is not less than 11%, preferably not less than 15%, more preferably not less than 20%, further preferably not less than 25%, further more preferably not less than 30%, based on all cells contained in the neural retinal tissue. Alternatively, it may be set such that the proportion of CRX-positive and TRβ2-positive cells is not less than 7%, preferably not less than 10%, more preferably not less than 11%, further preferably not less than 15%, further more preferably not less than 16%, not less than 20%, based on all cells contained in the neural retinal tissue.

In one embodiment of the present invention, the medium in step (1) and/or at least a part of the medium in step (2) may be a medium containing a dorsalization signal transmitter that suppresses expression of the ventral marker. When a dorsalization signal transmitter is contained, the order of addition of the thyroid gland hormone signal transduction pathway agonist and the dorsalization signal transmitter to a medium in the above-mentioned step (1)-step (2) may be simultaneous or either may be earlier.

By culturing in a medium containing a dorsalization signal transmitter in the aforementioned step (1) and/or step (2), among the photoreceptor precursors contained in the retinal tissue, the proportion of cone photoreceptor precursor can be further increased as compared to when the thyroid gland hormone signal transduction pathway agonist is acted alone. That is, by this step, a retinal tissue in which the proportion of any of PAX6-negative/CHX10-strongly positive cell, PAX6-positive/CHX10-negative cell and the like, namely bipolar cell, and any one of amacrine cell, ganglion cell, horizontal cell and the like is decreased, and the proportion of the photoreceptor precursor among the cells contained in the retinal tissue, particularly the proportion of cone photoreceptor precursor among the photoreceptor precursors, is simultaneously increased further can be produced.

Furthermore, by this step, it is possible to form an ectopic photoreceptor layer (photoreceptor precursor layer) in the cell layer on the basement membrane side such as an inner nuclear layer where bipolar cell, amacrine cell and the like exist, a ganglion cell layer where ganglion cell exists in a retinal tissue, and further increase the proportion of cone photoreceptor precursor among the contained photoreceptor precursors.

The retinal tissue thus produced has a higher proportion of cone photoreceptor precursor, and can be a retinal tissue more suitable for transplantation into the macula or the central part of the macula since, when transplanted, the physical distance between bipolar cells of the recipient and the photoreceptor precursor contained in the transplanted retinal tissue becomes shorter.

In step (1), the dorsalization signal transmitter may be added all the time when a dorsalization signal transmitter is added, or may be added during the process. Preferably, at least step (1) includes culturing in a medium containing a dorsalization signal transmitter.

In step (2), when a dorsalization signal transmitter is added, more preferably, the cells are cultured in a medium containing a dorsalization signal transmitter for at least a part of step (2), further preferably for the entire period.

Specifically, culturing in a medium containing a dorsalization signal transmitter may be started in any period between the "initial developmental stage" and the "stage where an emergence rate of cone photoreceptor precursor reaches maximum" and is not particularly limited. It is preferably started within about 40 days from the initial developmental stage, more preferably 20 days, further more preferably in the initial developmental stage.

The above-mentioned "stage where an emergence rate of cone photoreceptor precursor reaches maximum" may be identified by adding a thyroid gland hormone signal transduction pathway agonist to the medium. However, since the thyroid gland hormone signal transduction pathway agonist improves the emergence rate of cone photoreceptor precursor, thus making it difficult to identify the above-mentioned stage. Thus, it is preferable to culture the gland hormone signal transduction pathway agonist and dorsalization signal transmitter without adding them to the medium, and to identify the above-mentioned stags in advance.

The period of culturing in the presence of a thyroid gland hormone signal transduction pathway agonist, or a thyroid gland hormone signal transduction pathway agonist and a dorsalization signal transmitter may be any as long as the effect of the thyroid gland hormone signal transduction pathway agonist, or the thyroid gland hormone signal transduction pathway agonist and dorsalization signal transmitter continues until the above-mentioned "differentiation stage where emergence rate of cone photoreceptor precursor reaches maximum", preferably until a rod photoreceptor precursor emerges when cultured in the absence of a thyroid gland hormone signal transduction pathway agonist and/or dorsalization signal transmitter, and the thyroid gland hormone signal transduction pathway agonist can be conventionally set for not less than 20 days, preferably not less than 40 days, more preferably not less than 70 days, and the dorsalization signal transmitter is conventionally set for not less than 4 days, preferably not less than 20 days, more preferably not less than 40 days, not less than 70 days as appropriate. Specifically, for example, a thyroid gland hormone signal transduction pathway agonist is continued for preferably 20 days-40 days (corresponding to a period up to a differentiation stage where emergence rate of cone photoreceptor precursor reaches maximum), more preferably 40 days-70 days (corresponding to a stage where rod photoreceptor precursor emerges), further preferably 70 days-100 days, from the first emergence of ganglion cell, further more preferably from first emergence of ganglion cell to the whole of period of step (2). For example, a dorsalization signal transmitter is continued for not less than 4 days, preferably 20 days-50 days (corresponding to a period up to a differentiation stage where emergence rate of cone photoreceptor precursor reaches maximum), more preferably 50 days-70 days, further preferably 70 days-80 days (corresponding to a stage where rod photoreceptor precursor emerges), from the initial developmental stage, further more preferably from initial developmental stage to the whole of period of step (2). The period of culturing in the presence of a thyroid gland hormone signal transduction pathway agonist, or a thyroid gland hormone signal transduction pathway agonist and a dorsalization signal transmitter may be continued until a neural retinal tissue is used for a particular purpose (e.g., transplantation).

As one embodiment of the present invention, the above-mentioned production method in which the medium of at least a part of the period of step (2) contains a thyroid gland hormone signal transduction pathway agonist, or a thyroid gland hormone signal transduction pathway agonist and a dorsalization signal transmitter, and the obtained retinal tissue is a neural retinal tissue in the differentiation stage where Muller cell has emerged can be mentioned.

The concentration of the thyroid gland hormone signal transduction pathway agonist, or the thyroid gland hormone signal transduction pathway agonist and dorsalization signal transmitter necessary for performing differentiation until a differentiation stage with emergence Muller cell and preparing the above-mentioned neural retinal tissue, and the period of culturing in a medium containing them can be appropriately determined by those of ordinary skill in the art based on the descriptions of the above-mentioned 4. and 5. One embodiment of the above-mentioned neural retinal tissue is described below.

The proportion of the PAX6-positive/CHX10-negative cell in the retinal tissue is not more than 30%, preferably not more than 20%, more preferably not more than 15%, further more preferably not more than 10%. The proportion of the PAX6-negative/CHX10-strongly positive cell in the retinal tissue is not more than 10%, preferably not more than 5%. The total of the PAX6-positive/CHX10-negative cell and the PAX6-negative/CHX10-strongly positive cell in the retinal tissue is not more than 30%, preferably not more than 20%, more preferably not more than 14%.

The proportion of the photoreceptor precursor which is a CRX-positive cell in the retinal tissue is not less than 40%, preferably not less than 50%, more preferably not less than 57%, further more preferably not less than 66%. Alternatively, the number of RXR-γ-positive and NRL-negative cells in the CRX-positive cells in the retinal tissue in the differentiation stage is not less than 32%, preferably not less than 40%, more preferably not less than 54%, further more preferably not less than 57%.

In one embodiment, the retinal tissue characteristically contains an ectopic photoreceptor precursor and/or a photoreceptor. Here, the ectopic photoreceptor precursor and/or photoreceptor means a photoreceptor precursor and/or a photoreceptor present in a layer other than the photoreceptor layer (or outer nuclear layer) among the layers constituting the retina. In the retinal tissue, specifically, the proportion of the photoreceptor precursor contained in the above-mentioned ectopic photoreceptor layer (also called photoreceptor precursor layer) is not less than 10%, preferably not less than 15%, more preferably not less than 20%, further more preferably not less than 25%, of the total number of cells contained in the neural retinal tissue. The proportion of the above-mentioned ectopic photoreceptor precursor is not less than 30%, preferably not less than 40%, more preferably not less than 50%, further more preferably not less than 60%, of the photoreceptor precursor present in the outer nuclear layer.

As for culturing in a medium containing a dorsalization signal transmitter, the above-mentioned 5. can be specifically referred to.

6-1. Production Method of Neural Retinal Tissue that can be Matured into a Matured Neural Retinal Tissue As one embodiment of the present invention, the above-mentioned production method in which the medium of step (2) contains a thyroid gland hormone signal transduction pathway agonist, or a thyroid gland hormone signal transduction pathway agonist and a dorsalization signal transmitter, and the retinal tissue that can be matured into a matured neural retinal tissue and obtained in step (2) is a neural retinal tissue in a differentiation stage where emergence rate of cone photoreceptor precursor reaches maximum can be mentioned.

The concentration of the thyroid gland hormone signal transduction pathway agonist, or the thyroid gland hormone signal transduction pathway agonist and dorsalization signal transmitter necessary for performing differentiation until a differentiation stage where emergence rate of cone photoreceptor precursor reaches maximum and preparing the above-mentioned neural retinal tissue, and the period of culturing in a medium containing them can be appropriately determined by those of ordinary skill in the art based on the descriptions of the above-mentioned 4. and 5. One embodiment of the above-mentioned neural retinal tissue is described below.

The proportion of the photoreceptor precursor which is a CRX-positive cell in the retinal tissue is not less than 11%, preferably not less than 15%, more preferably not less than 20%, further more preferably not less than 25%, further more preferably not less than 30%. Alternatively, the proportion of cone photoreceptor precursor which is a CRX-positive and TRβ2-positive cell in the retinal tissue in the differentiation stage is not less than 7%, preferably not less than 10%, more preferably not less than 11%, further more preferably not less than 15%, further more preferably not less than 16%, not less than 20%.

In one embodiment, the CRX-positive cell and/or CRX-positive and TRβ2-positive cell in the above-mentioned retinal tissue preferably contains ectopic photoreceptor precursor that emerges on the basement membrane side from the neuroblastic layer (NBL). In addition, the proportions of the photoreceptor precursor that emerges on the apical surface side containing a neuroblastic layer (NBL) and the ectopic photoreceptor precursor that emerges on the basement membrane side from NBL are of a certain level, more preferably the same level. Specifically, the ratio of the proportions per area of photoreceptor precursors contained in the basement membrane side from NBL and the apical surface side containing NBL is 10:1 to 1:10, preferably 2:1 to 1:2, more preferably 10:7 to 7:10.

In one embodiment, the proportion of the OTX2-positive cell that expresses OTX2 gene said to be necessary for the differentiation of photoreceptor precursor is not less than 13%, preferably not less than 20%, more preferably not less than 24%, further more preferably not less than 29%, further more preferably not less than 30%, of the retinal tissue.

In one embodiment, irrespective of the presence or absence of the addition of the dorsalization signal transmitter, the proportion of OC2 that expresses in the cone photoreceptor precursor by the addition of the thyroid gland hormone signal transduction pathway agonist is 30-50%, preferably 35%-45%, more preferably 39-43%, based on the total number of cells in the retinal tissue, and it increases compared to no addition of the thyroid gland hormone signal transduction pathway agonist.

The neural retinal tissue can be produced by the aforementioned step (1) and step (2), and can be produced by culturing for 30-50 days, preferably 30-40 days, throughout the whole steps after recognition of emergence of the cone photoreceptor precursor.

In one embodiment of the present invention, a medium containing "a dorsalization signal transmitter at a concentration that suppresses expression of a ventral marker" is preferably used for the whole period of the aforementioned step (1) and step (2), and a medium containing a thyroid gland hormone signal transduction pathway agonist is used for the whole period of step (2). In addition, culturing in the presence of a dorsalization signal transmitter or a thyroid gland hormone signal transduction pathway agonist is preferably started in the initial developmental stage, or immediately after emergence of ganglion cell, as described in the above-mentioned 4. or 5.

In addition, the neural retinal tissue corresponds to an aggregate obtained on about day 60-70, preferably about day 65, from the start of suspension culture when, for example, the retinal tissue in an initial developmental stage uses a retinal tissue produced by the method described in the starting material production methods 1-4 as the starting material, and about day 65-75, preferably about day 70, from the start of suspension culture when a retinal tissue produced by the method described in the starting material production methods 5-7 is the starting material (namely, retinal tissue in the stage where cone photoreceptor precursor that emerges in neural retinal tissue reaches maximum).

Also, as one embodiment of the present invention, the above-mentioned production method in which the medium in at least a part of the period of step (2) (specifically, 40 days-70 days, preferably 70 days-100 days) contains a thyroid gland hormone signal transduction pathway agonist, or a thyroid gland hormone signal transduction pathway agonist and a dorsalization signal transmitter, and the obtained retinal tissue is a neural retinal tissue in a differentiation stage where rod photoreceptor precursor starts to emerge (or differentiation stage where bipolar cell starts to emerge) can be mentioned.

The concentration of the thyroid gland hormone signal transduction pathway agonist, or the thyroid gland hormone signal transduction pathway agonist and dorsalization signal transmitter necessary for performing differentiation until the differentiation stage where rod photoreceptor precursor starts to emerge (or differentiation stage where bipolar cell starts to emerge), and the period of culturing in a medium containing them can be appropriately determined by those of ordinary skill in the art based on the descriptions of the above-mentioned 4. and 5. One embodiment of the above-mentioned neural retinal tissue is described below.

The neural retinal tissue characteristically shows, in a stage where rod photoreceptor precursor starts to emerge (or stage where bipolar cell starts to emerge), a higher proportion of photoreceptor precursor and/or cone photoreceptor precursor than a neural retinal tissue in vivo or a retinal tissue produced in the absence of a thyroid gland hormone signal transduction pathway agonist. That is, the neural retinal tissue contains a CRX-positive cell in a proportion of not less than 20%, preferably not less than 25%, further preferably not less than 30%, further more preferably not less than 40%, further more preferably not less than 50%, of the total number of cells. In addition, in a neural retinal tissue in the differentiation stage, two cells on average, preferably not less than 3 cells on average, more preferably not less than 4 cells on average, are photoreceptor precursors (CRX-positive cells) along a straight line vertical to the tangent line of the apical surface. Also, these neural retinal tissues, preferably the retinal tissues in the differentiation stage, contain an ectopic photoreceptor precursor on the basement membrane side from the neuroblastic layer (NBL).

Here, the stage where rod photoreceptor precursor starts to emerge (or stage where bipolar cell starts to emerge) can be determined by those of ordinary skill in the art by specifying the stage where NRL-positive and CRX-positive cell (or CHX10-strongly positive and PAX6-negative cell) which is a rod photoreceptor precursor marker (or bipolar cell marker) starts to emerge using a conventional method such as immunostaining and the like. Specifically, the stage where the bipolar cell (or rod photoreceptor precursor) starts to emerge is a differentiation stage within 20 days, preferably 15 days, more preferably 10 days, further preferably 5 days, from the emergence of bipolar cell (or rod photoreceptor precursor) and containing neural retinal progenitor cell in a stage of differentiation into bipolar cell (or rod photoreceptor precursor). Whether the neural retinal progenitor cell is in a stage of differentiation into a bipolar cell (or rod photoreceptor precursor) can be determined by adding, to the culture medium, BrdU or EdU and the like to be incorporated into a neural retinal cell as proliferated cell in the retinal tissue and identifying, using an antibody whether the cell that has incorporated BrdU or EdU and the like expresses a marker of the bipolar cell (or rod photoreceptor precursor). For example, BrdU is added for a given period (e.g., 1 day from day 90, 91, 92, 93, 94-day 110 from the start of suspension culture, etc.) to the medium, retinal tissue is analyzed immediately thereafter, and when BrdU-positive and bipolar cell (or rod photoreceptor precursor) marker-positive cell can be observed, then the period (the very day in case of 1 day) of BrdU addition can be identified as a stage containing a neural retinal tissue in a stage of differentiation into bipolar cell (or rod photoreceptor precursor). Alternatively, it may also be identified as a stage where bipolar cell (or rod photoreceptor precursor) marker-positive cell is detected, and BLIMP1-positive cell known to be transiently expressed in a photoreceptor precursor is detected. At this time, since thyroid gland hormone signal transduction pathway agonist has an action of suppressing the emergence of a rod photoreceptor precursor, it is preferable to identify the above-mentioned differentiation stage in advance using a medium not containing a thyroid gland hormone signal transduction pathway agonist.

The neural retinal tissue can be produced by the aforementioned step (1) and step (2), and can be produced by culturing for 55-80 days, preferably 55-70 days, throughout the whole steps after recognition of emergence of the cone photoreceptor precursor. In one embodiment of the present invention, a medium containing "a dorsalization signal transmitter at a concentration that suppresses expression of a ventral marker" is used for the whole period of the aforementioned step (1) and step (2), and a medium containing a thyroid gland hormone signal transduction pathway agonist is used for the whole period of step (2). In addition, culturing in the presence of a dorsalization signal transmitter or a thyroid gland hormone signal transduction pathway agonist is preferably started immediately after emergence of ganglion cell, preferably from an initial developmental stage, as described in the above-mentioned 4. or 5.

The neural retinal tissue corresponds to an aggregate obtained on day 85-100, preferably about day 95, from the start of suspension culture when, for example, a retinal tissue in an initial developmental stage is produced by the above-mentioned starting material production methods 1-4. It corresponds to an aggregate obtained on day 90-105, preferably about day 100, from the start of suspension culture (namely, retinal tissue in a stage where bipolar cell (or rod photoreceptor precursor) starts to emerge) when it is produced by the above-mentioned starting material production methods 5-7.

As one embodiment of the present invention, a production method of a matured neural retinal tissue, or a neural retinal tissue that can be matured into a matured neural retinal tissue which includes the following steps can be specifically mentioned:
- (1') a step of producing a retinal tissue in an initial developmental stage by the method described in the starting material production methods 1-7,
- (2') a step of culturing the retinal tissue in an initial developmental stage formed in step (1') to obtain a retinal tissue containing a neural retinal progenitor cell, and in any stage between a differentiation stage immediately after emergence of a ganglion cell and a differentiation stage where emergence rate of a cone photoreceptor precursor reaches maximum, and
- (3') a step of culturing the retinal tissue obtained in step (2') in a medium containing a thyroid gland hormone signal transduction pathway agonist. Each step is as already explained, step (1') and step (2') can be continuously performed without identifying or isolating a retinal tissue in an initial developmental stage and without interruption between the steps.

As one embodiment of the present invention, a production method of a matured neural retinal tissue, or neural retinal tissue that can be matured into a matured neural retinal tissue, which includes the following steps can be specifically mentioned:
- (a1) a step of forming a cell aggregate by culturing pluripotent cells in suspension in a serum-free medium,
- (a2) a step of producing a retinal tissue in an initial developmental stage containing a retinal progenitor cell or a neural retinal progenitor cell by culturing in suspension the aggregate formed in step (a1) in a medium not containing an SHH signal transduction pathway agonist and containing a BMP signal transduction pathway agonist,
- (a3) a step of culturing the retinal tissue obtained in step (a2) to obtain a retinal tissue containing a neural retinal progenitor cell, and in any stage between a differentiation stage immediately after emergence of a ganglion cell and a differentiation stage where emergence rate of a cone photoreceptor precursor reaches maximum, and
- (a4) a step of culturing the retinal tissue obtained in step (a3) in a medium containing a thyroid gland hormone signal transduction pathway agonist. Each step is as already explained, step (a2) and step (a3) can be continuously performed without identifying or isolating a retinal tissue in an initial developmental stage and without interruption between the steps.

As one embodiment, a production method of a matured neural retinal tissue, or neural retinal tissue that can be matured into a matured neural retinal tissue, which includes the following steps can be specifically mentioned:
- (b1) a step of culturing pluripotent stem cells in the absence of feeder cells and in a medium containing 1) a TGFβ family signal transduction pathway inhibitor and/or an SHH signal transduction pathway agonist, and 2) a factor for maintaining undifferentiated state,
- (b2) a step of forming a cell aggregate by culturing the cells obtained in step (b1) in suspension,
- (b3) a step of producing a retinal tissue in an initial developmental stage containing a retinal progenitor cell or a neural retinal progenitor cell by culturing in suspension the aggregate formed in step (b2) in the presence of a BMP signal transduction pathway agonist,
- (b4) a step of culturing the retinal tissue obtained in step (b3) to obtain a retinal tissue containing a neural retinal progenitor cell, and in any stage between a differentiation stage immediately after emergence of a ganglion cell and a differentiation stage where emergence rate of a cone photoreceptor precursor reaches maximum, and
- (b5) a step of culturing the retinal tissue obtained in step (b4) in a medium containing a thyroid gland hormone signal transduction pathway agonist. Each step is as already explained, step (b3) and step (b4) can be continuously performed without identifying or isolating a retinal tissue in an initial developmental stage and without interruption between the steps.

As one embodiment, a production method of a matured neural retinal tissue or neural retinal tissue that can be matured into a matured neural retinal tissue, which includes the following steps, can be specifically mentioned:
- (c1) a step of culturing pluripotent stem cells in the absence of feeder cells and in a medium containing a factor for maintaining undifferentiated state, and optionally a TGFβ family signal transduction pathway inhibitor and/or an SHH signal transduction pathway agonist,
- (c2) a step of forming a cell aggregate by culturing the cells obtained in step (c1) in suspension in the presence of a SHH signal transduction pathway agonist and/or Wnt signal transduction pathway inhibitor,
- (c3) a step of producing a retinal tissue in an initial developmental stage and containing an retinal progenitor cell or a neural retinal progenitor cell by culturing the aggregate formed in step (c2) in suspension in the presence of a BMP signal transduction pathway agonist,
- (c4) a step of culturing the retinal tissue obtained in step (c3) to obtain a retinal tissue containing a neural retinal progenitor cell, and in any stage between a differentiation stage immediately after emergence of a ganglion cell and a differentiation stage where emergence rate of a cone photoreceptor precursor reaches maximum, and
- (c5) a step of culturing the retinal tissue obtained in step (c4) in a medium containing a thyroid gland hormone signal transduction pathway agonist. Each step is as already explained, step (c3) and step (c4) can be continuously performed without identifying or isolating a retinal tissue in an initial developmental stage and without interruption between the steps.

As one embodiment, a production method of a matured neural retinal tissue or neural retinal tissue that can be matured into a matured neural retinal tissue, which includes the following steps, can be specifically mentioned:
- (d1) a step of culturing pluripotent stem cells in the absence of feeder cells and in a medium containing a factor for maintaining undifferentiated state, and optionally a TGFβ family signal transduction pathway inhibitor and/or an SHH signal transduction pathway agonist,
- (d2) a step of forming a cell aggregate by culturing the cells obtained in step (d1) in suspension in the presence of in some cases a SHH signal transduction pathway agonist and/or Wnt signal transduction pathway inhibitor,
- (d3) a step of culturing the aggregate formed in step (c2) in suspension in the presence of a BMP signal transduction pathway agonist to obtain a cell aggregate containing a retinal progenitor cell or a neural retinal progenitor cell and having a content of CHX10-positive cell of not less than 20% and not more than 100%,
- (d4) a step of culturing the cell aggregate obtained in step (d3) in a serum-free medium or serum-containing medium each containing a Wnt signal transduction pathway agonist and in some case an FGF signal transduction pathway inhibitor for only a period before the emergence of a RPE65 gene-expressing cell, after which culturing the obtained "cell aggregate in which a RPE65 gene-expressing cell has not emerged" in a serum-free medium or serum-containing medium each not containing a Wnt signal transduction pathway agonist to obtain a retinal tissue in an initial developmental stage and containing a ciliary marginal zone-like structure, (d5) a step of culturing the retinal tissue obtained in step (d4) to obtain a retinal tissue containing a neural retinal progenitor cell, and in any stage between a differentiation stage immediately after emergence of a ganglion cell and a differentiation stage where emergence rate of a cone photoreceptor precursor reaches maximum, and (d6) a step of culturing the retinal tissue obtained in step (d5) in a medium containing a thyroid gland hormone signal transduction pathway agonist. Each step is as already explained, step (d4) and step (d5) can be continuously performed without identifying or isolating a retinal tissue in an initial developmental stage and without interruption between the steps.

As one embodiment of the present invention, a production method of a matured neural retinal tissue or neural retinal tissue that can be matured into a matured neural retinal tissue, which includes the following steps, can be specifically mentioned:

(a1) a step of forming an aggregate of pluripotent stem cells by culturing pluripotent cells in suspension in a serum-free medium containing a Wnt signal transduction pathway inhibitor, (e2) a step of producing a retinal tissue in an initial developmental stage and containing a retinal progenitor cell or a neural retinal progenitor cell by culturing the aggregate formed in step (e1) in suspension in a serum-free medium containing a basement membrane preparation, (e3) a step of culturing the retinal tissue obtained in step (e2) to obtain a retinal tissue containing a neural retinal progenitor cell, and in any stage between a differentiation stage immediately after emergence of a ganglion cell and a differentiation stage where emergence rate of a cone photoreceptor precursor reaches maximum, and (e4) a step of culturing the retinal tissue obtained in step (e3) in a medium containing a thyroid gland hormone signal transduction pathway agonist. Each step is as already explained, step (e2) and step (e3) can be continuously performed without identifying or isolating a retinal tissue in an initial developmental stage and without interruption between the steps.

As one embodiment of the present invention, a production method of a matured neural retinal tissue or neural retinal tissue that can be matured into a matured neural retinal tissue, which includes the following steps, can be specifically mentioned:

(f1) a step of forming an aggregate of pluripotent stem cells by culturing pluripotent cells in suspension in a serum-free medium containing a Wnt signal transduction pathway inhibitor, (f2) a step of culturing the aggregate formed in step (f1) in suspension in a serum-free medium containing a basement membrane preparation to obtain a cell aggregate containing a retinal progenitor cell or a neural retinal progenitor cell, in which CHX10-positive cells are present in a proportion of not less than 20% and not more than 100%, (f3) a step of culturing the cell aggregate obtained in step (f2) in a serum-free medium or serum-containing medium each containing a Wnt signal transduction pathway agonist and in some case an FGF signal transduction pathway inhibitor for only a period before the emergence of a RPE65 gene-expressing cell, after which culturing the obtained "cell aggregate in which a RPE65 gene-expressing cell has not emerged" in a serum-free medium or serum-containing medium each not containing a Wnt signal transduction pathway agonist to obtain a retinal tissue in an initial developmental stage and containing a ciliary marginal zone-like structure, (f4) a step of culturing the retinal tissue obtained in step (f3) to obtain a retinal tissue containing a neural retinal progenitor cell, and in any stage between a differentiation stage immediately after emergence of a ganglion cell and a differentiation stage where emergence rate of a cone photoreceptor precursor reaches maximum, and (f5) a step of culturing the retinal tissue obtained in step (f4) in a medium containing a thyroid gland hormone signal transduction pathway agonist. Each step is as already explained, step (f3) and step (f4) can be continuously performed without identifying or isolating a retinal tissue in an initial developmental stage and without interruption between the steps.

6-2. Production Method of Matured Neural Retinal Tissue

A matured neural retinal tissue can be produced by maturing the neural retinal tissue produced in the above-mentioned 6-1. in an appropriate medium. In this case, step (2) encompasses a maturation step. Specifically, an embodiment in which step (2) includes the following steps (2-1) and (2-2) can be mentioned:

(2-1) a step of culturing the retinal tissue obtained in step (1) in a medium containing a thyroid gland hormone signal transduction pathway agonist up to day 30-80 after recognition of emergence of the cone photoreceptor precursor, and (2-2) a step of culturing the retinal tissue obtained in step (2-1) in a medium optionally containing a thyroid gland hormone signal transduction pathway agonist for 60-120 days.

In the above-mentioned step (2-2), the step of culturing the cultured product obtained in step (2-1) in a medium can be appropriately performed by a method well known to those of ordinary skill in the art. The period of step (2-1) and step (2-2) is not particularly limited and culturing may be continued until a retinal tissue in a stage where Muller cell starts to emerge. Specifically, depending on the period required for step (1), when, for example, the retinal tissue produced by the method described in the starting material production methods 5-7 is the starting material, an appropriate period may be set such that the culturing is performed for a period corresponding to about day 33-day 75, preferably day 33-day 100, more preferably day 33-day 130, from the time point when pluripotent stem cell is subjected to suspension culture in step (2-1). Also, depending on the period required for step (1), for example, an appropriate period may be set such that the culturing is performed for a period corresponding to about day 75-day 190, preferably day 100-day 190, more preferably day 130-day 190, from the time point when pluripotent stem cell is subjected to suspension culture in step (2-2). Here, a tissue at about day 33-day 45 from the time point when pluripotent stem cell is subjected to suspension culture is a retinal tissue containing a neural retinal progenitor cell, and in a differentiation stage immediately after emergence of a ganglion cell (one embodiment includes a differentiation stage where cone photoreceptor precursor starts to emerge), a tissue at day 65-day 75 is a retinal tissue in a differentiation stage where emergence rate of cone photoreceptor precursor reaches maximum, a tissue at day 90-day 105 is a retinal tissue in a differentiation stage where bipolar cell (or rod photoreceptor precursor) starts to emerge, a tissue at day 120-day 140 is a retinal tissue in a differentiation stage where outer plexiform membrane can be formed, and a tissue at day 190 is a retinal tissue in a differentiation stage where Muller cell is observed.

For example, when a retinal tissue produced by the method described in the starting material production methods 1-4 is the starting material, an appropriate period may be set such that the culturing is performed for a period corresponding to about day 27-day 70, preferably day 27-day 95, more preferably day 27-day 130, from the time point when pluripotent stem cell is subjected to suspension culture in step (2-1). Also, depending on the period required for step (1), for example, an appropriate period may be set such that the culturing is performed for a period corresponding to about day 70-day 190, preferably day 95-day 190, more preferably day 130-day 190, from the time point when pluripotent stem cell is subjected to suspension culture in step (2-2). Here, a tissue at about day 27-day 40 from the time point when pluripotent stem cell is subjected to suspension culture is a retinal tissue containing a neural retinal progenitor cell, and in a differentiation stage immediately after emergence of a ganglion cell (one embodiment includes a differentiation stage where cone photoreceptor precursor starts to emerge), a tissue at day 60-day 70 is a retinal tissue in a differentiation stage where emergence rate of cone photoreceptor precursor reaches maximum, a tissue at day 85-day 100 is a retinal tissue in a differentiation stage where bipolar cell (or rod photoreceptor precursor) starts to emerge, a tissue at day 120-day 140 is a retinal tissue in a differentiation stage where outer plexiform membrane can be formed, and a tissue at day 190 is a retinal tissue in a differentiation stage where Muller cell is observed.

In a part of the period or all period of step (2-1) and step (2-2), a thyroid gland hormone signal transduction pathway agonist may be added, and a specific embodiment is as described in the above-mentioned 4.

In a part of the period or all period of step (2-1) and step (2-2), a medium containing a dorsalization signal transmitter at a concentration that suppresses expression of a ventral marker may be used, and a specific embodiment is as described in the above-mentioned 5.

Depending on the amount of the medium to be used, medium exchange of the medium in step (2-2) may be performed, for example, every 1 day-10 days, preferably 1 day-4 days, as appropriate. The composition thereof doe not need to be particularly changed. Since it is easy to maintain the continuous epithelial structure in a neural retinal tissue after a stage where a rod photoreceptor precursor emerges, medium change may be performed as appropriate. For example, the below-mentioned medium B may be changed to other medium. After the time when a rod photoreceptor precursor emerges, a serum-containing medium can be preferably used.

In the case of a neural retinal tissue in a stage where Muller cell emerges, any medium of serum-containing medium or serum-free medium can be preferably used as a medium that can maintain a continuous epithelial structure. Whether a rod photoreceptor precursor or Muller cell has emerged may be confirmed by conventionally-performed immunostaining using an antibody of a marker of a rod photoreceptor precursor or Muller cell and the like.

When a serum is added to a medium (e.g., the below-mentioned medium B) and culture is performed, final maturation of not less than 90%, preferably not less than 99%, of photoreceptor precursor among the photoreceptor precursors contained in the retinal tissue does not progress. The "final maturation" here means a state where a part, preferably not less than 15%, more preferably not less than 30%, further preferably not less than 60%, of a photoreceptor precursor or photoreceptor forms a synapse, or expresses a functional molecule such as visual pigment and the like. That is, the neural retinal tissue that has matured to a differentiation stage where Muller cells are observed but has not yet reached final maturation is preferably a neural retinal tissue in a stage where synapse formation has not occurred (or a state where a functional molecule such as a visual pigment and the like has not been expressed). It is known to those skilled in the art that, in a photoreceptor precursor (at least rod photoreceptor precursor) contained in the retinal tissue, neural circuit formation with bipolar cell can be promoted in a manner dependent on glutamic acid secreted from synaptic terminal of photoreceptor (non-patent document: Neuron, 87(6), 1248-60(2015)). Thus, from the aspect of suppressing neural circuit formation of photoreceptor precursor and bipolar cell in transplanted retinal tissue by not allowing progress of final maturation of photoreceptor precursor contained in the retinal tissue, namely, not causing a decrease in the efficiency of neural circuit formation of transplanted retinal tissue and bipolar cell of the recipient, a medium not containing glutamic acid is preferably used, more preferably, serum is added to the below-mentioned medium B and culture is performed.

Here, whether or not photoreceptor precursor is finally matured can be identified using a photoreceptor specific visual pigment such as S-opsin, L-opsin, M-opsin and the like, or an antibody against a functional factor necessary for light stimulus response. That is, a cell in which a functional molecule such as S-opsin, L-opsin, M-opsin, Rhodopsin, Cone-arrestin, arrestin, CNGA3, CNGA1, G alpha t2, G alpha t1, PDE6c, PDE6a, PDE6b and the like is expressed can be identified as a finally matured photoreceptor. Whether the photoreceptor precursor and a bipolar cell were contacted in the retinal tissue and formed a neural circuit can be identified by multiple staining using a combination of antibodies against for RIBEYE, CtBP2, which are expressed in a region where a photoreceptor and a bipolar cell formed the neural circuit, mGluR6 expressed in a bipolar cell in the region, Arrestin, Recoverin, cone specific Arrestin (Gene symbol; ARR3) which are expressed in the synaptic ending of the photoreceptor in the region, PNA said to be cone photoreceptor specific or ELFN1 said to be rod photoreceptor specific. Alternatively, formation of a neural circuit may also be identified by observing the synaptic ending of photoreceptor and the synapse structure of the bipolar cell using an electron microscope.

Conversely, when final maturation into a photoreceptor precursor is promoted and final differentiation into a photoreceptor expressing a visual pigment is performed, a method including culture using a medium containing glutamic acid and/or a medium not containing serum is preferable after step (2-2) (from the aspect of maintaining the layer structure of neural retinal tissue, preferably 150 days or later after a stage where photoreceptor precursor or photoreceptor first emerges). S-cone photoreceptor and rod photoreceptor are further matured by using the above-mentioned medium not containing a thyroid gland hormone signal transduction pathway agonist, and LM-cone photoreceptor is preferably matured by adding a dorsalization signal transmitter and a thyroid gland hormone signal transduction pathway agonist to the above-mentioned medium. The concentration of dorsalization signal transmitter and thyroid gland hormone signal transduction pathway agonist is not particularly limited. When T3 is used as a thyroid gland hormone signal transduction pathway agonist, for example, it can be added to a medium to fall within the range of 0.01 nM-100 nM; preferably 0.5-10 nM; more preferably 2-10 nM.

When T4 is used as a thyroid gland hormone signal transduction pathway agonist, for example, it can be added to a medium to fall within the range of 1 nM-500 µM; preferably 10 nM-50 µM; more preferably 20 nM-5 µM.

As a dorsalization signal transmitter for maturing a cone photoreceptor precursor into an LM cone photoreceptor, a dorsalization signal transmitter equivalent to a dorsalization signal transmitter at least of the level that suppresses expression of the above-mentioned ventral marker is preferably added. To prevent induction of expression of a visual pigment expressed in S cone photoreceptor, i.e., S-opsin, the above-mentioned dorsalization signal transmitter at a concentration that suppresses expression of a ventral marker is preferable. Specifically, when a BMP signal transduction pathway agonist, particularly BMP4, is used as a dorsalization signal transmitter, BMP4 is used at a concentration of preferably 0.01 nM-0.90 nM, more preferably 0.05 nM-0.45 nM, further preferably 0.05 nM-0.15 nM, further more preferably 0.1 nM-0.45 nM.

After step (2-2), the period required for a step of finally maturing a photoreceptor that expresses a visual pigment is not particularly limited, and appropriate culturing up to a differentiation stage of final maturation suitable for transplantation to a human body or functional analysis suffices. Specifically, when final maturation of S-cone photoreceptor is promoted, the period is not less than 10 days, preferably not less than 30 days, more preferably not less than 70 days, more preferably not less than 100 days, after step (2-2). When final maturation of LM-cone photoreceptor and rod photoreceptor is promoted, the period is specifically not less than 50 days, preferably not less than 70 days, more preferably not less than 100 days, more preferably not less than 150 days, after the above-mentioned step (2-1).

7. Medium

In the production method of the neural retinal tissue in the above-mentioned 6., the medium used in step (1) and/or step (2) is not particularly limited as long as a cell constituting neuronal cell, concretely retinal tissue, can survival therein. A medium conventionally used for culturing animal cells can be prepared as a basal medium.

Examples of the basal medium include media that can be used for culturing animal cell such as BME medium, BGJb medium, CMRL 1066 medium, Glasgow MEM (GMEM) medium, Improved MEM Zinc Option medium, IMDM medium, Medium 199 medium, Eagle MEM medium, αMEM medium, DMEM medium, F-12 medium, DMEM/F12 medium, IMDM/F12 medium, ham medium, RPMI1640 medium, Fischer's medium, or a mixed medium of these and the like.

To maintain continuous epithelial structure of neural retinal tissue, medium for maintaining a continuous epithelial tissue explained below can be used.

In the present specification, the medium for maintaining a continuous epithelial tissue contains at least one of a methyl group donor or a substrate of the methyl group donor at a concentration at which cell differentiation of a retinal progenitor cell or a neural retinal progenitor cell can be suppressed, and a neurite extension inhibitor at a concentration at which neurite extension can be suppressed. Preferably, the medium for maintaining a continuous epithelial tissue contains a methyl group donor or a substrate of the methyl group donor at a concentration at which cell differentiation of a retinal progenitor cell or a neural retinal progenitor cell is suppressed, and a neurite extension inhibitor at a concentration at which neurite extension is suppressed.

In vivo, a methyl group is transferred from a methyl donor to a DNA or a protein including histone by methyltransferase. In the present specification, a methyl group donor is a substance (methyl donor) that can donate a methyl group to be transferred to a DNA or a protein including histone. In the present specification, the substrate of the methyl group donor is a substrate necessary for biosynthesis of the aforementioned methyl donor. Specifically, the methyl group donor is, for example, S-adenosylmethionine (to be also referred to as SAM), and the substrate of the methyl group donor is, for example, methionine, S-methyl 5'-thioadenosine (sometimes to be abbreviated as MTA), homocysteine (sometimes to be abbreviated as Hcy) or the like. In the present invention, methionine is preferably used.

To determine whether cell differentiation of retinal progenitor cell or neural retinal progenitor cell is suppressed, for example, an evaluation target substance is reacted with a retinal tissue in an initial developmental stage and containing retinal progenitor cell or neural retinal progenitor cell and, after culturing for a period of time, the proportion of retinal progenitor cells or neural retinal progenitor cells in the retinal tissue may be identified, or the proportion of differentiated cells or differentiated cells that have ceased growing in the retinal tissue may be identified. Specifically, for example, after a certain period of time (e.g., 5 days-50 days) from the emergence of ganglion cells, a decrease rate of retinal progenitor cells or neural retinal progenitor cell; an increase rate of differentiated cells, cells that have stopped proliferating, or cells that express bHLH transcription factor necessary for terminal differentiation, each in the retinal tissue; or an expression level of bHLH transcription factor may be identified by immunostaining, quantitative PCR and the like. As a retinal progenitor cell or neural retinal progenitor marker, for example, a combination of RX and PAX6, a combination of RX, PAX6 and CHX10 or the like can be used. In addition, as a marker of differentiated cells contained in the retinal tissue, a marker of differentiated progenitor cells, or a marker of a bHLH transcription factor necessary for terminal differentiation, for example, BRN3, CRX, HuNu, Cath5, NeuroM, NGN1, NGN2, ISLET-1 (also referred to as ISL1), OLIG2 and the like can be used. As a marker for cells that have ceased cell proliferation due to cell differentiation, for example, p53, p27, p21 and the like can be used.

When methionine is used as a substrate of a methyl group donor, the concentration of methionine in the medium for maintaining a continuous epithelial tissue is generally more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L). The upper limit of the concentration of methionine in a medium for maintaining a continuous epithelial tissue is not particularly limited as long as maintenance of continuous epithelial tissue is achieved. It is generally not more than 100 mg/L (preferably not more than 75 mg/L). The range of methionine concentration in a medium for maintaining a continuous epithelial tissue is, for example, more than 17.24 mg/L and not more than 100 mg/L, preferably not less than 23.62 mg/L and not more than 75 mg/L, not less than 25 mg/L and not more than 75 mg/L, not less than 25.75 mg/L and not more than 75 mg/L, not less than 26 mg/L and not more than 75 mg/L, not less than 26.81 mg/L and not more than 75 mg/L, not less than 27 mg/L and not more than 75 mg/L, not less than 30 mg/L and not more than 75 mg/L. When a methyl group donor other than methionine or a substrate thereof is used, it is preferably used at a concentration affording an equivalent level of suppression of cell differentiation of retinal progenitor cell or neural retinal progenitor cell to that by the above-mentioned concentration of methionine.

In the present specification, the neurite extension inhibitor is a substance that suppresses neurite extension of ganglion cells. Specifically, neurite extension suppresses hormones such as glucocorticoid and the like, neurite extension suppressive proteins such as Semaphorin, Nogo, Mag, OMgp protein, chondroitin sulfate proteoglycan and the like, and the like can be mentioned. Examples of the glucocorticoid include corticosterone, cortisol, cortisone and the like. The neurite extension inhibitor is preferably glucocorticoid, more preferably corticosterone.

The extension suppressive action can be evaluated by, for example, adhesion culture of retinal tissues or ganglion cells contained in the retinal tissue in the presence of an evaluation target substance, followed by measurement of the length of the extended neurite by using image analysis software (e.g., Image J) and the like.

When corticosterone is used as a neurite extension inhibitor, the concentration of corticosterone in a medium for maintaining a continuous epithelial tissue is a concentration that suppresses neurite extension of ganglion cell and the like contained in the retinal tissue. It is generally not less than 0.1 nM (preferably, not less than 1 nM, not less than 5 nM, not less than 10 nM, not less than 50 nM, not less than 100 nM). The upper limit of the concentration of corticosterone in a medium for maintaining a continuous epithelial tissue is not particularly limited as long as maintenance of continuous epithelial tissue is achieved. It is generally not more than 10 μM (preferably not more than 5 μM, not more than 1 μM). The range of corticosterone concentration in a medium for maintaining a continuous epithelial tissue is, for example, 0.1 nM-10 μM, preferably, 1 nM-5 μM. When the above-mentioned neurite extension inhibitor other than corticosterone is used, it is preferably used at a concentration affording an equivalent level of neurite extension suppressive action to that by the above-mentioned concentration of corticosterone.

In one embodiment, a medium for maintaining a continuous epithelial tissue contains methionine and corticosterone at the above-mentioned concentrations. In one embodiment, a medium for maintaining a continuous epithelial tissue contains more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L) of methionine and not less than 0.1 nM (preferably not less than 1 nM, more preferably not less than 5 nM, further preferably not less than 10 nM, further preferably not less than 50 nM, further preferably not less than 100 nM) of corticosterone.

The medium for maintaining a continuous epithelial tissue may further contain acidic amino acid, antioxidant and retinal neuron protection substance. The concentration of each of them is preferably lower.

In the present specification, specific examples of acidic amino acid include glutamic acid and aspartic acid and each encompasses L form and D form. In the present specification, glutamic acid in an L form is indicated as L-glutamic acid, aspartic acid in an L form is indicated as L-aspartic acid, glutamic acid in a D form is indicated as D-glutamic acid, and aspartic acid in a D form is indicated as D-aspartic acid. In the present specification, when the D form and L form are not distinguished, they are indicated as "glutamic acid" and "aspartic acid".

The concentration of L-glutamic acid in a medium for maintaining a continuous epithelial tissue is preferably less than 50 μM (more preferably not more than 25 μM, further preferably not more than 12.5 μM, further more preferably not more than 1 μM, particularly preferably not more than 0.1 μM). In one embodiment, the concentration of glutamic acid in a medium for maintaining a continuous epithelial tissue is preferably less than 50 μM (more preferably not more than 25 μM, further preferably not more than 12.5 μM, further more preferably not more than 1 μM, particularly preferably not more than 0.1 μM).

The concentration of L-aspartic acid in a medium for maintaining a continuous epithelial tissue is preferably less than 50 μM (more preferably not more than 25 μM, further preferably not more than 12.5 μM, further more preferably not more than 1 μM, particularly preferably not more than 0.1 μM). In one embodiment, the concentration of aspartic acid contained in a medium for maintaining a continuous epithelial tissue is preferably less than 50 μM (more preferably not more than 10 μM, further preferably not more than 1 μM, further preferably not more than 0.1 μM).

In one preferable embodiment, a medium for maintaining a continuous epithelial tissue contains at least one (preferably both) of more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L) of methionine and not less than 0.1 nM (preferably not less than 1 nM, more preferably not less than 5 nM, further preferably not less than 10 nM, further preferably not less than 50 nM, further preferably not less than 100 nM) of corticosterone, and the concentration of L-glutamic acid is less than 50 μM (more preferably not more than 25 μM, further preferably not more than 12.5 μM, further more preferably not more than 1 μM, particularly preferably not more than 0.1 μM).

In a more preferable embodiment, a medium for maintaining a continuous epithelial tissue contains at least one (preferably both) of more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L) of methionine and not less than 0.1 nM (preferably not less than 1 nM, not less than 5 nM, not less than 10 nM, not less than 50 nM, not less than 100 nM) of corticosterone, and the concentration of L-glutamic acid is less than 50 μM (more preferably not more than 25 μM, further preferably not more than 12.5 μM, further more preferably not more than 1 μM, particularly preferably not more than 0.1 μM) and the concentration of L-aspartic acid is preferably less than 50 μM (more preferably not more than 25 μM, further preferably not more than 12.5 μM, further more preferably not more than 1 μM, particularly preferably not more than 0.1 μM).

In the present specification, examples of the antioxidant include glutathione, catalase, Superoxide dismutase, alpha-tocopherol, cysteine and the like. In one embodiment, the concentration of at least one, preferably plural, more preferably all antioxidants selected from the group consisting of glutathione, catalase, Superoxide dismutase, alpha-tocopherol, and cysteine in a medium for maintaining a continuous epithelial tissue is within the following ranges:

glutathione: not more than 100 ng/mL (preferably not more than 10 ng/mL, more preferably not more than 1 ng/mL, further preferably not more than 0.1 ng/mL);

catalase: not more than 100 U/mL (preferably not more than 10 U/mL, more preferably not more than 1 U/mL, further preferably not more than 0.1 U/mL);

Superoxide dismutase: not more than 100 U/mL (preferably not more than 10 U/mL, more preferably not more than 1 U/mL, further preferably not more than 0.1 U/mL);

alpha-tocopherol: not more than 50 nM (preferably not more than 5 nM, more preferably not more than 0.5 nM, further preferably not more than 0.05 nM); and cysteine: not more than 0.26 mM (preferably not more than 0.22 mM, more preferably not more than 0.18 mM, further preferably not more than 0.1 mM).

In one embodiment, the concentration of at least one, preferably plural, more preferably all antioxidants selected from the group consisting of glutathione, catalase, Superoxide dismutase, and alpha-tocopherol in a medium for maintaining a continuous epithelial tissue is a concentration that does not have an antioxidative action that influences the continuous epithelial structure, and the concentration of cysteine is not more than 0.26 mM (preferably not more than 0.22 mM, more preferably not more than 0.18 mM, further preferably not more than 0.1 mM). When other antioxidant is contained, the concentration thereof is preferably not more than a concentration that affords an antioxidative action equivalent to that of the above-mentioned antioxidant at the above-mentioned concentration, or a concentration that does not have an antioxidative action. The antioxidative action can be evaluated by directly measuring a part of active oxygen belonging to free radical by, for example, electron Spin resonance apparatus (Electron Spin Resonance, to be also referred to as ESR) in the presence of a spin trap agent. The antioxidative action can also be evaluated by other various methods for measuring active oxygen (e.g., measuring the amount of lipoperoxide produced due to active oxygen, the amount of 8-hydroxydeoxyguanosine or 8-nitroguanosine utilizable as oxidation stress markers and the like). For the measurement of the amount of active oxygen and the like, commercially available measurement kits (COSMO BIO, DOJINDO LABORATORIES, Thermo Fisher Scientific etc.) may be used.

In the present specification, examples of the retinal neuron protection substance include progesterone and the like. In one embodiment, the concentration of progesterone in a medium for maintaining a continuous epithelial tissue is not more than 100 nM, preferably not more than 50 nM, more preferably not more than 20 nM (or 6.3 µg/mL (20.033708 nM)), further preferably not more than 10 nM, further preferably not more than 3 nM. In one embodiment, the concentration of progesterone in a medium for maintaining a continuous epithelial tissue is a concentration that does not show a ganglion cell protective action. When other retinal neuron protection substance is contained, the concentration thereof is preferably not more than a concentration that affords a retinal neuron protective action equivalent to that of progesterone at the above-mentioned concentration, or a concentration that does not show a retinal neuron protective action. The retinal neuron protective action can be confirmed by, for example, identifying the proportion of ganglion cell contained in a retinal tissue, or the proportion of cleaved caspase-3 (known as an apoptosis marker)-positive ganglion cell, and identifying increase and decrease thereof. When the evaluation target substance shows a ganglion cell protective action, the proportion of the ganglion cells contained in a retinal tissue reacted with the substance for a given period increases and conversely, the proportion of the cleaved caspase-3-positive ganglion cells decreases compared to that without reaction with the substance. The proportion of the ganglion cells can be identified using immunohistostaining with antibody against the aforementioned ganglion cell markers (e.g., BRN3), DAPI staining, PI staining, Hoechst staining and the like.

In one preferable embodiment, a medium for maintaining a continuous epithelial tissue contains at least one (preferably both) of more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L) of methionine and not less than 0.1 nM (preferably not less than 1 nM, more preferably not less than 5 nM, further preferably not less than 10 nM, further preferably not less than 50 nM, further preferably not less than 100 nM) of corticosterone, the concentration of L-glutamic acid is less than 50 µM (more preferably not more than 25 µM, further preferably not more than 12.5 µM, further more preferably not more than 1 µM, particularly preferably not more than 0.1 µM), and further, the concentration of at least one, preferably plural, more preferably all compounds selected from the group consisting of L-aspartic acid, glutathione, catalase, Superoxide dismutase, alpha-tocopherol, cysteine and progesterone is within the following ranges:

L-aspartic acid: less than 50 µM (more preferably not more than 25 µM, further preferably not more than 12.5 µM, further more preferably not more than 1 µM, particularly preferably not more than 0.1 µM);

glutathione: not more than 100 ng/mL (preferably not more than 10 ng/mL, more preferably not more than 1 ng/mL, further preferably not more than 0.1 ng/mL);

catalase: not more than 100 U/mL (preferably not more than 10 U/mL, more preferably not more than 1 U/mL, further preferably not more than 0.1 U/mL); Superoxide dismutase: not more than 100 U/mL (preferably not more than 10 U/mL, more preferably not more than 1 U/mL, further preferably not more than 0.1 U/mL);

alpha-tocopherol: not more than 50 nM (preferably not more than 5 nM, more preferably not more than 0.5 nM, further preferably not more than 0.05 nM);

cysteine: not more than 0.26 mM (preferably not more than 0.22 mM, more preferably not more than 0.18 mM, further preferably not more than 0.1 mM); and progesterone: not more than 100 nM (preferably not more than 50 nM, more preferably not more than 20 nM (or 6.3 µg/mL (20.033708 nM)), further preferably not more than nM, further preferably not more than 3 nM).

The medium for maintaining a continuous epithelial tissue may further contain hypoxanthine, thymidine and vitamin B12. The concentration of each of them is preferably lower.

In one embodiment, the concentration of hypoxanthine in a medium for maintaining a continuous epithelial tissue is, for example, less than 15 µM (preferably not more than 7.5 µM, more preferably not more than 3.75 µM, further preferably not more than 1 µM, further more preferably not more than 0.1 µM (e.g., 0 µM)).

In one embodiment, the concentration of thymidine in a medium for maintaining a continuous epithelial tissue is less than 1.5 µM (preferably not more than 0.75 µM, more preferably not more than 0.375 µM, further preferably not more than 0.1 µM, further more preferably not more than 0.01 µM (e.g., 0 µM)).

In one embodiment, the concentration of vitamin B12 in a medium for maintaining a continuous epithelial tissue is less than 0.5 µM (preferably not more than 0.253 µM, more preferably not more than 0.129 µM, further preferably not more than 0.005 µM).

In a preferable embodiment, the concentration of 2 or 3 compounds selected from the group consisting of hypoxanthine, thymidine and vitamin B12 in a medium for maintaining a continuous epithelial tissue is within the aforementioned ranges.

In one preferable embodiment, a medium for maintaining a continuous epithelial tissue contains at least one (preferably both) of more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L) of methionine and not less than 0.1 nM (preferably not less than 1 nM, more preferably not less than 5 nM, further preferably not less than 10 nM, further preferably not less than 50 nM, further preferably not less than 100 nM) of corticosterone, the concentration of L-glutamic acid is less than 50 µM (more preferably not more than 25 µM, further preferably not more than 12.5 µM, further more preferably not more than 1 µM, particularly preferably not more than 0.1 µM), and the concentration of at least one, preferably plural, more preferably all compounds selected from the group consisting of L-aspartic acid, glutathione, catalase, Superoxide dismutase, alpha-tocopherol, cysteine, progesterone, hypoxantine, thymidine and vitamin B12 is within the following ranges:

L-aspartic acid: less than 50 µM (more preferably not more than 25 µM, further preferably not more than 12.5 µM, further more preferably not more than 1 µM, particularly preferably not more than 0.1 µM);

glutathione: not more than 100 ng/mL (preferably not more than 10 ng/mL, more preferably not more than 1 ng/mL, further preferably not more than 0.1 ng/mL);

catalase: not more than 100 U/mL (preferably not more than 10 U/mL, more preferably not more than 1 U/mL, further preferably not more than 0.1 U/mL);

Superoxide dismutase: not more than 100 U/mL (preferably not more than 10 U/mL, more preferably not more than 1 U/mL, further preferably not more than 0.1 U/mL);

alpha-tocopherol: not more than 50 nM (preferably not more than 5 nM, more preferably not more than 0.5 nM, further preferably not more than 0.05 nM);

cysteine: not more than 0.26 mM (preferably not more than 0.22 mM, more preferably not more than 0.18 mM, further preferably not more than 0.1 mM);

progesterone: not more than 100 nM (preferably not more than 50 nM, more preferably not more than 20 nM (or 6.3 µg/mL (20.033708 nM)), further preferably not more than 10 nM, further preferably not more than 3 nM);

hypoxanthine: less than 15 µM (preferably not more than 7.5 µM, more preferably not more than 3.75 µM, further preferably not more than 1 µM, further more preferably not more than 0.1 µM (e.g., 0 µM));

thymidine: less than 1.5 µM (preferably not more than 0.75 µM, more preferably not more than 0.375 µM, further preferably not more than 0.1 µM, further more preferably not more than 0.01 µM (e.g., 0 µM)); and vitamin B12: less than 0.5 µM (preferably not more than 0.253 µM, more preferably not more than 0.129 µM, further preferably not more than 0.005 µM).

In one preferable embodiment, a medium for maintaining a continuous epithelial tissue has the following composition:

methionine: more than 17.24 mg/L (preferably not less than 23.62 mg/L, not less than 25 mg/L, not less than 25.75 mg/L, not less than 26 mg/L, not less than 26.81 mg/L, not less than 27 mg/L, not less than 30 mg/L);

corticosterone: not less than 0.1 nM (preferably not less than 1 nM, more preferably not less than 5 nM, further preferably not less than 10 nM, further preferably not less than 50 nM, further preferably not less than 100 nM);

L-glutamic acid: less than 50 µM (more preferably not more than 25 µM, further preferably not more than 12.5 µM, further more preferably not more than 1 µM, particularly preferably not more than 0.1 µM);

L-aspartic acid: less than 50 µM (more preferably not more than 25 µM, further preferably not more than 12.5 µM, further more preferably not more than 1 µM, particularly preferably not more than 0.1 µM);

hypoxanthine: less than 15 µM (preferably not more than 7.5 µM, more preferably not more than 3.75 µM, further preferably not more than 1 µM, further more preferably not more than 0.1 µM (e.g., 0 µM));

thymidine: less than 1.5 µM (preferably not more than 0.75 µM, more preferably not more than 0.375 µM, further preferably not more than 0.1 µM, further more preferably not more than 0.01 µM (e.g., 0 µM)); and vitamin B12: less than 0.5 µM (preferably not more than 0.253 µM, more preferably not more than 0.129 µM, further preferably not more than 0.005 µM).

In the embodiment, the concentration of at least one, preferably plural, more preferably all compounds selected from the group consisting of glutathione, catalase, Superoxide dismutase, alpha-tocopherol, L-cysteine and progesterone is within the following ranges:

glutathione: not more than 100 ng/mL (preferably not more than 10 ng/mL, more preferably not more than 1 ng/mL, further preferably not more than 0.1 ng/mL);

catalase: not more than 100 U/mL (preferably not more than 10 U/mL, more preferably not more than 1 U/mL, further preferably not more than 0.1 U/mL);

Superoxide dismutase: not more than 100 U/mL (preferably not more than 10 U/mL, more preferably not more than 1 U/mL, further preferably not more than 0.1 U/mL);

alpha-tocopherol: not more than 50 nM (preferably not more than 5 nM, more preferably not more than 0.5 nM, further preferably not more than 0.05 nM);

cysteine: not more than 0.26 mM (preferably not more than 0.22 mM, more preferably not more than 0.18 mM, further preferably not more than 0.1 mM); and progesterone: not more than 100 nM (preferably not more than 50 nM, more preferably not more than 20 nM (6.3 µg/mL), further preferably not more than 10 nM, further preferably not more than 3 nM).

A medium for maintaining a continuous epithelial tissue can be prepared by appropriately blending a commercially available medium.

Examples of the basal medium that can be used for preparing a medium for maintaining a continuous epithelial tissue include a medium not containing at least one of the aforementioned acidic amino acid, antioxidant and retinal neuron protection substances such as progesterone and the like (e.g., acidic amino acid), preferably two or more (e.g., acidic amino acid and any other substance), more preferably not containing all, or within the aforementioned concentration ranges. In one embodiment of the basal medium, one, preferably two, more preferably three, of hypoxanthine, thymidine and vitamin B12 are within the aforementioned concentration ranges. In one embodiment of the basal medium, hypoxanthine and thymidine are not contained, and the concentration of vitamin B12 is within the aforementioned concentration range.

As a basal medium that can be used for the preparation of a medium for maintaining a continuous epithelial tissue, a medium in which the concentration of at least one of methyl group donor (e.g., S-adenosylmethionine), substrate of methyl group donor (e.g., methionine, MTA, Hcy) and neurite extension inhibitor (e.g., corticosterone) is in the aforementioned concentration range is preferable. A medium for maintaining a continuous epithelial tissue can be prepared by appropriately supplementing necessary substances to the basal medium that fall within the above-mentioned concentration ranges.

The basal medium that can be used for the preparation of a medium for maintaining a continuous epithelial tissue may be appropriately selected from commercially available basal media according to the above-mentioned selection criteria and based on the ingredient table published by the manufacturer. Examples of the basal medium that can be used for the preparation of a medium for maintaining a continuous epithelial tissue include commercially available Neurobasal medium (including Neurobasal-A medium, phenol red-free Neurobasal medium and the like), Improved MEM Zinc Option medium, MEM, DMEM, Leibovitz's L-15, E-MEM, G-MEM and the like. In addition, it is also possible to order and purchase a medium with individual customized components to and from a medium manufacturer. Also, a medium customized according to the aforementioned description to be a basal medium usable for the preparation of a medium for maintaining a continuous epithelial tissue may be used.

A supplemental medium may be appropriately blended to supplement corticosterone. Specific examples of the supplemental medium include B27 supplement and the like. As one embodiment of the medium for maintaining a continuous epithelial tissue, specifically, a medium in which B27 supplement is blended with Neurobasal medium can be mentioned. The medium may contain L-glutamine, taurine, serum and the like as appropriate Neurobasal medium is a known basal medium developed for nerve cell culture (J. Neurosci. Res., vol. 35, p. 567-576, 1993). While Neurobasal medium has been partially modified from the report, it is available as a commercially available Neurobasal medium from a medium manufacturer (e.g., manufactured by Thermo Fisher Scientific, 21103049). The composition of Neurobasal medium (21103049) available from Thermo Fisher Scientific does not contain acidic amino acids (L-glutamic acid and L-aspartic acid), progesterone, hypoxanthine or thymidine, has high methionine concentration (30 mg/L), high cysteine concentration (0.26 mM), and low vitamin B12 concentration (0.005 µM) compared to DMEM/F12. The specific composition is as follows.

TABLE 1-1

| Components | Molecular Weight | Concentration (mg/L) | mM |
|---|---|---|---|
| Amino Acids | | | |
| Glycine | 75 | 30 | 0.4 |
| L-alanine | 89 | 2 | 0.02247191 |
| L-Arginine hydrochloride | 211 | 84 | 0.39810428 |
| L-Asparagine-H$_2$O | 150 | 0.83 | 0.005533333 |
| L-Cysteine | 121 | 31.5 | 0.2603306 |
| L-Histidine hydrochloride-H$_2$O | 210 | 42 | 0.2 |
| L-Isoleucine | 131 | 105 | 0.8015267 |
| L-Leucine | 131 | 105 | 0.8015267 |
| L-Lysine hydrochloride | 183 | 146 | 0.7978142 |
| L-Methionine | 149 | 30 | 0.20134228 |
| L-Phenylalanine | 165 | 66 | 0.4 |
| L-Proline | 115 | 7.76 | 0.06747826 |
| L-Serine | 105 | 42 | 0.4 |
| L-Threonine | 119 | 95 | 0.79831934 |
| L-Tryptophan | 204 | 16 | 0.078431375 |
| L-Tyrosine | 181 | 72 | 0.39779004 |
| L-Valine | 117 | 94 | 0.8034188 |
| Vitamins | | | |
| Choline chloride | 140 | 4 | 0.028571429 |
| D-Calcium pantothenate | 477 | 4 | 0.008385744 |
| Folic Acid | 441 | 4 | 0.009070295 |
| Niacinamide | 122 | 4 | 0.032786883 |
| Pyridoxal hydrochloride | 204 | 4 | 0.019607844 |
| Riboflavin | 376 | 0.4 | 0.00106383 |
| Thiamine hydrochloride | 337 | 4 | 0.011869436 |
| Vitamin B12 | 1355 | 0.0068 | 0.00000502 |
| i-Inositol | 180 | 7.2 | 0.04 |

TABLE 1-2

| Inorganic Salts | | | |
|---|---|---|---|
| Calcium Chloride (CaCl$_2$) (anhyd.) | 111 | 200 | 1.8018018 |
| Ferric Nitrate (Fe(NO$_3$)$_3$—9H$_2$O) | 404 | 0.1 | 0.000248 |
| Magnesium Chloride (anhydrous) | 95 | 77.3 | 0.8136842 |
| Potassium Chloride (KCl) | 75 | 400 | 5.3333335 |
| Sodium Bicarbonate (NaHCO$_3$) | 84 | 2200 | 26.190475 |
| Sodium Chloride (NaCl) | 58 | 3000 | 51.724136 |
| Sodium Phosphate monobasic (NaH$_2$PO$_4$—H$_2$O) | 138 | 125 | 0.9057971 |
| Zinc sulfate (ZnSO$_4$—7H$_2$O) | 288 | 0.194 | 0.000674 |
| Other Components | | | |
| D-Glucose (Dextrose) | 180 | 4500 | 25 |
| HEPES | 238 | 2600 | 10.92437 |
| Phenol Red | 376.4 | 8.1 | 0.021519661 |
| Sodium Pyruvate | 110 | 25 | 0.22727273 |

B27 supplement is a known supplemental medium developed for nerve cell culture (J. Neurosci. Res., vol. 35, p. 567-576, 1993). B27 supplement is generally used by adding to a basal medium such as Neurobasal medium and the like at a volume ratio of about 2%. B27 supplement containing corticosterone and combined with Neurobasal medium can be used as the medium for maintaining a continuous epithelial tissue. For example, B27 supplement containing corticosterone is added to a basal medium containing methionine (Neurobasal medium etc.) such that the aforementioned methionine concentration and corticosterone concentration would be achieved, whereby the medium for maintaining a continuous epithelial tissue can be prepared.

B27 supplement (J. Neurosci. Res., vol. 35, p. 567-576, 1993) can be purchased from, for example, a medium manufacturer (e.g., Thermo Fisher Scientific, 12587010), and the composition is as follows.

TABLE 2

| Components | mM |
|---|---|
| Vitamins | |
| Biotin | n/a |
| DL Alpha Tocopherol Acetate | n/a |
| DL Alpha-Tocopherol | n/a |
| Proteins | |
| BSA, fatty acid free Fraction V | n/a |
| Catalase | n/a |
| Human Recombinant Insulin | n/a |
| Human Transferrin | n/a |
| Superoxide Dismutase | n/a |
| Other Components | |
| Corticosterone | n/a |
| D-Galactose | n/a |
| Ethanolamine HCl | n/a |
| Glutathione (reduced) | n/a |
| L-Carnitine HCl | n/a |
| Linoleic Acid | n/a |
| Linolenic Acid | n/a |
| Progesterone | n/a |
| Putrescine 2HCl | n/a |
| Sodium Selenite | n/a |
| T3 (triodo-I-thyronine) | n/a |

In another embodiment, the medium for maintaining a continuous epithelial tissue includes a medium containing Neurobasal medium supplemented with B27 supplement at a volume ratio of one or more (preferably two or more, more preferably three or more) based on the cell proliferation basal medium (e.g., DMEM/F12 mixed medium (DMEM: F12=1:1)).

The cell proliferation basal medium is not particularly limited and a commercially available basal medium can be used alone or in an appropriate mixture. The cell proliferation basal medium may contain an appropriately additive (supplement), and a specific supplement is, for example, N2 supplement.

The concentration of L-methionine, L-glutamic acid, L-aspartic acid, L-cysteine, hypoxanthine, thymidine, and vitamin B12 in a medium obtained by adding B27 supplement (Thermo Fisher Scientific, 12587010) to the above-mentioned commercially available Neurobasal medium (Thermo Fisher Scientific, 21103049), and a medium obtained by mixing a medium obtained by adding B27 supplement to Neurobasal medium and a medium obtained by adding N2 supplement to DMEM/F12 mixed medium (DMEM:F12=1:1) at a ratio of 3:1, 2:1 or 1:1 is, for example, as shown below.

In one embodiment, a medium having a composition of L-methionine, L-glutamic acid, L-aspartic acid, L-cysteine, hypoxanthine, thymidine, and vitamin B12 at concentrations equivalent to those shown in Table 3 can be used as a medium for maintaining a continuous epithelial tissue. Here, the "equivalent concentration" independently means that it includes the range of ±20% (preferably ±10%, more preferably ±5%, further preferably ±2.5%, and further more preferably ±1%) for the concentration of each factor.

In one embodiment, a medium having a composition of L-methionine, L-glutamic acid, L-aspartic acid, hypoxanthine, thymidine, and vitamin B12 at concentrations equivalent to those shown in Table 3, wherein the concentration of at least one, preferably plural, more preferably all compounds selected from the group consisting of corticosterone, glutathione, catalase, Superoxide dismutase, alpha-tocopherol, L-cysteine and progesterone is within the following ranges can be used as a medium for maintaining a continuous epithelial tissue:

corticosterone: not less than 0.1 nM (preferably not less than 1 nM, more preferably not less than 5 nM, further preferably not less than 10 nM, further preferably not less than 50 nM, further preferably not less than 100 nM);

glutathione: not more than 100 ng/mL (preferably not more than 10 ng/mL, more preferably not more than 1 ng/mL, further preferably not more than 0.1 ng/mL);

catalase: not more than 100 U/mL (preferably not more than 10 U/mL, more preferably not more than 1 U/mL, further preferably not more than 0.1 U/mL);

Superoxide dismutase: not more than 100 U/mL (preferably not more than 10 U/mL, more preferably not more than 1 U/mL, further preferably not more than 0.1 U/mL);

alpha-tocopherol: not more than 50 nM (preferably not more than 5 nM, more preferably not more than 0.5 nM, further preferably not more than 0.05 nM);

cysteine: not more than 0.26 mM (preferably not more than 0.22 mM, more preferably not more than 0.18 mM, further preferably not more than 0.1 mM); and progesterone: not more than 100 nM (preferably not more than 50 nM, more preferably not more than 20 nM (or not more than 6.3 µg/mL (20.033708 nM)), further preferably not more than 10 nM, further preferably not more than 3 nM).

The medium for maintaining a continuous epithelial tissue may contain L-glutamine, taurine, N2 and the like as appropriate. The concentration of taurine is generally 1 µM-1000

TABLE 3

| | Neurobasal + B27 | (1) Neurobasal + B27 (2) DMEM/F12 + N2 (1):(2) = 3:1 | (1) Neurobasal + B27 (2) DMEM/F12 + N2 (1):(2) = 2:1 | (1) Neurobasal + B27 (2) DMEM/F12 + N2 (1):(2) = 1:1 |
|---|---|---|---|---|
| L-methionine | 30 mg/L | 26.81 mg/L | 25.75 mg/L | 23.62 mg/L |
| L-glutamic acid | 0 µM | 12.5 µM | 16.67 µM | 25 µM |
| L-aspartic acid | 0 µM | 12.5 µM | 16.67 µM | 25 µM |
| L-cysteine | 31.5 mg/L (0.26 mM) | 28.015 mg/L (0.22 mM) | 26.853 mg/L (0.207 mM) | 24.53 mg/L (0.135 mM) |
| hypoxanthine | 0 µM | 3.75 µM | 5 µM | 7.5 µM |
| thymidine | 0 µM | 0.375 µM | 0.5 µM | 0.75 µM |
| vitamin B12 | 6.8 µg/L (0.005 µM) | 175.1 µg/L (0.12875 µM) | 231.2 µg/L (0.17 µM) | 343.4 µg/L (0.275 µM) |

μM, preferably 10 μM-500 μM. When N2 is contained, it is more preferable to add glucocorticoid such as corticosterone and the like at the aforementioned concentration without adding B27.

The medium for maintaining a continuous epithelial tissue may contain, as long as continuous epithelial tissues can be maintained, one or more additives appropriately selected from, though not limited to, adjusting agents such as buffering agent (e.g., HEPES), salt (e.g., inorganic salt such as sodium chloride, sodium hydrogen carbonate and the like) or antioxidant (e.g., 2-mercaptoethanol, antioxidant is not contained in one embodiment) and the like, nutritional supplements such as amino acid (e.g., non-essential amino acid, acidic amino acid is not contained in one embodiment), fatty acid, sugar, vitamin, lipid, pyruvic acid and the like, antibiotic (e.g., penicillin, streptomycin), extracellular matrix (e.g., Matrigel, laminin, laminin fragment, laminin511-E8 fragment), dye (e.g., phenol red) and the like, which are generally contained in a medium.

The medium for maintaining a continuous epithelial tissue may be either a serum-containing medium or a serum-free medium. It is preferably a serum-containing medium. The concentration of serum in the serum-containing medium is generally 0.1-20% (v/v), preferably 0.1-12% (v/v) (e.g., 10% (v/v)). In the present specification, the concentration change of the composition contained in the medium due to the addition of serum at a concentration of 0.1-20% (v/v) is not to be considered.

The medium to be used in step (1) of the above-mentioned 6. is specifically, for example, DMEM/F12 medium containing about 10% FBS, about 1% N2 supplement (manufactured by Thermo Scientific) and about 100 μM taurine (hereinafter to be referred to as medium A).

The medium to be used in step (2) of the above-mentioned 6. is specifically, for example, the above-mentioned medium A and Neurobasal medium containing about 10% FBS, about 2% B27 supplement (manufactured by Thermo Scientific), about 200 mM glutamine and about 100 μM taurine (hereinafter to be referred to as medium B).

In addition, the aforementioned medium B may be appropriately mixed with the above-mentioned medium A and the like and used. For example, medium A and medium B may be appropriately mixed at a ratio of 4:1-1:4 and used. Alternatively, the ratio of medium B in the mixed medium may also be increased step by step.

Medium A can be preferably used up to a differentiation stage where photoreceptor or photoreceptor precursor emerges.

A mixed medium of medium A and medium B can be preferably used up to a differentiation stage where emergence rate of photoreceptor precursor reaches maximum.

Medium B can be preferably used after the differentiation stage where emergence rate of a cone photoreceptor precursor reaches maximum. Since it is easy to maintain the continuous epithelial structure in a neural retinal tissue after a stage where a rod photoreceptor precursor emerges, medium B may be changed as appropriate to other medium.

The medium to be used in the aforementioned steps (2-1) and/or (2-2) is not particularly limited and a medium conventionally used for culturing animal cells can be prepared as a basal medium. Examples of the basal medium include media that can be used for culturing animal cell such as BME medium, BGJb medium, CMRL 1066 medium, Glasgow MEM (GMEM) medium, Improved MEM Zinc Option medium, IMDM medium, Medium 199 medium, Eagle MEM medium, αMEM medium, DMEM medium, F-12 medium, DMEM/F12 medium, IMDM/F12 medium, ham medium, RPMI1640 medium, Fischer's medium, or a mixed medium of these and the like.

In step (2-1) and/or (2-2), the continuous epithelial structure of the neural retinal tissue is desirably maintained. Thus, examples of the medium include the above-mentioned medium A, as well as the aforementioned medium B, and a mixed medium of medium A and medium B.

Preferably, medium A can be used up to a differentiation stage where photoreceptor or photoreceptor precursor emerges.

A mixed medium of medium A and medium B can be preferably used up to a differentiation stage where the emergence rate of photoreceptor precursor reaches maximum.

After the differentiation stage where emergence rate of photoreceptor precursor reaches maximum, medium B can be preferably used. The continuous epithelial structure can be easily maintained in a neural retinal tissue after the differentiation stage where rod photoreceptor precursor emerges. Thus, medium B may be changed as appropriate to other medium.

The "continuous epithelial structure" in the retinal tissue means a structure in which the retinal tissue has an apical surface unique to the epithelial tissue and the apical surface is formed on the surface of the retinal tissue continuously and generally parallel to at least photoreceptor layer (outer nuclear layer) or neuroblastic layer among the respective layers forming the neural retinal layer. That is, the continuous epithelial structure does not have a structure seen in a rosette-like structure in which the apical surface is divided. For example, in the case of a cell aggregate containing a retinal tissue prepared from pluripotent stem cells, the apical surface is formed on the surface of the aggregate, and not less than 10, preferably not less than 30, more preferably not less than 100, further preferably not less than 400 photoreceptor or photoreceptor precursors are regularly and continuously arranged in the tangential direction with respect to the surface. The number of photoreceptors or photoreceptor precursors arranged continuously correlates with the size of the neural retinal tissue contained in the cell aggregate. In the present specification, the tangential direction with respect to the epithelial tissue refers to a direction in which every single cell forming the apical surface in the epithelial tissue is arranged and it is a parallel direction or transverse direction relative to the epithelial tissue (or epithelial sheet).

In one embodiment, an apical surface is formed on the surface of the neural retinal tissue, and photoreceptors or photoreceptor precursors are regularly and continuously arranged along the apical surface.

In the case of a retinal tissue in a stage where the emergence rate of photoreceptors or photoreceptor precursors is low (e.g., retinal tissue in an initial developmental stage), it is known to those of ordinary skill in the art that the layer containing proliferating neural retinal progenitor cell is called a "neuroblastic layer". In addition, the surface of a retinal tissue in such stage may sometimes contain, in addition to photoreceptors and photoreceptor precursors, a neural retinal progenitor cell that has polarity and can form the apical surface, a cell that divides and proliferates from the neural retinal progenitor cell and/or a cell in a stage of differentiation from a neural retinal progenitor cell into a cell constituting the neural retina. By continuing culture of the retinal tissue in such a state under the conditions that maintain the "continuous epithelial structure", a retinal tissue in which photoreceptors or photoreceptor precursors are regularly and continuously arranged along the apical surface formed on the surface of the neural retinal tissue is obtained.

In one embodiment, the area of the apical surface present on the surface of the retinal tissue is not less than 30%, preferably not less than 50%, more preferably not less than 80%, further more preferably not less than 95%, on average relative to the surface area of the retinal tissue. The area of the apical surface present on the surface of the retinal tissue can be measured as described below by staining an apical surface marker.

In the present specification, the "rosette-like structure" in the retinal tissue refers to a structure in which cells are arranged radially or spirally while surrounding a central lumen. In the retinal tissue in which the rosette-like structure is formed, the apical surface and photoreceptors or photoreceptor precursors exist along the center (lumen), and the apical surface is divided for each rosette-like structure.

In the present specification, the "apical surface" refers to a 50-100 nm surface (surface layer) formed on the side opposite from the basement membrane side where the layer (basement membrane) produced by epithelial cell is present in an epithelial tissue. The surface is rich in mucopolysaccharide (positive for PAS staining) and contains a large amount of laminin and type IV collagen. In one embodiment, in a retinal tissue whose developmental stage has progressed to the extent that photoreceptors or photoreceptor precursors are observed, an outer limiting membrane formed and it refers to a surface in contact with a photoreceptor layer (outer nuclear layer) in which photoreceptors and photoreceptor precursors are present. Such apical surface can be identified by an immunostaining method or the like well known to those skilled in the art and by using an antibody against an apical surface marker (e.g., atypical-PKC (hereinafter sometimes to be abbreviated as aPKC), E-cadherin, N-cadherin). In an initial developmental stage, even when photoreceptor or photoreceptor precursor has not emerged or even when photoreceptor or photoreceptor precursor has not emerged to sufficiently cover the surface of retinal tissue, the epithelial tissue has polarity, and the apical surface expresses the above-mentioned apical surface marker.

Whether or not the retinal tissue has a continuous epithelial structure can be confirmed by the continuity of the apical surface of the retinal tissue (that is, an undivided form). The continuity of the apical surface is determined by, for example, immunostaining a marker on the apical surface (e.g., aPKC, E-cadherin, N-cadherin), a marker for photoreceptor or photoreceptor precursor located on the apical surface side (e.g., Crx or recoverin) and analyzing the obtained images and the like for positional relationship between the apical surface, the photoreceptor layer, and each retinal layer. As for retinal layers other than the apical surface and photoreceptor layer (outer nuclear layer), the continuity can be identified by DAPI staining PI staining, Hoechst staining, each including staining of the cell nucleus, or immunostaining with a marker protein (Rx, Chx10, Ki67, Crx etc.) or the like localized in the cell nucleus.

Whether or not a rosette-like structure was generated can be determined by fixing cell aggregates with 4% paraformaldehyde and so on, preparing frozen sections, and observing dysplasia (e.g., divided apical surface or invasion of apical surface into cell aggregate) of rosette-like structure by immunostaining or the like that is generally performed using antibodies against apical surface markers aPKC, E-cadherin, N-cadherin, and DAPI that specifically stains nucleus and the like.

In one embodiment of the present invention, an aggregate containing a retinal tissue having a continuous epithelial structure, namely, an aggregate containing a retinal tissue having a photoreceptor or a progenitor cell thereof continuously present in not less than at least 50% (preferably not less than 60%, not less than 70%, not less than 80%, not less than 85%, not less than 90%) of a surface of the retinal tissue can be mentioned. In addition, a preparation containing the aggregate and a medium for maintaining a continuous epithelial tissue is also within the scope of the present invention.

As one embodiment of the retinal tissue having a continuous epithelial structure of the present invention, an aggregate containing a retinal tissue in which the area of the apical surface present on the surface of the retinal tissue is not less than at least 50% (preferably not less than 60%, not less than 70%, not less than 80%, not less than 85%, not less than 90%) based on the surface area of the retinal tissue can be mentioned. In one embodiment of the present invention, the diameter in the major axis direction is not less than 0.5 mm (preferably not less than 0.6 mm, not less than 0.8 mm, not less than 1.0 mm, not less than 1.2 mm, not less than 1.4 mm, not less than 1.6 mm, not less than 1.8 mm, not less than 2.0 mm, not less than 2.2 mm, not less than 2.4 mm, not less than 2.6 mm, not less than 2.8 mm, not less than 2.9 mm). An aggregate containing a retinal tissue having a continuous epithelial structure can be mentioned. A retinal tissue to be transplanted is preferably large since a wide area of a retinal tissue of a recipient with a disorder can be covered. Generally, a retinal tissue exceeding 0.5 mm-1.0 mm easily produces a rosette structure during transplantation. However, the present invention can provide an aggregate containing a retinal tissue having a continuous epithelial structure, without producing a rosette structure even with a retinal tissue exceeding 0.5 mm-1.0 mm. The structure of the retinal tissue is as described in the below-mentioned "8. Neural retinal tissue".

Here, the diameter in the major axis direction of a retinal tissue means, for example, when measuring based on images taken with a stereomicroscope, the length of the longest straight line connecting any two points in the outer circumference (contour, surface) of the retinal tissue. Some aggregates containing a retinal tissue contain multiple retinal tissues overlapping with one another (e.g., clover type). A person skilled in the art can easily determine whether multiple retinal tissues are present. In this case, the diameter in the major axis direction of the retinal tissue means the diameter in the major axis direction of each retinal tissue in the aggregate, and the diameter in the major axis direction of at least one retinal tissue only needs to be not less than 0.5 mm. Preferably, the diameters in the major axis direction of all retinal tissues in the aggregate are not less than 0.5 mm. More specifically, the length of the longest straight line connecting any two points in the outer circumference separated by two overlapping circles or ellipses in terms of shape (more specifically, when the continuous positional information of the outer circumference of the aggregate containing a retinal tissue is hypothetically determined, the point at which continuity of the curve is lost in the curve obtained when the positional information is plotted on the horizontal axis and the slope of the tangent line at the position is plotted on the vertical axis) is measured. Furthermore, some aggregates containing a retinal tissue contain a retinal pigment epithelial cell and/or a ciliary marginal zone. Also in this case, similar to when multiple retinal tissues are present in an aggregate, the length of the longest straight line connecting any two points in the outer circumference separated by a contact point between a retinal pigment epithelium and/or a ciliary marginal zone and a retinal tissue is measured.

The proportion of the cells expressing RAX, CHX10 and/or CRX in a retinal tissue is preferably not less than 50%, not less than 60%, not less than 70%, not less than 80%, not less than 85%, not less than 90%, not less than 95%.

When the aggregate contains multiple retinal tissues, the proportion of the number of aggregates containing a retinal tissue satisfying the above-mentioned conditions based on the whole number is preferably at least not less than 50% (preferably not less than 60%, not less than 70%, not less than 80%, not less than 85%, not less than 90%, not less than 95%).

The medium for maintaining a continuous epithelial tissue contained in the preparation containing the aggregate and the medium is a medium for maintaining a continuous epithelial tissue defined in the present specification. The prepared product may contain, for example, antibiotic, antiseptic, stabilizer, preservative and the like as long as a continuous epithelial tissue can be maintained.

8. Neural Retinal Tissue

The neural retinal tissue obtained by the methods described in the above-mentioned 4., 5. and 6. is also within the scope of the present invention. That is, neural retinal tissues with various maturation degrees according to the culture period can be obtained by the methods described in the above-mentioned 4., 5. and 6. Neural retinal tissues with different maturation degrees are each explained in the following.

(1) Matured Neural Retinal Tissue

A neural retinal tissue obtained by continuously culturing by the method described in the above-mentioned 4. for not less than 180-200 days from the start of suspension culture is a matured neural retinal tissue rich in cone photoreceptor precursor, and containing photoreceptor precursor and photoreceptor and Muller cell. In the neural retinal tissue, the proportion of ganglion cell, amacrine cell, horizontal cell, and bipolar cell is lower, and the proportion of photoreceptor precursor and photoreceptor, and further, cone photoreceptor precursor and cone photoreceptor, is higher than in a neural retinal tissue in vivo. That is, a neural retinal tissue in which the proportion of PAX6-positive/CHX10-negative cell (that is, any of ganglion cell, amacrine cell, horizontal cell), and the proportion of PAX6-negative/CHX10-strongly positive cell (that is, bipolar cell) are both low, these cells are contained at not more than 30%, preferably not more than 20%, more preferably not more than 15%, of the total number of cells, and not more than 8%, preferably not more than 6%, more preferably not more than 5%, of the total number of cells, further, the CRX-positive cell (that is, photoreceptor precursor) is contained at not less than 35%, preferably not less than 40%, more preferably not less than 45%, further more preferably not less than 50%, further more preferably not less than 53%, of the total number of cells and/or the CRX-positive and RXR-γ-positive and NRL-negative cell (that is, cone photoreceptor precursor) is contained at not less than 25%, preferably not less than 32%, more preferably not less than 35%, further more preferably not less than 40%, further more preferably not less than 44%, of the total number of cells is also within the scope of the present invention.

In addition, a neural retinal tissue obtained by continuously culturing by the method described in the above-mentioned 5. for not less than 180-200 days from the start of suspension culture is a matured neural retinal tissue rich in cone photoreceptor precursor, and containing photoreceptor precursor and photoreceptor, and Muller cell. In the neural retinal tissue, the proportion of photoreceptor precursor in the whole cells and/or cone photoreceptor precursor in photoreceptor precursor is higher as compared to a retinal tissue produced in the absence of a dorsalization signal transmitter. That is, in a stage where Muller cell is found, the proportion of a total of the PAX6-positive/CHX10-negative cell (that is, any of ganglion cell, amacrine cell, horizontal cell) and the PAX6-negative/CHX10-strongly positive cell (that is, bipolar cell) is low, and is not more than 30%, preferably not more than 25%, more preferably not more than 20%, of the total number of cells. Furthermore, a neural retinal tissue in which CRX-positive cell (that is, photoreceptor precursor) is contained at not less than 40%, preferably not less than 53%, more preferably not less than 57%, of the total number of cells and/or CRX-positive and RXR-γ-positive and NRL-negative cell is contained at not less than 32%, preferably not less than 44%, more preferably not less than 54%, of the total number of cells is also within the scope of the present invention.

The above-mentioned neural retinal tissue in which the dorsalization signal transmitter is an SHH signal transduction pathway inhibitor shows a low proportion of ganglion cell, amacrine cell, horizontal cell and bipolar cell, and a high proportion of photoreceptor precursor and photoreceptor in the whole cells; and/or a high proportion of cone photoreceptor precursor in photoreceptor precursor; and/or a high proportion of cone photoreceptor in photoreceptor, as compared to a retinal tissue produced in the absence of a dorsalization signal transmitter, or in the presence of a dorsalization signal transmitter such as BMP4 and the like. That is, in a stage where Muller cell is found, the proportion of a total of the PAX6-positive/CHX10-negative cell (that is, any of ganglion cell, amacrine cell, horizontal cell) and the PAX6-negative/CHX10-strongly positive cell (that is, bipolar cell) is low, and is not more than 30%, preferably not more than 25%, more preferably not more than 20%, of the total number of cells. Furthermore, a neural retinal tissue in which CRX-positive cell (that is, photoreceptor precursor) is contained at not less than 40%, preferably not less than 53%, more preferably not less than 57%, further more preferable not less than 66%, of the total number of cells and/or CRX-positive and RXR-γ-positive and NRL-negative cell is contained at not less than 32%, preferably not less than 44%, more preferably not less than 54%, further more preferably not less than 57%, of the total number of cells is also within the scope of the present invention.

In addition, a neural retinal tissue obtained by the methods described in the above-mentioned 4., 5. and 6. contains ectopic photoreceptor precursor and/or photoreceptor. Here, the ectopic photoreceptor precursor and/or photoreceptor means photoreceptor precursor and/or photoreceptor present in a layer other than the photoreceptor layer among the cell layers constituting the retina. In the neural retinal tissue, when preferably applied to a retinal tissue of the living body, an ectopic CRX-positive cell (that is, photoreceptor precursor or photoreceptor) emerges on the basement membrane side, in detail, a region corresponding to the basement membrane side from the outer nuclear layer, namely, a region extending from the neural retinal progenitor cell layer in a neural retinal tissue in a developing stage including a neural retinal progenitor cell to the ganglion cell layer, in other words, the neuroblastic layer and a region on the basement membrane side from the neuroblastic layer, and an ectopic photoreceptor layer (also called photoreceptor precursor layer) can be formed in a cell layer on the basement membrane side such as an inner nuclear layer containing bipolar cell and amacrine cell and the like, a ganglion cell layer containing ganglion cell and the like among the respective layers constituting the retinal tissue along with a maturation. Thus, it is a retinal tissue suitable for transplantation since, when transplanted, the special or physical distance between bipolar cells of the recipient and the photoreceptor precursor contained in the transplanted retinal tissue becomes shorter.

That is, the neural retinal tissue is a retinal tissue characterized by a low proportion of ganglion cell, amacrine cell, horizontal cell, and bipolar cell, and further, a high proportion of cone photoreceptor precursor in photoreceptor precursor and/or cone photoreceptor in photoreceptor, and a retinal tissue in which the above-mentioned ectopic photoreceptor layer (also called photoreceptor precursor layer) can be formed is also within the scope of the present invention.

In the retinal tissue, the proportion of a photoreceptor precursor contained in the above-mentioned ectopic photoreceptor layer (also called photoreceptor precursor layer) is specifically not less than 10%, preferably not less than 15%, more preferably not less than 20%, further more preferably not less than 25%, of the total number of cells contained in the neural retinal tissue. The proportion of the above-mentioned ectopic photoreceptor precursor in the photoreceptor precursor present in the outer nuclear layer is not less than 30%, preferably not less than 40%, more preferably not less than 50%, further more preferably not less than 60%.

Any of the aforementioned matured neural retinal tissues constitutes a cell aggregate containing a continuous epithelial structure, and can be formed such that the apical surface of the surface is in contact with the culture medium side.

(2) Neural Retinal Tissue with Moderate Maturation Degree

A neural retinal tissue obtained by continuously culturing by the method described in the above-mentioned 4. for about 65 days-75 days from the start of suspension culture, that can be differentiated into the matured neural retinal tissue described in the above-mentioned (1) is also within the scope of the present invention. The neural retinal tissue is rich in cone photoreceptor or cone photoreceptor precursor and, in one embodiment, in a differentiation stage where emergence rate of a cone photoreceptor precursor reaches maximum. The neural retinal tissue has a high proportion of photoreceptor precursor and/or cone photoreceptor precursor in a stage where emergence rate of cone photoreceptor precursor reaches maximum than a neural retinal tissue in vivo or a retinal tissue produced in the absence of thyroid gland hormone signal transduction pathway agonist. That is, a neural retinal tissue in a stage where emergence rate of cone photoreceptor precursor reaches maximum, and containing CRX-positive cell at not less than 10%, preferably not less than 11%, more preferably not less than 15%, further preferably not less than 20%, of the total number of cells; and/or CRX-positive and TRβ2-positive cell at not less than 7%, preferably not less than 10%, further preferably not less than 11%, of the total number of cells is also within the scope of the present invention.

A neural retinal tissue obtained by continuously culturing by the method described in the above-mentioned 5. for about 65 days-75 days from the start of suspension culture, that can be differentiated into the matured neural retinal tissue described in the above-mentioned (1) is also within the scope of the present invention. The neural retinal tissue is rich in cone photoreceptor or cone photoreceptor precursor and, in one embodiment, in a differentiation stage where emergence rate of a cone photoreceptor precursor reaches maximum. In the neural retinal tissue, the proportion of photoreceptor precursor in the whole cells and/or cone photoreceptor precursor in photoreceptor precursor is higher as compared to a retinal tissue produced in the absence of a dorsalization signal transmitter. That is, a neural retinal tissue in a stage where emergence rate of cone photoreceptor precursor reaches maximum, and containing CRX-positive cell at not less than 20%, more preferably not less than 25%, further preferably not less than 29%, of the total number of cells; and/or CRX-positive and TRβ2-positive cell at not less than 11%, preferably not less than 13%, further preferably not less than 15%, of the total number of cells is also within the scope of the present invention.

Among the neural retinal tissues obtained by the method described in the above-mentioned 5., when an SHH signal transduction pathway inhibitor was used as a dorsalization signal transmitter, the neural retinal tissue is characterized by a higher proportion of photoreceptor precursor in the whole cells as compared to a retinal tissue produced in the absence of a dorsalization signal transmitter or in the presence of a dorsalization signal transmitter such as BMP4 and the like. That is, a neural retinal tissue in a stage where emergence rate of cone photoreceptor precursor reaches maximum, and containing CRX-positive cell at not less than 20%, more preferably not less than 25%, further preferably not less than 30%, of the total number of cells is also within the scope of the present invention.

As a neural retinal tissue obtained by continuously culturing for about 65 days-75 days from the start of suspension culture of the present invention, a neural retinal tissue containing CRX-positive cell (that is, photoreceptor precursor) at not less than 20% and/or CRX-positive/TRβ2-positive cell (that is, cone photoreceptor precursor that emerges in the initial developmental stage) at not less than 10% can be mentioned. The neural retinal tissue can be produced by culturing in the presence of a thyroid gland hormone signal transduction pathway agonist. In addition, a neural retinal tissue characterized by the presence of an ectopic CRX-positive cell (that is, photoreceptor precursor) in, when applied to a living body, a region corresponding to the basement membrane side from the outer nuclear layer, namely, a region extending from the neural retinal progenitor cell layer to the ganglion cell layer, in other words, the neuroblastic layer in a neural retinal tissue in a developing stage including a neural retinal progenitor cell and a region on the basement membrane side from the neuroblastic layer can be mentioned. That is, the neural retinal tissue is a retinal tissue suitable for transplantation since, when transplanted, the special or physical distance between bipolar cells of the recipient and the photoreceptor precursor contained in the transplanted retinal tissue becomes shorter. In addition, the neural retinal tissue is a retinal tissue characterized in that it shows a high proportion of photoreceptor precursor and/or cone photoreceptor precursor in photoreceptor precursor, and the proportions of the photoreceptor precursor that emerges on the apical surface side containing a neuroblastic layer (NBL) and the ectopic photoreceptor precursor that emerges on the basement membrane side from NBL are of a certain level, more preferably the same level. Here, "certain level, preferably the same level" specifically means that the ratio of the proportions per area of photoreceptor precursors contained in the basement membrane side from NBL and the apical surface side containing NBL is 10:1 to 1:10, preferably 2:1 to 1:2, more preferably 10:7 to 7:10.

A neural retinal tissue obtained by continuously culturing by the method described in the above-mentioned 4. for about 90 days-105 days from the start of suspension culture, that can be differentiated into the matured neural retinal tissue described in the above-mentioned (1) is also within the scope of the present invention. The neural retinal tissue is rich in cone photoreceptor or cone photoreceptor precursor and, in one embodiment, in a differentiation stage where rod photoreceptor precursor or rod photoreceptor precursor (or bipolar cell) starts to emerge. The neural retinal tissue characteristically shows a higher proportion of photoreceptor precursor and/or cone photoreceptor precursor than a neural retinal tissue in vivo or a retinal tissue produced in the absence of a thyroid gland hormone signal transduction pathway agonist in a stage where rod photoreceptor precursor starts to emerge. That is, a neural retinal tissue containing CRX-positive cell at not less than 20%, preferably not less than 25%, further preferably not less than 30%, of the total number of cells in a stage where rod photoreceptor precursor starts to emerge is also within the scope of the present invention. In addition, a neural retinal tissue in the differentiation stage where two cells on average, preferably not less than 3 cells on average, more preferably not less than 4 cells on average, are photoreceptor precursors (CRX-positive cells) along a straight line vertical to the tangent line of the apical surface is also within the scope of the present invention. Also, these neural retinal tissues, preferably the retinal tissues in the differentiation stage, contain an ectopic photoreceptor precursor on the basement membrane side from the neuroblastic layer (NBL).

A neural retinal tissue obtained by continuously culturing by the method described in the above-mentioned 5. for about 90 days-105 days from the start of suspension culture, that can be differentiated into the matured neural retinal tissue described in the above-mentioned (1) is also within the scope of the present invention. The neural retinal tissue is rich in cone photoreceptor or cone photoreceptor precursor and, in one embodiment, in a differentiation stage where rod photoreceptor precursor or rod photoreceptor (or bipolar cell) starts to emerge. The neural retinal tissue characteristically shows a higher proportion of photoreceptor precursor and/or cone photoreceptor precursor than a neural retinal tissue in vivo or a retinal tissue produced in the absence of a thyroid gland hormone signal transduction pathway agonist in a stage where rod photoreceptor precursor (or bipolar cell) starts to emerge. That is, a neural retinal tissue containing CRX-positive cell at not less than 25%, preferably not less than 30%, further preferably not less than 40%, further more preferably not less than 50%, of the total number of cells in a stage where rod photoreceptor precursor (or bipolar cell) starts to emerge is also within the scope of the present invention. In addition, a neural retinal tissue in the differentiation stage where two cells on average, preferably not less than 3 cells on average, more preferably not less than 4 cells on average, are photoreceptor precursors (CRX-positive cells) along a straight line vertical to the tangent line of the apical surface is also within the scope of the present invention. Also, these neural retinal tissues, preferably the retinal tissues in the differentiation stage, contain an ectopic photoreceptor precursor on the basement membrane side from the neuroblastic layer (NBL).

As a preferable embodiment of the neural retinal tissue of the present invention, neural retinal tissue having at least one, preferably 3, more preferably 2 in addition to the above-mentioned (3), further preferably 3 in addition to the above-mentioned (3), further more preferably all, of the following characteristics can be mentioned:

(1) the number of CRX-positive cells is not less than 10%, preferably not less than 20%, further preferably not less than 25%, more preferably not less than 30%;
(2) the number of CRX-positive and TRβ2-positive cells is not less than 10%, preferably not less than 15%; and
(3) an ectopic CRX-positive cell is present in a region corresponding to the basement membrane side from the neuroblastic layer (NBL) (or basement membrane side from the outer nuclear layer);
(4) a ratio of ectopic photoreceptor precursor that emerges on the basement membrane side from the neuroblastic layer (NBL) and photoreceptor precursor that emerges on the apical surface side containing a neuroblastic layer is 10:1-1:10 (e.g., 1:1);
(5) a continuous epithelial rate is not less than 50%, preferably not less than 80%, more preferably not less than 95%.

The neural retinal cell of the present invention is, in one embodiment, a retinal tissue in a stage where the proportion of cone photoreceptor precursor that emerges in the neural retinal tissue is maximum. Here, the stage where the proportion of cone photoreceptor precursor is maximum can be identified by examining the time when the proportion of differentiation of cone photoreceptor precursor from neural retinal progenitor cell becomes maximum by the aforementioned method. Specifically, it corresponds to a neural retinal tissue (or cell aggregate containing neural retinal tissue) corresponding to 30-50 days, preferably 30-40 days, after recognition of the emergence of cone photoreceptor precursor, or a neural retinal tissue (or cell aggregate containing neural retinal tissue) on about day 60-70 from the start of suspension culture when, for example, a retinal tissue produced by the method described in the starting material production methods 1-4 is the starting material, or a neural retinal tissue (or cell aggregate containing neural retinal tissue) on about day 65-75 from the start of suspension culture when, for example, a retinal tissue produced by the method described in the starting material production methods 5-7 is the starting material.

As a preferable embodiment of the neural retinal tissue of the present invention, neural retinal tissue having at least one, preferably 2, more preferably the above-mentioned (1) and (2), further preferably 2 in addition to (3), further more preferably all, of the following characteristics can be mentioned:

(1) the number of CRX-positive cells is not less than 25%, preferably not less than 30%, more preferably not less than 40%, further more preferably not less than 50%;
(2) two cells on average, preferably not less than 3 cells on average, more preferably not less than 4 cells on average, are photoreceptor precursors (CRX-positive cells) along a straight line vertical to the tangent line of the apical surface; and
(3) ectopic photoreceptor precursor is contained on the basement membrane side from the neuroblastic layer (NBL);
(4) a continuous epithelial rate is not less than 50%, preferably not less than 80%, more preferably not less than 95%.

The neural retinal cell of the present invention is, in one embodiment, a retinal tissue in a stage where rod photoreceptor precursor starts to emerge in the neural retinal tissue. Here, the stage where the rod photoreceptor precursor starts to emerge can be identified by examining the time when the marker of the rod photoreceptor precursor, specifically CRX and NRL-positive cell (or CHX10-strongly positive and PAX6-negative cell), starts to emerge in the neural retinal tissue. Alternatively, it can also be identified by specifying the stage where bipolar cell starts to emerge, which is a stage similar to the stage where rod photoreceptor precursor starts to emerge. Here, the stage where the bipolar cell starts to emerge can be identified by specifying the stage where the marker of the bipolar cell, i.e., CHX10-strongly positive and PAX6-negative cell, starts to emerge in the neural retinal tissue. Specifically, the stage where the rod photoreceptor precursor (or bipolar cell) starts to emerge is a differentiation stage within 20 days, preferably 15 days, more preferably 10 days, further preferably 5 days, from the emergence of rod photoreceptor precursor (or bipolar cell) and containing neural retinal progenitor cell in a stage of differentiation into rod photoreceptor precursor (or bipolar cell). Whether the neural retinal progenitor cell is in a stage of differentiation into a rod photoreceptor precursor (or bipolar cell) can be determined by adding, to the culture medium, BrdU or EdU and the like to be incorporated into a neural retinal cell as proliferated cell in the retinal tissue and identifying, using an antibody whether the cell that has incorporated BrdU or EdU and the like expresses a marker of the rod photoreceptor precursor (or bipolar cell). For example, BrdU is added for a given period (e.g., 1 day from day 90, 91, 92, 93, 94-day 110 from the start of suspension culture, etc.) to the medium, retinal tissue is analyzed immediately thereafter, and when BrdU-positive and bipolar cell (or rod photoreceptor precursor) marker-positive cell can be observed, then the period (the very day in case of 1 day) of BrdU addition can be identified as a stage containing a neural retinal tissue in a stage of differentiation into bipolar cell (or rod photoreceptor precursor). Alternatively, it may also be identified as a stage where bipolar cell (or rod photoreceptor precursor) marker-positive cell is detected, and BLIMP1-positive cell known to transiently express in a photoreceptor precursor is detected. More specifically, it corresponds to a neural retinal tissue (or cell aggregate containing neural retinal tissue) corresponding to 55-80 days, preferably 55-70 days, after recognition of the emergence of cone photoreceptor precursor, or a neural retinal tissue on about day 85-100 from the start of suspension culture when, for example, a retinal tissue produced by the method described in the starting material production methods 1-4 is the starting material, or in the case of a neural retinal tissue (or cell aggregate containing neural retinal tissue) produced by the above-mentioned production methods 5, 6 and/or 7, the neural retinal tissue corresponds to a neural retinal tissue on day 90-day 105 from the start of suspension culture (corresponding to days 55-80, preferably days 55-70 after recognition of emergence of the cone photoreceptor precursor).

As a preferable embodiment of the neural retinal tissue of the present invention, neural retinal tissue having at least 3, preferably 5, more preferably 4 in addition to the above-mentioned (1) and (7), further preferably 5 in addition to the above-mentioned (1) and (7), further preferably all, of the following characteristics can be mentioned:
  (1) CRABP or CRALBP-positive cell is contained;
  (2) PAX6-positive/CHX10-negative cell is contained at not more than 30%, preferably not more than 20%, more preferably not more than 15%, further more preferably not more than 10%;
  (3) PAX6-negative/CHX10-strongly positive cell is contained at not more than 10%, preferably not more than 5%;
  (4) the total of PAX6-positive/CHX10-negative cell and PAX6-negative/CHX10-strongly positive cell is not more than 30%, preferably not more than 20%, more preferably not more than 14%;
  (5) CRX-positive cell is contained at not less than 40%, preferably not less than 50%, more preferably not less than 57%, further more preferably not less than 66%;
  (6) the number of RXR-γ-positive and NRL-negative cells in the CRX-positive cells is not less than 32%, preferably not less than 40%, more preferably not less than 54%, further more preferably 57%;
  (7) ectopic CRX-positive cell is present in a region corresponding to the basement membrane side from the outer nuclear layer; and
  (8) a continuous epithelial rate is not less than 50%, preferably not less than 80%, more preferably not less than 95%.

The neural retinal cell of the present invention is, in one embodiment, a retinal tissue differentiated to the extent that Muller cell is found in the neural retinal tissue. Here, the Muller cell can be identified by detecting a well-known marker, for example, CRABP-positive cell and/or CRALBP-positive cell. Specifically, for example, in the case of a retinal tissue (or cell aggregate containing retinal tissue) produced by the above-mentioned production methods 1-3, 4, 5, 6 and/or 7, the neural retinal tissue corresponds to a neural retinal tissue on day 180-day 200 from the start of suspension culture.

Particularly, when a BMP signal transduction pathway agonist such as BMP4 and the like is used as a dorsalization signal transmitter in the production method of the above-mentioned 5., a cone photoreceptor precursor selective neural retinal tissue in which a rod photoreceptor precursor is scarcely present in the photoreceptor precursor contained in the retinal tissue, in addition to the above-mentioned characteristics, can be produced. In addition, when an SHH signal transduction pathway inhibitor such as Cyclopamine-KAAD and the like is used as a dorsalization signal transmitter in the production method of the above-mentioned 5., a neural retinal tissue having a low proportion of bipolar cell a high proportion of photoreceptor precursor and a high proportion of cone photoreceptor precursor contained in the retinal tissue, in addition to the above-mentioned characteristics, can be produced. These neural retinal tissues are also within the scope of the present invention.

A neural retinal tissue that can be differentiated into any of the aforementioned matured neural retinal tissues constitutes a cell aggregate containing a continuous epithelial structure, and can be formed such that the apical surface of the surface is in contact with the culture medium side. The proportion of the apical surface adjacent to the medium side to the surface of the neural retinal tissue is not less than 50%, preferably not less than 80%, more preferably not less than 95%.

As the aforementioned "matured neural retinal tissue" or "neural retinal tissue that can be differentiated into matured neural retinal tissue" obtained by the method of the present invention, the form of a cell aggregate with an average diameter size of 1-2 mm, specifically about 1.3 mm, can be mentioned. In addition, a cell aggregate population in which at least 60%, preferably not less than 70%, 80%, more preferably 85%, 90%, 95% of aggregates have a size of not less than 1.0 mm is also within the scope of the present invention. The cell aggregate population includes a cell aggregate of not less than 1.5 mm, preferably not less than 2.0 mm, further preferably not less than 2.5 mm, 2.9 mm.

9. Pharmaceutical Composition

The present invention provides a pharmaceutical composition containing an effective amount of a neural retinal tissue. The pharmaceutical composition contains an effective amount of the neural retinal tissue of the present invention and a pharmaceutically acceptable carrier.

As a pharmaceutically acceptable carrier, a physiological aqueous solvent (saline, buffer, serum-free medium etc.) can be used. Where necessary, in a transplantation therapy, a medicament containing a tissue or cells to be transplanted may contain conventionally used preservative, stabilizer, reducing agent, isotonizing agent and the like.

The pharmaceutical composition of the present invention can be produced as a suspension by suspending the neural retinal tissue of the present invention in an appropriate physiological aqueous solvent. Where necessary, the composition may be cryopreserved by adding a cryopreservative, and when in use, thawed and washed with buffer for use of a transplantation therapy.

The neural retinal tissue of the present invention can take various forms suitable for medical use. it may take various shapes such as a sheet shape, a column shape, a lump shape, a plug shape and the like can be processed into a shape suitable for administration by appropriate molding. The sheet shape is preferable from the viewpoint of superior therapeutic effect, convenience, and the like.

The neural retinal tissue of the present invention may be cut in an appropriate size with a tool such as tweezers and the like to prepare a retinal tissue section of administration. In addition, a sparse retinal tissue section cut into a sheet like form can be used as a sheet agent. When forming a sheet, a suitable sheet or mesh sheet made of a biocompatible polymer, monomer, or gel for the purpose of extending the neural retinal tissue of the present invention may also be used.

That is, a pharmaceutical composition containing a retinal tissue section cut out from the neural retinal tissue of the present invention is also within the scope of the present invention.

A retinal cell suspension for administration can be prepared by dispersing the neural retinal tissue of the present invention by using a cell dispersant containing protease such as papain and the like. In addition, it is also possible to separate a cell desirable as an active ingredient from the cells contained in the cell suspension by the use of specific antibody, aptamer, peptide, and the like of an antigen protein expressed by the target cell, and provide a pharmaceutical composition thereof.

That is, a pharmaceutical composition containing a cell suspension prepared by dispersing and/or purifying the neural retinal tissue of the present invention is also within the scope of the present invention.

In the neural retinal tissue of the present invention, it was found that the proportion of bipolar cell, amacrine cell and the like not desirable for forming synapses with recipient cells can be reduced, ectopic photoreceptor precursor can be allowed to emerge also in the area where synapse formation with recipient cells is easy, which is on the basement membrane side from the outer nuclear layer, and the proportion of the photoreceptor precursor can be increased. That is, the present invention can produce a retinal tissue for transplantation which is useful as a pharmaceutical product used for regenerative medicine.

The transplantation site of the retinal tissue for transplantation is not particularly limited as long as it is an eye region where regeneration of photoreceptor cells is required. It is particularly useful as a retinal tissue for transplantation into the macula or the center of the macula, since the proportion of cone photoreceptor precursor is high.

8. Treatment Method

The neural retinal tissue of the present invention is useful for a transplantation therapy for a disease due to (caused by) a disorder of the retinal tissue, or a disorder of the retinal cell contained therein. Thus, the present invention provides a therapeutic drug for a disease due to a disorder of a retinal tissue, which contains a neural retinal tissue of the present invention, and a treatment method including administering the therapeutic drug to patients. The neural retinal tissue of the present invention can be used as a therapeutic drug for a disease based on a disorder of a retinal tissue or to supplement a retinal tissue to the corresponding damaged site in a damaged state of the retinal tissue. A disease due to a disorder of a retinal tissue, and a damaged state of a retinal tissue can be treated by transplanting a retinal cell produced by the production method of the present invention to a patient with a disease due to a disorder of a retinal tissue, or a damaged state of a retinal tissue, who requires transplantation, to supplement the disordered retinal tissue itself. Examples of the disease due to a disorder of a retinal tissue include retinal denaturation, retinitis pigmentosa, age-related macular degeneration, organic mercury poisoning, chloroquine retinopathy, glaucoma, diabetic retinopathy, retinopathy of newborn babies, and the like.

Among the neural retinal tissues of the present invention, a neural retinal tissue rich in photoreceptor precursor and/or photoreceptor, further a neural retinal tissue containing photoreceptor precursor and/or photoreceptor rich in cone photoreceptor precursor and/or cone photoreceptor, are useful as pharmaceutical compositions for transplantation into a region of patients' eyes where cone photoreceptor is abundant. The region where cone photoreceptor precursor and/or cone photoreceptor are/is abundant is specifically a region containing a Rod-free zone. The region containing a Rod-free zone includes a region having a macular-like structure, preferably macula. That is, the retinal tissue of the present invention rich in cone photoreceptor precursor and containing photoreceptor is useful as a pharmaceutical composition for transplantation into the macula, preferably more central region of the macula, of patients. The diseases that require transplantation to the macula include conditions such as age-related macular degeneration, where visual acuity in light place (i.e., visual acuity in the daytime) is reduced, visual field constriction in light place, total blindness, and the like, and the composition can be utilized to improve or treat these.

In transplantation therapy, rejection due to the difference in histocompatibility antigens often poses a problem. The problem can be solved by using pluripotent stem cells (e.g., induced pluripotent stem cells) established from the somatic cells of the transplantation recipient. That is, in a preferable embodiment, by using pluripotent stem cells (e.g., induced pluripotent stem cells) established from the somatic cell of the recipient as pluripotent stem cells in the method of present invention, a neural tissue or neural cell which is immunological self to the recipient is produced, and they are transplanted to the recipient.

In addition, an allogenic retinal tissue or retinal cell may be produced from pluripotent stem cells (e.g., induced pluripotent stem cells) established from the somatic cell of others who are immunologically compatible with the recipient (e.g., compatible in part or all of HLA type and MHC type), and transplanted to the recipient.

11. Toxicity, Efficacy Evaluation Method

Since the neural retinal tissue of the present invention is useful as a material for disease study or drug discovery in a screening or toxicity evaluation for a medicament for treating a disease due to a disorder of a retinal tissue, it can be used as a reagent for evaluating toxicity or efficacy of a test substance. For example, iPS cells are generated from a human patient with a disease due to a disorder of a retinal tissue, particularly a hereditary disease, and using the iPS cells, the retinal tissue of the present invention is produced by the method of the present invention. The retinal tissue can reproduce the disorder of retinal tissue causing the disease of the patient in vitro. Therefore, the present invention provides a method for evaluating toxicity or efficacy of a test substance, which includes contacting a test substance with a retinal tissue produced by the production method of the present invention and detecting an influence of the substance on the tissue.

For example, a retinal tissue having a particular disorder (e.g., hereditary disorder) which is produced by the production method of the present invention is cultured in the presence or absence (negative control) of a test substance. Then, the severity of disorder of the retinal tissue treated with a test substance is compared with that of the negative control. As a result, a test substance that reduced the severity of the disorder can be selected as a candidate substance for a medicament for treating the disease resulting from the disorder. For example, a test substance that improves the physiological activity (e.g., survival promotion or maturation) of the retinal tissue produced by the production method of the present invention can be searched for as a candidate substance of a pharmaceutical product. Alternatively, an induced pluripotent stem cell is prepared from a somatic cell having a gene mutation that causes a particular disorder such as a disease having a disorder of a retinal tissue and the like, a test substance is added to a retinal progenitor cell or retinal layer-specific neuron produced by differentiation induction of the cell by the production method of the present invention, and a candidate of a test substance effective as a therapeutic drug or prophylactic drug for the disorder can be searched for based on whether they show the disorder as an index.

For toxicity evaluation, the neural retinal tissue of the present invention is cultured in the presence or absence (negative control) of a test substance. Then, the severity of toxicity on the retinal tissue treated with the test substance is compared with that of the negative control. As a result, a test substance that exerted toxicity as compared to the negative control can be judged as a substance having toxicity to the retinal tissue.

That is, the present invention encompasses a method for evaluating toxicity including the following steps:
(step 1) a step of culturing the neural retinal tissue of the present invention under viable culture conditions for a given time in the presence of a test substance, and measuring the severity of cell injury,
(step 2) a step of culturing a retinal tissue produced by the production method of the present invention under viable culture conditions for a given time in the absence of test substance or in the presence of a positive control, and measuring the severity of cell injury,
(step 3) a step of evaluating the toxicity of the test substance in step 1, based on the difference in the results measured in (step 1) and (step 2).

As used herein, "in the absence of a test substance" encompasses adding only a culture medium or a solvent used to dissolve the test substance instead of adding a test substance. In addition, "positive control" means a known compound having toxicity. Examples of the method for measuring the severity of cell injury include a method for measuring the number of viable cells, for example, a method for measuring intracellular ATP amount, a method for measuring the number of viable cells by cell staining (e.g., nucleus staining) and morphology observation and the like.

In (step 3), as a method for evaluating the toxicity of a test substance, the measurement value in step 1 and the measurement value of the negative control in (step 2) are compared, and when the severity of cell injury in step 1 is higher, the test substance can be judged to have toxicity. In addition, the measurement value in step 1 and the measurement value of the positive control in (step 2) are compared, and when the severity of cell injury in step 1 is the same or above, the test substance can be judged to have toxicity.

The obtained neural retinal tissue may be used as it is as a reagent for evaluating toxicity or efficacy. The neural retinal tissue is subjected to a dispersion treatment (e.g., trypsin/EDTA treatment or papain treatment), and the obtained cells are subjected to a selection using FACS or MACS, whereby highly pure neural retinal progenitor cells can also be obtained. In addition, the photoreceptor precursor (S cone photoreceptor precursor, L cone photoreceptor precursor, M cone photoreceptor precursor, or rod photoreceptor precursor) contained in the neural retinal tissue may be differentiated, after final maturation, into photoreceptors (S cone photoreceptor, L cone photoreceptor, M cone photoreceptor, or rod photoreceptor) expressing a visual pigment and used as a reagent for evaluating toxicity and efficacy.

EXAMPLE

While the present invention is explained in more detail by referring to the Examples, the present invention is not limited thereto.

Example 1 (Production Example of Cell Aggregate Containing Retinal Tissue Using Human ES Cell and Method for Cutting Out Retinal Tissue)

CRX:Venus knock-in human ES cells (derived from KhES-1; Nakano, T. et al. Cell Stem Cell 2012, 10(6), 771-785) were cultured according to the methods described in "Ueno, M. et al. PNAS 2006, 103(25), 9554-9559" and "Watanabe, K. et al. Nat Biotech 2007, 25, 681-686". As a medium for culturing human ES cells, DMEM/F12 medium (Sigma) supplemented with 20% KSR (KNOCKOUT™ serum replacement medium; Invitrogen), 0.1 mM 2-mercaptoethanol, 2 mM L-glutamine, 1× non-essential amino acid (Thermo Fisher Scientific, 11140050), 7.5 ng/ml bFGF was used.

A cell aggregate containing a retinal tissue in an initial developmental stage was prepared by the method described in "Kuwahara et al. Nat Commun 2015, 19(6), 6286-" after modification in part. That is, the aforementioned cultured ES cells were individually dispersed using TRYPLE™ Express cell dispersion solution (Invitrogen), and the individually dispersed human ES cells were suspended in 100 μL of a serum-free medium in a cell non-adhesive 96 well culture plate (SUMILON spheroid plate, SUMITOMO BAKELITE CO., LTD.) at 9×10³ cells per well to allow rapid formation of aggregates, after which they were cultured at 37° C., 5% $CO_2$. As the serum-free medium therefor, a serum-free medium obtained by adding 10% KSR, 450 μM 1-monothioglycerol, 1× Chemically defined lipid concentrate, 5 mg/mL BSA, 20 μM Y27632 to a 1:1 mixture of F-12 medium and IMDM medium was used. At 6 days after the start of suspension culture, BMP4 at a final concentration of 1.5 nM was added and suspension culture was continued. A half amount of the culture medium in the well was exchanged with the above-mentioned medium not supplemented with a BMP signal transduction pathway agonist every 3 or 4 days. A cell aggregate containing a retinal tissue at day 18 from the start of suspension culture was cultured in suspension in a serum-free medium (DMEM/F12 medium supplemented with 1% N2 supplement) containing 3 μM CHIR99021 and 5 μM SU5402 for 4 days, namely, up to day 22 from the start of suspension culture. Thereafter, suspension culture of the cell aggregate containing the retinal tissue was continued until it was appropriately used for analysis and the like. As the culture medium during this period, serum-containing media shown in the following [1] to [3] were used and the cell aggregate was cultured under 5% $CO_2$ conditions.

[1] day 22 to day 38 from the start of suspension culture; DMEM/F12 medium supplemented with 10% fetal calf serum, 1% N2 supplement, and 100 μM taurine (hereinafter to be referred to as medium A).

[2] day 38 to day 60 from the start of suspension culture; a 1:3 mixed medium of medium A, and Neurobasal medium supplemented with 10% fetal calf serum, 2% B27 supplement, 200 mM glutamine, and 100 μM taurine (hereinafter to be referred to as medium B).

[3] after day 60 or later from the start of suspension culture: medium B.

The most portion of the cell aggregate that is not the retinal tissue was visually checked and then appropriately excised using tweezers to cut out the retinal tissue from the cell aggregate containing retinal tissue and appropriately used for analysis. FIG. 1a, b show an example in which a retinal tissue was cut out from a cell aggregate containing a retinal tissue on day 35 from the start of suspension culture. Furthermore, thereafter, a cell aggregate containing a retinal tissue cultured according to the above-mentioned culture method was observed under a fluorescent microscope (Biorevo BZ-9000, Keyence). As a result, by day 42 after the start of suspension culture, green fluorescence exhibited by knock-in CRX:Venus could be observed in almost all retinal tissues (FIG. 1c, d). Therefrom it could be confirmed that a photoreceptor precursor emerges by day 42.

Example 2

The cell aggregates containing a retinal tissue shown in Example 2 were prepared by respectively adding T3 or dorsalization signal transmitter BMP4 or Cyclopamine-KAAD as follows in the method described in Example 1.

[1]-T3 group (FIG. 2a); culture was performed as described in Example 1 and cultured up to day 74 from the start of suspension culture.

[2] +T3 group (FIG. 2b); using the culture medium described in Example 1, 60 nM T3 was further added from day 38 from the start of suspension culture to the completion of suspension culture, and cultured up to day 69 from the start of suspension culture.

[3] +T3+BMP group (FIG. 2c); using the culture medium described in Example 1, 0.15 nM BMP4 and 60 nM T3 were each added from day 22, day 38 from the start of suspension culture to the completion of suspension culture, and cultured up to day 69 from the start of suspension culture.

[4] +T3+Cyclopamine-KAAD group (FIG. 2d); using the culture medium described in Example 1, 500 nM Cyclopamine-KAAD and 60 nM T3 were each added from day 22, day 38 from the start of suspension culture to the completion of suspension culture, and cultured up to day 69 from the start of suspension culture.

A cell aggregate containing a retinal tissue cultured under the above conditions was observed under a fluorescent microscope (Biorevo BZ-9000, Keyence). As a result, green fluorescence shown by knocked-in CRX:Venus was observed more in the retinal tissue of +T3 group than in the retinal tissue of −T3 group (FIG. 2a, b). Furthermore, green fluorescence shown by knocked-in CRX:Venus was observed still more in the retinal tissue of +T3+BMP group and +T3+Cyclopamine-KAAD group than in the retinal tissue of +T3 group (FIG. 2c, d).

From these, it was found that thyroid gland hormone signal transduction pathway agonist such as T3 and the like has an action of increasing photoreceptor precursor in a retinal tissue. When thyroid gland hormone signal transduction pathway agonist and dorsalization signal transmitter were allowed to act in combination, an action of further increasing photoreceptor precursor was found as compared to when thyroid gland hormone signal transduction pathway agonist was allowed to act alone.

Example 3

The cell aggregates containing a retinal tissue shown in Example 3 were prepared by respectively adding 100 nM 9-cis retinoic acid, T3 or dorsalization signal transmitter (BMP4) as follows in the method described in Example 1.

[1]-T3 group (FIG. 3a); using the culture medium described in Example 1, 100 nM 9-cis retinoic acid was further added from day 38 from the start of suspension culture to the completion of suspension culture, and cultured up to day 74 from the start of suspension culture.

[2] +T3 group (FIG. 3b); using the culture medium described in Example 1, 100 nM 9-cis retinoic acid and 60 nM T3 were further added from day 38 from the start of suspension culture to the completion of suspension culture, and cultured up to day 74 from the start of suspension culture.

[3] +T3+BMP group (FIG. 3c); using the culture medium described in Example 1, 0.45 nM BMP4 was added from day 22 from the start of suspension culture, 100 nM 9-cis retinoic acid and 60 nM T3 were added from day 38 from the start of suspension culture to the completion of suspension culture, and cultured up to day 74 from the start of suspension culture.

A cell aggregate containing a retinal tissue cultured under the above conditions was observed under a fluorescent microscope (Biorevo BZ-9000, Keyence). As a result, green fluorescence shown by knocked-in CRX:Venus was observed more in the retinal tissue of +T3 group than in the retinal tissue of −T3 group (FIG. 3a, b). Furthermore, green fluorescence shown by knocked-in CRX:Venus was observed still more in the retinal tissue of +T3+BMP group than in the retinal tissue of +T3 group (FIG. 3c).

From these, it was found that thyroid gland hormone signal transduction pathway agonist has an action of increasing photoreceptor precursor in a retinal tissue irrespective of the presence or absence of 9-cis retinoic acid. When thyroid gland hormone signal transduction pathway agonist and dorsalization signal transmitter were allowed to act in combination, an action of further increasing photoreceptor precursor was found as compared to when thyroid gland hormone signal transduction pathway agonist was allowed to act alone irrespective of the presence or absence of 9-cis retinoic acid.

Example 4

The cell aggregates containing a retinal tissue shown in Example 4 were prepared by respectively adding T3 or dorsalization signal transmitter (BMP4) as follows in the method described in Example 1.
- [1] -T3 group (FIG. 4a, FIG. 4e, FIG. 4i); using the culture medium described in Example 1, culture was performed without addition up to day 75 from the start of suspension culture.
- [2] +T3 group (FIG. 4b, FIG. 4f, FIG. 4j); using the culture medium described in Example 1, 60 nM T3 was further added from day 38 from the start of suspension culture to the completion of suspension culture, and cultured up to day 71 from the start of suspension culture.
- [3] +T3+BMP group (FIG. 4c, FIG. 4g, FIG. 4k); using the culture medium described in Example 1, 0.15 nM BMP4 and 60 nM T3 were further added respectively from day 22, day 38 from the start of suspension culture to the completion of suspension culture, and cultured up to day 71 from the start of suspension culture.
- [4] +T3+Cyclopamine-KAAD group (FIG. 4d, FIG. 4h, FIG. 4l); using the culture medium described in Example 1, 500 nM Cyclopamine-KAAD and 60 nM T3 were further added respectively from day 22, day 38 from the start of suspension culture to the completion of suspension culture, and cultured up to day 71 from the start of suspension culture.

Figure 4:
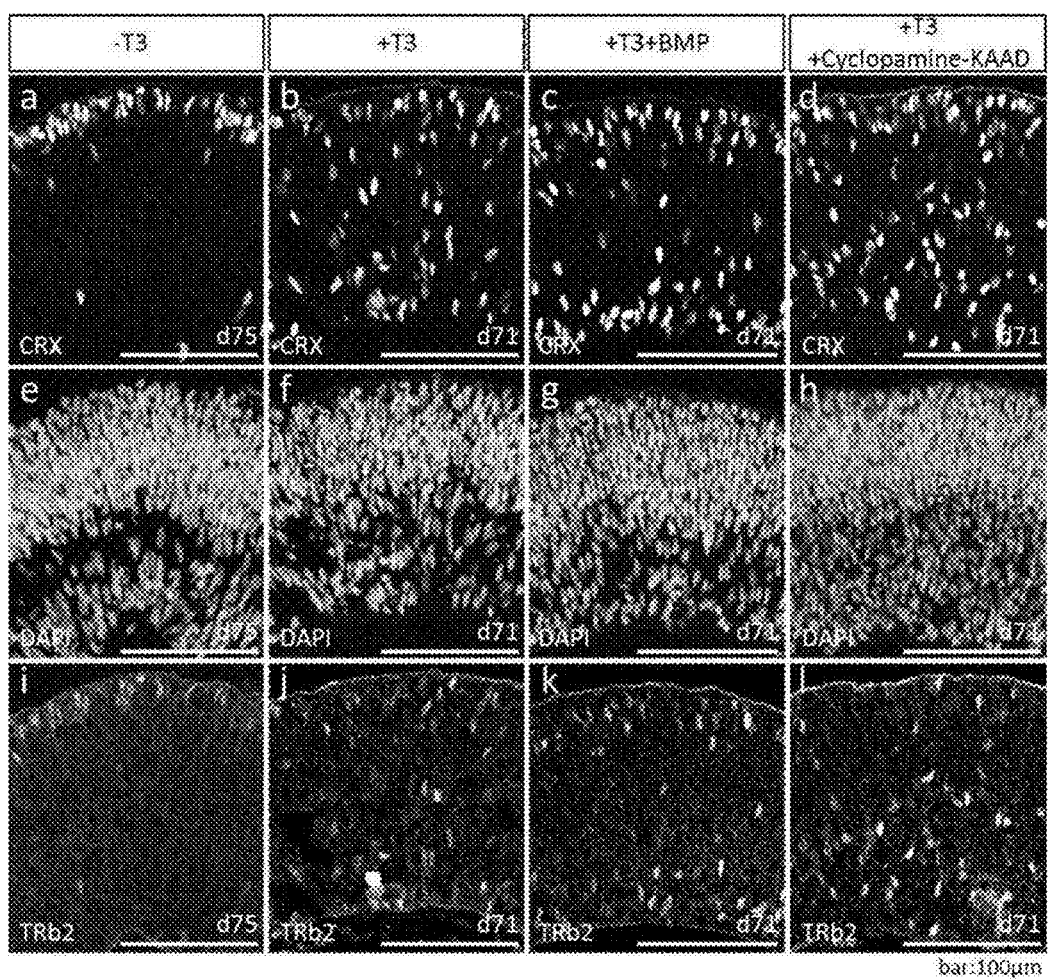
FIG. 4 shows the results obtained by culturing cell aggregates containing a retinal tissue produced from human ES cells up to about day 71-75 from the start of suspension culture, preparing a section of the collected cell aggregates containing the retinal tissue, performing immunostaining using an anti-CRX antibody, an anti-TRβ2 antibody, and DAPI by a conventional method, and analyzing CRX-positive cells and TRβ2-positive cells among CRX-positive cells. Compared to the T3 no-addition group (−T3; a, e, i), it is clear that CRX-positive cell and CRX-positive and TRβ2-positive cell increased in T3 addition group (+T3; b, f, j). When a dorsalization signal transmitter was added in addition to T3 (+T3+BMP4; c, g, k, +T3+Cyclopamine-KAAD; d, h, l), it is clear that CRX-positive cell and CRX-positive and TRβ2-positive cell further increased. Particularly, it is clear that CRX-positive cell and CRX-positive and TRβ2-positive cell further increased in +T3+Cyclopamine-KAAD group as compared to +T3+BMP4 group. These cells emerge ectopically not only the apical surface side but also the basement membrane side (neuroblastic layer and ganglion cell layer) and it is clear that the proportion thereof is almost of the same level in the basement membrane side from the neuroblastic layer and other regions. In this differentiation stage, the CRX-positive cell, and CRX-positive and TRβ2-positive cell are photoreceptor precursor and cone photoreceptor precursor.

After fixing cell aggregates containing retinal tissue cultured under the above conditions with 4% para-formaldehyde, cryosections were prepared and subjected to immunostaining using CRX, TRβ2(TRb2) antibody, or DAPI staining for staining the cell nucleus. As a result of observation with a fluorescence microscope, CRX-positive cell which is a photoreceptor precursor was found more in the retinal tissue of +T3 group as compared to the retinal tissue of -T3 group (FIG. 4a, b). Also, as compared to the retinal tissue of -T3 group, in the retinal tissue of +T3 group, it is also present in a region other than the apical surface (photoreceptor layer, outer nuclear layer) and neuroblastic layer, where photoreceptor precursor is originally present in retinal tissue in the fetal stage, namely, a region extending from neural retinal progenitor cell layer to ganglion cell layer (region on the basement membrane side from neuroblastic layer), and ectopic CRX-positive cell was found at the same level as in the apical surface (photoreceptor layer, outer nuclear layer) and neuroblastic layer where photoreceptor progenitor cells are originally present (FIG. 4a, b).

Furthermore, many ectopic CRX-positive cells were found in the retinal tissues of +T3+BMP4 group and +T3+Cyclopamine-KAAD group, as in the retinal tissue of +T3 group, still more CRX-positive cells were found on the whole (FIG. 4b, c, d).

From these, similar to what is shown in Examples 2, 3, thyroid gland hormone signal transduction pathway agonist was found to have an action of increasing photoreceptor precursor of a retinal tissue on about day 70 from the start of suspension culture. In addition, it was found that when thyroid gland hormone signal transduction pathway agonist and dorsalization signal transmitter were allowed to act in combination, photoreceptor precursor was further increased as compared to when thyroid gland hormone signal transduction pathway agonist was allowed to act alone. Furthermore, it was found that photoreceptor precursor that is increased by thyroid gland hormone signal transduction pathway agonist, or by thyroid gland hormone signal transduction pathway agonist and dorsalization signal transmitter in combination, also ectopically emerges in a region extending from the neural retinal progenitor cell layer to the ganglion cell layer.

In addition, the CRX-positive cell at this time contained a cell that expresses TRβ2 in a retinal tissue cultured under any conditions, namely, cone photoreceptor precursor (FIG. 4i, j, k, l). These cone photoreceptor precursors that emerge in the initial developmental stage were found in a greater number in the retinal tissue of +T3 group as compared to -T3 group, like photoreceptor precursor (FIG. 4i, j). Like photoreceptor precursor, in the retinal tissue of -T3 group, cone photoreceptor precursor that emerges in the initial developmental stage was scarcely found in a region extending from neural retinal progenitor cell layer to ganglion cell layer. In the retinal tissue of +T3 group, many ectopic cone photoreceptor precursors that emerge in the initial developmental stage were found in a region extending from neural retinal progenitor cell layer to ganglion cell layer (FIG. 4i, j). On the other hand, the retinal tissues of +T3+BMP4 group and +T3+Cyclopamine-KAAD group showed the same tendency as in the retinal tissue of +T3 group, and a greater number of cone photoreceptor precursors that emerge in the initial developmental stage were found (FIG. 4j, k, l).

From these, it was found that thyroid gland hormone signal transduction pathway agonist such as T3 and the like has an action of increasing cone photoreceptor precursor that emerge in the initial developmental stage of retinal tissue on about day 70 from the start of suspension culture. In addition, it was found that when thyroid gland hormone signal transduction pathway agonist and dorsalization signal transmitter were allowed to act in combination, an action of further increasing cone photoreceptor precursors that emerge in the initial developmental stage was found as compared to when thyroid gland hormone signal transduction pathway agonist was allowed to act alone. Furthermore, it was found that cone photoreceptor precursors that emerge in the initial developmental stage and are increased by thyroid gland hormone signal transduction pathway agonist, or photoreceptor progenitor cell that emerge in the initial developmental stage and is increased by thyroid gland hormone signal transduction pathway agonist and dorsalization signal transmitter in combination also ectopically emerges in a region extending from the neural retinal progenitor cell layer to the ganglion cell layer.

Example 5

The cell aggregates containing a retinal tissue shown in Example 5 were prepared by respectively adding T3 or dorsalization signal transmitter as follows in the method described in Example 1.

[1] -T3 group (FIG. 5a, FIG. 5g, FIG. 5m); using the culture medium described in Example 1, culture was performed without addition up to day 191 from the start of suspension culture.
[2] +T3 group (FIG. 5b, FIG. 5h, FIG. 5n); using the culture medium described in Example 1, 60 nM T3 was further added from day 38 to day 130 from the start of suspension culture, and thereafter cultured up to day 188 from the start of suspension culture. From day 130 to day 188, medium B described in Example 1 was used.
[3] +BMP group (FIG. 5c, FIG. 5i, FIG. 5o); using the culture medium described in Example 1, 0.15 nM BMP4 was further added from day 22 to day 100 from the start of suspension culture, and thereafter cultured up to day 191 from the start of suspension culture. From day 100 to day 191, medium [3] described in Example 1 was used.
[4] +T3+BMP group (FIG. 5d, FIG. 5j, FIG. 5p); using the culture medium described in Example 1, 0.15 nM BMP4 was further added from day 22 to day 100 from the start of suspension culture, 60 nM T3 was added from day 38 to day 130 from the start of suspension culture, and thereafter cultured up to day 188 from the start of suspension culture. From day 130 to day 188, medium [3] described in Example 1 was used.
[5] +Cyclopamine-KAAD group (FIG. 5e, FIG. 5k, FIG. 5q); using the culture medium described in Example 1, 500 nM Cyclopamine-KAAD was further added from day 22 to day 100 from the start of suspension culture, and thereafter cultured up to day 191 from the start of suspension culture. From day 100 to day 191, medium [3] described in Example 1 was used.
[6] +T3+Cyclopamine-KAAD group (FIG. 5f, FIG. 5l, FIG. 5r); using the culture medium described in Example 1, 500 nM Cyclopamine-KAAD was further added from day 22 to day 100 from the start of suspension culture, 60 nM T3 was added from day 38 to day 130 from the start of suspension culture, and thereafter cultured up to day 188 from the start of suspension culture. From day 130 to day 188, medium [3] described in Example 1 was used.

After fixing cell aggregates containing retinal tissue cultured under the above conditions with 4% para-formaldehyde, cryosections were prepared and subjected to immunostaining using PAX6 antibody, CHX10 antibody, or DAPI staining for staining the cell nucleus. In the retina of a living body, PAX6-positive/CHX10-positive cell is considered to be a neural retinal progenitor cell, and PAX6-strongly positive/CHX10-negative cell is considered to be any of ganglion cell, horizontal cell, amacrine cell. The PAX6-negative/CHX10-strongly positive cell is considered to be bipolar cell.

As a result of observation with a fluorescent microscope, PAX6-positive/CHX10-positive cell contained in a cell aggregate containing a retinal tissue was similarly found under any conditions, and a remarkable difference was not found. In -T3 group, +BMP group and +Cyclopamine-KAAD group, i.e., groups without addition of T3, many PAX6-strongly positive/CHX10-negative cells were found in a region seemingly on the basement membrane side from the inner nuclear layer containing ganglion cell layer (FIG. 5a, c, e). Also, many PAX6-negative/CHX10-strongly positive cells were found in a region seemingly on the apical surface side of the inner nuclear layer (FIG. 5g, i, k). On the other hand, the proportions of PAX6-strongly positive/CHX10-negative cell, PAX6-negative/CHX10-strongly positive cell markedly decreased in the retinal tissues of +T3 group, +T3+BMP group and +T3+Cyclopamine-KAAD group, i.e., groups added with T3, as compared to groups with no addition (FIG. 5b, d, f, h, j, l).

From these, it was found that thyroid gland hormone signal transduction pathway agonist such as T3 and the like can markedly decrease the proportion of PAX6-strongly positive/CHX10-negative cell (any of ganglion cell, amacrine cell, horizontal cell) and PAX6-negative/CHX10-strongly positive cell (bipolar cell). Therefore, it was found to be useful for regenerative medicine as a retinal tissue for transplantation containing photoreceptor precursor. In a stage of about day 188-day 191 from the start of suspension culture when maturation proceeded to the extent Muller cell was found, BRN3-positive cell, i.e., ganglion cell, found in a stage of about day 70 or about day 100 from the start of suspension culture died and was scarcely found. On the other hand, the proportions of Calretinin-positive cell expressed in amacrine cell, Calbindin-positive cell, LIM1-positive cell and the like expressed in horizontal cell, decreased like PAX6-strongly positive/CHX10-negative cell.

Example 6

The cell aggregates containing a retinal tissue shown in Example 6 were prepared by respectively adding T3 or dorsalization signal transmitter (BMP4 or Cyclopamine-KAAD) as follows in the method described in Example 1.
[1] -T3 group (FIG. 6a, FIG. 6e, FIG. 6i, FIG. 6m); using the culture medium described in Example 1, culture was performed without addition up to day 191 from the start of suspension culture.
[2] +T3 group (FIG. 6b, FIG. 6f, FIG. 6j, FIG. 6n); using the culture medium described in Example 1, 60 nM T3 was further added from day 38 to day 130 from the start of suspension culture, and thereafter cultured up to day 192 from the start of suspension culture. From day 130 to day 192, medium [3] described in Example 1 was used.
[3] +T3+BMP group (FIG. 6c, FIG. 6g, FIG. 6k, FIG. 6o); using the culture medium described in Example 1, 0.15 nM BMP4 was further added from day 22 to day 100 from the start of suspension culture, 60 nM T3 was added from day 38 to day 130 from the start of suspension culture, and thereafter cultured up to day 188 from the start of suspension culture. From day 130 to day 188, medium [3] described in Example 1 was used.
[4] +T3+Cyclopamine-KAAD group (FIG. 6d, FIG. 6h, FIG. 6l, FIG. 6p); using the culture medium described in Example 1, 500 nM Cyclopamine-KAAD was further added from day 22 to day 100 from the start of suspension culture, 60 nM T3 was added from day 38 to day 130 from the start of suspension culture, and thereafter cultured up to day 193 from the start of suspension culture. From day 130 to day 193, medium [3] described in Example 1 was used.

After fixing cell aggregates containing retinal tissue cultured under the above conditions with 4% para-formaldehyde, cryosections were prepared. The cryosections were subjected to immunostaining using GFP antibody, NRL antibody, RXR-γ (RXRg) antibody, or DAPI staining for staining the cell nucleus. GFP-positive cell is a photoreceptor precursor that expresses fluorescent protein Venus knocked-in at the CRX gene locus. In general, NRL-positive cell is considered to be a rod photoreceptor (or rod photoreceptor precursor), and RXR-γ-positive cell is considered to be a cone photoreceptor (or cone photoreceptor precursor) among the photoreceptors (or photoreceptor precursors). As a result of observation with a fluorescent microscope, in +T3 group, +T3+BMP group, +T3+Cyclopamine-KAAD group, the proportion of photoreceptor precursor was markedly high among the cells contained in the retinal tissue, as compared to −T3 group (FIG. 6a, b, c, d). On the other hand, many nuclei of cells seemingly other than photoreceptor precursor, namely, PAX6-strongly positive/CHX10-negative cell and the like described in Example 5 were present on the basement membrane side from the outer nuclear layer (layer in which nucleus of photoreceptor precursor is accumulated) in −T3 group. Such cells markedly decreased in +T3 group, +T3+BMP group, +T3+Cyclopamine-KAAD group, the cells present in this region were replaced with ectopic photoreceptor precursors (FIG. 6a, b, c, d, m, n, o, p). Furthermore, RXR-γ-positive and NRL-negative cone photoreceptor precursor increased among CRX:Venus-positive photoreceptor precursors in all of +T3 group, +T3+BMP group, +T3+Cyclopamine-KAAD group as compared to −T3 group (FIG. 6a, b, c, d, e, f, g, h, i, j, k, l).

Example 7

The number of CRX-positive cells contained in retinal tissues produced by the method described in Example 4, and the numbers of TRβ2-positive cells in CRX-positive cells were measured using image analysis software (Image J), the results of which are shown (FIG. 7). As a control group, a cell aggregate containing retinal tissue when only a dorsalization signal transmitter was added and 60 nM T3 was not added, such as +BMP4 group, +Cyclopamine-KAAD group and the like, was also prepared and measured in the same manner. As a result of the measurement, about 10.6% was CRX-positive cell in the control group without addition of T3, whereas 17.0%, 14.1% were CRX-positive cells respectively in +BMP4 group, +Cyclopamine-KAAD group. In contrast, it was 22.8% in the control group added with T3, and 29.1%, 30.7% were CRX-positive cells in groups containing a combination of T3 and dorsalization signal transmitter, namely, a group added with BMP4 in addition to T3 and a group added with Cyclopamine-KAAD in addition to T3, respectively. In a control group without addition of T3, about 6.8% was CRX-positive and TRβ2-positive cell, whereas 10.8%, 8.1% were CRX-positive and TRβ2-positive cells respectively in +BMP4 group, +Cyclopamine-KAAD group. In contrast, it was 11.3% in +T3 group, and 16.0%, 15.0% were CRX-positive and TRβ2-positive cells in groups containing a combination of T3 and dorsalization signal transmitter, namely, a group added with BMP4 in addition to T3 and a group added with Cyclopamine-KAAD in addition to T3, respectively.

Example 8

The PAX6-negative/CHX10-strongly positive cells (bipolar cells) or PAX6-strongly positive/CHX10-negative cells (any of ganglion cell, amacrine cell, horizontal cell) contained in the retinal tissue produced by the method described in Example 5 were measured using image analysis software (Image J), the results of which are shown (FIG. 8). In control group, +BMP group or +Cyclopamine-KAAD group without addition of T3, 8.03%, 15.49%, 8.65% were respectively PAX6-negative/CHX10-strongly positive cells. In contrast, it was 4.29% in +T3 group, and 8.50%, 4.38% were PAX6-negative/CHX10-strongly positive cells in groups containing a combination of T3 and dorsalization signal transmitter, namely, +T3+BMP4 group, +T3+Cyclopamine-KAAD group, respectively. On the other hand, in control group, +BMP group or +Cyclopamine-KAAD group which are without addition of T3, 32.54%, 24.60%, 24.50% were respectively PAX6-strongly positive/CHX10-negative cells. In contrast, it was 13.83% in +T3 group, and 9.78%, 8.65% were PAX6-strongly positive/CHX10-negative cells in groups containing T3 and dorsalization signal transmitter in combination, namely, +T3+BMP4 group, +T3+Cyclopamine-KAAD group, respectively.

Example 9

CRX:Venus-positive cell (photoreceptor precursor), RXR-γ-positive and NRL-negative cell (cone photoreceptor precursor) among CRX:Venus-positive cells or NRL-positive cell (rod photoreceptor precursor) among CRX:Venus-positive cells, which are contained in the retinal tissue produced by the method described in Example 6, were measured using image analysis software (Image J), the results of which are shown (FIG. 9). As a control group, a cell aggregate containing retinal tissue when 60 nM T3 was not added, such as +BMP4 group, +Cyclopamine-KAAD group and the like, was also prepared and measured using image analysis software (Image J) in the same manner. As a result of the measurement, 35.5%, 37.7%, 41.7% were CRX-positive cells respectively in control group, +BMP group or +Cyclopamine-KAAD group without addition of T3. In contrast, it was 53.4% in +T3 group, and 57.9%, 66.6% were CRX-positive cells in groups containing a combination of T3 and dorsalization signal transmitter, namely, +T3+BMP4 group, +T3+Cyclopamine-KAAD group, respectively. On the other hand, control group, +BMP group or +Cyclopamine-KAAD group which are without addition of T3, 22.7%, 31.3%, 30.2% were respectively RXR-γ-positive and NRL-negative cell among CRX-positive cells. In contrast, it was 44.1% in +T3 group, and 54.2%, 57.5% were RXR-γ-positive and NRL-negative cell among CRX-positive cells in groups containing a combination of T3 and dorsalization signal transmitter, namely, +T3+BMP4 group, +T3+Cyclopamine-KAAD group, respectively. Furthermore, in control group, +BMP group or +Cyclopamine-KAAD group which are without addition of T3, 12.8%, 6.1%, 11.5% were respectively NRL-positive cells among CRX-positive cells. In contrast, it was 9.4% in +T3 group, and 3.7%, 9.1% were NRL-positive cells among CRX-positive cells respectively in groups containing a combination of T3 and dorsalization signal transmitter, namely, +T3+BMP4 group, +T3+Cyclopamine-KAAD group.

Example 10

The cell aggregates containing a retinal tissue shown in Example 10 were prepared by respectively adding T3 or dorsalization signal transmitter as follows in the method described in Example 1.
  [1]-T3 group; using the culture medium described in Example 1, culture was performed without addition up to day 100-105 from the start of suspension culture.
  [2] +T3 group; using the culture medium described in Example 1, culture was performed, 60 nM T3 was added from day 38 from the start of suspension culture, and cultured up to day 100-105 from the start of suspension culture.
  [3] +T3+BMP group; using the culture medium described in Example 1, 0.15 nM BMP4 was added from day 22-day 100 from the start of suspension culture, 60 nM T3 was further added from day 38 from the start of suspension culture to the completion of suspension culture, and cultured up to day 100-105 from the start of suspension culture.

[4] +T3+Cyclopamine-KAAD group; using the culture medium described in Example 1, 500 nM Cyclopamine-KAAD was added from day 22-day 100 from the start of suspension culture, 60 nM T3 was further added from day 38 from the start of suspension culture to the completion of suspension culture, and cultured up to day 100-105 from the start of suspension culture.

A cell aggregate containing retinal tissue which was cultured under the above conditions was fixed with 4% para-formaldehyde, cryosections were prepared, subjected to immunostaining using an anti-CRX antibody, anti-Ki67 antibody, or DAPI staining for staining the cell nucleus and observed with a fluorescent microscope, the results of which are shown (FIG. 10, left). As a result of observation, it was found that CRX-positive cell which is a photoreceptor precursor remarkably increased in the retinal tissue of +T3 group as compared to the retinal tissue of −T3 group. Particularly, the thickness of the photoreceptor precursor layer present on the apical surface was about 2, 3 times greater in +T3 group as compared to −T3 group. These results were also found in +T3+BMP4 group, +T3+Cyclopamine-KAAD group. In addition, a layer containing Ki67-positive proliferative neural retinal progenitor cell, i.e., neuroblastic layer, was found also in a neural retinal tissue on about day 100 from the start of suspension culture. As compared to the retinal tissue of −T3 group, in the retinal tissue of +T3 group, many photoreceptor precursors are contained in a retinal tissue in sites other than the apical surface (photoreceptor layer, outer nuclear layer) where photoreceptor precursor is originally present in the fetal stage, namely, a neuroblastic layer where Ki67-positive neural retinal progenitor cells are present and ganglion cell layer on the basement membrane side therefrom, it is found that ectopic photoreceptor precursors are contained. Such results were also found in +T3+Cyclopamine-KAAD group. On the other hand, even though such ectopic photoreceptor precursor was also found in +T3+BMP4 group, it was not found as many times as in +T3 group or +T3+Cyclopamine-KAAD group, and it was suggested that emergence of photoreceptor precursor was less in this differentiation stage as compared to that in +T3 group and +T3+Cyclopamine-KAAD.

Then, the proportion of CRX-positive cells contained in a neural retinal tissue prepared under similar conditions was measured using image analysis software (Image J), the results of which are shown in a graph (FIG. 10, right). As a result, the proportion of CRX-positive cells contained in the neural retinal tissues of −T3 group, +T3 group, +T3+BMP4 group, and +T3+Cyclopamine-KAAD group was 17.1%, 30.0%, 42.9%, and 50.1%, respectively, and it was found that the content of CRX-positive cell becomes higher in the order of −T3 group, +T3 group, +T3+BMP4 group, +T3+Cyclopamine-KAAD group.

From these, thyroid gland hormone signal transduction pathway agonist was found to have an action of increasing photoreceptor precursor of a retinal tissue on about day 100 from the start of suspension culture. In addition, it was found that when thyroid gland hormone signal transduction pathway agonist and dorsalization signal transmitter were allowed to act in combination, photoreceptor precursor was further increased as compared to when thyroid gland hormone signal transduction pathway agonist was allowed to act alone.

When the results of these Examples are considered together, it was found that thyroid gland hormone signal transduction pathway agonist markedly reduces the proportion of unnecessary cells, causes emergence of ectopic photoreceptor precursor also on the basement membrane side from the outer nuclear layer, and further increases the proportion of photoreceptor precursor markedly. That is, it was found that thyroid gland hormone signal transduction pathway agonist makes it possible to produce a retinal tissue for transplantation which is useful as a pharmaceutical product to be used for regenerative medicine.

It was found that when a dorsalization signal transmitter and a thyroid gland hormone signal transduction pathway agonist are acted in combination, similarly, it markedly reduces the proportion of unnecessary cells, markedly increases the proportion of photoreceptor precursor and further increases the proportion of cone photoreceptor precursor among the photoreceptor precursors. Particularly, it was found that when the dorsalization signal transmitter is BMP4, rods are almost absent in photoreceptor precursor and it is possible to prepare a region with a particularly high cone proportion. Also, it was found that when the dorsalization signal transmitter is Cyclopamine-KAAD which is an SHH signal transduction pathway inhibitor, a retinal tissue with a high cone proportion can be prepared without increasing the proportion of bipolar cell considered to be unnecessary for transplantation, as compared to when the dorsalization signal transmitter is BMP4. That is, it was found that when thyroid gland hormone signal transduction pathway agonist is allowed to act in combination with a dorsalization signal transmitter, a pharmaceutical composition useful as a retinal tissue for transplantation into the macula or the center of the macula can be produced.

Example 11

The cell aggregates were prepared by adding T3 or dorsalization signal transmitter as follows to the methods described in Examples 1, 4, 5, 6, 10. The results are shown in FIG. 11. In FIG. 11, +T3 group is a group added with T3, +T3+BMP4 group is a group added with BMP4 in addition to T3, +T3+Cyclopamine-KAAD group is a group added with Cyclopamine-KAAD in addition to T3, T3 was added to 60 nM, BMP4 was added to 0.15 nM, and Cyclopamine-KAAD was added to 500 nM in the medium.

[1] +T3 group; using the culture medium described in Example 1, 60 nM T3 was added from day 38 from the start of suspension culture, and cultured up to day 69, 104, or 188 from the start of suspension culture. T3 was added up to day about 130 from the start of suspension culture at the longest and cultured.

[2] +T3+BMP group; using the culture medium described in Example 1, 0.15 nM BMP4 was added from day 22 from the start of suspension culture, 60 nM T3 was further added from day 38, and cultured up to day 69, 105, or 188-192 from the start of suspension culture. BMP4 was added up to day about 100 from the start of suspension culture and T3 was added up to day about 130 from the start of suspension culture and cultured.

[3] +T3+Cyclopamine-KAAD group; using the culture medium described in Example 1, 500 nM Cyclopamine-KAAD was added from day 22 from the start of suspension culture, 60 nM T3 was further added from day 38, and cultured up to day 69, 105, or 188 from the start of suspension culture. Cyclopamine-KAAD was added up to day about 100 from the start of suspension culture and T3 was added up to day about 130 from the start of suspension culture and cultured.

The cell aggregate containing retinal tissue which was cultured under the above conditions was observed with a fluorescent microscope (Biorevo BZ-9000, Keyence) and images were obtained. As a result, it was found that the cell aggregate had a cavity inside and an epithelial structure was formed. Furthermore, it was found that the diameter in the major axis direction sometimes exceeded 2 mm when the cell aggregate is big (FIG. 11-1).

Furthermore, a cell aggregate containing retinal tissue which was cultured up to day 188 from the start of suspension culture in the same manner was fixed with 4% paraformaldehyde, cryosections were prepared, subjected to immunostaining using an anti-GFP antibody, and observed with a fluorescent microscope (FIG. 11-2). As a result of the observation, it was found that CRX:Venus-positive cells stained with an anti-GFP antibody, namely, photoreceptor precursors, were continuously and regularly arranged on the surface of the cell aggregate. That is, it was found that these cell aggregates were retinal tissues having a continuous epithelial structure and not containing a rosette-like structure even on day 188 from suspension culture. Furthermore, from this Figure, it was found that not only the photoreceptor layer (outer nuclear layer) near apical surface but also many ectopic photoreceptor precursors were observed.

Furthermore, cell aggregates containing retinal tissue which were cultured in the same manner up to day about 70, day about 100, day about 190 from the start of suspension culture were observed with a fluorescent microscope (Biorevo BZ-9000, Keyence) and images were obtained. The obtained images were measured for the diameter in the major axis by using analysis software (Image J). Using the measurement data, the mean (FIG. 11-3, left graph) and the diameter in the major axis of individual cell aggregates containing retinal tissue were plotted in a graph (FIG. 11-3, right graph). The mean was analyzed and it was found that cell aggregates containing retinal tissue in any stage showed a size of not less than 1.1 mm on average. From the plotted graph, it was found that most of them were cell aggregates of not less than 1.0 mm containing retinal tissue, and cell aggregates of not less than 1.5 mm containing retinal tissue were also found easily. It was found that a long diameter in the major axis reached almost 3.0 mm (2.93 mm) in the cell aggregates containing retinal tissue. The numerical value indicated in the plotted graph shows the size of diameter in the major axis of each cell aggregate.

INDUSTRIAL APPLICABILITY

According to the production method of the present invention, a retinal tissue suitable for transplantation in which the proportion of a photoreceptor precursor contained in a neural retinal tissue has been increased and the proportion of unnecessary cells such as amacrine cell, ganglion cell and the like has been reduced can be provided. In addition, the retinal tissue of the present invention is useful as a pharmaceutical composition.

This application is based on a patent application No. 2017-177188 filed in Japan (filing date: Sep. 14, 2017), the contents of which are incorporated in full herein.

The invention claimed is:
1. A method for suppressing differentiation of a ganglion cell, an amacrine cell, a horizontal cell and/or a bipolar cell in a neural retinal tissue with a layer comprising a photoreceptor precursor and/or a photoreceptor, comprising steps:
 (1) differentiating pluripotent stem cells in a first medium into a retinal tissue comprising a neural retinal progenitor cell and in any stage between a differentiation stage immediately after emergence of a ganglion cell and a differentiation stage where emergence rate of a cone photoreceptor precursor reaches maximum, and
 (2) suspension culturing the retinal tissue obtained in step (1) in a second medium containing a thyroid gland hormone signal transduction pathway agonist,
 thereby obtaining the retinal tissue as an aggregate,
 wherein a ratio of ganglion cells, amacrine cells, horizontal cells, and/or bipolar cells to other cells is less than the ratio in the retinal tissue obtained by steps (1) and (2) except for the absence of a thyroid gland hormone signal transduction pathway agonist in the second medium, and
 wherein the first medium and/or the second medium in at least a part of step (2) is a medium containing a dorsalization signal transmitter selected from a group consisting of BMP signal transduction pathway agonist and SHH signal transduction pathway inhibitor at a concentration that suppresses expression of a ventral marker.
2. The method according to claim 1, wherein the step (2) is performed up to a differentiation stage where a rod photoreceptor precursor and/or a bipolar cell emerge(s).
3. The method according to claim 1, wherein the step (2) is performed up to a differentiation stage where an outer plexiform membrane is formed.
4. The method according to claim 1, wherein the step (2) is performed up to a differentiation stage where a Muller cell emerges.
5. The method according to claim 1, wherein the method suppresses formation of PAX6-negative/CHX10-strongly positive cell and PAX6-positive/CHX10-negative cell.
6. The method according to claim 1, wherein the thyroid gland hormone signal transduction pathway agonist is triiodothyronine or thyroxine.
7. The method according to claim 6, wherein the triiodothyronine has a concentration of 1-100 nM.
8. The method according to claim 1, wherein the retinal tissue containing a neural retinal progenitor cell and in a differentiation stage immediately after emergence of a ganglion cell in the step (1) is a retinal tissue having a neural retinal progenitor cell content of not less than 50% based on the total number of cells.
9. A method for producing matured neural retinal tissue, or a neural retinal tissue that can be matured into a matured neural retinal tissue, comprising steps:
 (1) differentiating pluripotent stem cells into a retinal tissue in an initial developmental stage, and
 (2) culturing the retinal tissue obtained in step (1) in a first medium to obtain a retinal tissue containing a neural retinal progenitor cell and in any stage between a differentiation stage immediately after emergence of a ganglion cell and a differentiation stage where emergence rate of a cone photoreceptor precursor reaches maximum, and
 (3) suspension culturing the retinal tissue obtained in step (2) in a second medium containing a thyroid gland hormone signal transduction pathway agonist,
 thereby obtaining the retinal tissue as an aggregate,
 wherein a ratio of ganglion cells, amacrine cells, horizontal cells, and/or bipolar cells to other cells is less than the ratio in the retinal tissue obtained by steps (1), (2), and (3) except for the absence of a thyroid gland hormone signal transduction pathway agonist in the second medium, and wherein the first medium and/or the second medium in at least a part of step (3) is a medium containing a dorsalization signal transmitter selected from a group consisting of BMP signal transduction pathway agonist and SHH signal transduction pathway inhibitor at a concentration that suppresses expression of a ventral marker.

10. The production method according to claim 9, wherein the second medium in step (3) comprises a dorsalization signal transmitter at a concentration that suppresses expression of a ventral marker.

11. The production method according to claim 9, wherein the first medium in step (2) comprises a dorsalization signal transmitter at a concentration that suppresses expression of a ventral marker.

12. The production method according to claim 9, wherein the matured neural retinal tissue has the following characteristics (i)-(iii):
   (i) the proportion of the number of cells of the photoreceptor precursor and photoreceptor is not less than 40% based on the total number of cells;
   (ii) a content of cone photoreceptor precursor and cone photoreceptor contained in photoreceptor precursor and photoreceptor is not less than 70%; and
   (iii) a proportion of the number of cells of a bipolar cell, a ganglion cell, an amacrine cell and a horizontal cell is not more than 30% based on the total number of cells.

13. The production method according to claim 9, wherein the neural retinal tissue that can be matured into a matured neural retinal tissue has the following characteristics (i)-(ii):
   (i) the proportion of the number of cells of photoreceptor precursor and photoreceptor (CRX-positive cell) is not less than 11% based on the total number of cells; and
   (ii) the proportion of the number of cells of CRX-positive and TRβ2-positive cells is not less than 7% based on the total number of cells; and
   culturing is continued for 30-50 days, after recognition of emergence of the cone photoreceptor precursor.

14. The production method according to claim 9, wherein the neural retinal tissue that can be matured into a matured neural retinal tissue has the following characteristics (i)-(ii):
   (i) the proportion of the photoreceptor precursor and photoreceptor (CRX-positive cells) is not less than 25% based on the total number of cells; and
   (ii) the photoreceptor precursor and/or photoreceptor (CRX-positive cell) are/is in contact with the apical surface, and at least two cells are present side by side along a straight line vertical to the tangent line of the apical surface; and
   culturing is continued for 55-80 days after recognition of emergence of the cone photoreceptor precursor.

15. The production method according to claim 9, wherein the step (3) includes the following steps (3-1) and (3-2):
   (3-1) culturing the retinal tissue obtained in step (2) in a medium containing a thyroid gland hormone signal transduction pathway agonist up to day 30-80 after recognition of emergence of the cone photoreceptor precursor, and
   (3-2) culturing the retinal tissue obtained in step (3-1) in a medium for 60-120 days in the presence of or in the absence of thyroid gland hormone signal transduction pathway agonist.

16. The production method according to claim 15, wherein the medium used in step (3-2) is a medium containing a thyroid gland hormone signal transduction pathway agonist and/or a dorsalization signal transmitter at a concentration that suppresses expression of a ventral marker.

17. The production method according to claim 1 or 9, wherein the dorsalization signal transmitter is BMP4.

18. The production method according to claim 17, wherein the BMP4 has a concentration of 0.05-0.45 nM.

19. The production method according to claim 1 or 9, wherein the dorsalization signal transmitter is Cyclopamine-KAAD.

20. The production method according to claim 19, wherein the Cyclopamine-KAAD has a concentration of 0.01-100 μM.

21. The production method according to claim 15, wherein the medium used in step (3-2) is a medium for maintaining a continuous epithelial structure.

* * * * *